US007335759B2

(12) United States Patent
Corona Villegas et al.

(10) Patent No.: US 7,335,759 B2

(45) Date of Patent: Feb. 26, 2008

(54) **RECOMBINANT IMMUNOGENS FOR THE GENERATION OF ANTIVENOMS TO THE VENOM OF SCORPIONS OF THE GENUS *CENTRUROIDES***

(75) Inventors: Miguel Corona Villegas, Cuernavaca City (MX); Ma Consuelo Garcia Rodríguez, Cuernavaca City (MX); Georgina Gurrola Briones, Cuernavaca City (MX); Norma Adriana Valdez Cruz, Cuernavaca City (MX); Baltazar Becerril Luján, Cuernavaca City (MX); Lourival Domingos Possani Postay, Cuernavaca City (MX)

(73) Assignee: Universidad Nacional Autónoma de México (UNAM) (MX)

( * ) Notice: Subject to any disclaimer, the term of this patent is extended or adjusted under 35 U.S.C. 154(b) by 0 days.

(21) Appl. No.: 10/721,793

(22) Filed: Nov. 26, 2003

(65) Prior Publication Data

US 2005/0065331 A1 Mar. 24, 2005

Related U.S. Application Data

(60) Provisional application No. 60/430,067, filed on Dec. 2, 2002.

(51) Int. Cl.
*C07H 21/04* (2006.01)
*C12P 21/06* (2006.01)
*A61K 39/00* (2006.01)

(52) U.S. Cl. ................ 536/23.4; 435/320.1; 435/69.1; 424/178.1

(58) Field of Classification Search ..................... None
See application file for complete search history.

(56) References Cited

U.S. PATENT DOCUMENTS

| | | | |
|---|---|---|---|
| 4,806,346 | A | 2/1989 | Hum et al. |
| 4,814,433 | A | 3/1989 | Fredrickson |
| 4,849,352 | A | 7/1989 | Sullivan et al. |
| 4,940,670 | A | 7/1990 | Rhodes |
| 5,328,834 | A | 7/1994 | Ngo et al. |
| 5,443,976 | A | 8/1995 | Carroll |
| 5,733,742 | A | 3/1998 | Landon |
| 5,888,511 | A | 3/1999 | Skurkovich et al. |
| 5,904,922 | A | 5/1999 | Carroll |
| 6,333,032 | B1 | 12/2001 | Skurkovich et al. |
| 6,448,054 | B1 | 9/2002 | Poznansky et al. |
| 6,534,059 | B2 | 3/2003 | Skurkovich et al. |
| 6,709,655 | B2 | 3/2004 | Lopez de Silanes et al. |
| 2003/0049725 | A1 | 3/2003 | Heavner et al. |
| 2003/0215448 | A1 | 11/2003 | Skurkovich et al. |
| 2003/0223995 | A1 | 12/2003 | Skurkovich et al. |
| 2003/0224005 | A1 | 12/2003 | Skurkovich et al. |
| 2003/0228310 | A1 | 12/2003 | Skurkovich et al. |
| 2004/0062768 | A1 | 4/2004 | Skurkovich et al. |
| 2004/0086508 | A1 | 5/2004 | Skurkovich et al. |

FOREIGN PATENT DOCUMENTS

| | | | |
|---|---|---|---|
| WO | WO 92/22324 | A1 | 12/1992 |
| WO | WO 01/58469 | A1 | 8/2001 |

OTHER PUBLICATIONS

Becerril, B., et al., "Cloning and characterization of cDNAs that code for $Na^+$-channel-blocking toxins of the scorpion *Centruroides noxius* Hoffman," *Gene 128*:165-171, Elsevier Science Publishers B.V. (1993).

Couraud, F., et al., "Two types of scorpion toxin receptor sites, one Related to the Activation, the Other to the inactivation of the action potential sodium channel," *Toxicon 20*: 9-16, Pergamon Press, Ltd. (1982).

Dehesa-Dávila, M. and Possani, L.D., "Scorpionism and serotherapy in Mexico," *Toxicon 32*:1015-1018, Elsevier Science, Ltd. (1994).

Dehesa-Davila, M., et al., "Clinical toxicology of scorpion stings," in *Handbook of Clinical Toxicology of Animal Venoms and Poisons*, Ch. 18, Meier, J., and White, J., eds., CRC Press, Boca Raton, LA, pp. 221-238 (1995).

Edman, P. and Begg, G., "A protein sequenator," *Eur. J. Biochem. 1*:80-91, Blackwell Science, Ltd. on behalf of the Federation of European Biochemical Societies (1967).

Garcia, C., et al., "Isolation, characterization and comparison of novel crustacean toxin with a mammalian toxin from the venom of the Scorpion *Centruroides noxius* Hoffman," *Comp. Biochem. Physiol. 116B*: 315-322, Elsevier Science, Inc. (1997).

Legros, C., et al., "Use of fusion protein constructs to generate potent immunotherapy and protection against scorpion toxins," *Vaccine 20*:934-942, Elsevier Science, Ltd. (Dec. 2001).

Licea, A.F., et al., "FAB fragments of the monoclonal antibody BCF2 are capable of neutralizing the whole soluble venom from the Scorpion *Centruroides noxius* Hoffman," *Toxicon 34*:843-847, Elsevier Science, Ltd. (1996).

Maraboto Martinez, J.A., et al., "Panorama Epidemiológico de las Intoxicaciones Causadas por Animales Ponzoñosos en la Población Derechohabiente del IMSS 1990-1998," in *3ª Reunión de Expertos en Envenenamiento por Animales Ponzoñosos*, Instituto de Biotecnologia, Universidad Nacional Autónoma de México, Alcapulco, Gro., México pp. 1-14 (1999).

Nonner, W., "Effects of *Leiurus* scorpion venom on the "gating" current in myelinated nerve," *Adv. Cytopharmacol. 3*:345-352. Raven Press (1979).

(Continued)

*Primary Examiner*—Robert Mondesi
*Assistant Examiner*—Anand Desai
(74) *Attorney, Agent, or Firm*—Sterne, Kessler, Goldstein & Fox P.L.L.C.

(57) ABSTRACT

The invention concerns genes and fusion of genes that code for scorpion toxins and the corresponding polypeptides. The invention also concerns the use of the polypeptides as immunogens for the generation of antibodies that can recognize and neutralize components of scorpion venom as well as for vaccines to prevent envenomation from stings of scorpions of the genus *Centruroides*, and to immunogenic matrices for the purification of specific immunoglobulins.

20 Claims, 4 Drawing Sheets

OTHER PUBLICATIONS

Possani, L.D., et al., "Scorpion toxins from *Centruroides noxius* and *Tityus serrulatus,*" *Biochem. J. 229*:739-750, Biochemical Society/ Portland Press (1985).

Possani, L.D., et al., "Scorpion toxins specific for $NA^{+-}$channels," *Eur. J. Biochem. 264*:287-300, Blackwell Science, Ltd. on behalf of the Federation of European Biochemical Societies (1999).

Possani, L.D., et al., "Peptides and genes coding for scorpion toxins that affect ion-channels," *Biochimie 82*: 861-868, Editions Scientifiques Elsevier (2000).

Soraida Calderon-Aranda, E., et al., "Neutralizing capacity of murine sera Induced by different antigens of scorpion venom," *Toxicon 31*: 327-337, Pergamon Press, Ltd. (1993).

Soraida Calderon-Aranda, E., et al., "The use of syntheitic peptides can be a misleading approach to generate vaccines against scorpion toxins," *Vaccine 13*:1198-1206, Elsevier Science, Ltd. (1995).

Strichartz, G., et al., "An integrated view of the molecular toxinology of sodium channel grating in excitable cells," *Ann. Rev. Neurosci. 10*:237-267, Annual Reviews, Inc. (1987).

Zamudio, F., et al., "Amino acid sequence and immunological characterization with monoclonal antibodies of two toxins from the venom of the Scorpion *Centruroides noxius* Hoffman," *Eur. J. Biochem. 204*:281-292, Blackwell Science, Ltd. on behalf of the Federation of European Biochemical Societies (1992).

English translation of Maraboto Martinez, J.A., et al., "Intoxications caused by poisonous animals among IMSS right-holders, 1990-1998. An epidemiological overview," in *3ª Reunión de Expertos en Envenenamiento por Animales Ponzoñosos*, Instituto de Biotecnologia, Universidad Nacional Autónoma de México, Alcapulco, Gro., México pp. 1-14 (1999), translated by Amador Rodriquez, J.C. (Dec. 2004), Document AT3.

Cain, B.s., et al., "The Physiologic Basis for Anticytokine Clinical Trials in the Treatment of Sepsis," *J. Am. Coll. Surg. 186*:337-351, American College of Surgeons (1998).

Dick, A.D., et al., "Neutralizing TNF-alpha Activity Modulates T-cell Phenotype and Function in Experimental Autoimmune Uveoretinitis," *J. Autoimmun.* (*Abs.*) 11:255-264, Academic Press (1998).

Fekade, D., et al., "Prevention of Jarisch-Herxheimer Reactions by Treatment with Antibodies Against Tumor Necrosis Factor α," *N. Engl. J. Med. 335*:311-315, Massachusetts Medical Society (1996).

Fox, D.A., et al., "Cytokine Blockade as a New Strategy to Treat Rheumatoid Arthritis," *Arch. Intern. Med. 160*:437-444, American Medical Association (Feb. 2000).

Krueger, J.G., "The immunologic basis for the treatment of psoriasis with new biologic agents," *J. Am. Acad. Dermatol. 46*:1-23, American Academy of Dermatology, Inc. (Jan. 2002).

Lisman, K.A., et al., "Managing Heart Failure with Immunomodulatory Agents," *Cardiol. Clin. 19*:617-625, W.B. Saunders Co. (Nov. 2001).

Luger, T., "Treatment of immune-mediated skin diseases: future perspectives," *Eur. J. Dermatol. 11*:343-347, accessed at http://www.john-libbey-eurotext.fr/en/revues/medecine/ejd/e-docs/00/01/88/A6/article.md, John Libbey Eurotext (2003).

Martin, G.S., "Current Management Strategies for Severe Sepsis and Septic Shock," Presented at Chest 2001: $67^{th}$ Annual Scientific Assembly of the American College of Chest Physicians, Nov. 4-8, 2001, Philadelphia, PA.

Present, D.H., et al., "Infliximab for the Treatment of Fistulas in Patients with Crohn's Disease," *N. Engl. J. Med. 340*:1398-1405, Massachusetts Medical Society (1999).

Qian, Y., et al., "Topical Soluble Tumor Necrosis Factor Receptor Type I Suppresses Ocular Chemokine Gene Expression and Rejection of Allogenic Corneal Transplants," *Arch. Ophthalmol. 118*:1666-1671, American Medical Association (2000).

Stapcynski, J.S., "Shock, Septic," accessed at http://emedicine.com/EMERG/topic533.htm, eMedicine.com Inc., 25 pages (Jul. 25, 2002).

Torres, P.F., and Kijlstra, A., "The role of cytokines in corneal immunopathology," *Ocul. Immunol. Inflamm. 9*:9-24, Swets & Zeitlinger (2001).

Zhu, S., et al., "Early Expression of Proinflammatory Cytokines Interleukin-1 and Tumor Necrosis Factor-α after Corneal Transplantation," *J. Interferon Cytokine Res. 19*:661-669, Mary Ann Liebert, Inc. (1999).

English translation of Secretaria de Salud, "Potency of Anti-Poison Sera," in *Farmacopea de los Estados Unidos Mexicanos*, vol. II, Secretaría de Salud, Mexico City, MX, pp. 1756-1757 (2000).

English language translation of Secretarí de Salud, "Pyrogen Tests," in *Farmacopea de los Estados Unidos Mexicanos*, vol I, Secretarí de Salud, Mexico City, MX, pp. 334-335 (2000).

International Search Report for International Patent Application No. PCT/MX02/0013, European Patent Office, Netherlands, mailed Aug. 16, 2002.

Dialog File 351, Accession No. 9271133, English language abstract for Spanish Patent No. 2 106 183.

RECOMBINANT IMMUNOGENS FOR THE GENERATION OF ANTIVENOMS TO THE VENOM OF SCORPIONS OF THE GENUS *CENTRUROIDES*

This application claims the benefit of priority of U.S. Provisional Application No. 60/430,067 filed Dec. 2, 2002 which is incorporated herein by reference.

BACKGROUND OF THE INVENTION

Field of the Invention

The present invention relates to the isolated genes that code for scorpion toxins (particularly, toxins that affect the sodium and Erg type potassium channels), to fusions of said genes with fragments of genes from other proteins, to the genetic constructions they comprise, to the isolated recombinant fusion proteins and recombinant peptides that comprise the primary sequence of the toxins in question, to their use as immunogens or antigens for the generation of antibodies that can recognize and neutralize components of the scorpion venom from which the toxin genes were obtained, to their use as vaccines to prevent envenomation from stings of scorpions of the genus *Centruroides*, and to their use as part of an immunogenic matrix for the purification of specific immunoglobulins.

Scorpion venom is a complex mixture of peptides, which can be classified in two groups based on the number of amino acids: long chain toxins with 60-76 amino acids (Possani, L. D., et al., *Eur. J. Biochem.* 264:287-300 (1999)), which block the Na+ channels of excitable cells and short chain toxins with 29-41 amino acids that affect the $K^+$ channels (Possani, L. D., et al., *Biochemie* 82:861-868 (2000)), including the Erg type channels (Ether a go go).

The toxins that modify the $Na^+$ channels are, in turn, classified as a and β toxins (Couraud, F., et al., *Toxicon* 20:9-16 (1982)). The α-toxins mainly modify the inactivation mechanism of the $Na^+$ channels, while the β-toxins preferentially modify their activation mechanism (Strichartz, G., et al., *Annu. Rev. Neurosci* 10:237-267 (1987)).

Scorpion venom is composed of several peptides that can be toxic for a large variety of animals, some are toxic for mammals, others for insects, others for crustaceans, etc. (Possani, L. D., et al., *Eur. J. Biochem.* 264:287-300 (1999)).

There are approximately 221 species and subspecies of scorpions in Mexico, but only eight are medically important and are those that belong to the genus *Centruroides*, of which the species *Centruroides noxius* Hoffmann, *C. limpidus limpidus* Krash, *C. elegans* and *C. sculpturatus* are some of the most dangerous (Calderón-Aranda, et al., *Toxicon* 31:327-337 (1993)). From 1981 to 1990, approximately 250,000 cases of stings in humans were reported, with some 300 deaths (Calderón-Aranda, E. S., et al., Vaccine 13:1198-1206 (1995)), while from 1996-1998, of the cases that were reported among the population covered by the Mexican Social Security Institute, there were 429,561 cases of intoxication caused by scorpion stings (Esteba Maraboto, J. A., and Turrubiate Guillén, N. (1999). Panorama epidemiológico de las intoxicaciones causadas por animales ponzoñosos en la población derechohabiente del IMSS 1990-1998.5[a] Reunión de expertos en Envenenamiento por Animales Ponzofoñosos. Instituto de Biotecnología/UNAM Cuernavaca, Morelos, Mexico, 17 Feb., 1999). Hence scorpionism is considered to be a public health problem in Mexico.

In the United States, although the incidence of scorpion stings is much lower than in Mexico, there is a health problem caused by the scorpion *C. sculpturatus* of Arizona. This low incidence of cases of envenomation from this scorpion means a very small potential market, which has discouraged the large pharmaceutical companies from developing and producing efficacious antivenoms, and therefore cases are usually attended with intensive therapy, that is, relieving the symptoms caused by means of intensive care. In general, symptoms following a scorpion sting include: pain, cough, hypersensitivity, hyperexcitability, excessive salivation and vomiting. When two or more of these symptoms are present, antiscorpion serum is administered to counteract the effects, since cases of severe envenomation can cause heart and/or lung failure (Normer, W., *Adv. Cytopharmacol.* 3:345-351 (1979)), which can cause the death of the individual who has been stung.

Perhaps the most successful strategy in treating scorpion envenomation is the use of hyperimmune sera or monoclonal antibodies that can neutralize or delay the toxic effect of the scorpion toxins (serotherapy). In this sense, serotherapy studies have been conducted with polyclonal antibodies (Dehesa-Dávila, M., and Possani, L. D., *Toxicon* 32: 1015-1018 (1994)) and monoclonal antibodies (Dehesa-Dávila, M., et al., "Cinical toxicology of scorpion stings." In: *Handbook of Clinical Toxicology of Animal Venoms and Poisons*, pp. 201-238 (Meier, J. and White, J. Eds.). New York, CRC Press (1995); Zamudio, F., et al., *Eur. J. Biochem.* 204:281-292 (1992)); similarly, there are products on the market obtained from hyperimmune anti-scorpion horse sera, that after being fractionated, are enzymatically digested to obtain the $F(ab)_2$ fragment (for example, the one prepared by Instituto Bioclón S. A., in Mexico). However, these sera are prepared by immunizing horses with the macerated telson of a large number of scorpions. Once this maceration has been prepared, it is centrifuged and the horse is inoculated with the soluble part. This procedure is carried out by macerating a mixture of telsons from several scorpion species, such as *C. noxius, C. limpidus limpidus* and *C. suffusus suffusus* (in Mexico) (Dehesa-Dávila, M., and Possani, L. D., *Toxicon* 32: 1015-1018 (1994)).

After several immunizations, the horse serum is obtained and whole immunoglobulins of the horse are purified. The antibodies are subsequently digested with pepsin to obtain the immunoglobulin fragments, $F(ab)_2$, responsible for neutralizing the venom.

The preparation described above has the disadvantage of containing a mixture of very varied antibodies, since, as mentioned earlier, scorpion venom is composed of dozens of peptides, only a few of which are active against mammals. Hence, the antibodies directed against these toxins are found in a very small proportion with respect to the total population of antibodies, meaning that it is necessary to apply a high dose of the preparation in order to be able to neutralize the effect of the toxins. Since this is an exogenous protein, the larger the amount the greater the risk of provoking an anaphylactic shock or serum sickness in patients, and the greater the possibility of provoking secondary effects in persons to whom this neutralizing preparation is applied on more than one occasion.

Due to the above, there is a need to remove the immunoglobulins not associated with the neutralizing effect of these sera, since their administration can produce an undesirable immune response (crossed autoimmunity, for example), induce nephrotoxicity, serum sickness and, in serious cases, anaphylactic shock.

In the case of the use of monoclonal antibodies, there are other disadvantages such as the presence of pollutants in the culture mediums that contain antibodies expressed by a hybridoma of interest, such as cells or nucleic acids. In the same way, antibody aggregates can also act as immunogens and cause an undesirable immune response in the organism receiving the therapy.

Together with the failed attempts to generate a reliable vaccine, and until more adequate, safe peptides for vaccination are determined, the most viable alternative with greatest purity, at least in the short term, for protection from scorpion stings is the use of anti-scorpion fabotherapics.

Furthermore, independent of whether or not adequate vaccines are produced to prevent intoxication from scorpion venom, there will be the constant need to have an effective reagent (anti-scorpion antiserum or purified anti-scorpion antibodies) for administration to non-vaccinated, intoxicated individuals available for immediate use in the field, since the time in which the venom exerts its toxic effect and can even provoke death in the affected organism is very short (0.33 hrs. in mice) (Zamudio, F., et al., *Eur. J. Biochem.* 204:281-292 (1992)).

For this reason, there is interest in constantly improving the production of the anti-scorpion antivenoms to be administered in order to neutralize the toxic activity of the scorpion venom in affected individuals.

Legros et al. (2002) published a report in which clones of mammal specific toxins I, II and III of *Androctonus australis* were used to produce recombinant peptides fused to the maltose binding protein (MBP). The fusion proteins were subsequently employed to generate antibodies in rabbits and proved to have a neutralizing effect on the toxic fraction (for mammals) that was separated from the scorpion venom, producing a sustained response. Hence, it is suggested that these recombinant peptides can even be used as a vaccine against the sting of this scorpion.

DETAILED DESCRIPTION OF THE INVENTION

Figure 1:
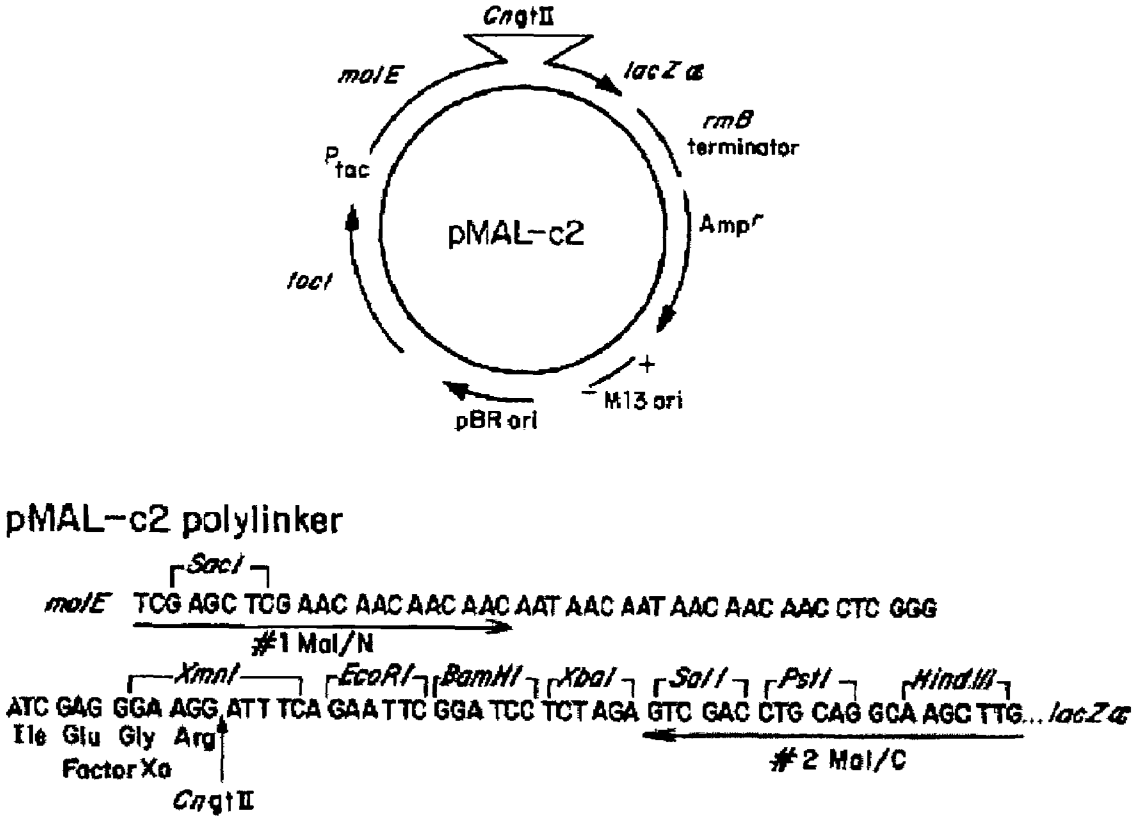
FIG. 1. Shows the construction for the expression of recombinant peptide Cn5. A) shows the scheme of the expression vector pMal-C where the insert corresponding to clone CngtII is shown. B shows the information of the polylinker of the expression vector pMal-C, including the positions recognized by the restriction enzymes and factor Xa, and the position where CngtII was inserted.

One way of improving the antivenoms being currently produced is to enrich the mixtures of scorpion venoms that are used as immunogens or antigens with selected toxins whose effect is known as being especially toxic for mammals. To this end, it would be necessary to purify large amounts of toxins from large amounts of venom. One interesting alternative is to substitute these native toxins with synthetic peptides or peptides produced using recombinant DNA techniques. Although feasible, chemical synthesis of the peptide is not economically recommendable on a large scale, while to be able to produce said recombinant peptides it is necessary to have the nucleotide sequences coding for these toxins.

It may prove even better to prepare a chemical composition consisting of a mixture of those toxins specific for mammals or alternatively a mixture of synthetic or recombinant peptides that have the same primary sequence as said toxins for use as an immunogen instead of the whole venoms for the generation of antibodies in mammals. It is postulated that said mixture of antibodies would have a clear advantage over those currently produced, since it would have been generated only against mammal specific toxins and would have greater venom neutralizing activity per milligram of exogenous protein administered to the organism affected by the venom.

Another way of improving the antivenoms currently produced is to separate those antibodies or their fragments that really participate in the neutralization of mammal specific toxins. To this end, it would be useful to have an antigenic matrix to which those antibodies against said toxins are specifically bound (immunoaffinity). This can be achieved by binding said isolated toxins to an inert material by way of support. Again, it is necessary to have sufficient amounts of said toxins or, alternatively, recombinant or synthetic peptides with the same primary sequence as the toxins in question.

In order to be able to have sufficient amounts of peptides with the same primary sequence as the toxins that are potentially specific for mammals, which can be used to improve the antivenoms currently produced as mentioned in the paragraphs above, the inventors of the present invention decided to isolate and sequence several cDNA clones of toxins from different scorpions of potential interest to health in several regions, such as *Centruroides exilicauda, C. limpidus limpidus* Karsh, *C. noxius* Hoffman, *C. elegans* and *C. gracilis* from Mexico and *C. sculpturatus* Ewing from the United States. The isolation and cloning of these genes is described in detail in examples 1 to 7. As shown in Table 1, it was possible to isolate and clone a total of 71 clones of toxins from 6 species of scorpions of the genus *Centruroides,* 49 of which are specific for sodium channels and 22 for Erg type potassium channels.

TABLE 1

71 clones of genes of toxins isolated from scorpions of the genus *Centruroides*

| Species | A | A1 | B | C | D | E |
|---|---|---|---|---|---|---|
| *C. exilicauda* | Cex1 | 1 | SEQ ID NO: 1 | SEQ ID NO: 2 | SEQ ID NO: 3 | SEQ ID NO: 4 |
| *C. exilicauda* | Cex2 | 1 | SEQ ID NO: 5 | SEQ ID NO: 6 | SEQ ID NO: 7 | SEQ ID NO: 8 |
| *C. exilicauda* | Cex12 | 1 | SEQ ID NO: 9 | SEQ ID NO: 10 | SEQ ID NO: 11 | SEQ ID NO: 12 |
| *C. exilicauda* | Cex13 | 1 | SEQ ID NO: 13 | SEQ ID NO: 14 | SEQ ID NO: 15 | SEQ ID NO: 16 |
| *C. exilicauda* | Cex3 | 1 | SEQ ID NO: 17 | SEQ ID NO: 18 | SEQ ID NO: 19 | SEQ ID NO: 20 |
| *C. exilicauda* | Cex4 | 1 | SEQ ID NO: 21 | SEQ ID NO: 22 | SEQ ID NO: 23 | SEQ ID NO: 24 |
| *C. exilicauda* | Cex5 | 1 | SEQ ID NO: 25 | SEQ ID NO: 26 | SEQ ID NO: 27 | SEQ ID NO: 28 |
| *C. exilicauda* | Cex6 | 1 | SEQ ID NO: 29 | SEQ ID NO: 30 | SEQ ID NO: 31 | SEQ ID NO: 32 |
| *C. exilicauda* | Cex7 | 1 | SEQ ID NO: 33 | SEQ ID NO: 34 | SEQ ID NO: 35 | SEQ ID NO: 36 |
| *C. exilicauda* | Cex8 | 1 | SEQ ID NO: 37 | SEQ ID NO: 38 | SEQ ID NO: 39 | SEQ ID NO: 40 |
| *C. exilicauda* | Cex9 | 1 | SEQ ID NO: 41 | SEQ ID NO: 42 | SEQ ID NO: 43 | SEQ ID NO: 44 |
| *C. exilicauda* | Cex10 | 1 | SEQ ID NO: 45 | SEQ ID NO: 46 | SEQ ID NO: 47 | SEQ ID NO: 48 |
| *C. exilicauda* | Cex11 | 1 | SEQ ID NO: 49 | SEQ ID NO: 50 | SEQ ID NO: 51 | SEQ ID NO: 52 |
| *C. limpidus limpidus* | Cll2b | 1 | SEQ ID NO: 53 | SEQ ID NO: 54 | SEQ ID NO: 55 | SEQ ID NO: 56 |
| *C. limpidus limpidus* | Cll3 | 1 | SEQ ID NO: 57 | SEQ ID NO: 58 | SEQ ID NO: 59 | SEQ ID NO: 60 |
| *C. limpidus limpidus* | Cll4 | 1 | SEQ ID NO: 61 | SEQ ID NO: 62 | SEQ ID NO: 63 | SEQ ID NO: 64 |
| *C. limpidus limpidus* | Cll5b | 1 | SEQ ID NO: 65 | SEQ ID NO: 66 | SEQ ID NO: 67 | SEQ ID NO: 68 |
| *C. limpidus limpidus* | Cll5c | 1 | SEQ ID NO: 69 | SEQ ID NO: 70 | SEQ ID NO: 71 | SEQ ID NO: 72 |
| *C. limpidus limpidus* | Cll6 | 1 | SEQ ID NO: 73 | SEQ ID NO: 74 | SEQ ID NO: 75 | SEQ ID NO: 76 |
| *C. limpidus limpidus* | Cll7 | 1 | SEQ ID NO: 77 | SEQ ID NO: 78 | SEQ ID NO: 79 | SEQ ID NO: 80 |
| *C. limpidus* limpidus | Cll8 | 1 | SEQ ID NO: 81 | SEQ ID NO: 82 | SEQ ID NO: 83 | SEQ ID NO: 84 |
| *C. noxius* | Cn4b | 1 | SEQ ID NO: 85 | SEQ ID NO: 86 | SEQ ID NO: 87 | SEQ ID NO: 88 |
| *C. noxius* | Cn10b | 1 | SEQ ID NO: 89 | SEQ ID NO: 90 | SEQ ID NO: 91 | SEQ ID NO: 92 |
| *C. elegans* | Ce3 | 1 | SEQ ID NO: 93 | SEQ ID NO: 94 | SEQ ID NO: 95 | SEQ ID NO: 96 |
| *C. elegans* | Ce5 | 1 | SEQ ID NO: 97 | SEQ ID NO: 98 | SEQ ID NO: 99 | SEQ ID NO: 100 |
| *C. elegans* | Ce6 | 1 | SEQ ID NO: 101 | SEQ ID NO: 102 | SEQ ID NO: 103 | SEQ ID NO: 104 |
| *C. elegans* | Ce6b | 1 | SEQ ID NO: 105 | SEQ ID NO: 106 | SEQ ID NO: 107 | SEQ ID NO: 108 |
| *C. elegans* | Ce7 | 1 | SEQ ID NO: 109 | SEQ ID NO: 110 | SEQ ID NO: 111 | SEQ ID NO: 112 |
| *C. elegans* | Ce13 | 1 | SEQ ID NO: 113 | SEQ ID NO: 114 | SEQ ID NO: 115 | SEQ ID NO: 116 |
| *C. elegans* | Ce13b | 1 | SEQ ID NO: 117 | SEQ ID NO: 118 | SEQ ID NO: 119 | SEQ ID NO: 120 |
| *C. gracilis* | Cg1 | 1 | SEQ ID NO: 121 | SEQ ID NO: 122 | SEQ ID NO: 123 | SEQ ID NO: 124 |
| *C. gracilis* | Cg1b | 1 | SEQ ID NO: 125 | SEQ ID NO: 126 | SEQ ID NO: 127 | SEQ ID NO: 128 |
| *C. gracilis* | Cg2 | 1 | SEQ ID NO: 129 | SEQ ID NO: 130 | SEQ ID NO: 131 | SEQ ID NO: 132 |
| *C. gracilis* | Cg3 | 1 | SEQ ID NO: 133 | SEQ ID NO: 134 | SEQ ID NO: 135 | SEQ ID NO: 136 |
| *C. sculpturatus* | CsEv1d | 1 | SEQ ID NO: 137 | SEQ ID NO: 138 | SEQ ID NO: 139 | SEQ ID NO: 140 |
| *C. sculpturatus* | CsEv1c | 1 | SEQ ID NO: 141 | SEQ ID NO: 142 | SEQ ID NO: 143 | SEQ ID NO: 144 |
| *C. sculpturatus* | CsEv3b | 1 | SEQ ID NO: 145 | SEQ ID NO: 146 | SEQ ID NO: 147 | SEQ ID NO: 148 |
| *C. sculpturatus* | CsEIa | 1 | SEQ ID NO: 149 | SEQ ID NO: 150 | SEQ ID NO: 151 | SEQ ID NO: 152 |
| *C. sculpturatus* | CsEv2c | 1 | SEQ ID NO: 153 | SEQ ID NO: 154 | SEQ ID NO: 155 | SEQ ID NO: 156 |
| *C. sculpturatus* | CsEv2b | 1 | SEQ ID NO: 157 | SEQ ID NO: 158 | SEQ ID NO: 159 | SEQ ID NO: 160 |
| *C. sculpturatus* | CsEv2d | 1 | SEQ ID NO: 161 | SEQ ID NO: 162 | SEQ ID NO: 163 | SEQ ID NO: 164 |
| *C. sculpturatus* | CsEv1b | 1 | SEQ ID NO: 165 | SEQ ID NO: 166 | SEQ ID NO: 167 | SEQ ID NO: 168 |
| *C. sculpturatus* | CsEv1e | 1 | SEQ ID NO: 169 | SEQ ID NO: 170 | SEQ ID NO: 171 | SEQ ID NO: 172 |
| *C. sculpturatus* | CsEv2a | 1 | SEQ ID NO: 173 | SEQ ID NO: 174 | SEQ ID NO: 175 | SEQ ID NO: 176 |
| *C. sculpturatus* | CsE9b | 1 | SEQ ID NO: 177 | SEQ ID NO: 178 | SEQ ID NO: 179 | SEQ ID NO: 180 |
| *C. sculpturatus* | CsE9 | 1 | SEQ ID NO: 181 | SEQ ID NO: 182 | SEQ ID NO: 183 | SEQ ID NO: 184 |
| *C. sculpturatus* | CsE8 | 1 | SEQ ID NO: 185 | SEQ ID NO: 186 | SEQ ID NO: 187 | SEQ ID NO: 188 |
| *C. sculpturatus* | CsE3 | 1 | SEQ ID NO: 189 | SEQ ID NO: 190 | SEQ ID NO: 191 | SEQ ID NO: 192 |
| *C. sculpturatus* | CsE1x | 1 | SEQ ID NO: 193 | SEQ ID NO: 194 | SEQ ID NO: 195 | SEQ ID NO: 196 |
| *C. exilicauda* | CexErg1 | 2 | SEQ ID NO: 197 | SEQ ID NO: 198 | SEQ ID NO: 199 | SEQ ID NO: 200 |
| *C. exilicauda* | CexErg2 | 2 | SEQ ID NO: 201 | SEQ ID NO: 202 | SEQ ID NO: 203 | SEQ ID NO: 204 |
| *C. exilicauda* | CexErg3 | 2 | SEQ ID NO: 205 | SEQ ID NO: 206 | SEQ ID NO: 207 | SEQ ID NO: 208 |
| *C. exilicauda* | CexErg4 | 2 | SEQ ID NO: 209 | SEQ ID NO: 210 | SEQ ID NO: 211 | SEQ ID NO: 212 |
| *C. limpidus limpidus* | Cll Erg1 | 2 | SEQ ID NO: 213 | SEQ ID NO: 214 | SEQ ID NO: 215 | SEQ ID NO: 216 |
| *C. limpidus limpidus* | Cll Erg2 | 2 | SEQ ID NO: 217 | SEQ ID NO: 218 | SEQ ID NO: 219 | SEQ ID NO: 220 |
| *C. limpidus limpidus* | Cll Erg3 | 2 | SEQ ID NO: 221 | SEQ ID NO: 222 | SEQ ID NO: 223 | SEQ ID NO: 224 |
| *C. limpidus limpidus* | Cll Erg4 | 2 | SEQ ID NO: 225 | SEQ ID NO: 226 | SEQ ID NO: 227 | SEQ ID NO: 228 |
| *C. noxius* | Cn Erg3 | 2 | SEQ ID NO: 229 | SEQ ID NO: 230 | SEQ ID NO: 231 | SEQ ID NO: 232 |
| *C. noxius* | Cn Erg4 | 2 | SEQ ID NO: 233 | SEQ ID NO: 234 | SEQ ID NO: 235 | SEQ ID NO: 236 |
| *C. noxius* | Cn Erg5 | 2 | SEQ ID NO: 237 | SEQ ID NO: 238 | SEQ ID NO: 239 | SEQ ID NO: 240 |
| *C. elegans* | CeErg1 | 2 | SEQ ID NO: 241 | SEQ ID NO: 242 | SEQ ID NO: 243 | SEQ ID NO: 244 |
| *C. elegans* | CeErg2 | 2 | SEQ ID NO: 245 | SEQ ID NO: 246 | SEQ ID NO: 247 | SEQ ID NO: 248 |

TABLE 1-continued 71 clones of genes of toxins isolated from scorpions of the genus *Centruroides*

| Species | A | A1 | B | C | D | E |
|---|---|---|---|---|---|---|
| *C. elegans* | CeErg3 | 2 | SEQ ID NO: 249 | SEQ ID NO: 250 | SEQ ID NO: 251 | SEQ ID NO: 252 |
| *C. gracilis* | CgErg1 | 2 | SEQ ID NO: 253 | SEQ ID NO: 254 | SEQ ID NO: 255 | SEQ ID NO: 256 |
| *C. gracilis* | CgErg2 | 2 | SEQ ID NO: 257 | SEQ ID NO: 258 | SEQ ID NO: 259 | SEQ ID NO: 260 |
| *C. gracilis* | CgErg3 | 2 | SEQ ID NO: 261 | SEQ ID NO: 262 | SEQ ID NO: 263 | SEQ ID NO: 264 |
| *C. sculpturatus* | CsErg1 | 2 | SEQ ID NO: 265 | SEQ ID NO: 266 | SEQ ID NO: 267 | SEQ ID NO: 268 |
| *C. sculpturatus* | CsErg2 | 2 | SEQ ID NO: 269 | SEQ ID NO: 270 | SEQ ID NO: 271 | SEQ ID NO: 272 |
| *C. sculpturatus* | CsErg3 | 2 | SEQ ID NO: 273 | SEQ ID NO: 274 | SEQ ID NO: 275 | SEQ ID NO: 276 |
| *C. sculpturatus* | CsErg4 | 2 | SEQ ID NO: 277 | SEQ ID NO: 278 | SEQ ID NO: 279 | SEQ ID NO: 280 |
| *C. sculpturatus* | CsErg5 | 2 | SEQ ID NO: 281 | SEQ ID NO: 282 | SEQ ID NO: 283 | SEQ ID NO: 284 |

A. Name given to the clone by the inventors
A1. Type of channel that modifies the native toxin, according to information on homologous toxins:
1. Sodium channels
2. Erg type potassium channels (ether a go go)
B. Sequence number of the complete clone
C. Number of the amino acid sequence encoded by the complete clone B
D. Number of the nucleotide sequence of the coding fragment of the mature peptide (same primary sequence as the native toxin)
E. Number of the amino acid sequence encoded by fragment D Naturally occurring toxins in the scorpion venom will raise specific antibodies in a stung individual In certain embodiments of the invention, the antibodies are specific against only a particular polypeptide and/or the toxin from a particular *Centruroides* species. Such polypeptides may be used as part of a composition, where the polypeptide is bound covalently or through hydrophobic or hydrophilic interaction to a substrate. The substrate may then be used as part of a diagnostic device.

Another embodiment of the invention comprises a device using the substrate described in the previous paragraph. Such a device may be used to detect the presence of species-specific antibodies in an individual stung by a species of *Centruroides* scorpion. A method to dianose whether the scorpion that stunag an individual belongs to a particular species of *Centruroides* scoprion comprises contacting such a diagnostic device with a sample from a stung individual, and detecting the presence of antibodies from the individual that had been stung by the scorpion. If present, the antibodies raised against a particular naturally occurring toxin will bind to the polypeptides of the device. The bound antibodies can then be detected by methods and optical detecting systems well-known to those of ordinary skill in the art. Such methods and devices may for example, be based on immuno-enzymatic, immuno-fluorescenct or immuno-chromatographic techniques.

A significant amount of toxins and their genes including the respective signal peptide are now known. From comparative analyses of the nucleotide and/or amino acid sequences, it can be seen that there are some highly conserved regions, like those equivalent to the first 6 amino acids of the signal peptide and part of the 3' uncoding region (UTR). Based on the foregoing, it is possible to design degenerate oligonucleotides corresponding to the amino ends of the signal peptide and the carboxyl end of the toxin, which can be amplified by PCR using the messenger RNA present in the telson of the scorpion in question. The sequences that hybridize with said oligos generate clones that comprise the coding sequence of the toxin and its peptide signal. These are cloned in a useful vector for rapid identification, as is the case of the vector PKS- (Stratagene, La Jolla, Calif., USA) that has Beta galactosidase as marker in such a way that when X-gal is present in the solid culture medium the colonies that received inserts (clones) lose Beta galactosidase activity and grow with a white color, while this enzyme remains intact in the colonies that received no insert and generates blue colonies. The white colonies are cultivated in order to amplify their plasmid DNA (that presumably comprises some of the clones of interest) which is subsequently sequenced to determine the nucleotide sequence and the deduced amino acid sequence.

Another alternative for oligonucleotide design is to purify some of the toxins present in the scorpion venom in question and obtain the amino acid sequence of the amino region (at least the first 8 amino acids) and use them to design specific oligonucleotides with which to try to obtain, in particular, the clones of these toxins, or rather, based on the homology between the amino acid sequences obtained, design a degenerate oligonucleotide to try to obtain the clones present in the telson that are homologous to the oligonucleotide that has been designed. In both cases, the clones obtained will comprise the coding sequence of the just the toxin without the signal peptide.

Another strategy to be used should there be no further information on the possible expected clones consists of using, instead of an oligonucleotide corresponding to the 3' region of the clone, a poly T oligonucleotide that should hybridize with the PolyA site present in all cDNAs independently of the direct oligo used, the one from the amino region of the signal peptide or of the mature peptide.

The choice of the strategy to be followed in each case will depend on the elements available such as the knowledge of the total or partial amino acid sequence of the toxins of interest or an analysis by mass spectrometry of one or more toxins of the venom of the scorpion in question, the sequence of other toxins from the same scorpion or from other related scorpions, the information on the signal peptide toxin sequence of the same scorpion or other related scorpions, to name but a few.

The peptide or toxin purification procedures using raw venoms from the different scorpions can begin with chromatographic columns that separate fractions based on screening of molecular mass, followed by ion exchange resins and HPLC using reverse phase columns. At present, most laboratories use direct separations of peptides by HPLC or use it directly after a simple separation by molecular mass of the soluble venoms (Possani, L. D., et al., *Eur. J. Biochem.* 264:287-300 (1999)). To this end, the whole venom of the scorpion in question is obtained by electrostimulation of the telson and is subsequently centrifuged before beginning the purification processes.

It is known that some of the polypeptide precursors of the toxins suffer postranslational modifications in both the amino and carboxyl ends: in the amino end a signal peptide of 18 to 21 amino acids is normally eliminated by means of a signal peptidase. In the carboxyl end, the extra basic amino acids (Arg and/or Lys) are processed by a carboxypeptidase. Several mechanisms have been discovered for the postranslational processing of the carboxyl end, typically the basic residue(s) of the end are removed. When a glycine residue precedes one or two basic residues of the amino group of the glycine residue, it is used to amidate to the amino acid residue that precedes it. If a glycine precedes a group of three basic residues, the basic triad is removed without there being any amidation (Possani, L. D., et al., *Eur. J. Biochem.* 264:287-300 (1999)). It will therefore be appropriate if the recombinant peptides being produced have a primary sequence the most similar possible to the mature toxin, that is, without the signal peptide and without the amino acids of the carboxyl end that are eliminated when the toxin is processed, when this is the case.

In order for the genes or clones of the present invention to be used in the generation of better antivenoms, they should first be expressed in a heterologue system, as for example *Escherichia coli, Pichia pastoris*, Baculovirus or others, for either the corresponding recombinant peptide or a fusion protein comprising said peptide to then be used as immunogen (antigen) or component of an immunogen for the production of antibodies in mammals.

It is clear that in order to be expressed in a heterologue system, the genes or clones of the present invention should be introduced in genetic constructions that are compatible with the expression in said systems. Some examples of these could be the Protein Expression and Purification System of New England Biolabs where plasmid pMal-C is used in *E. coli* to express the proteins of interest as fusion proteins bound to the maltose binding protein. Another system could be the one used by Legros' group (Legros, C., et al., *Vaccine* 20:934-942 (2002)), pMal-p from the same supplier.

Before inserting the genes or clones of the present invention in said genetic constructions, it is necessary to edit them to eliminate any fragment of 3' and 5' uncoding regions (UTR). In order to edit the genes or clones of the present invention, it is necessary to synthesize oligonucleotides that, for the direct oligonucleotide, comprise the first amino acids (from 6 to 9) of the amino terminal region to be expressed, either the signal peptide, if it is to be included in the expressed protein, or the mature peptide if the signal peptide is to be excluded and, for the reverse oligonucleotide, the last 6-9 amino acids of the carboxyl terminal region of the mature peptide. In the cases of those toxins that are known to be postranslationally processed, it will be convenient for the reverse oligo to be designed leaving out the amino acid residue(s) that are known to be eliminated with the processing. Subsequently, using both oligonucleotides as primers and the clone or gene of interest as template, a PCR amplification reaction is performed to obtain the DNA that codes only for the mature peptide or for the mature peptide plus the signal peptide. It can also be recommendable to take advantage of the direct oligo to include a methionine residue just before the first amino acid This, at some moment, will permit cleavage of the recombinant peptide once the fusion protein has been expressed through the application of cyanogen bromide (Possani, L. D., et al., *Biochem. J.* 229:739-750 (1985))

In order to demonstrate the feasibility of using any of the genes or clones isolated from scorpions of the genus *Centruroides*, including those of the present invention, for industrial production of the recombinant peptide whose primary sequence is identical to that of the encoded toxin, that is, the native toxin, either in free form or fused with part of other proteins producing a larger polypeptide, the inventors of the present invention carried out a construction (shown in FIG. 1) using clone CngtII (Becerril, B., et al., *Gene* 128:165-171 (1993)), that codes for a well-known, characterized toxin of *Centruroides noxius* Hoffmann, Cn5 (García, C., et al., *Com. Biochem. Physiol.* 116B (3):315-322 (1997)), in which this clone was fused to the maltose binding protein. This is illustrated in detail in examples 8 and 9. The fusion protein expressed was used to generate antibodies in mammals as can be seen in example 10, while in example 11 the use is illustrated of said antibodies in the neutralization in vivo of a known toxin specific for mammals whose amino acid sequence is similar to that of Cn5 and which has proved to be one of the most important in its toxic effect, Cn2 (Zamudio, F., et al., *Eur. J. Biochem.* 204:281-292 (1992); García, C., et al., *Com. Biochem. Physiol.* 116B (3):315-322 (1997)).

Any of the clones of the present invention can, like CngtII, be edited by designing specific oligos which, as mentioned earlier, can be used for the insertion of some methionine or some other sequence that permits its purification, for example, by amplifying them by PCR using the clone of choice as template, obtaining DNA fragments that comprise the corresponding sequence reported in column D, Table 1. Constructions can be made with said fragments in commercial systems, such as plasmids pMalC and pMal-p of the Protein Expression and Purification System (New England Biolabs), or in manufactured expression systems that comprise said DNA fragments fused to heterologue protein coding fragments or fragments of the same, transforming hosts into bacteria such as the CMK strain of *Escherichia coli* or any other expression host for which the selected expression system is appropriate.

On cultivating said cells of the recombinant host, these cells will express (after induction) the fusion protein that will comprise the corresponding sequence reported in column E, Table 1.

It is known that the genetic code is degenerate, that is, that for one same amino acid there is generally more than one encoding codon. The difference between these codons is the third of the bases. It is obvious to an expert in the state of the technique that it is possible to substitute some bases in the encoding nucleotide sequence of the clones of the present invention referred to in column B or in the edited sequences of column D, Table 1, that encode exactly the same amino acid sequences as those referred to in column E, Table 1. This may be particularly useful when it is wished to express said peptides of the present invention in different recombinant hosts, for it is known that different types of hosts have a "preference" of use towards certain codons for determined amino acids. Such "silent mutations" fall within the scope of the present invention, since the products of their expression are again the peptides referred to in column E, Table 1, of the present invention.

Recombinant peptides for the present invention shall be understood to be those peptides obtained by recombinant methods that comprise the primary sequence reported in column E, Table 1.

Thus, the present invention also refers to the use of the recombinant peptides of the present invention, either free or as part of fusion proteins, as vaccines to prevent envenomation from the venom of scorpions of the genus *Centruroides* and the pharmaceutical preparations of said vaccine. Administration of the peptides may be by intravenous, subcutaneous, intramuscular, intravaginal, intraperitoneal, intranasal, oral or other mucous routes. Additionally, the hyperimmune sera or antibodies (obtained following injection of the polypeptides of the invention) that can neutralize or delay the toxic effect of the scorpion toxins can be used to treat envenomation (serotherapy).

The vaccines of the present invention comprise one or more of the recombinant peptides of the present invention, either free or as fusion proteins that, in turn, comprise the primary sequence of the peptides of the present invention. Since the folding of the recombinant peptides expressed in heterologue hosts is not the same as that of the native toxin, said vaccine is also sufficiently innocuous to be administered without danger of intoxication, it is stable and compatible with vaccine carriers.

An effective amount of the vaccine should be administered that is capable of producing an immune response in a mammal, where "effective amount" is defined as an amount of recombinant peptides from the present invention or any fusion protein comprising the same. The necessary amount will vary depending on whether the peptides of the present invention are used or fusion proteins comprising these peptides and on the antigenicity of said fusion protein and on the species and weight of the subject to be vaccinated, but it can be estimated by standard techniques.

Pharmaceutically useful compositions can be formulated as vaccines that comprise one or more of the recombinant peptides of the present invention or any fusion protein including said peptides, according to known methods such as the addition of a pharmaceutically acceptable carrier. In order to form a pharmaceutically acceptable composition suitable for effective administration, said composition shall contain an effective amount of one or more of the recombinant peptides of the present invention or any fusion protein including said recombinant peptides.

The pharmaceutical compositions of the vaccines of the present invention can include a pharmaceutically acceptable adjuvant such as aluminum or calcium gels, modified muramyl dipeptides, monophosphorylated lipids, liposomes, delayed release capsules, polyglycolic acids and polyamino acids. Polyglycolic and polyamino acids are also useful for the oral administration of vaccines. Some examples of aluminum gels useful as adjuvants include precipitated aluminum salts such as aluminum phosphate and hydroxide. Some preservatives such as thimerosal, dextrane and glycerine can be added to stabilize the final vaccine. If it is wished to have the vaccines in injectable form, immunologically acceptable diluents or carriers can be included.

The vaccine of the present invention or the pharmaceutical compositions of the same can be administered to mammals locally and/or systemically through the conventional routes such as the intravenous, subcutaneous, intramuscular, intravaginal, intraperitoneal, intranasal, oral or other mucous routes to arouse an efficacious immune response to protect against the venom of scorpions of the genus *Centruroides*. The vaccine can be optionally administered in sole or multiple doses with the object of sustaining antibody levels.

The pharmaceutic compositions of the vaccines of the present invention should be administered to an individual in such amounts that they contain effective amounts of the vaccine of the present invention. The effective amount will vary according to a variety of factors such as species, condition, weight, sex and age of the individual to be treated. Another factor includes the administration route used.

Another scope of the present invention is based on the fact that the recombinant peptides of the present invention, either free or as fusion proteins, can also be used to generate an immunogenic matrix when bound either covalently or through hydrophobic or hydrophilic interactions to some substrate like polyacrylamide, polyvinyl, activated aldehyde agarose (U.S. Pat. Nos. 5,904,922 and 5,443,976), sepharose, carboxymethyl cellulose or some other, in such a way that the matrix is capable of specifically binding either antibodies (raised against the whole venom of scorpions of the genus *Centruroides* or against the same venoms enriched with some of the recombinant peptides of the present invention, or against mixtures of recombinant peptides of the present invention) or the F(ab) or F(ab)2 fragments obtained from hydrolysis of said antibodies, and is useful in the purification by immunoaffinity of said antibodies or F(ab) or $F(ab)_2$ fragments, which is why said use in the antigenic matrix and said antigenic matrix are included in the scope of the present invention.

Materials and Methods

Scorpions of the species *Centruroides exilicauda* were collected in Baja California, Mexico. Only 2 animals were used for clone isolation.

Scorpions of the species *C. limpidus limpidus* Karsh were collected in Guerrero, Mexico. Only 5 animals were used for clone isolation.

Scorpions of the species *C. noxius* Hoffmann were collected in Nayarit, Mexico. Only 1 animal was used for clone isolation.

Scorpions of the species *C. elegans* were collected in Jalisco, Mexico. Only 5 animals were used for clone isolation.

Scorpions of the species *C. gracilis* were collected in Veracruz, Mexico. Only 1 animal was used for clone isolation.

Scorpions of the species *C. sculpturatus* Ewing were collected in Tucson Ariz. Only 5 animals were used for clone isolation.

All the reagents used are of an analytical grade.

Obtaining the Scorpion Venom

The venom of each scorpion was obtained by electrostimulating the telson. The mixture of the venom from all the scorpions of the same species was centrifuged at 10,000 g for 15 min. The supernatant was quantified by absorbance at 280 nm, lyophilized and stored at −40° C. until it was used.

Purification of Toxins from the Venoms

The toxins were purified in three sequential chromatographic steps:

i) In the first place, using a molecular filter in a medium Sephadex G-50 column (Amersham Pharmacia Biotech AB, Uppsala Sweden). Columns of 200×0.9 cm were used with a 30 ml/hr flow of 20 mM ammonium acetate Buffer pH 4.7 for approximately 10 hr.

ii) The different fractions of interest obtained in the preceding step were separated by ion exchange in 30×0.9 cm columns packed with CMC-32 (Whatman, England). They were run for approximately 15 hr with a 30 ml/hr flow of ammonium acetate buffer pH 4.7 in a gradient of 0.0.5 M NaCl applying 250 ml on each side.

iii) The fractions of interest obtained from the preceding step were subsequently separated by HPLC in a C-18 reverse phase analytic column (Vidac, Hisperia, Calif., USA), with 0-60% solution B gradient for 60 min with a flow of 1 ml/min. Solution A is water with 0.12% trifluoroacetic acid (TFA) (TFA) (Pierce, Rockford, Ill., USA) and solution B is acetonitrile (Pierce, Rockford, Ill., USA) with 0.10% TFA. The apparatus used was a Waters (Millipore Co., Milford, Mass., USA) model 625 LC System with a Waters 996 Diode Photoarray Detector.

The readings of the different eluted fractions from Sephadex G-50 and CMC-32 were read in a Beckman DU-50 spectrophotometer at 280 nm.

Partial or Total Sequencing of Peptides

Peptide sequentiation was performed following the automatic Edman degradation method (Edman, P. and Begg, G., *Eur. J. Biochem.* 1:80-91 (1967)) with a Beckman LF300 sequencer.

Isolation of Clones from Scorpion Toxins

The RNAm from the poisonous glands (telsons) of the scorpions of each species was isolated using the method of Chirgwin et al. (1979). Total RNA (approximately 500 ng) was used to synthesis cDNA through the use of an oligonucleotide which is a 22mer polyT22NN, followed by two degenerate nucleotides (N). Synthesis of the first chain was performed in a first chain 1× buffer (50 mM Tris-HCl, pH 8.3, 75 mM KCl, 3 mM $MgCl_2$), 10 mM dithiothreitol (DTT), 0.5 mM dNTPs, 200 units of reverse transcriptase M-MLV (Gibco-BRL, Gran Islands, N.Y., USA), 0.5 mM oligo (T)22NN, RNAse inhibitor units (Boehringer Mannheim, Frankfurt, Germany), in a final volume of 20 ml. The mixture was pre-incubated for 5 min at 65° C., and then for 5 min. at 50° C. and 30 min. at 42° C. The DTT and enzyme were added to the reaction when the mixture reached 42° C., just before the final 30 min.

For the polymerase chain reaction (PCR), a sample was taken of the first chain reaction (2 ml) to which was added a Vent DNA polymerase 1× buffer (10 mM KCl, 10 mM $(NH_4)_2$ $SO_4$, 20 mM Tris-HCl, pH 8.8, 2 mM $MgSO_4$, 0.1% Triton X-100, at 25° C.), 200 mM dNTPs, 0.25 mM of the direct oligonucleotide (in the 5'-3' sense), 0.25 mm of the reverse oligonucleotide (in the 3'-5' sense) and two units of Vent DNA Polymerase (New England Biolabs, Beverly Mass., USA) in a final volume of 50 ml. The reaction was carried out using a Perking Elmer 9600 thermocycler with the following protocol: Incubation of the mixture for 3 min at 94° C., 5 min a 55° C. before adding the enzyme, followed by 30 s at 72° for the first cycle. The mixture was then incubated at 94° C. for 30 s followed by 30 s at 52° C. per cycle and 30 s at 72° C. per cycle, and repeated 32 times before a final step of 10 min at 72° C.

The PCR products were purified in a Centricon 100 column (Amicon, Beverly, Mass., USA) following the manufacture's instructions. They were subsequently bound to the EcoRV site of plasmid PKS-. These constructions were used to transform *E. coli* DH5-alpha cells. The selection of clones that comprised some insert was done by plating the transforming cells in Petri dishes with LB/agar in the presence of X.Gal, choosing the white colonies for plasmid amplification. The plasmid DNA were sequenced in both chains using fluorescent nucleotides in a Perkin Elmer Applied Biosystems apparatus (Foster City, Calif., USA) as described by the manufacturer.

In order to better illustrate how the clones or genes and recombinant peptides of the present invention were obtained and their modes of use, the following specific examples are provided to better help the reader in the different aspects of the practice of the present invention. Given that these specific examples are simply illustrative, in no case should the following descriptions be considered as limiting the scope of the following invention:

EXAMPLES

Example 1

Isolation and Cloning of the Genes of *C. exilicauda* Toxins

The venom was processed as indicated in the materials and methods section in order to purify toxins and the amino region of the isolated toxins was sequenced as described in the materials and methods section.

The first chain was then obtained and amplified by PCR as mentioned in the materials and methods section. The direct oligonucleotide used in this case was initially oligonucleotide D1 which is a 25mer with the sequence 5'-gagatgaattcgttgttgatgatya-3' (SEQ ID NO: 286) and R1 as reverse oligonucleotide with sequence 5'-gcaattaagaagcgttacaata-3' (SEQ ID NO: 287).

Five clones were obtained with this first strategy (first amplification reaction) (SEQ ID NO: 1, SEQ ID NO: 5, SEQ ID NO: 9, SEQ ID NO: 13 and SEQ ID NO: 17), four of which, as well as the coding sequence of the mature peptide, also presented the coding sequence of the complete sequence of the signal peptide and one of them only included the sequence corresponding to the carboxyl region of the signal peptide. The number of clones isolated with this first amplification reaction proved to be less than the number of toxins directly isolated from the venom, and it was thus decided to design another direct oligonucleotide whose sequence is 5'-gmaarggarggttatc-3' (SEQ ID NO: 288), benefiting from the fact that all the signal peptides of known toxins finish with an Ala in the carboxyl end and from the homologies between the amino regions of the toxins that had already been partially sequenced.

A further amplification reaction was then performed using this new oligonucleotide and 5 additional clones were found (SEQ ID NO: 21, SEQ ID NO: 25, SEQ ID NO: 29, SEQ ID NO: 33 and SEQ ID NO: 37), all of which showed sequences corresponding to the mature peptide and only the last amino acid of the signal peptide.

A new amplification reaction was performed with a third oligo 5'-raaggasggt tatccb-3' (SEQ ID NO: 289) and three additional clones were obtained (SEQ. ID. No: 41, SEQ ID NO: 45 and SEQ ID NO: 49).

Example 2

Isolation and Cloning of the Genes of the Sodium Toxins from *C. limpidus limpidus*

The first chain was obtained and amplified by PCR as mentioned in the materials and methods section. The direct oligonucleotide used in this case was initially the same D1 oligonucleotide (SEQ ID NO: 286) and R1 as reverse oligonucleotide (SEQ ID NO: 287).

With this first strategy (first PCR), 7 clones were obtained (SEQ ID NO: SEQ ID NO: 53, SEQ ID NO: 57, SEQ ID NO: 61, SEQ ID NO: 65, SEQ ID NO: 69, SEQ ID NO: 73 and SEQ ID NO: 77) with the complete coding sequence of the signal peptide and the mature peptide. In this case, a genomic clone was also obtained (SEQ ID NO: 81) whose complete sequence could not be sequenced clearly, and hence only the coding sequence of the last 4 amino acids of the carboxyl region of the signal peptide plus the complete mature peptide are presented. The presence of genomic clones in whole RNA preparations is not common. It can only be explained if the genomic DNA was not completely removed from the preparation, as could be the case here.

Example 3

Isolation and Cloning of the Genes of the Sodium Toxins of *C. noxius* Hoffmann

The first chain was obtained and amplified by PCR as mentioned in the materials and methods section. The direct oligonucleotide used in this case was initially the same oligonucleotide D1 (SEQ ID NO: 286) and R1 as reverse oligonucleotide (SEQ ID NO: 287).

Two clones were obtained with this strategy (SEQ ID NO: 85 y SEQ ID NO: 89,), with the complete coding sequence of the signal peptide and mature peptide.

Example 4

Isolation and Cloning of the Genes of the Sodium Toxins of *C. elegans*

The first chain was obtained and amplified by PCR as mentioned in the materials and methods section. The direct oligonucleotide used in this case was the same oligonucleotide D1 (SEQ ID NO: 286) and R1 as reverse oligonucleotide (SEQ ID NO: 287).

Seven clones were obtained with this strategy (SEQ ID NO: 93, SEQ ID NO: 97, SEQ ID NO: 101, SEQ ID NO: 105, SEQ ID NO: 109, SEQ ID NO: 113 and SEQ ID NO: 117), all of which had the complete coding sequence of the signal peptide and the mature peptide.

Example 5

Isolation and Cloning of the Genes of the Sodium Toxins of *C. gracilis*

The first chain was obtained and amplified by PCR as mentioned in the materials and methods section. The direct oligonucleotide used in this case was the same oligonucleotide D1 (SEQ ID NO: 286) and R1 as reverse oligonucleotide (SEQ ID NO: 287).

Four clones were obtained with this strategy (SEQ ID NO: 121, SEQ ID NO: 125, SEQ ID NO: 129 and SEQ ID NO: 133), all of which had the complete coding sequence of the signal peptide and the mature peptide.

Example 6

Isolation and Cloning of the Genes of the Sodium Toxins of *C. sculpturatus*

The first chain was obtained and amplified by PCR as mentioned in the materials and methods section. The direct oligonucleotide used in this case was the same oligonucleotide D1 (SEQ ID NO:286) and R1 as reverse oligonucleotide (SEQ ID NO: 287).

Fifteen clones were obtained with this strategy (SEQ ID NO: 137, SEQ ID NO: 141, SEQ ID NO: 145, SEQ ID NO: 149, SEQ ID NO: 153, SEQ ID NO: 157, SEQ ID NO: 161, SEQ ID NO: 165, SEQ ID NO: 169, SEQ ID NO: 173, SEQ ID NO: 177, SEQ ID NO: 181, SEQ ID NO: 185, SEQ ID NO: 189 and SEQ ID NO: 193), all of which had the complete coding sequence of the signal peptide and mature peptide.

Example 7

Isolation and Cloning of the Genes of the ERG Type Potassium Toxins of 6 Species of Scorpions of the Genus *Centruroides*

The first chain was obtained and amplified in two PCR reactions for each one of the species of scorpions separately, as mentioned in the materials and methods section. The direct oligonucleotide used in this case was 5'-gatagagat-agctgtgttgataaatca-3' (SEQ ID NO: 292) and as reverse oligonucleotide 5'-mmtaatctttatttttc-3' (SEQ ID NO:290) for one of the reactions and ErgR2 5'-aatttgcggaaatttmm-3' (SEQ ID NO:291) for the other.

Four clones of *C. exilicauda* were obtained from both reactions (SEQ. ID. NO: 197, SEQ ID NO: 201, SEQ ID NO: 205 and SEQ ID NO: 209); 4 clones of *C. limpidus limpidus* (SEQ. ID. NO: 231, SEQ ID NO: 217, SEQ ID NO: 221 and SEQ ID NO: 225); 3 clones of *C. noxius* (SEQ. ID. NO: 229, SEQ ID NO: 233 and SEQ ID NO: 237); 3 clones of *C. elegans* (SEQ. ID. NO: 241, SEQ ID NO: 245 and SEQ ID NO: 249); 3 of *C. gracilis* (SEQ. ID. NO: 253, SEQ ID NO: 257 and SEQ ID NO: 261); and 5 clones of *C. sculpturatus* (SEQ. ID. NO: 265, SEQ ID NO: 269, SEQ ID NO: 273, SEQ ID NO: 277 and SEQ ID NO: 281).

Example 8

Genetic Construction for the Heterologue Expression of a Fusion Protein of a Toxin of a Scorpion of the Genus *Centruroides*

Clone CngtII that codes for the toxin Cn5 was obtained from a cDNA library as described in Becerril et al., 1993. In order to edit it, two specific oligonucleotides were designed and synthesized, direct oligo 5'-atgaaagaaggttatctggtaaac-3' (SEQ. ID. NO:293), that comprises amino acids 1 to 7 of the Cn5 toxin, permitted removal of the signal peptide and the inclusion of a methionine codon just before amino acid 1 in order to permit cleavage of peptide Cn5 with cyanogen bromide after its expression, permitting release of the recombinant peptide using the expressed fusion protein. The reverse oligo 5'-ttagctgcaagatttattaggaag-3' (SEQ. ID. NO:294) was designed to eliminate the last two amino acids that are not present in the mature Cn5 toxin (Lys 67 and Lys 68). The DNA coding for peptide Cn5 was amplified by PCR using clone CngtII as template and the designed oligos as primers. This DNA was bound to a plasmid pMalC XmaI site of the Protein Expression and Purification System (New England Biolabs), which has a specific factor Xa site that permits enzyme cleavage of the fusion protein. FIG. 1 shows the generated construction in which the peptide Cn5 sequence was confirmed by sequencing both chains.

Example 9

Heterologue Expression of the Fusion Protein Comprising Recombinant Peptide Cn5

Once the inserts (DNA coding for peptide Cn5) had been bound to plasmid pMalC as in the above example, they were transformed into *Escherichia coli* strain CMK (Sambrook, J., et al., "*Molecular cloning a laboratory manual.*" Second Edition, Cold Spring Harbor Laboratory Press, New York (1989)). Five ml of cultures were grown overnight in 500 ml of Luria Broth supplemented with 2.5 g glucose and 200 mg/ml ampicillin. The expression of the recombinant protein was induced when the culture reached an absorbance value of 0.5 to 600 nm, and it was harvested 3.5 hr. later. The cells were processed and the fusion protein was purified using affinity chromatography, following the supplier's protocol.

Figure 2:
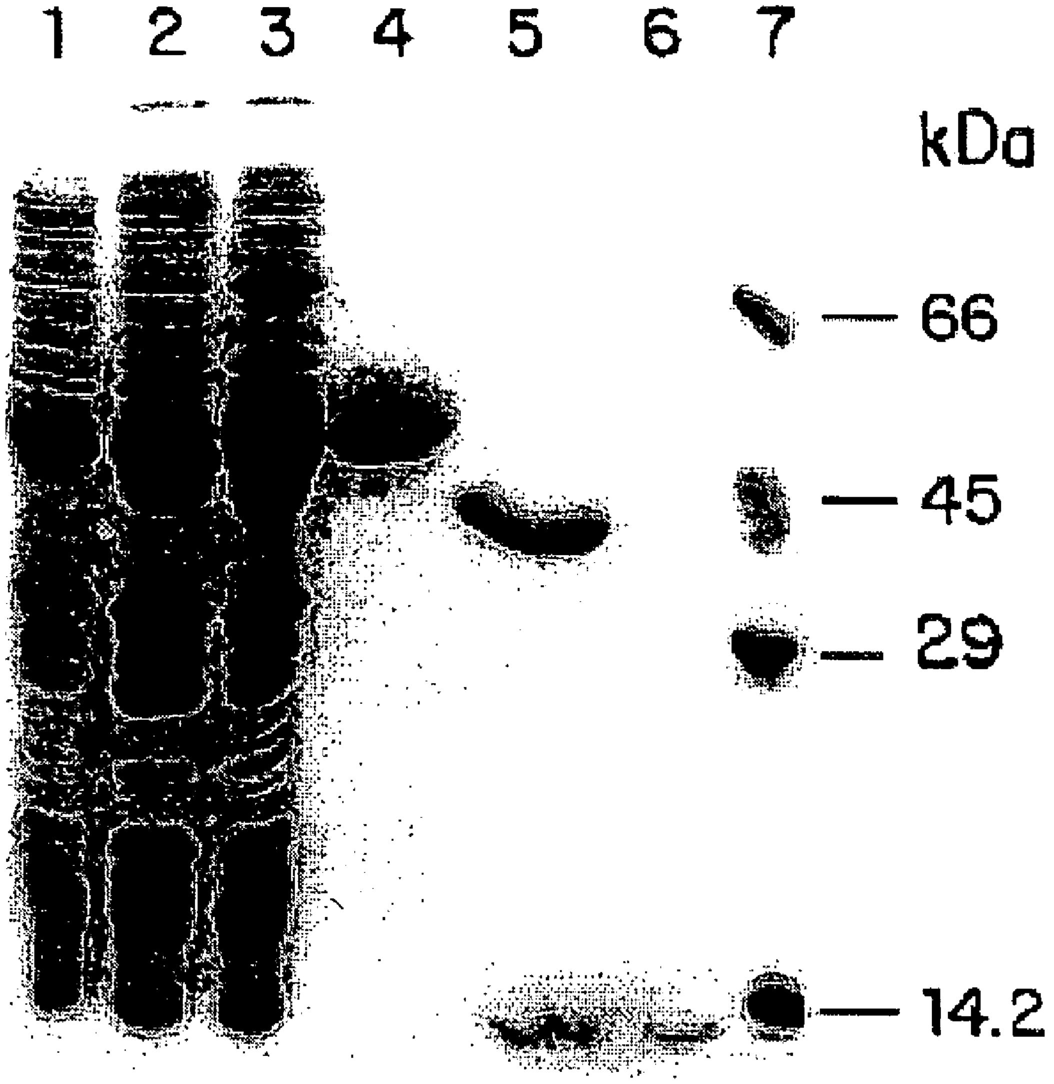
FIG. 2. Shows a 10% SDS PAGE gel dyed with Coomasie blue. Lanes 1, 2 and 3 contain the cell extracts of non-transformed, transformed but not induced and transformed and induced *E. coli*, respectively. The fusion protein FP obtained after purification by affinity chromatography using the extract of transformed, induced *E. coli* cells is in lane 4. Lane 5 shows fusion protein (FP) after digestion by factor Xa giving rise to the maltose binding protein and the recombinant peptide Cn5. Native toxin Cn5 is in lane 6. Lane 7 depicts the molecular weight markers that are indicated to the right of the figure.

The fusion protein (FP) was expressed in the cytoplasm of the *E. coli* cells, comprising protein sequence Mal E (maltose binding protein) plus peptide Cn5 sequence. After extraction of cytoplasm from the culture cell pack, the expression yield of the FP was in the order of 50 mg/L. The presence of hybrid FP was shown using SDS PAGE where the presence of the product with the expected molecular mass was observed (lane 4, FIG. 2, where the product can be seen after being purified by affinity). After digestion with factor Xa, proteins can be observed corresponding to the size expected of the maltose binding protein and the size of the Cn5 (see lane 5, FIG. 2).

Figure 3:
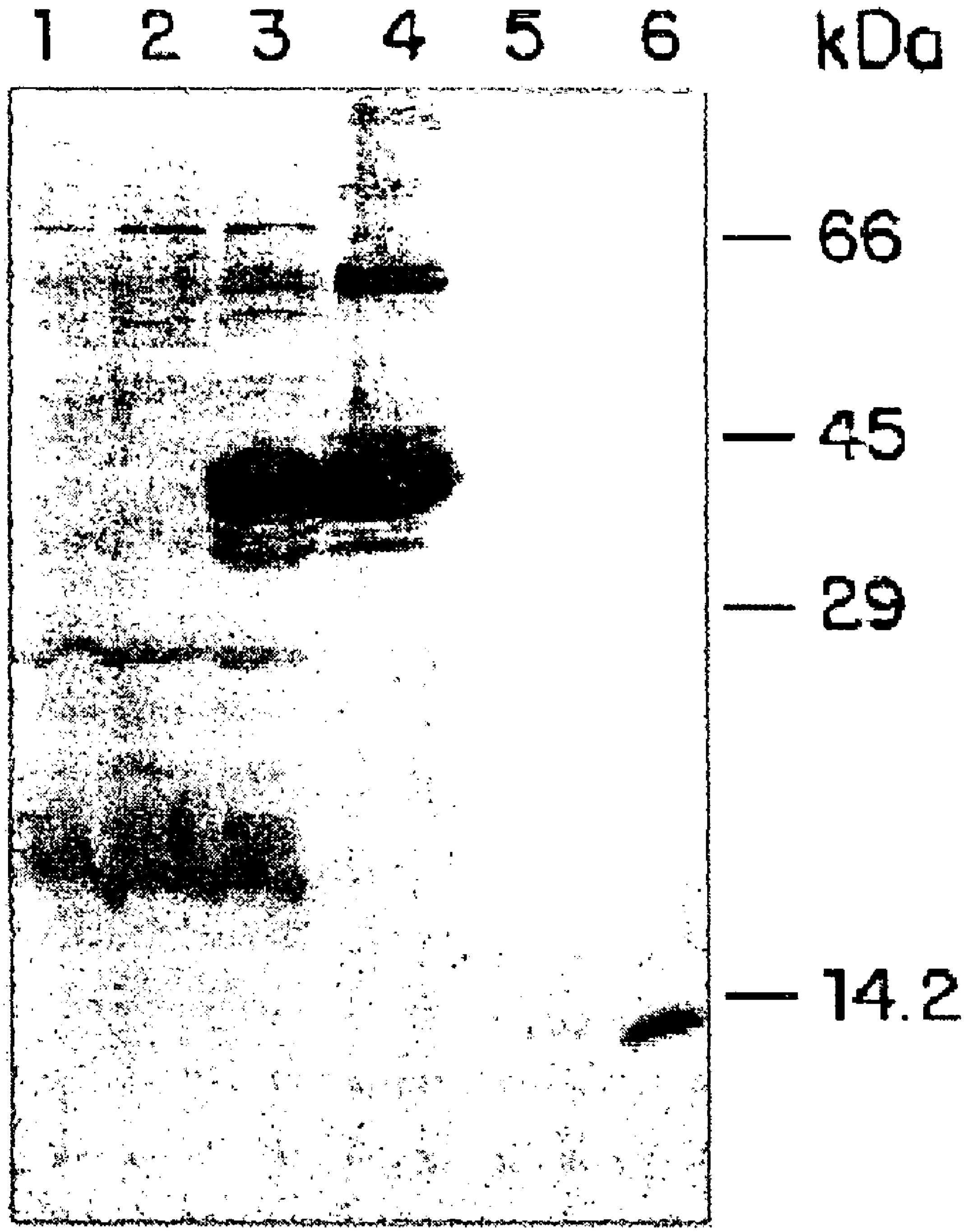
FIG. 3. Shows a western blot developed with anti native toxin Cn5 rabbit serum. The contents of the lanes are the same as in FIG. 2.

Specific recognition assays were conducted by immunoblot using antibodies generated against native toxin Cn5 as in example 10. This is shown in FIG. 3. Lanes 3 and 4 present a positive recognition of the FP comprising peptide Met-Cn5, while in lane 5, where the FP was applied after being digested with factor Xa, only peptide Met-Cn5 is recognized, contrary to Mal E. Lane 6 shows native toxin Cn5 as control, which is clearly recognized by the antibodies.

Peptide Met-Cn5 was purified by HPLC (data not shown) and the peptide was sequenced by automatic Edman degradation unequivocally confirming the first 10 amino acids, including the extra methionine. The final yield of expression of clone CngtII (peptide Met-Cn5) was calculated at 5 mg/L.

In this way the feasibility was proved of using any clone or isolated gene from the telson of scorpions of the genus *Centruroides*, including those of the present invention, for their heterologue expression, thus obtaining either a fusion protein comprising the primary sequence of the toxin encoded by the gene or clone used or a recombinant peptide comprising said sequence, and that said product is able to specifically bind antibodies generated against the native toxin (encoded by the gene in question), which can be used to purify specific antibodies to that toxin using a mixture of antibodies generated against a mixture of several toxins, among which the native toxin (encoded by the gene in question) can be found, as could be the case of the whole venom of a scorpion of the genus *Centruroides* or mixtures of venoms of more than one scorpion.

Example 10

Use of a Fusion Protein Comprising a Primary Sequence Identical to that of a Native Toxin of a Scorpion of the Genus *Centruroides*, as Immunogen in Rabbits for the Development of Polyclonal Antibodies The fusion protein (FP) obtained in the above example was used as immunogen for the development of polyclonal antibodies in rabbits. To this end, female new Zealand rabbits were used (2 kg starting weight). 100 mg of FP or the native toxin Cn5 were applied in Freund's complete adjuvant (1 ml) for the first dose. The 3 subsequent doses were applied in Freund's incomplete adjuvant (1 ml) every 15 days. All the applications were subcutaneous. The rabbits were bled 9 days after the fourth immunization to obtain the sera.

The sera were titered by ELISA, to which end Costar plates with 96 wells were covered with 150 ng per well of fusion peptide (FP) dissolved in a 120 mM sodium bicarbonate buffer pH 9.5 overnight at 4° C. Subsequently, the plates were blocked with 3% bovine serum albumin (BSA) in a PBS buffer (150 mM sodium chloride and 15 mM sodium phosphate, pH7.4) for 1 hr at 37° C. Two-fold serial dilutions were prepared for the serum beginning with a 1:50 dilution with a PBS buffer containing Tween-20 0.1% and BSA 1%.

After incubating for 2 hr. at 37° C., the plates were washed in a washing solution (0.1% Tween-20 in PBS). Anti-rabbit goat antibodies were used coupled to horse-radish peroxidase (Biorad, Hercules, Calif.) as second antibodies. After 1 hour at 37° C., the plates were washed and ortho-phenylenediamine plus hydrogen peroxide were added as substrates. The enzyme reaction was stopped by the addition of sulfuric acid 4N. Absorbance was monitored at 492 nm in a microplate reader (EIA model 1550, Biorad, Hercules, Calif.). Preimmune rabbit serum was used as control.

Figure 4:
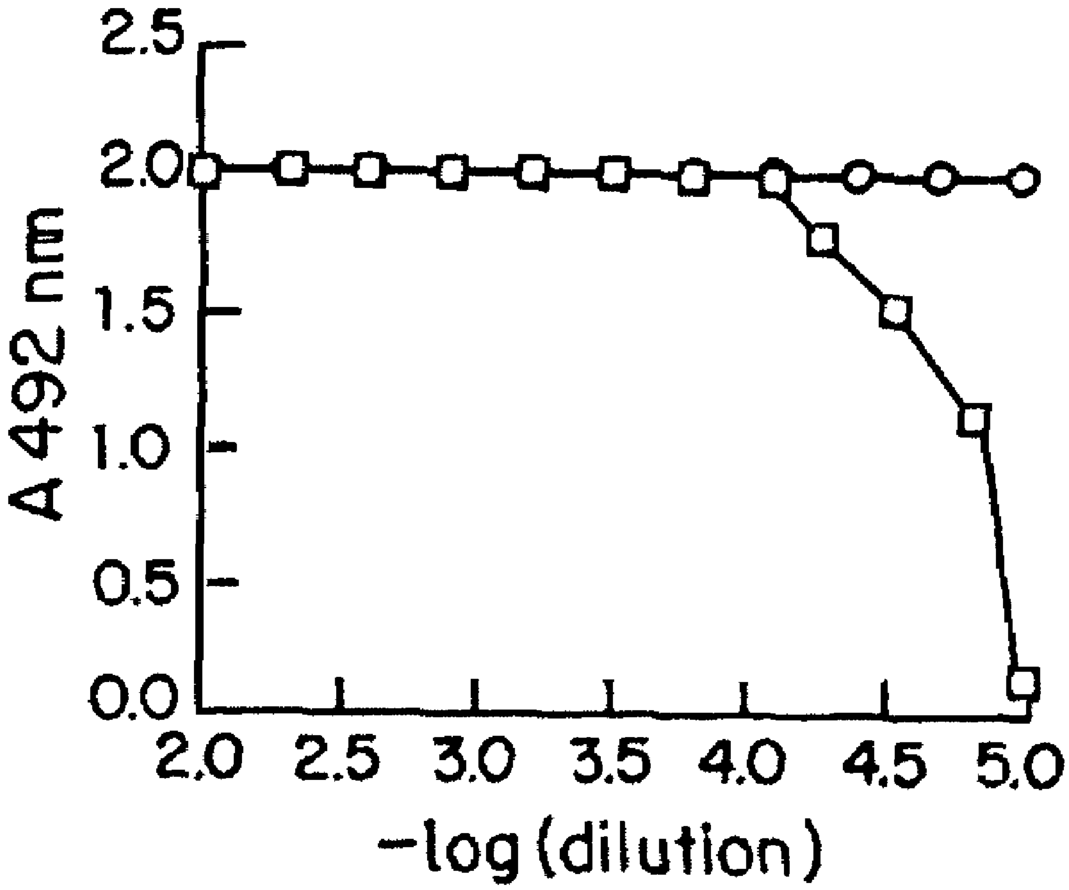
FIG. 4. Titration by ELISA of anti-native toxin Cn5 and anti-fusion protein (FP) sera, obtained from immunized rabbits. The open boxes correspond to titration of the anti Cn5 serum and the open circles correspond to titration of anti-FP serum.

As can be seen in FIG. 4, the fusion protein produced antibodies that recognized the same FP in an excellent way in comparison to the antibodies generated against native toxin Cn5.

Example 11

Use of the Antibodies Generated Against the Fusion Protein that Comprises the Amino Acid Sequence of Peptide Cn5 to Neutralize a Specific Toxin for Mammals In Vivo As mentioned earlier, toxin Cn2 is one of the principal toxins of the venom of *C. noxius* Hoffmann responsible for the intoxication of mammals and has similarities at primary sequence level with Cn5. The antibodies generated against native Cn5 and against the fusion protein, both generated in rabbits as shown in example 10, to neutralize toxin Cn2 were therefore tested.

To this end, several values of the LD50 of toxin Cn2 were mixed with 250 ml of both immune (anti-Cn5 and anti-FP) and preimmune (taken before beginning the immunization scheme) (control) rabbit serum and were incubated at room temperature for 1 hr and gently stirred. After this period, non-immune CD1 mice, 8 weeks old, were injected subcutaneously with the mixtures and their rates of survival 24 hr after the challenge were recorded (See Table 2).

TABLE 2

| | Survival rates in mice challenged with toxin Cn2 incubated with the sera | | |
|---|---|---|---|
| LD50 of Cn2 | Serum | Survival Rate (live/total) | Percentage |
| 1.0 | Pre-immune | 0/6 | 0 |
| 1.0 | Anti-Cn5 | 7/7 | 100 |
| 1.5 | Anti-Cn5 | 7/7 | 100 |
| 2.0 | Anti-Cn5 | 6/7 | 86 |
| 1.0 | Anti-FP | 5/6 | 83 |

1 LD50 of Cn2 = 0.6 μg/20 g (Licea, A. F., et al., Centruroides noxius Hoffmann. Toxicon 34: 843-847 (1996)).

The anti-Cn5 antibodies proved to have total protection capacity in the challenged mice with up to 2.5 LD50 of Cn2, while the anti-FP antibodies proved to have a reasonable protective capacity with 1 DL50. These results are especially significant considering that the mice challenged with a DL50 preincubated with pre-immune serum should have had a survival rate of 50%, however for this experiment in particular it worked with DL 100 (all the control mice died). This effect has been observed in the laboratory when a recently prepared toxin is used. Meanwhile, observe the challenge experiment (table 2) on the same day under the same conditions with mice from sibling litters.

SUMMARY

The present invention refers to 71 clones of scorpions of the genus *Centruroides* that code for toxins affecting sodium and Erg type potassium channels; to genetic constructions that comprise the coding fragment of said toxins; the recombinant proteins that include in their sequence the sequence of the mature peptides encoded by the clones of the present invention; and their uses as immunogens or antigens for the generation of specific antibodies in mammals; as part of an immunogenic matrix for fractionating by immunoaffinity the antivenoms currently produced; and as a vaccine.

Similarly, the present invention also refers to expression vectors that comprise the coding sequence of the toxins of the present invention, to the recombinant hosts comprising said vectors, and to the methods used for their expression.

All publications, patents and patent publications cited herein are incorporated by reference in their entirety into the disclosure. The foregoing specification, including the specific embodiments and examples, are intended to be illustrative and not limiting. Numerous other variations and modifications can be effected without departing from the true spirit and scope of the present invention.

---

SEQUENCE LISTING

```
<160> NUMBER OF SEQ ID NOS: 294

<210> SEQ ID NO 1
<211> LENGTH: 299
<212> TYPE: DNA
<213> ORGANISM: Centruroides exilicauda
<220> FEATURE:
<221> NAME/KEY: CDS
<222> LOCATION: (4)..(264)
<223> OTHER INFORMATION: Product= Sodium-channel modifier toxin
      precursor In the mature peptide, the last Cys is amidated,
      and the last Gly and the last 2 basic aminoacids are cut
<220> FEATURE:
<221> NAME/KEY: 5'UTR
<222> LOCATION: (1)..(3)
<223> OTHER INFORMATION:
<220> FEATURE:
<221> NAME/KEY: mat_peptide
<222> LOCATION: (61)..()
<223> OTHER INFORMATION: Product= Sodium-channel modifier toxin
<220> FEATURE:
<221> NAME/KEY: sig_peptide
<222> LOCATION: (4)..(60)
<223> OTHER INFORMATION:
<220> FEATURE:
<221> NAME/KEY: 3'UTR
<222> LOCATION: (268)..(299)
<223> OTHER INFORMATION:

<400> SEQUENCE: 1

aag atg aac tcg ttg ttg atg atc act gct tgt ttg gcc ctg atc gga       48
    Met Asn Ser Leu Leu Met Ile Thr Ala Cys Leu Ala Leu Ile Gly
                    -15                 -10                 -5

aca gtg tgg gca aag gaa ggt tat ctg gta agc aag agc acg ggc tgc       96
Thr Val Trp Ala Lys Glu Gly Tyr Leu Val Ser Lys Ser Thr Gly Cys
            -1  1               5                   10

aaa tac gag tgc ttt tgg ttg gga aaa aac gaa ggc tgc gat aag gaa      144
Lys Tyr Glu Cys Phe Trp Leu Gly Lys Asn Glu Gly Cys Asp Lys Glu
        15                  20                  25

tgc aaa gcg ccg aac caa gga ggt ggt tac ggc tat tgc cac gct ttc      192
Cys Lys Ala Pro Asn Gln Gly Gly Gly Tyr Gly Tyr Cys His Ala Phe
    30                  35                  40

gca tgc tgg tgc gaa aat ttg ccc gaa agt aca ccg act tat ccc att      240
Ala Cys Trp Cys Glu Asn Leu Pro Glu Ser Thr Pro Thr Tyr Pro Ile
45                  50                  55                  60

cct ggt aat gaa aac gac ttt tta ttgtccacca acagaaatat tgtaacgctt     294
Pro Gly Asn Glu Asn Asp Phe Leu
                65
```

-continued

```
cttaa                                                              299


<210> SEQ ID NO 2
<211> LENGTH: 87
<212> TYPE: PRT
<213> ORGANISM: Centruroides exilicauda

<400> SEQUENCE: 2

Met Asn Ser Leu Leu Met Ile Thr Ala Cys Leu Ala Leu Ile Gly Thr
                -15                 -10                 -5

Val Trp Ala Lys Glu Gly Tyr Leu Val Ser Lys Ser Thr Gly Cys Lys
        -1  1               5                   10

Tyr Glu Cys Phe Trp Leu Gly Lys Asn Glu Gly Cys Asp Lys Glu Cys
    15                  20                  25

Lys Ala Pro Asn Gln Gly Gly Gly Tyr Gly Tyr Cys His Ala Phe Ala
30                  35                  40                  45

Cys Trp Cys Glu Asn Leu Pro Glu Ser Thr Pro Thr Tyr Pro Ile Pro
                50                  55                  60

Gly Asn Glu Asn Asp Phe Leu
            65


<210> SEQ ID NO 3
<211> LENGTH: 195
<212> TYPE: DNA
<213> ORGANISM: Centruroides exilicauda
<220> FEATURE:
<221> NAME/KEY: CDS
<222> LOCATION: (1)..(195)
<223> OTHER INFORMATION: Product= Sodium-channel modifier toxin

<400> SEQUENCE: 3

aag gaa ggt tat ctg gta agc aag agc acg ggc tgc aaa tac gag tgc       48
Lys Glu Gly Tyr Leu Val Ser Lys Ser Thr Gly Cys Lys Tyr Glu Cys
1               5                   10                  15

ttt tgg ttg gga aaa aac gaa ggc tgc gat aag gaa tgc aaa gcg ccg       96
Phe Trp Leu Gly Lys Asn Glu Gly Cys Asp Lys Glu Cys Lys Ala Pro
            20                  25                  30

aac caa gga ggt ggt tac ggc tat tgc cac gct ttc gca tgc tgg tgc      144
Asn Gln Gly Gly Gly Tyr Gly Tyr Cys His Ala Phe Ala Cys Trp Cys
        35                  40                  45

gaa aat ttg ccc gaa agt aca ccg act tat ccc att cct ggt aaa tca      192
Glu Asn Leu Pro Glu Ser Thr Pro Thr Tyr Pro Ile Pro Gly Lys Ser
    50                  55                  60

tgc                                                                  195
Cys
65


<210> SEQ ID NO 4
<211> LENGTH: 65
<212> TYPE: PRT
<213> ORGANISM: Centruroides exilicauda

<400> SEQUENCE: 4

Lys Glu Gly Tyr Leu Val Ser Lys Ser Thr Gly Cys Lys Tyr Glu Cys
1               5                   10                  15

Phe Trp Leu Gly Lys Asn Glu Gly Cys Asp Lys Glu Cys Lys Ala Pro
            20                  25                  30

Asn Gln Gly Gly Gly Tyr Gly Tyr Cys His Ala Phe Ala Cys Trp Cys
        35                  40                  45

Glu Asn Leu Pro Glu Ser Thr Pro Thr Tyr Pro Ile Pro Gly Lys Ser
```

-continued

```
    50                  55                  60

Cys
65


<210> SEQ ID NO 5
<211> LENGTH: 317
<212> TYPE: DNA
<213> ORGANISM: Centruroides exilicauda
<220> FEATURE:
<221> NAME/KEY: CDS
<222> LOCATION: (4)..(264)
<223> OTHER INFORMATION: Product= Sodium-channel modifier toxin
      precursor In the mature peptide, the last Cys is amidated,
      and the last Gly and the last 2 basic aminoacids are cut
<220> FEATURE:
<221> NAME/KEY: 3'UTR
<222> LOCATION: (268)..(317)
<223> OTHER INFORMATION:
<220> FEATURE:
<221> NAME/KEY: 5'UTR
<222> LOCATION: (1)..(3)
<223> OTHER INFORMATION:
<220> FEATURE:
<221> NAME/KEY: mat_peptide
<222> LOCATION: (61)..()
<223> OTHER INFORMATION: Product= Sodium-channel modifier toxin
<220> FEATURE:
<221> NAME/KEY: sig_peptide
<222> LOCATION: (4)..(60)
<223> OTHER INFORMATION:

<400> SEQUENCE: 5

aag atg aac tcg ttg ttg atg atc act gct tgt ttg gcc ctg atc gga       48
    Met Asn Ser Leu Leu Met Ile Thr Ala Cys Leu Ala Leu Ile Gly
                    -15                 -10                 -5

aca gtg tgg gca aag gaa ggt tat ctg gta agc aag agc acg ggc tgc       96
Thr Val Trp Ala Lys Glu Gly Tyr Leu Val Ser Lys Ser Thr Gly Cys
            -1  1               5                   10

aaa tac gag tgc ttt tgg ttg gga aaa aac gaa ggc tgc gat aag gaa      144
Lys Tyr Glu Cys Phe Trp Leu Gly Lys Asn Glu Gly Cys Asp Lys Glu
        15                  20                  25

tgc aaa gcg ccg aac caa gga ggt ggt tac ggc tat tgc cac gct ttc      192
Cys Lys Ala Pro Asn Gln Gly Gly Gly Tyr Gly Tyr Cys His Ala Phe
    30                  35                  40

gca tgc tgg tgc gaa aat ttg ccc gaa agt aca ccg act tat ccc att      240
Ala Cys Trp Cys Glu Asn Leu Pro Glu Ser Thr Pro Thr Tyr Pro Ile
45                  50                  55                  60

cct ggt aaa tca tgc ggc aaa aaa taatgaaaac gactttttat tgtccaccaa     294
Pro Gly Lys Ser Cys Gly Lys Lys
                65

cagaaatatt gtaacgcttc taa                                            317


<210> SEQ ID NO 6
<211> LENGTH: 87
<212> TYPE: PRT
<213> ORGANISM: Centruroides exilicauda

<400> SEQUENCE: 6

Met Asn Ser Leu Leu Met Ile Thr Ala Cys Leu Ala Leu Ile Gly Thr
                -15                 -10                 -5

Val Trp Ala Lys Glu Gly Tyr Leu Val Ser Lys Ser Thr Gly Cys Lys
        -1  1               5                   10

Tyr Glu Cys Phe Trp Leu Gly Lys Asn Glu Gly Cys Asp Lys Glu Cys
    15                  20                  25

Lys Ala Pro Asn Gln Gly Gly Gly Tyr Gly Tyr Cys His Ala Phe Ala
```

-continued

```
30                  35                  40                  45

Cys Trp Cys Glu Asn Leu Pro Glu Ser Thr Pro Thr Tyr Pro Ile Pro
                50                  55                  60

Gly Lys Ser Cys Gly Lys Lys
            65


<210> SEQ ID NO 7
<211> LENGTH: 195
<212> TYPE: DNA
<213> ORGANISM: Centruroides exilicauda
<220> FEATURE:
<221> NAME/KEY: CDS
<222> LOCATION: (1)..(195)
<223> OTHER INFORMATION: Product= Sodium-channel modifier toxin

<400> SEQUENCE: 7

aag gaa ggt tat ctg gta agc aag agc acg ggc tgc aaa tac gag tgc       48
Lys Glu Gly Tyr Leu Val Ser Lys Ser Thr Gly Cys Lys Tyr Glu Cys
1               5                   10                  15

ttt tgg ttg gga aaa aac gaa ggc tgc gat aag gaa tgc aaa gcg ccg       96
Phe Trp Leu Gly Lys Asn Glu Gly Cys Asp Lys Glu Cys Lys Ala Pro
            20                  25                  30

aac caa gga ggt ggt tac ggc tat tgc cac gct ttc gca tgc tgg tgc      144
Asn Gln Gly Gly Gly Tyr Gly Tyr Cys His Ala Phe Ala Cys Trp Cys
        35                  40                  45

gaa aat ttg ccc gaa agt aca ccg act tat ccc att cct ggt aaa tca      192
Glu Asn Leu Pro Glu Ser Thr Pro Thr Tyr Pro Ile Pro Gly Lys Ser
    50                  55                  60

tgc                                                                  195
Cys
65


<210> SEQ ID NO 8
<211> LENGTH: 65
<212> TYPE: PRT
<213> ORGANISM: Centruroides exilicauda

<400> SEQUENCE: 8

Lys Glu Gly Tyr Leu Val Ser Lys Ser Thr Gly Cys Lys Tyr Glu Cys
1               5                   10                  15

Phe Trp Leu Gly Lys Asn Glu Gly Cys Asp Lys Glu Cys Lys Ala Pro
            20                  25                  30

Asn Gln Gly Gly Gly Tyr Gly Tyr Cys His Ala Phe Ala Cys Trp Cys
        35                  40                  45

Glu Asn Leu Pro Glu Ser Thr Pro Thr Tyr Pro Ile Pro Gly Lys Ser
    50                  55                  60

Cys
65


<210> SEQ ID NO 9
<211> LENGTH: 313
<212> TYPE: DNA
<213> ORGANISM: Centruroides exilicauda
<220> FEATURE:
<221> NAME/KEY: CDS
<222> LOCATION: (4)..(255)
<223> OTHER INFORMATION: Product= Sodium-channel modifier toxin
      precursor In the mature peptide, the last 2 basic aminoacids
      are cut
<220> FEATURE:
<221> NAME/KEY: 3'UTR
<222> LOCATION: (259)..(313)
<223> OTHER INFORMATION:
<220> FEATURE:
```

-continued

```
<221> NAME/KEY: sig_peptide
<222> LOCATION: (4)..(60)
<223> OTHER INFORMATION:
<220> FEATURE:
<221> NAME/KEY: mat_peptide
<222> LOCATION: (61)..()
<223> OTHER INFORMATION: Product= Sodium-channel modifier toxin

<400> SEQUENCE: 9

aag atg aac tcg ttg ttg atg atc act act tgt ttg att cta gtc ggt       48
    Met Asn Ser Leu Leu Met Ile Thr Thr Cys Leu Ile Leu Val Gly
                    -15                 -10                 -5

acc gtg tgg gca aac gat ggt tat ttg ttt gac aag aga aag cgc tgc       96
Thr Val Trp Ala Asn Asp Gly Tyr Leu Phe Asp Lys Arg Lys Arg Cys
            -1  1               5                   10

aca ctc gaa tgc ata gac aag aca gga gac aaa aat tgc gat aga aat      144
Thr Leu Glu Cys Ile Asp Lys Thr Gly Asp Lys Asn Cys Asp Arg Asn
        15                  20                  25

tgc aag aag gaa gga ggt agt ttt ggc aaa tgc tct tat tct gca tgc      192
Cys Lys Lys Glu Gly Gly Ser Phe Gly Lys Cys Ser Tyr Ser Ala Cys
    30                  35                  40

tgg tgc aaa gga ttg ccc gga att aca ccg att tca cgt act cct ggt      240
Trp Cys Lys Gly Leu Pro Gly Ile Thr Pro Ile Ser Arg Thr Pro Gly
45                  50                  55                  60

aaa aca tgt aga aaa taatggcaac ttgtttttat tgtgcaccaa cagaaatatt      295
Lys Thr Cys Arg Lys
                65

gtaacgcttc ttaattgc                                                  313


<210> SEQ ID NO 10
<211> LENGTH: 84
<212> TYPE: PRT
<213> ORGANISM: Centruroides exilicauda

<400> SEQUENCE: 10

Met Asn Ser Leu Leu Met Ile Thr Thr Cys Leu Ile Leu Val Gly Thr
                -15                 -10                 -5

Val Trp Ala Asn Asp Gly Tyr Leu Phe Asp Lys Arg Lys Arg Cys Thr
        -1  1               5                   10

Leu Glu Cys Ile Asp Lys Thr Gly Asp Lys Asn Cys Asp Arg Asn Cys
    15                  20                  25

Lys Lys Glu Gly Gly Ser Phe Gly Lys Cys Ser Tyr Ser Ala Cys Trp
30                  35                  40                  45

Cys Lys Gly Leu Pro Gly Ile Thr Pro Ile Ser Arg Thr Pro Gly Lys
                50                  55                  60

Thr Cys Arg Lys
            65


<210> SEQ ID NO 11
<211> LENGTH: 249
<212> TYPE: DNA
<213> ORGANISM: Centruroides exilicauda
<220> FEATURE:
<221> NAME/KEY: CDS
<222> LOCATION: (1)..(249)
<223> OTHER INFORMATION: Product= Sodium-channel modifier toxin

<400> SEQUENCE: 11

aag atg aac tcg ttg ttg atg atc act act tgt ttg att cta gtc ggt       48
Lys Met Asn Ser Leu Leu Met Ile Thr Thr Cys Leu Ile Leu Val Gly
1               5                   10                  15

acc gtg tgg gca aac gat ggt tat ttg ttt gac aag aga aag cgc tgc       96
```

-continued

```
Thr Val Trp Ala Asn Asp Gly Tyr Leu Phe Asp Lys Arg Lys Arg Cys
            20                  25                  30

aca ctc gaa tgc ata gac aag aca gga gac aaa aat tgc gat aga aat      144
Thr Leu Glu Cys Ile Asp Lys Thr Gly Asp Lys Asn Cys Asp Arg Asn
        35                  40                  45

tgc aag aag gaa gga ggt agt ttt ggc aaa tgc tct tat tct gca tgc      192
Cys Lys Lys Glu Gly Gly Ser Phe Gly Lys Cys Ser Tyr Ser Ala Cys
    50                  55                  60

tgg tgc aaa gga ttg ccc gga att aca ccg att tca cgt act cct ggt      240
Trp Cys Lys Gly Leu Pro Gly Ile Thr Pro Ile Ser Arg Thr Pro Gly
65                  70                  75                  80

aaa aca tgt                                                          249
Lys Thr Cys


<210> SEQ ID NO 12
<211> LENGTH: 83
<212> TYPE: PRT
<213> ORGANISM: Centruroides exilicauda

<400> SEQUENCE: 12

Lys Met Asn Ser Leu Leu Met Ile Thr Thr Cys Leu Ile Leu Val Gly
1               5                   10                  15

Thr Val Trp Ala Asn Asp Gly Tyr Leu Phe Asp Lys Arg Lys Arg Cys
            20                  25                  30

Thr Leu Glu Cys Ile Asp Lys Thr Gly Asp Lys Asn Cys Asp Arg Asn
        35                  40                  45

Cys Lys Lys Glu Gly Gly Ser Phe Gly Lys Cys Ser Tyr Ser Ala Cys
    50                  55                  60

Trp Cys Lys Gly Leu Pro Gly Ile Thr Pro Ile Ser Arg Thr Pro Gly
65                  70                  75                  80

Lys Thr Cys


<210> SEQ ID NO 13
<211> LENGTH: 273
<212> TYPE: DNA
<213> ORGANISM: Centruroides exilicauda
<220> FEATURE:
<221> NAME/KEY: CDS
<222> LOCATION: (1)..(219)
<223> OTHER INFORMATION: Product= Sodium-channel modifier toxin
      precursor
<220> FEATURE:
<221> NAME/KEY: 3'UTR
<222> LOCATION: (223)..(273)
<223> OTHER INFORMATION:
<220> FEATURE:
<221> NAME/KEY: mat_peptide
<222> LOCATION: (22)..()
<223> OTHER INFORMATION: Product= Sodium-channel modifier toxin
<220> FEATURE:
<221> NAME/KEY: sig_peptide
<222> LOCATION: (1)..(21)
<223> OTHER INFORMATION: Carboxy term of signal peptide

<400> SEQUENCE: 13

gct aca gga aat gtg tgg gca aag gac ggt tat ctg gtg atc att aaa       48
Ala Thr Gly Asn Val Trp Ala Lys Asp Gly Tyr Leu Val Ile Ile Lys
        -5              -1  1               5

acg ggc tgc aaa tac aat tgc tat ata ttg gga aaa aac aaa tac tgc       96
Thr Gly Cys Lys Tyr Asn Cys Tyr Ile Leu Gly Lys Asn Lys Tyr Cys
10                  15                  20                  25

aat tcg gaa tgc aaa gag gta ggt gct ggt tac ggc tat tgc tat gct      144
Asn Ser Glu Cys Lys Glu Val Gly Ala Gly Tyr Gly Tyr Cys Tyr Ala
                30                  35                  40
```

-continued

```
ttt ggg tgc tgg tgc gaa gga tta ccc gaa agt ata ccg acc tgg ccc      192
Phe Gly Cys Trp Cys Glu Gly Leu Pro Glu Ser Ile Pro Thr Trp Pro
            45                  50                  55

ctt cct gat aaa aca tgt ggc aca aaa taatggcaac gtctttttat            239
Leu Pro Asp Lys Thr Cys Gly Thr Lys
        60                  65

tgtccaccaa cagaaatatt gtaacgcttc ttaa                                273


<210> SEQ ID NO 14
<211> LENGTH: 73
<212> TYPE: PRT
<213> ORGANISM: Centruroides exilicauda

<400> SEQUENCE: 14

Ala Thr Gly Asn Val Trp Ala Lys Asp Gly Tyr Leu Val Ile Ile Lys
        -5              -1  1               5

Thr Gly Cys Lys Tyr Asn Cys Tyr Ile Leu Gly Lys Asn Lys Tyr Cys
10                  15                  20                  25

Asn Ser Glu Cys Lys Glu Val Gly Ala Gly Tyr Gly Tyr Cys Tyr Ala
                30                  35                  40

Phe Gly Cys Trp Cys Glu Gly Leu Pro Glu Ser Ile Pro Thr Trp Pro
            45                  50                  55

Leu Pro Asp Lys Thr Cys Gly Thr Lys
        60                  65


<210> SEQ ID NO 15
<211> LENGTH: 219
<212> TYPE: DNA
<213> ORGANISM: Centruroides exilicauda
<220> FEATURE:
<221> NAME/KEY: CDS
<222> LOCATION: (1)..(219)
<223> OTHER INFORMATION: Product= Sodium-channel modifier toxin

<400> SEQUENCE: 15

gct aca gga aat gtg tgg gca aag gac ggt tat ctg gtg atc att aaa       48
Ala Thr Gly Asn Val Trp Ala Lys Asp Gly Tyr Leu Val Ile Ile Lys
1               5                   10                  15

acg ggc tgc aaa tac aat tgc tat ata ttg gga aaa aac aaa tac tgc       96
Thr Gly Cys Lys Tyr Asn Cys Tyr Ile Leu Gly Lys Asn Lys Tyr Cys
            20                  25                  30

aat tcg gaa tgc aaa gag gta ggt gct ggt tac ggc tat tgc tat gct      144
Asn Ser Glu Cys Lys Glu Val Gly Ala Gly Tyr Gly Tyr Cys Tyr Ala
        35                  40                  45

ttt ggg tgc tgg tgc gaa gga tta ccc gaa agt ata ccg acc tgg ccc      192
Phe Gly Cys Trp Cys Glu Gly Leu Pro Glu Ser Ile Pro Thr Trp Pro
    50                  55                  60

ctt cct gat aaa aca tgt ggc aca aaa                                  219
Leu Pro Asp Lys Thr Cys Gly Thr Lys
65                  70


<210> SEQ ID NO 16
<211> LENGTH: 73
<212> TYPE: PRT
<213> ORGANISM: Centruroides exilicauda

<400> SEQUENCE: 16

Ala Thr Gly Asn Val Trp Ala Lys Asp Gly Tyr Leu Val Ile Ile Lys
1               5                   10                  15

Thr Gly Cys Lys Tyr Asn Cys Tyr Ile Leu Gly Lys Asn Lys Tyr Cys
            20                  25                  30
```

-continued

```
Asn Ser Glu Cys Lys Glu Val Gly Ala Gly Tyr Gly Tyr Cys Tyr Ala
        35                  40                  45

Phe Gly Cys Trp Cys Glu Gly Leu Pro Glu Ser Ile Pro Thr Trp Pro
    50                  55                  60

Leu Pro Asp Lys Thr Cys Gly Thr Lys
65                  70


<210> SEQ ID NO 17
<211> LENGTH: 261
<212> TYPE: DNA
<213> ORGANISM: Centruroides exilicauda
<220> FEATURE:
<221> NAME/KEY: CDS
<222> LOCATION: (1)..(207)
<223> OTHER INFORMATION: Product= Sodium-channel modifier toxin
      precursor In the mature peptide, the last Cys is amidated, and
      the last Gly and the last 2 basic aminoacids are cut
<220> FEATURE:
<221> NAME/KEY: 3'UTR
<222> LOCATION: (211)..(261)
<223> OTHER INFORMATION:
<220> FEATURE:
<221> NAME/KEY: sig_peptide
<222> LOCATION: (1)..(3)
<223> OTHER INFORMATION: Carboxy-end of the signal peptide
<220> FEATURE:
<221> NAME/KEY: mat_peptide
<222> LOCATION: (4)..()
<223> OTHER INFORMATION: Product= Sodium-channel modifier toxin

<400> SEQUENCE: 17

gca aag gat ggt tat ctg gta aac aag agc acg ggc tgc aaa tac gag       48
Ala Lys Asp Gly Tyr Leu Val Asn Lys Ser Thr Gly Cys Lys Tyr Glu
-1  1               5                   10                  15

tgc ttt tgg ttg gga aaa aac gaa ttc tgc gat aag gaa tgc aaa gcg       96
Cys Phe Trp Leu Gly Lys Asn Glu Phe Cys Asp Lys Glu Cys Lys Ala
                20                  25                  30

aag aac caa gga ggt agt tac ggc tat tgc tac tct ttc gca tgc tgg      144
Lys Asn Gln Gly Gly Ser Tyr Gly Tyr Cys Tyr Ser Phe Ala Cys Trp
            35                  40                  45

tgc gaa ggt ttg ccc gaa agt aca tcg act tat cct ctt cct aat aaa      192
Cys Glu Gly Leu Pro Glu Ser Thr Ser Thr Tyr Pro Leu Pro Asn Lys
        50                  55                  60

tca tgc ggc aga aaa taatggcaaa gactttttat tgtccatcaa cagaaatatt      247
Ser Cys Gly Arg Lys
    65

gtaacgcttc ttaa                                                       261


<210> SEQ ID NO 18
<211> LENGTH: 69
<212> TYPE: PRT
<213> ORGANISM: Centruroides exilicauda

<400> SEQUENCE: 18

Ala Lys Asp Gly Tyr Leu Val Asn Lys Ser Thr Gly Cys Lys Tyr Glu
-1  1               5                   10                  15

Cys Phe Trp Leu Gly Lys Asn Glu Phe Cys Asp Lys Glu Cys Lys Ala
                20                  25                  30

Lys Asn Gln Gly Gly Ser Tyr Gly Tyr Cys Tyr Ser Phe Ala Cys Trp
            35                  40                  45

Cys Glu Gly Leu Pro Glu Ser Thr Ser Thr Tyr Pro Leu Pro Asn Lys
        50                  55                  60

Ser Cys Gly Arg Lys
```

-continued

```
    65


<210> SEQ ID NO 19
<211> LENGTH: 204
<212> TYPE: DNA
<213> ORGANISM: Centruroides exilicauda
<220> FEATURE:
<221> NAME/KEY: CDS
<222> LOCATION: (1)..(204)
<223> OTHER INFORMATION: Product= Sodium-channel modifier toxin

<400> SEQUENCE: 19

aag gat ggt tat ctg gta aac aag agc acg ggc tgc aaa tac gag tgc       48
Lys Asp Gly Tyr Leu Val Asn Lys Ser Thr Gly Cys Lys Tyr Glu Cys
1               5                   10                  15

ttt tgg ttg gga aaa aac gaa ttc tgc gat aag gaa tgc aaa gcg aag       96
Phe Trp Leu Gly Lys Asn Glu Phe Cys Asp Lys Glu Cys Lys Ala Lys
            20                  25                  30

aac caa gga ggt agt tac ggc tat tgc tac tct ttc gca tgc tgg tgc      144
Asn Gln Gly Gly Ser Tyr Gly Tyr Cys Tyr Ser Phe Ala Cys Trp Cys
        35                  40                  45

gaa ggt ttg ccc gaa agt aca tcg act tat cct ctt cct aat aaa tca      192
Glu Gly Leu Pro Glu Ser Thr Ser Thr Tyr Pro Leu Pro Asn Lys Ser
    50                  55                  60

tgc ggc aga aaa                                                      204
Cys Gly Arg Lys
65


<210> SEQ ID NO 20
<211> LENGTH: 68
<212> TYPE: PRT
<213> ORGANISM: Centruroides exilicauda

<400> SEQUENCE: 20

Lys Asp Gly Tyr Leu Val Asn Lys Ser Thr Gly Cys Lys Tyr Glu Cys
1               5                   10                  15

Phe Trp Leu Gly Lys Asn Glu Phe Cys Asp Lys Glu Cys Lys Ala Lys
            20                  25                  30

Asn Gln Gly Gly Ser Tyr Gly Tyr Cys Tyr Ser Phe Ala Cys Trp Cys
        35                  40                  45

Glu Gly Leu Pro Glu Ser Thr Ser Thr Tyr Pro Leu Pro Asn Lys Ser
    50                  55                  60

Cys Gly Arg Lys
65


<210> SEQ ID NO 21
<211> LENGTH: 314
<212> TYPE: DNA
<213> ORGANISM: Centruroides exilicauda
<220> FEATURE:
<221> NAME/KEY: mat_peptide
<222> LOCATION: (58)..()
<223> OTHER INFORMATION: Product= Sodium-channel modifier toxin
      In the mature peptide, the last Cys is amidated, and the last Gly
      and the last 2 basic aminoacids are cut
<220> FEATURE:
<221> NAME/KEY: 3'UTR
<222> LOCATION: (265)..(314)
<223> OTHER INFORMATION:
<220> FEATURE:
<221> NAME/KEY: sig_peptide
<222> LOCATION: (1)..(57)
<223> OTHER INFORMATION:
<220> FEATURE:
<221> NAME/KEY: CDS
<222> LOCATION: (1)..(261)
```

-continued

```
<223> OTHER INFORMATION: Product= Sodium-channel modifier toxin
      precursor

<400> SEQUENCE: 21

atg aat tcg ttg ttg atg atc act gct tgt ttg ttc ctg atc gga aca       48
Met Asn Ser Leu Leu Met Ile Thr Ala Cys Leu Phe Leu Ile Gly Thr
                -15                 -10                 -5

gtg tgg gca aag gaa ggt tat ctg gta aac aag agc acg ggc tgc aaa       96
Val Trp Ala Lys Glu Gly Tyr Leu Val Asn Lys Ser Thr Gly Cys Lys
        -1  1               5                   10

tac gag tgc ttt tgg ttg gga aaa aac gaa ttc tgc gat aag gaa tgc      144
Tyr Glu Cys Phe Trp Leu Gly Lys Asn Glu Phe Cys Asp Lys Glu Cys
    15                  20                  25

aaa gcg aag aac caa gga ggt agt tac ggc tat tgc tac tct ttc gca      192
Lys Ala Lys Asn Gln Gly Gly Ser Tyr Gly Tyr Cys Tyr Ser Phe Ala
30                  35                  40                  45

tgc tgg tgc gaa ggt ttg ccc gaa agt aca tcg act tat cct ctt cct      240
Cys Trp Cys Glu Gly Leu Pro Glu Ser Thr Ser Thr Tyr Pro Leu Pro
                50                  55                  60

aat aaa tca tgc ggc aga aaa taatggcaaa gactttttat tgtccatcaa         291
Asn Lys Ser Cys Gly Arg Lys
            65

cagaaatatt gtaacgcttc tta                                            314


<210> SEQ ID NO 22
<211> LENGTH: 87
<212> TYPE: PRT
<213> ORGANISM: Centruroides exilicauda

<400> SEQUENCE: 22

Met Asn Ser Leu Leu Met Ile Thr Ala Cys Leu Phe Leu Ile Gly Thr
                -15                 -10                 -5

Val Trp Ala Lys Glu Gly Tyr Leu Val Asn Lys Ser Thr Gly Cys Lys
        -1  1               5                   10

Tyr Glu Cys Phe Trp Leu Gly Lys Asn Glu Phe Cys Asp Lys Glu Cys
    15                  20                  25

Lys Ala Lys Asn Gln Gly Gly Ser Tyr Gly Tyr Cys Tyr Ser Phe Ala
30                  35                  40                  45

Cys Trp Cys Glu Gly Leu Pro Glu Ser Thr Ser Thr Tyr Pro Leu Pro
                50                  55                  60

Asn Lys Ser Cys Gly Arg Lys
            65


<210> SEQ ID NO 23
<211> LENGTH: 195
<212> TYPE: DNA
<213> ORGANISM: Centruroides exilicauda
<220> FEATURE:
<221> NAME/KEY: CDS
<222> LOCATION: (1)..(195)
<223> OTHER INFORMATION: Product= Sodium-channel modifier toxin

<400> SEQUENCE: 23

aag gaa ggt tat ctg gta aac aag agc acg ggc tgc aaa tac gag tgc       48
Lys Glu Gly Tyr Leu Val Asn Lys Ser Thr Gly Cys Lys Tyr Glu Cys
1               5                   10                  15

ttt tgg ttg gga aaa aac gaa ttc tgc gat aag gaa tgc aaa gcg aag       96
Phe Trp Leu Gly Lys Asn Glu Phe Cys Asp Lys Glu Cys Lys Ala Lys
            20                  25                  30

aac caa gga ggt agt tac ggc tat tgc tac tct ttc gca tgc tgg tgc      144
Asn Gln Gly Gly Ser Tyr Gly Tyr Cys Tyr Ser Phe Ala Cys Trp Cys
```

-continued 35 40 45 gaa ggt ttg ccc gaa agt aca tcg act tat cct ctt cct aat aaa tca 192
Glu Gly Leu Pro Glu Ser Thr Ser Thr Tyr Pro Leu Pro Asn Lys Ser
50 55 60 tgc 195
Cys
65

<210> SEQ ID NO 24
<211> LENGTH: 65
<212> TYPE: PRT
<213> ORGANISM: Centruroides exilicauda

<400> SEQUENCE: 24

Lys Glu Gly Tyr Leu Val Asn Lys Ser Thr Gly Cys Lys Tyr Glu Cys
1 5 10 15

Phe Trp Leu Gly Lys Asn Glu Phe Cys Asp Lys Glu Cys Lys Ala Lys
20 25 30

Asn Gln Gly Gly Ser Tyr Gly Tyr Cys Tyr Ser Phe Ala Cys Trp Cys
35 40 45

Glu Gly Leu Pro Glu Ser Thr Ser Thr Tyr Pro Leu Pro Asn Lys Ser
50 55 60

Cys
65

<210> SEQ ID NO 25
<211> LENGTH: 261
<212> TYPE: DNA
<213> ORGANISM: Centruroides exilicauda
<220> FEATURE:
<221> NAME/KEY: CDS
<222> LOCATION: (1)..(207)
<223> OTHER INFORMATION: Product= Sodium-channel modifier toxin precursor In the mature peptide, the last Cys is amidated, and the last Gly and the last 2 basic aminoacids are cut
<220> FEATURE:
<221> NAME/KEY: 3'UTR
<222> LOCATION: (211)..(261)
<223> OTHER INFORMATION:
<220> FEATURE:
<221> NAME/KEY: mat_peptide
<222> LOCATION: (4)..()
<223> OTHER INFORMATION: Product= Sodium-channel modifier toxin
<220> FEATURE:
<221> NAME/KEY: sig_peptide
<222> LOCATION: (1)..(3)
<223> OTHER INFORMATION: Carboxy-end of the signal peptide

<400> SEQUENCE: 25 gca aag gac ggt tat ctg gta agc aag agc acg ggc tgc aaa tac gag 48
Ala Lys Asp Gly Tyr Leu Val Ser Lys Ser Thr Gly Cys Lys Tyr Glu
-1 1 5 10 15 tgc ttt tgg ttg gga aaa aac gaa ggc tgc gat aag gaa tgc aaa gcg 96
Cys Phe Trp Leu Gly Lys Asn Glu Gly Cys Asp Lys Glu Cys Lys Ala
20 25 30 ccg aac caa gga ggt ggt tac ggc tat tgc cac gct ttc gca tgc tgg 144
Pro Asn Gln Gly Gly Gly Tyr Gly Tyr Cys His Ala Phe Ala Cys Trp
35 40 45 tgc gaa aat ttg ccc gaa agt aca ccg act tat ccc att cct ggt aaa 192
Cys Glu Asn Leu Pro Glu Ser Thr Pro Thr Tyr Pro Ile Pro Gly Lys
50 55 60 tca tgc ggc aaa aaa taatgaaaac gactttttat tgtcctccaa cagaaatatt 247
Ser Cys Gly Lys Lys
65

-continued

```
gtaacgcttc ttaa                                                      261


<210> SEQ ID NO 26
<211> LENGTH: 69
<212> TYPE: PRT
<213> ORGANISM: Centruroides exilicauda

<400> SEQUENCE: 26

Ala Lys Asp Gly Tyr Leu Val Ser Lys Ser Thr Gly Cys Lys Tyr Glu
-1  1               5                   10                  15

Cys Phe Trp Leu Gly Lys Asn Glu Gly Cys Asp Lys Glu Cys Lys Ala
            20                  25                  30

Pro Asn Gln Gly Gly Gly Tyr Gly Tyr Cys His Ala Phe Ala Cys Trp
        35                  40                  45

Cys Glu Asn Leu Pro Glu Ser Thr Pro Thr Tyr Pro Ile Pro Gly Lys
    50                  55                  60

Ser Cys Gly Lys Lys
    65


<210> SEQ ID NO 27
<211> LENGTH: 195
<212> TYPE: DNA
<213> ORGANISM: Centruroides exilicauda
<220> FEATURE:
<221> NAME/KEY: CDS
<222> LOCATION: (1)..(195)
<223> OTHER INFORMATION: Product= Sodium-channel modifier toxin

<400> SEQUENCE: 27

aag gac ggt tat ctg gta agc aag agc acg ggc tgc aaa tac gag tgc       48
Lys Asp Gly Tyr Leu Val Ser Lys Ser Thr Gly Cys Lys Tyr Glu Cys
1               5                   10                  15

ttt tgg ttg gga aaa aac gaa ggc tgc gat aag gaa tgc aaa gcg ccg       96
Phe Trp Leu Gly Lys Asn Glu Gly Cys Asp Lys Glu Cys Lys Ala Pro
            20                  25                  30

aac caa gga ggt ggt tac ggc tat tgc cac gct ttc gca tgc tgg tgc      144
Asn Gln Gly Gly Gly Tyr Gly Tyr Cys His Ala Phe Ala Cys Trp Cys
        35                  40                  45

gaa aat ttg ccc gaa agt aca ccg act tat ccc att cct ggt aaa tca      192
Glu Asn Leu Pro Glu Ser Thr Pro Thr Tyr Pro Ile Pro Gly Lys Ser
    50                  55                  60

tgc                                                                  195
Cys
65


<210> SEQ ID NO 28
<211> LENGTH: 65
<212> TYPE: PRT
<213> ORGANISM: Centruroides exilicauda

<400> SEQUENCE: 28

Lys Asp Gly Tyr Leu Val Ser Lys Ser Thr Gly Cys Lys Tyr Glu Cys
1               5                   10                  15

Phe Trp Leu Gly Lys Asn Glu Gly Cys Asp Lys Glu Cys Lys Ala Pro
            20                  25                  30

Asn Gln Gly Gly Gly Tyr Gly Tyr Cys His Ala Phe Ala Cys Trp Cys
        35                  40                  45

Glu Asn Leu Pro Glu Ser Thr Pro Thr Tyr Pro Ile Pro Gly Lys Ser
    50                  55                  60

Cys
65
```

```
<210> SEQ ID NO 29
<211> LENGTH: 261
<212> TYPE: DNA
<213> ORGANISM: Centruroides exilicauda
<220> FEATURE:
<221> NAME/KEY: CDS
<222> LOCATION: (1)..(207)
<223> OTHER INFORMATION: Product= Sodium-channel modifier toxin
      precursor In the mature peptide, the last Cys is amidated,
      and the last Gly and the last 2 basic aminoacids are cut
<220> FEATURE:
<221> NAME/KEY: 3'UTR
<222> LOCATION: (211)..(261)
<223> OTHER INFORMATION:
<220> FEATURE:
<221> NAME/KEY: sig_peptide
<222> LOCATION: (1)..(3)
<223> OTHER INFORMATION: Carboxy-end of the signal peptide
<220> FEATURE:
<221> NAME/KEY: mat_peptide
<222> LOCATION: (4)..()
<223> OTHER INFORMATION: Product= Sodium-channel modifier toxin

<400> SEQUENCE: 29

gca agg gaa ggt tat ctg gta aac aag agc acg ggc tgc aaa tac gag       48
Ala Arg Glu Gly Tyr Leu Val Asn Lys Ser Thr Gly Cys Lys Tyr Glu
-1  1               5                   10                  15

tgc ttt tgg ttg gga aaa aac gaa ttc tgc gat aag gaa tgc aaa gcg       96
Cys Phe Trp Leu Gly Lys Asn Glu Phe Cys Asp Lys Glu Cys Lys Ala
                20                  25                  30

aag aac caa gga ggt agt tac ggc tat tgc tac tct ttc gca tgc tgg      144
Lys Asn Gln Gly Gly Ser Tyr Gly Tyr Cys Tyr Ser Phe Ala Cys Trp
            35                  40                  45

tgc gaa ggt ttg ccc gaa agt aca tcg act tat cct ctt cct aat aaa      192
Cys Glu Gly Leu Pro Glu Ser Thr Ser Thr Tyr Pro Leu Pro Asn Lys
        50                  55                  60

tca tgc ggc aga aaa taatggcaaa gactttttat tgtccatcaa cagaaatatt      247
Ser Cys Gly Arg Lys
    65

gtaacgcttc ttaa                                                      261


<210> SEQ ID NO 30
<211> LENGTH: 69
<212> TYPE: PRT
<213> ORGANISM: Centruroides exilicauda

<400> SEQUENCE: 30

Ala Arg Glu Gly Tyr Leu Val Asn Lys Ser Thr Gly Cys Lys Tyr Glu
-1  1               5                   10                  15

Cys Phe Trp Leu Gly Lys Asn Glu Phe Cys Asp Lys Glu Cys Lys Ala
                20                  25                  30

Lys Asn Gln Gly Gly Ser Tyr Gly Tyr Cys Tyr Ser Phe Ala Cys Trp
            35                  40                  45

Cys Glu Gly Leu Pro Glu Ser Thr Ser Thr Tyr Pro Leu Pro Asn Lys
        50                  55                  60

Ser Cys Gly Arg Lys
    65


<210> SEQ ID NO 31
<211> LENGTH: 195
<212> TYPE: DNA
<213> ORGANISM: Centruroides exilicauda
<220> FEATURE:
<221> NAME/KEY: CDS
```

-continued

```
<222> LOCATION: (1)..(195)
<223> OTHER INFORMATION: Product= Sodium-channel modifier toxin

<400> SEQUENCE: 31

agg gaa ggt tat ctg gta aac aag agc acg ggc tgc aaa tac gag tgc       48
Arg Glu Gly Tyr Leu Val Asn Lys Ser Thr Gly Cys Lys Tyr Glu Cys
1               5                   10                  15

ttt tgg ttg gga aaa aac gaa ttc tgc gat aag gaa tgc aaa gcg aag       96
Phe Trp Leu Gly Lys Asn Glu Phe Cys Asp Lys Glu Cys Lys Ala Lys
            20                  25                  30

aac caa gga ggt agt tac ggc tat tgc tac tct ttc gca tgc tgg tgc      144
Asn Gln Gly Gly Ser Tyr Gly Tyr Cys Tyr Ser Phe Ala Cys Trp Cys
        35                  40                  45

gaa ggt ttg ccc gaa agt aca tcg act tat cct ctt cct aat aaa tca      192
Glu Gly Leu Pro Glu Ser Thr Ser Thr Tyr Pro Leu Pro Asn Lys Ser
    50                  55                  60

tgc                                                                  195
Cys
65


<210> SEQ ID NO 32
<211> LENGTH: 65
<212> TYPE: PRT
<213> ORGANISM: Centruroides exilicauda

<400> SEQUENCE: 32

Arg Glu Gly Tyr Leu Val Asn Lys Ser Thr Gly Cys Lys Tyr Glu Cys
1               5                   10                  15

Phe Trp Leu Gly Lys Asn Glu Phe Cys Asp Lys Glu Cys Lys Ala Lys
            20                  25                  30

Asn Gln Gly Gly Ser Tyr Gly Tyr Cys Tyr Ser Phe Ala Cys Trp Cys
        35                  40                  45

Glu Gly Leu Pro Glu Ser Thr Ser Thr Tyr Pro Leu Pro Asn Lys Ser
    50                  55                  60

Cys
65


<210> SEQ ID NO 33
<211> LENGTH: 261
<212> TYPE: DNA
<213> ORGANISM: Centruroides exilicauda
<220> FEATURE:
<221> NAME/KEY: CDS
<222> LOCATION: (1)..(207)
<223> OTHER INFORMATION: Product= Sodium-channel modifier toxin
      precursor In the mature peptide, the last Cys is amidated, and the
      last Gly and the last 2 basic aminoacids are cut
<220> FEATURE:
<221> NAME/KEY: 3'UTR
<222> LOCATION: (211)..(261)
<223> OTHER INFORMATION:
<220> FEATURE:
<221> NAME/KEY: sig_peptide
<222> LOCATION: (1)..(3)
<223> OTHER INFORMATION:
<220> FEATURE:
<221> NAME/KEY: mat_peptide
<222> LOCATION: (4)..()
<223> OTHER INFORMATION: Product= Sodium-channel modifier toxin

<400> SEQUENCE: 33

gca agg gag ggt tat ctg gta agc aag agc acg ggc tgc aaa tac gag       48
Ala Arg Glu Gly Tyr Leu Val Ser Lys Ser Thr Gly Cys Lys Tyr Glu
-1  1               5                   10                  15

tgc ttt tgg ttg gga aaa aac gaa ggc tgc gat aag gaa tgc aaa gcg       96
```

-continued

```
Cys Phe Trp Leu Gly Lys Asn Glu Gly Cys Asp Lys Glu Cys Lys Ala
                20                  25                  30

ccg aac caa gga ggt ggt tac ggc tat tgc cac gct ttc gca tgc tgg      144
Pro Asn Gln Gly Gly Gly Tyr Gly Tyr Cys His Ala Phe Ala Cys Trp
            35                  40                  45

tgc gaa aat ttg ccc gaa agt aca ccg act tat ccc att cct ggt aaa      192
Cys Glu Asn Leu Pro Glu Ser Thr Pro Thr Tyr Pro Ile Pro Gly Lys
        50                  55                  60

tca tgc ggc aaa aaa taatggcaaa gactttttat tgtccatcaa cagaaatatt      247
Ser Cys Gly Lys Lys
    65

gtaacgcttc ttaa                                                      261


<210> SEQ ID NO 34
<211> LENGTH: 69
<212> TYPE: PRT
<213> ORGANISM: Centruroides exilicauda

<400> SEQUENCE: 34

Ala Arg Glu Gly Tyr Leu Val Ser Lys Ser Thr Gly Cys Lys Tyr Glu
-1  1               5                   10                  15

Cys Phe Trp Leu Gly Lys Asn Glu Gly Cys Asp Lys Glu Cys Lys Ala
                20                  25                  30

Pro Asn Gln Gly Gly Gly Tyr Gly Tyr Cys His Ala Phe Ala Cys Trp
            35                  40                  45

Cys Glu Asn Leu Pro Glu Ser Thr Pro Thr Tyr Pro Ile Pro Gly Lys
        50                  55                  60

Ser Cys Gly Lys Lys
    65


<210> SEQ ID NO 35
<211> LENGTH: 195
<212> TYPE: DNA
<213> ORGANISM: Centruroides exilicauda
<220> FEATURE:
<221> NAME/KEY: CDS
<222> LOCATION: (1)..(195)
<223> OTHER INFORMATION: Product= Sodium-channel modifier toxin

<400> SEQUENCE: 35

agg gag ggt tat ctg gta agc aag agc acg ggc tgc aaa tac gag tgc       48
Arg Glu Gly Tyr Leu Val Ser Lys Ser Thr Gly Cys Lys Tyr Glu Cys
1               5                   10                  15

ttt tgg ttg gga aaa aac gaa ggc tgc gat aag gaa tgc aaa gcg ccg       96
Phe Trp Leu Gly Lys Asn Glu Gly Cys Asp Lys Glu Cys Lys Ala Pro
            20                  25                  30

aac caa gga ggt ggt tac ggc tat tgc cac gct ttc gca tgc tgg tgc      144
Asn Gln Gly Gly Gly Tyr Gly Tyr Cys His Ala Phe Ala Cys Trp Cys
        35                  40                  45

gaa aat ttg ccc gaa agt aca ccg act tat ccc att cct ggt aaa tca      192
Glu Asn Leu Pro Glu Ser Thr Pro Thr Tyr Pro Ile Pro Gly Lys Ser
    50                  55                  60

tgc                                                                  195
Cys
65


<210> SEQ ID NO 36
<211> LENGTH: 65
<212> TYPE: PRT
<213> ORGANISM: Centruroides exilicauda

<400> SEQUENCE: 36
```

```
Arg Glu Gly Tyr Leu Val Ser Lys Ser Thr Gly Cys Lys Tyr Glu Cys
1               5                   10                  15

Phe Trp Leu Gly Lys Asn Glu Gly Cys Asp Lys Glu Cys Lys Ala Pro
            20                  25                  30

Asn Gln Gly Gly Gly Tyr Gly Tyr Cys His Ala Phe Ala Cys Trp Cys
        35                  40                  45

Glu Asn Leu Pro Glu Ser Thr Pro Thr Tyr Pro Ile Pro Gly Lys Ser
    50                  55                  60

Cys
65


<210> SEQ ID NO 37
<211> LENGTH: 254
<212> TYPE: DNA
<213> ORGANISM: Centruroides exilicauda
<220> FEATURE:
<221> NAME/KEY: CDS
<222> LOCATION: (1)..(201)
<223> OTHER INFORMATION: Product= Sodium-channel modifier toxin
      precursor In the mature peptide, the last Cys is amidated, and the
      last Gly and the last 2 basic aminoacids are cut
<220> FEATURE:
<221> NAME/KEY: 3'UTR
<222> LOCATION: (205)..(254)
<223> OTHER INFORMATION:
<220> FEATURE:
<221> NAME/KEY: sig_peptide
<222> LOCATION: (1)..(3)
<223> OTHER INFORMATION: Carboxy-end of the signal peptide
<220> FEATURE:
<221> NAME/KEY: mat_peptide
<222> LOCATION: (4)..()
<223> OTHER INFORMATION: Product= Sodium-channel modifier toxin

<400> SEQUENCE: 37

gca aag gaa ggt tat ctg gtg aac ata tac acg ggc tgc aaa tac agt       48
Ala Lys Glu Gly Tyr Leu Val Asn Ile Tyr Thr Gly Cys Lys Tyr Ser
-1  1               5                   10                  15

tgc tgg ttg ttg gga gaa aac gaa tat tgc att gcg gaa tgc aaa gag       96
Cys Trp Leu Leu Gly Glu Asn Glu Tyr Cys Ile Ala Glu Cys Lys Glu
                20                  25                  30

ata gga gct ggt tac ggc tat tgc cac ggt ttt ggg tgc tgg tgc gaa      144
Ile Gly Ala Gly Tyr Gly Tyr Cys His Gly Phe Gly Cys Trp Cys Glu
            35                  40                  45

caa ttt cca gaa aat aaa ccg tct tat ccc tat cct gaa aaa tca tgc      192
Gln Phe Pro Glu Asn Lys Pro Ser Tyr Pro Tyr Pro Glu Lys Ser Cys
        50                  55                  60

ggc aga aaa taagtaacgt ctttttattg tctgcgcaaa agaattattg              241
Gly Arg Lys
    65

taacgcttct taa                                                       254


<210> SEQ ID NO 38
<211> LENGTH: 67
<212> TYPE: PRT
<213> ORGANISM: Centruroides exilicauda

<400> SEQUENCE: 38

Ala Lys Glu Gly Tyr Leu Val Asn Ile Tyr Thr Gly Cys Lys Tyr Ser
-1  1               5                   10                  15

Cys Trp Leu Leu Gly Glu Asn Glu Tyr Cys Ile Ala Glu Cys Lys Glu
                20                  25                  30

Ile Gly Ala Gly Tyr Gly Tyr Cys His Gly Phe Gly Cys Trp Cys Glu
```

-continued

```
            35                  40                  45

Gln Phe Pro Glu Asn Lys Pro Ser Tyr Pro Tyr Pro Glu Lys Ser Cys
        50                  55                  60

Gly Arg Lys
    65


<210> SEQ ID NO 39
<211> LENGTH: 189
<212> TYPE: DNA
<213> ORGANISM: Centruroides exilicauda
<220> FEATURE:
<221> NAME/KEY: CDS
<222> LOCATION: (1)..(189)
<223> OTHER INFORMATION: Product= Sodium-channel modifier toxin

<400> SEQUENCE: 39

aag gaa ggt tat ctg gtg aac ata tac acg ggc tgc aaa tac agt tgc       48
Lys Glu Gly Tyr Leu Val Asn Ile Tyr Thr Gly Cys Lys Tyr Ser Cys
1               5                   10                  15

tgg ttg ttg gga gaa aac gaa tat tgc att gcg gaa tgc aaa gag ata       96
Trp Leu Leu Gly Glu Asn Glu Tyr Cys Ile Ala Glu Cys Lys Glu Ile
            20                  25                  30

gga gct ggt tac ggc tat tgc cac ggt ttt ggg tgc tgg tgc gaa caa      144
Gly Ala Gly Tyr Gly Tyr Cys His Gly Phe Gly Cys Trp Cys Glu Gln
        35                  40                  45

ttt cca gaa aat aaa ccg tct tat ccc tat cct gaa aaa tca tgc          189
Phe Pro Glu Asn Lys Pro Ser Tyr Pro Tyr Pro Glu Lys Ser Cys
    50                  55                  60


<210> SEQ ID NO 40
<211> LENGTH: 63
<212> TYPE: PRT
<213> ORGANISM: Centruroides exilicauda

<400> SEQUENCE: 40

Lys Glu Gly Tyr Leu Val Asn Ile Tyr Thr Gly Cys Lys Tyr Ser Cys
1               5                   10                  15

Trp Leu Leu Gly Glu Asn Glu Tyr Cys Ile Ala Glu Cys Lys Glu Ile
            20                  25                  30

Gly Ala Gly Tyr Gly Tyr Cys His Gly Phe Gly Cys Trp Cys Glu Gln
        35                  40                  45

Phe Pro Glu Asn Lys Pro Ser Tyr Pro Tyr Pro Glu Lys Ser Cys
    50                  55                  60


<210> SEQ ID NO 41
<211> LENGTH: 254
<212> TYPE: DNA
<213> ORGANISM: Centruroides exilicauda
<220> FEATURE:
<221> NAME/KEY: CDS
<222> LOCATION: (1)..(204)
<223> OTHER INFORMATION: Product= Sodium-channel modifier toxin
      precursor In the mature peptide, the last Cys is amidated, and
      the last Gly and the last 2 basic aminoacids are cut
<220> FEATURE:
<221> NAME/KEY: 3'UTR
<222> LOCATION: (205)..(254)
<223> OTHER INFORMATION:

<400> SEQUENCE: 41

aag gac ggt tat ccg gtg gag gtc acg ggc tgc aaa aag tct tgc tat       48
Lys Asp Gly Tyr Pro Val Glu Val Thr Gly Cys Lys Lys Ser Cys Tyr
1               5                   10                  15

aaa ttg gga gaa aac aaa ttc tgc aat agg gaa tgc aaa atg aag cac       96
```

-continued

```
Lys Leu Gly Glu Asn Lys Phe Cys Asn Arg Glu Cys Lys Met Lys His
            20                  25                  30

cga gga ggt agt tac ggc tat tgc tat ttt ttt ggg tgc tat tgc gaa      144
Arg Gly Gly Ser Tyr Gly Tyr Cys Tyr Phe Phe Gly Cys Tyr Cys Glu
        35                  40                  45

gga ttg gcc gaa agt aca ccg act tgg ccc ctt cct aat aaa tca tgc      192
Gly Leu Ala Glu Ser Thr Pro Thr Trp Pro Leu Pro Asn Lys Ser Cys
    50                  55                  60

ggc aaa aaa taa tggcaacgct gttctattgg ccaccaacgg aaatatttaa          244
Gly Lys Lys
65
cgcttcttaa                                                           254


<210> SEQ ID NO 42
<211> LENGTH: 67
<212> TYPE: PRT
<213> ORGANISM: Centruroides exilicauda

<400> SEQUENCE: 42

Lys Asp Gly Tyr Pro Val Glu Val Thr Gly Cys Lys Lys Ser Cys Tyr
1               5                   10                  15

Lys Leu Gly Glu Asn Lys Phe Cys Asn Arg Glu Cys Lys Met Lys His
            20                  25                  30

Arg Gly Gly Ser Tyr Gly Tyr Cys Tyr Phe Phe Gly Cys Tyr Cys Glu
        35                  40                  45

Gly Leu Ala Glu Ser Thr Pro Thr Trp Pro Leu Pro Asn Lys Ser Cys
    50                  55                  60

Gly Lys Lys
65


<210> SEQ ID NO 43
<211> LENGTH: 192
<212> TYPE: DNA
<213> ORGANISM: Centruroides exilicauda
<220> FEATURE:
<221> NAME/KEY: CDS
<222> LOCATION: (1)..(192)
<223> OTHER INFORMATION: Product= Sodium-channel modifier toxin

<400> SEQUENCE: 43

aag gac ggt tat ccg gtg gag gtc acg ggc tgc aaa aag tct tgc tat       48
Lys Asp Gly Tyr Pro Val Glu Val Thr Gly Cys Lys Lys Ser Cys Tyr
1               5                   10                  15

aaa ttg gga gaa aac aaa ttc tgc aat agg gaa tgc aaa atg aag cac       96
Lys Leu Gly Glu Asn Lys Phe Cys Asn Arg Glu Cys Lys Met Lys His
            20                  25                  30

cga gga ggt agt tac ggc tat tgc tat ttt ttt ggg tgc tat tgc gaa      144
Arg Gly Gly Ser Tyr Gly Tyr Cys Tyr Phe Phe Gly Cys Tyr Cys Glu
        35                  40                  45

gga ttg gcc gaa agt aca ccg act tgg ccc ctt cct aat aaa tca tgc      192
Gly Leu Ala Glu Ser Thr Pro Thr Trp Pro Leu Pro Asn Lys Ser Cys
    50                  55                  60


<210> SEQ ID NO 44
<211> LENGTH: 64
<212> TYPE: PRT
<213> ORGANISM: Centruroides exilicauda

<400> SEQUENCE: 44

Lys Asp Gly Tyr Pro Val Glu Val Thr Gly Cys Lys Lys Ser Cys Tyr
1               5                   10                  15

Lys Leu Gly Glu Asn Lys Phe Cys Asn Arg Glu Cys Lys Met Lys His
```

-continued

```
            20                  25                  30

Arg Gly Gly Ser Tyr Gly Tyr Cys Tyr Phe Phe Gly Cys Tyr Cys Glu
        35                  40                  45

Gly Leu Ala Glu Ser Thr Pro Thr Trp Pro Leu Pro Asn Lys Ser Cys
    50                  55                  60


<210> SEQ ID NO 45
<211> LENGTH: 258
<212> TYPE: DNA
<213> ORGANISM: Centruroides exilicauda
<220> FEATURE:
<221> NAME/KEY: CDS
<222> LOCATION: (1)..(204)
<223> OTHER INFORMATION: Product= Sodium-channel modifier toxin
      precursor In the mature peptide, the last Cys is amidated, and the
      last Gly and the last 2 basic aminoacids are cut
<220> FEATURE:
<221> NAME/KEY: 3'UTR
<222> LOCATION: (205)..(258)
<223> OTHER INFORMATION:

<400> SEQUENCE: 45

aag gac ggt tat ctg gtg gag gtc acg ggc tgc aaa aag tct tgc tat       48
Lys Asp Gly Tyr Leu Val Glu Val Thr Gly Cys Lys Lys Ser Cys Tyr
1               5                   10                  15

aaa ttg gga gaa aac aaa ttc tgc aat agg gaa tgc aaa atg aag cac       96
Lys Leu Gly Glu Asn Lys Phe Cys Asn Arg Glu Cys Lys Met Lys His
            20                  25                  30

cga gga ggt agt tac ggc tat tgc tat ttt ttt ggg tgc tat tgc gaa      144
Arg Gly Gly Ser Tyr Gly Tyr Cys Tyr Phe Phe Gly Cys Tyr Cys Glu
        35                  40                  45

gga ttg gcc gaa agt aca ccg act tgg ccc ctt cct aat aaa tca tgc      192
Gly Leu Ala Glu Ser Thr Pro Thr Trp Pro Leu Pro Asn Lys Ser Cys
    50                  55                  60

ggc aaa aaa taa tggcaacgct gttctattgg ccaccaacgg aaatatttaa          244
Gly Lys Lys
65

cgcttcttaa ttgc                                                      258


<210> SEQ ID NO 46
<211> LENGTH: 67
<212> TYPE: PRT
<213> ORGANISM: Centruroides exilicauda

<400> SEQUENCE: 46

Lys Asp Gly Tyr Leu Val Glu Val Thr Gly Cys Lys Lys Ser Cys Tyr
1               5                   10                  15

Lys Leu Gly Glu Asn Lys Phe Cys Asn Arg Glu Cys Lys Met Lys His
            20                  25                  30

Arg Gly Gly Ser Tyr Gly Tyr Cys Tyr Phe Phe Gly Cys Tyr Cys Glu
        35                  40                  45

Gly Leu Ala Glu Ser Thr Pro Thr Trp Pro Leu Pro Asn Lys Ser Cys
    50                  55                  60

Gly Lys Lys
65


<210> SEQ ID NO 47
<211> LENGTH: 192
<212> TYPE: DNA
<213> ORGANISM: Centruroides exilicauda
<220> FEATURE:
<221> NAME/KEY: CDS
<222> LOCATION: (1)..(192)
```

-continued

```
<223> OTHER INFORMATION: Product= Sodium-channel modifier toxin

<400> SEQUENCE: 47

aag gac ggt tat ctg gtg gag gtc acg ggc tgc aaa aag tct tgc tat       48
Lys Asp Gly Tyr Leu Val Glu Val Thr Gly Cys Lys Lys Ser Cys Tyr
1               5                   10                  15

aaa ttg gga gaa aac aaa ttc tgc aat agg gaa tgc aaa atg aag cac       96
Lys Leu Gly Glu Asn Lys Phe Cys Asn Arg Glu Cys Lys Met Lys His
            20                  25                  30

cga gga ggt agt tac ggc tat tgc tat ttt ttt ggg tgc tat tgc gaa      144
Arg Gly Gly Ser Tyr Gly Tyr Cys Tyr Phe Phe Gly Cys Tyr Cys Glu
        35                  40                  45

gga ttg gcc gaa agt aca ccg act tgg ccc ctt cct aat aaa tca tgc      192
Gly Leu Ala Glu Ser Thr Pro Thr Trp Pro Leu Pro Asn Lys Ser Cys
    50                  55                  60


<210> SEQ ID NO 48
<211> LENGTH: 64
<212> TYPE: PRT
<213> ORGANISM: Centruroides exilicauda

<400> SEQUENCE: 48

Lys Asp Gly Tyr Leu Val Glu Val Thr Gly Cys Lys Lys Ser Cys Tyr
1               5                   10                  15

Lys Leu Gly Glu Asn Lys Phe Cys Asn Arg Glu Cys Lys Met Lys His
            20                  25                  30

Arg Gly Gly Ser Tyr Gly Tyr Cys Tyr Phe Phe Gly Cys Tyr Cys Glu
        35                  40                  45

Gly Leu Ala Glu Ser Thr Pro Thr Trp Pro Leu Pro Asn Lys Ser Cys
    50                  55                  60


<210> SEQ ID NO 49
<211> LENGTH: 252
<212> TYPE: DNA
<213> ORGANISM: Centruroides exilicauda
<220> FEATURE:
<221> NAME/KEY: CDS
<222> LOCATION: (1)..(201)
<223> OTHER INFORMATION: Product= Sodium-channel modifier toxin
      precursor In the mature peptide, the last Cys is amidated, and the
      last Gly and the last 2 basic aminoacids are cut
<220> FEATURE:
<221> NAME/KEY: 3'UTR
<222> LOCATION: (202)..(252)
<223> OTHER INFORMATION:

<400> SEQUENCE: 49

aag gag ggt tat ccg gtg aac ata tac acg ggc tgc aaa tac agt tgc       48
Lys Glu Gly Tyr Pro Val Asn Ile Tyr Thr Gly Cys Lys Tyr Ser Cys
1               5                   10                  15

tgg ttg ttg gga gaa aac gaa tat tgc att gcg gaa tgc aaa gag ata       96
Trp Leu Leu Gly Glu Asn Glu Tyr Cys Ile Ala Glu Cys Lys Glu Ile
            20                  25                  30

gga gct ggt tac ggc tat tgc cac ggt ttt ggg tgc tgg tgc gaa caa      144
Gly Ala Gly Tyr Gly Tyr Cys His Gly Phe Gly Cys Trp Cys Glu Gln
        35                  40                  45

ttt cca gaa aat aaa ccg tct tat ccc tat cct gaa aaa tca tgc ggc      192
Phe Pro Glu Asn Lys Pro Ser Tyr Pro Tyr Pro Glu Lys Ser Cys Gly
    50                  55                  60

aga aaa taa tagcaacgtc tttttattgt ctgccaaaag aattattgta              241
Arg Lys
65

acgcttctta a                                                         252
```

-continued

<210> SEQ ID NO 50
<211> LENGTH: 66
<212> TYPE: PRT
<213> ORGANISM: Centruroides exilicauda

<400> SEQUENCE: 50

```
Lys Glu Gly Tyr Pro Val Asn Ile Tyr Thr Gly Cys Lys Tyr Ser Cys
1               5                   10                  15

Trp Leu Leu Gly Glu Asn Glu Tyr Cys Ile Ala Glu Cys Lys Glu Ile
            20                  25                  30

Gly Ala Gly Tyr Gly Tyr Cys His Gly Phe Gly Cys Trp Cys Glu Gln
        35                  40                  45

Phe Pro Glu Asn Lys Pro Ser Tyr Pro Tyr Pro Glu Lys Ser Cys Gly
    50                  55                  60

Arg Lys
65
```

<210> SEQ ID NO 51
<211> LENGTH: 189
<212> TYPE: DNA
<213> ORGANISM: Centruroides exilicauda
<220> FEATURE:
<221> NAME/KEY: CDS
<222> LOCATION: (1)..(189)
<223> OTHER INFORMATION: Product= Sodium-channel modifier toxin

<400> SEQUENCE: 51

```
aag gag ggt tat ccg gtg aac ata tac acg ggc tgc aaa tac agt tgc       48
Lys Glu Gly Tyr Pro Val Asn Ile Tyr Thr Gly Cys Lys Tyr Ser Cys
1               5                   10                  15

tgg ttg ttg gga gaa aac gaa tat tgc att gcg gaa tgc aaa gag ata       96
Trp Leu Leu Gly Glu Asn Glu Tyr Cys Ile Ala Glu Cys Lys Glu Ile
            20                  25                  30

gga gct ggt tac ggc tat tgc cac ggt ttt ggg tgc tgg tgc gaa caa      144
Gly Ala Gly Tyr Gly Tyr Cys His Gly Phe Gly Cys Trp Cys Glu Gln
        35                  40                  45

ttt cca gaa aat aaa ccg tct tat ccc tat cct gaa aaa tca tgc          189
Phe Pro Glu Asn Lys Pro Ser Tyr Pro Tyr Pro Glu Lys Ser Cys
    50                  55                  60
```

<210> SEQ ID NO 52
<211> LENGTH: 63
<212> TYPE: PRT
<213> ORGANISM: Centruroides exilicauda

<400> SEQUENCE: 52

```
Lys Glu Gly Tyr Pro Val Asn Ile Tyr Thr Gly Cys Lys Tyr Ser Cys
1               5                   10                  15

Trp Leu Leu Gly Glu Asn Glu Tyr Cys Ile Ala Glu Cys Lys Glu Ile
            20                  25                  30

Gly Ala Gly Tyr Gly Tyr Cys His Gly Phe Gly Cys Trp Cys Glu Gln
        35                  40                  45

Phe Pro Glu Asn Lys Pro Ser Tyr Pro Tyr Pro Glu Lys Ser Cys
    50                  55                  60
```

<210> SEQ ID NO 53
<211> LENGTH: 322
<212> TYPE: DNA
<213> ORGANISM: Centruroides limpidus limpidus
<220> FEATURE:
<221> NAME/KEY: CDS -continued

```
<222> LOCATION: (5)..(265)
<223> OTHER INFORMATION: Product= Sodium-channel modifier toxin
      precursor In the mature peptide, the last Asn  is amidated, and the
      last Gly and the last  basic aminoacid are cut
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:
<220> FEATURE:
<221> NAME/KEY: 3'UTR
<222> LOCATION: (269)..(322)
<223> OTHER INFORMATION:
<220> FEATURE:
<221> NAME/KEY: 5'UTR
<222> LOCATION: (1)..(4)
<223> OTHER INFORMATION:

<400> SEQUENCE: 53

gaag atg aat tcg ttg ttg atg atc act gct tgt ttg gcc ctg gtc gga      49
     Met Asn Ser Leu Leu Met Ile Thr Ala Cys Leu Ala Leu Val Gly
                    -15                 -10                 -5

aca gtg tgg gca aag gaa ggt tat ctg gta aac cac tcc acg ggg tgc       97
Thr Val Trp Ala Lys Glu Gly Tyr Leu Val Asn His Ser Thr Gly Cys
            -1  1               5                   10

aaa tac gaa tgc tat aaa ttg gga gac aac gat tat tgc cta agg gaa      145
Lys Tyr Glu Cys Tyr Lys Leu Gly Asp Asn Asp Tyr Cys Leu Arg Glu
        15                  20                  25

tgc aaa cag cag tac gga aaa ggt gct ggt ggc tat tgc tac gct ttt      193
Cys Lys Gln Gln Tyr Gly Lys Gly Ala Gly Gly Tyr Cys Tyr Ala Phe
    30                  35                  40

ggg tgc tgg tgc aca cat ttg tac gaa caa gcg gtg gtc tgg ccc ctt      241
Gly Cys Trp Cys Thr His Leu Tyr Glu Gln Ala Val Val Trp Pro Leu
45                  50                  55                  60

cct aag aaa aca tgc aac gga aaa taatggcaac gactttttat tgtccaccaa     295
Pro Lys Lys Thr Cys Asn Gly Lys
                65

cagaaatatt gtaacgcttc ttaattg                                        322


<210> SEQ ID NO 54
<211> LENGTH: 87
<212> TYPE: PRT
<213> ORGANISM: Centruroides limpidus limpidus

<400> SEQUENCE: 54

Met Asn Ser Leu Leu Met Ile Thr Ala Cys Leu Ala Leu Val Gly Thr
                -15                 -10                 -5

Val Trp Ala Lys Glu Gly Tyr Leu Val Asn His Ser Thr Gly Cys Lys
        -1  1               5                   10

Tyr Glu Cys Tyr Lys Leu Gly Asp Asn Asp Tyr Cys Leu Arg Glu Cys
    15                  20                  25

Lys Gln Gln Tyr Gly Lys Gly Ala Gly Gly Tyr Cys Tyr Ala Phe Gly
30                  35                  40                  45

Cys Trp Cys Thr His Leu Tyr Glu Gln Ala Val Val Trp Pro Leu Pro
                50                  55                  60

Lys Lys Thr Cys Asn Gly Lys
            65


<210> SEQ ID NO 55
<211> LENGTH: 198
<212> TYPE: DNA
```

-continued

```
<213> ORGANISM: Centruroides limpidus limpidus
<220> FEATURE:
<221> NAME/KEY: CDS
<222> LOCATION: (1)..(198)
<223> OTHER INFORMATION: Product= Sodium-channel modifier toxin Cll4

<400> SEQUENCE: 55

aag gaa ggt tat ctg gta aac cac tcc acg ggg tgc aaa tac gaa tgc       48
Lys Glu Gly Tyr Leu Val Asn His Ser Thr Gly Cys Lys Tyr Glu Cys
1               5                   10                  15

tat aaa ttg gga gac aac gat tat tgc cta agg gaa tgc aaa cag cag       96
Tyr Lys Leu Gly Asp Asn Asp Tyr Cys Leu Arg Glu Cys Lys Gln Gln
            20                  25                  30

tac gga aaa ggt gct ggt ggc tat tgc tac gct ttt ggg tgc tgg tgc      144
Tyr Gly Lys Gly Ala Gly Gly Tyr Cys Tyr Ala Phe Gly Cys Trp Cys
        35                  40                  45

aca cat ttg tac gaa caa gcg gtg gtc tgg ccc ctt cct aag aaa aca      192
Thr His Leu Tyr Glu Gln Ala Val Val Trp Pro Leu Pro Lys Lys Thr
    50                  55                  60

tgc aac                                                              198
Cys Asn
65


<210> SEQ ID NO 56
<211> LENGTH: 66
<212> TYPE: PRT
<213> ORGANISM: Centruroides limpidus limpidus

<400> SEQUENCE: 56

Lys Glu Gly Tyr Leu Val Asn His Ser Thr Gly Cys Lys Tyr Glu Cys
1               5                   10                  15

Tyr Lys Leu Gly Asp Asn Asp Tyr Cys Leu Arg Glu Cys Lys Gln Gln
            20                  25                  30

Tyr Gly Lys Gly Ala Gly Gly Tyr Cys Tyr Ala Phe Gly Cys Trp Cys
        35                  40                  45

Thr His Leu Tyr Glu Gln Ala Val Val Trp Pro Leu Pro Lys Lys Thr
    50                  55                  60

Cys Asn
65


<210> SEQ ID NO 57
<211> LENGTH: 322
<212> TYPE: DNA
<213> ORGANISM: Centruroides limpidus limpidus
<220> FEATURE:
<221> NAME/KEY: CDS
<222> LOCATION: (5)..(265)
<223> OTHER INFORMATION: Product= Sodium-channel modifier toxin
      precursor In the mature peptide, the last Tyr  is amidated, and the
      last Gly and the last  basic aminoacid are cut
<220> FEATURE:
<221> NAME/KEY: 3'UTR
<222> LOCATION: (269)..(322)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:
```

-continued

```
<400> SEQUENCE: 57

gaag atg aat tcg ttg ttg atg atc act gct tgt ttg gcc gtg atc gga      49
     Met Asn Ser Leu Leu Met Ile Thr Ala Cys Leu Ala Val Ile Gly
                     -15                 -10                 -5

aca gtg tgg gca aag gaa ggt tat att gta aac tac tac gat ggc tgc       97
Thr Val Trp Ala Lys Glu Gly Tyr Ile Val Asn Tyr Tyr Asp Gly Cys
            -1  1               5                   10

aaa tac gca tgt ctt aaa tta gga gag aac gat tat tgc tta agg gaa      145
Lys Tyr Ala Cys Leu Lys Leu Gly Glu Asn Asp Tyr Cys Leu Arg Glu
        15                  20                  25

tgc aaa gcg aga tac tac aaa tct gct ggc ggc tat tgc tac gct ttt      193
Cys Lys Ala Arg Tyr Tyr Lys Ser Ala Gly Gly Tyr Cys Tyr Ala Phe
    30                  35                  40

gcg tgc tgg tgc aca cat ttg tac gaa caa gcg gtg gtc tgg ccc ctt      241
Ala Cys Trp Cys Thr His Leu Tyr Glu Gln Ala Val Val Trp Pro Leu
45                  50                  55                  60

cct aat aaa aca tgc tac gga aaa taatggcaac gactttttat tgtccaccaa     295
Pro Asn Lys Thr Cys Tyr Gly Lys
                65

cagaaatatt gtaacgcttc ttaattg                                        322


<210> SEQ ID NO 58
<211> LENGTH: 87
<212> TYPE: PRT
<213> ORGANISM: Centruroides limpidus limpidus

<400> SEQUENCE: 58

Met Asn Ser Leu Leu Met Ile Thr Ala Cys Leu Ala Val Ile Gly Thr
                -15                 -10                 -5

Val Trp Ala Lys Glu Gly Tyr Ile Val Asn Tyr Tyr Asp Gly Cys Lys
        -1  1               5                   10

Tyr Ala Cys Leu Lys Leu Gly Glu Asn Asp Tyr Cys Leu Arg Glu Cys
    15                  20                  25

Lys Ala Arg Tyr Tyr Lys Ser Ala Gly Gly Tyr Cys Tyr Ala Phe Ala
30                  35                  40                  45

Cys Trp Cys Thr His Leu Tyr Glu Gln Ala Val Val Trp Pro Leu Pro
                50                  55                  60

Asn Lys Thr Cys Tyr Gly Lys
            65


<210> SEQ ID NO 59
<211> LENGTH: 198
<212> TYPE: DNA
<213> ORGANISM: Centruroides limpidus limpidus
<220> FEATURE:
<221> NAME/KEY: CDS
<222> LOCATION: (1)..(198)
<223> OTHER INFORMATION: Product= Sodium-channel modifier toxin

<400> SEQUENCE: 59

aag gaa ggt tat att gta aac tac tac gat ggc tgc aaa tac gca tgt       48
Lys Glu Gly Tyr Ile Val Asn Tyr Tyr Asp Gly Cys Lys Tyr Ala Cys
1               5                   10                  15

ctt aaa tta gga gag aac gat tat tgc tta agg gaa tgc aaa gcg aga       96
Leu Lys Leu Gly Glu Asn Asp Tyr Cys Leu Arg Glu Cys Lys Ala Arg
            20                  25                  30

tac tac aaa tct gct ggc ggc tat tgc tac gct ttt gcg tgc tgg tgc      144
Tyr Tyr Lys Ser Ala Gly Gly Tyr Cys Tyr Ala Phe Ala Cys Trp Cys
        35                  40                  45

aca cat ttg tac gaa caa gcg gtg gtc tgg ccc ctt cct aat aaa aca      192
```

-continued

```
Thr His Leu Tyr Glu Gln Ala Val Val Trp Pro Leu Pro Asn Lys Thr
    50                  55                  60

tgc tac                                                           198
Cys Tyr
65


<210> SEQ ID NO 60
<211> LENGTH: 66
<212> TYPE: PRT
<213> ORGANISM: Centruroides limpidus limpidus

<400> SEQUENCE: 60

Lys Glu Gly Tyr Ile Val Asn Tyr Tyr Asp Gly Cys Lys Tyr Ala Cys
1               5                   10                  15

Leu Lys Leu Gly Glu Asn Asp Tyr Cys Leu Arg Glu Cys Lys Ala Arg
            20                  25                  30

Tyr Tyr Lys Ser Ala Gly Gly Tyr Cys Tyr Ala Phe Ala Cys Trp Cys
        35                  40                  45

Thr His Leu Tyr Glu Gln Ala Val Val Trp Pro Leu Pro Asn Lys Thr
    50                  55                  60

Cys Tyr
65


<210> SEQ ID NO 61
<211> LENGTH: 322
<212> TYPE: DNA
<213> ORGANISM: Centruroides limpidus limpidus
<220> FEATURE:
<221> NAME/KEY: CDS
<222> LOCATION: (5)..(265)
<223> OTHER INFORMATION: Product= Sodium-channel modifier toxin
      precursor In the mature peptide, the last Asn  is amidated, and
      the last Gly and the last  basic aminoacid are cut
<220> FEATURE:
<221> NAME/KEY: 3'UTR
<222> LOCATION: (269)..(322)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:

<400> SEQUENCE: 61

gaag atg aat tcg ttg ttg atg atc act gct tgt ttg gcc ctg ata gga      49
     Met Asn Ser Leu Leu Met Ile Thr Ala Cys Leu Ala Leu Ile Gly
                     -15                 -10                 -5

aca gtg tgg gca aag gaa ggt tat att gta aac tac cac gat ggc tgc       97
Thr Val Trp Ala Lys Glu Gly Tyr Ile Val Asn Tyr His Asp Gly Cys
            -1  1               5                   10

aaa tac gaa tgc tat aaa ttg gga gac aac gat tat tgc tta agg gaa      145
Lys Tyr Glu Cys Tyr Lys Leu Gly Asp Asn Asp Tyr Cys Leu Arg Glu
        15                  20                  25

tgc aaa ttg aga tac gga aaa ggt gct ggc ggc tat tgc tac gct ttt      193
Cys Lys Leu Arg Tyr Gly Lys Gly Ala Gly Gly Tyr Cys Tyr Ala Phe
    30                  35                  40

ggg tgc tgg tgc aca cat ttg tac gaa caa gcg gtg gtc tgg ccc ctt      241
Gly Cys Trp Cys Thr His Leu Tyr Glu Gln Ala Val Val Trp Pro Leu
45                  50                  55                  60
```

-continued

```
cca aag aaa aga tgc aat gga aaa taatggcaac gactttttat tgtccaccaa     295
Pro Lys Lys Arg Cys Asn Gly Lys
                65

cagaaatatt gtaacgcttc ttaattg                                        322


<210> SEQ ID NO 62
<211> LENGTH: 87
<212> TYPE: PRT
<213> ORGANISM: Centruroides limpidus limpidus

<400> SEQUENCE: 62

Met Asn Ser Leu Leu Met Ile Thr Ala Cys Leu Ala Leu Ile Gly Thr
                -15                 -10                 -5

Val Trp Ala Lys Glu Gly Tyr Ile Val Asn Tyr His Asp Gly Cys Lys
        -1  1               5                   10

Tyr Glu Cys Tyr Lys Leu Gly Asp Asn Asp Tyr Cys Leu Arg Glu Cys
    15                  20                  25

Lys Leu Arg Tyr Gly Lys Gly Ala Gly Gly Tyr Cys Tyr Ala Phe Gly
30                  35                  40                  45

Cys Trp Cys Thr His Leu Tyr Glu Gln Ala Val Val Trp Pro Leu Pro
                50                  55                  60

Lys Lys Arg Cys Asn Gly Lys
            65


<210> SEQ ID NO 63
<211> LENGTH: 198
<212> TYPE: DNA
<213> ORGANISM: Centruroides limpidus limpidus
<220> FEATURE:
<221> NAME/KEY: CDS
<222> LOCATION: (1)..(198)
<223> OTHER INFORMATION: Product= Sodium-channel modifier toxin

<400> SEQUENCE: 63

aag gaa ggt tat att gta aac tac cac gat ggc tgc aaa tac gaa tgc       48
Lys Glu Gly Tyr Ile Val Asn Tyr His Asp Gly Cys Lys Tyr Glu Cys
1               5                   10                  15

tat aaa ttg gga gac aac gat tat tgc tta agg gaa tgc aaa ttg aga       96
Tyr Lys Leu Gly Asp Asn Asp Tyr Cys Leu Arg Glu Cys Lys Leu Arg
            20                  25                  30

tac gga aaa ggt gct ggc ggc tat tgc tac gct ttt ggg tgc tgg tgc      144
Tyr Gly Lys Gly Ala Gly Gly Tyr Cys Tyr Ala Phe Gly Cys Trp Cys
        35                  40                  45

aca cat ttg tac gaa caa gcg gtg gtc tgg ccc ctt cca aag aaa aga      192
Thr His Leu Tyr Glu Gln Ala Val Val Trp Pro Leu Pro Lys Lys Arg
    50                  55                  60

tgc aat                                                              198
Cys Asn
65


<210> SEQ ID NO 64
<211> LENGTH: 66
<212> TYPE: PRT
<213> ORGANISM: Centruroides limpidus limpidus

<400> SEQUENCE: 64

Lys Glu Gly Tyr Ile Val Asn Tyr His Asp Gly Cys Lys Tyr Glu Cys
1               5                   10                  15

Tyr Lys Leu Gly Asp Asn Asp Tyr Cys Leu Arg Glu Cys Lys Leu Arg
            20                  25                  30
```

-continued

```
Tyr Gly Lys Gly Ala Gly Gly Tyr Cys Tyr Ala Phe Gly Cys Trp Cys
        35                  40                  45

Thr His Leu Tyr Glu Gln Ala Val Val Trp Pro Leu Pro Lys Lys Arg
    50                  55                  60

Cys Asn
65


<210> SEQ ID NO 65
<211> LENGTH: 322
<212> TYPE: DNA
<213> ORGANISM: Centruroides limpidus limpidus
<220> FEATURE:
<221> NAME/KEY: CDS
<222> LOCATION: (5)..(265)
<223> OTHER INFORMATION: Product= Sodium-channel modifier toxin
      precursor In the mature peptide,  the last 2 basic aminoacids
      are cut
<220> FEATURE:
<221> NAME/KEY: 3'UTR
<222> LOCATION: (269)..(322)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:

<400> SEQUENCE: 65

gaag atg aat tcg ttg ttg atg atc act gct tgt ttg gcc gag atc gga      49
     Met Asn Ser Leu Leu Met Ile Thr Ala Cys Leu Ala Glu Ile Gly
                     -15                 -10                 -5

aca gtg tgg gca aaa gaa ggt tat ctg gta aac aag agc acg ggc tgc       97
Thr Val Trp Ala Lys Glu Gly Tyr Leu Val Asn Lys Ser Thr Gly Cys
            -1  1               5                   10

aaa tac ggt tgc ttc tgg ttg gga aaa aac gaa aac tgc gat aag gaa      145
Lys Tyr Gly Cys Phe Trp Leu Gly Lys Asn Glu Asn Cys Asp Lys Glu
        15                  20                  25

tgc aaa gcg aaa aac caa gga ggt agt tac ggc tat tgc tac tct ttt      193
Cys Lys Ala Lys Asn Gln Gly Gly Ser Tyr Gly Tyr Cys Tyr Ser Phe
    30                  35                  40

gcc tgc tgg tgc gaa ggt ttg ccc gat agt aca ccg act tat ccc ctt      241
Ala Cys Trp Cys Glu Gly Leu Pro Asp Ser Thr Pro Thr Tyr Pro Leu
45                  50                  55                  60

cct aat aaa tcg tgc agc aaa aaa taatggcaac gtctttttat tgtccaccaa     295
Pro Asn Lys Ser Cys Ser Lys Lys
                65

cagaaatatt gtaacgcttc ttaattg                                        322


<210> SEQ ID NO 66
<211> LENGTH: 87
<212> TYPE: PRT
<213> ORGANISM: Centruroides limpidus limpidus

<400> SEQUENCE: 66

Met Asn Ser Leu Leu Met Ile Thr Ala Cys Leu Ala Glu Ile Gly Thr
                -15                 -10                 -5

Val Trp Ala Lys Glu Gly Tyr Leu Val Asn Lys Ser Thr Gly Cys Lys
        -1  1               5                   10
```

-continued

```
Tyr Gly Cys Phe Trp Leu Gly Lys Asn Glu Asn Cys Asp Lys Glu Cys
    15                  20                  25

Lys Ala Lys Asn Gln Gly Gly Ser Tyr Gly Tyr Cys Tyr Ser Phe Ala
30                  35                  40                  45

Cys Trp Cys Glu Gly Leu Pro Asp Ser Thr Pro Thr Tyr Pro Leu Pro
                50                  55                  60

Asn Lys Ser Cys Ser Lys Lys
            65


<210> SEQ ID NO 67
<211> LENGTH: 198
<212> TYPE: DNA
<213> ORGANISM: Centruroides limpidus limpidus
<220> FEATURE:
<221> NAME/KEY: CDS
<222> LOCATION: (1)..(198)
<223> OTHER INFORMATION: Product= Sodium-channel modifier toxin

<400> SEQUENCE: 67

aaa gaa ggt tat ctg gta aac aag agc acg ggc tgc aaa tac ggt tgc       48
Lys Glu Gly Tyr Leu Val Asn Lys Ser Thr Gly Cys Lys Tyr Gly Cys
1               5                   10                  15

ttc tgg ttg gga aaa aac gaa aac tgc gat aag gaa tgc aaa gcg aaa       96
Phe Trp Leu Gly Lys Asn Glu Asn Cys Asp Lys Glu Cys Lys Ala Lys
            20                  25                  30

aac caa gga ggt agt tac ggc tat tgc tac tct ttt gcc tgc tgg tgc      144
Asn Gln Gly Gly Ser Tyr Gly Tyr Cys Tyr Ser Phe Ala Cys Trp Cys
        35                  40                  45

gaa ggt ttg ccc gat agt aca ccg act tat ccc ctt cct aat aaa tcg      192
Glu Gly Leu Pro Asp Ser Thr Pro Thr Tyr Pro Leu Pro Asn Lys Ser
    50                  55                  60

tgc agc                                                              198
Cys Ser
65


<210> SEQ ID NO 68
<211> LENGTH: 66
<212> TYPE: PRT
<213> ORGANISM: Centruroides limpidus limpidus

<400> SEQUENCE: 68

Lys Glu Gly Tyr Leu Val Asn Lys Ser Thr Gly Cys Lys Tyr Gly Cys
1               5                   10                  15

Phe Trp Leu Gly Lys Asn Glu Asn Cys Asp Lys Glu Cys Lys Ala Lys
            20                  25                  30

Asn Gln Gly Gly Ser Tyr Gly Tyr Cys Tyr Ser Phe Ala Cys Trp Cys
        35                  40                  45

Glu Gly Leu Pro Asp Ser Thr Pro Thr Tyr Pro Leu Pro Asn Lys Ser
    50                  55                  60

Cys Ser
65


<210> SEQ ID NO 69
<211> LENGTH: 322
<212> TYPE: DNA
<213> ORGANISM: Centruroides limpidus limpidus
<220> FEATURE:
<221> NAME/KEY: CDS
<222> LOCATION: (5)..(265)
<223> OTHER INFORMATION: Product= Sodium-channel modifier toxin
      precursor In the mature peptide,  the last 2 basic aminoacids
      are cut
<220> FEATURE:
```

-continued

<221> NAME/KEY: 3'UTR
<222> LOCATION: (269)..(322)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:

<400> SEQUENCE: 69

```
gaag atg aat tcg ttg ttg atg atc act gct tgt ttg gtc cta ttc gga      49
     Met Asn Ser Leu Leu Met Ile Thr Ala Cys Leu Val Leu Phe Gly
                     -15                 -10                 -5

aca gtg tgg gca aaa gaa ggt tat ctg gta aac aag agc acg ggc tgc       97
Thr Val Trp Ala Lys Glu Gly Tyr Leu Val Asn Lys Ser Thr Gly Cys
            -1  1               5                   10

aaa tac ggt tgc ttc tgg ttg gga aaa aac gaa aac tgc gat atg gaa      145
Lys Tyr Gly Cys Phe Trp Leu Gly Lys Asn Glu Asn Cys Asp Met Glu
        15                  20                  25

tgc aaa gcg aaa aac caa gga ggt agt tac ggc tat tgc tac tct ttt      193
Cys Lys Ala Lys Asn Gln Gly Gly Ser Tyr Gly Tyr Cys Tyr Ser Phe
    30                  35                  40

gcc tgc tgg tgc gaa ggt ttg ccc gat agt aca ccg act tat ccc ctt      241
Ala Cys Trp Cys Glu Gly Leu Pro Asp Ser Thr Pro Thr Tyr Pro Leu
45                  50                  55                  60

cct aat aaa tcg tgc agc aaa aaa taatggcaac gtctttttat tgtccaccaa     295
Pro Asn Lys Ser Cys Ser Lys Lys
                65

cagaaatatt gtaacgcttc ttaattg                                        322
```

<210> SEQ ID NO 70
<211> LENGTH: 87
<212> TYPE: PRT
<213> ORGANISM: Centruroides limpidus limpidus

<400> SEQUENCE: 70

```
Met Asn Ser Leu Leu Met Ile Thr Ala Cys Leu Val Leu Phe Gly Thr
                -15                 -10                 -5

Val Trp Ala Lys Glu Gly Tyr Leu Val Asn Lys Ser Thr Gly Cys Lys
        -1  1               5                   10

Tyr Gly Cys Phe Trp Leu Gly Lys Asn Glu Asn Cys Asp Met Glu Cys
    15                  20                  25

Lys Ala Lys Asn Gln Gly Gly Ser Tyr Gly Tyr Cys Tyr Ser Phe Ala
30                  35                  40                  45

Cys Trp Cys Glu Gly Leu Pro Asp Ser Thr Pro Thr Tyr Pro Leu Pro
                50                  55                  60

Asn Lys Ser Cys Ser Lys Lys
            65
```

<210> SEQ ID NO 71
<211> LENGTH: 198
<212> TYPE: DNA
<213> ORGANISM: Centruroides limpidus limpidus
<220> FEATURE:
<221> NAME/KEY: CDS
<222> LOCATION: (1)..(198)
<223> OTHER INFORMATION: Product= Sodium-channel modifier toxin -continued

<400> SEQUENCE: 71 aaa gaa ggt tat ctg gta aac aag agc acg ggc tgc aaa tac ggt tgc 48
Lys Glu Gly Tyr Leu Val Asn Lys Ser Thr Gly Cys Lys Tyr Gly Cys
1 5 10 15 ttc tgg ttg gga aaa aac gaa aac tgc gat atg gaa tgc aaa gcg aaa 96
Phe Trp Leu Gly Lys Asn Glu Asn Cys Asp Met Glu Cys Lys Ala Lys
20 25 30 aac caa gga ggt agt tac ggc tat tgc tac tct ttt gcc tgc tgg tgc 144
Asn Gln Gly Gly Ser Tyr Gly Tyr Cys Tyr Ser Phe Ala Cys Trp Cys
35 40 45 gaa ggt ttg ccc gat agt aca ccg act tat ccc ctt cct aat aaa tcg 192
Glu Gly Leu Pro Asp Ser Thr Pro Thr Tyr Pro Leu Pro Asn Lys Ser
50 55 60 tgc agc 198
Cys Ser
65

<210> SEQ ID NO 72
<211> LENGTH: 66
<212> TYPE: PRT
<213> ORGANISM: Centruroides limpidus limpidus

<400> SEQUENCE: 72

Lys Glu Gly Tyr Leu Val Asn Lys Ser Thr Gly Cys Lys Tyr Gly Cys
1 5 10 15

Phe Trp Leu Gly Lys Asn Glu Asn Cys Asp Met Glu Cys Lys Ala Lys
20 25 30

Asn Gln Gly Gly Ser Tyr Gly Tyr Cys Tyr Ser Phe Ala Cys Trp Cys
35 40 45

Glu Gly Leu Pro Asp Ser Thr Pro Thr Tyr Pro Leu Pro Asn Lys Ser
50 55 60

Cys Ser
65

<210> SEQ ID NO 73
<211> LENGTH: 316
<212> TYPE: DNA
<213> ORGANISM: Centruroides limpidus limpidus
<220> FEATURE:
<221> NAME/KEY: CDS
<222> LOCATION: (5)..(259)
<223> OTHER INFORMATION: Product= Sodium-channel modifier toxin precursor In the mature peptide, the last Ser is amidated, and the last Gly and the last basic aminoacid are cut
<220> FEATURE:
<221> NAME/KEY: 3'UTR
<222> LOCATION: (263)..(316)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:

<400> SEQUENCE: 73 gaag atg aac tcg ttg ttg atg att att ggt tgt ttg gtc ctg atc gga 49
Met Asn Ser Leu Leu Met Ile Ile Gly Cys Leu Val Leu Ile Gly
-15 -10 -5

-continued

```
aca gtg tgg aca aag gaa ggt tat ctg gtg aac atg aaa acg ggc tgc       97
Thr Val Trp Thr Lys Glu Gly Tyr Leu Val Asn Met Lys Thr Gly Cys
            -1  1               5                   10

aaa tac ggg tgc tat gaa ttg ggt gac aac ggt tac tgc gat agg aaa      145
Lys Tyr Gly Cys Tyr Glu Leu Gly Asp Asn Gly Tyr Cys Asp Arg Lys
        15                  20                  25

tgc aaa gcg gag agc ggt aac tac ggc tat tgc tat act gtt ggg tgc      193
Cys Lys Ala Glu Ser Gly Asn Tyr Gly Tyr Cys Tyr Thr Val Gly Cys
    30                  35                  40

tgg tgc gaa gga ttg ccc aat agt aaa ccg act tgg ccc ctt cct ggt      241
Trp Cys Glu Gly Leu Pro Asn Ser Lys Pro Thr Trp Pro Leu Pro Gly
45                  50                  55                  60

aaa tca tgc agc gga aaa taatagcaac gtctttttat tgtccaccaa             289
Lys Ser Cys Ser Gly Lys
                65

cagaaatatt gtaacgcttc ttaattg                                        316


<210> SEQ ID NO 74
<211> LENGTH: 85
<212> TYPE: PRT
<213> ORGANISM: Centruroides limpidus limpidus

<400> SEQUENCE: 74

Met Asn Ser Leu Leu Met Ile Ile Gly Cys Leu Val Leu Ile Gly Thr
                -15                 -10                 -5

Val Trp Thr Lys Glu Gly Tyr Leu Val Asn Met Lys Thr Gly Cys Lys
        -1  1               5                   10

Tyr Gly Cys Tyr Glu Leu Gly Asp Asn Gly Tyr Cys Asp Arg Lys Cys
    15                  20                  25

Lys Ala Glu Ser Gly Asn Tyr Gly Tyr Cys Tyr Thr Val Gly Cys Trp
30                  35                  40                  45

Cys Glu Gly Leu Pro Asn Ser Lys Pro Thr Trp Pro Leu Pro Gly Lys
                50                  55                  60

Ser Cys Ser Gly Lys
            65


<210> SEQ ID NO 75
<211> LENGTH: 192
<212> TYPE: DNA
<213> ORGANISM: Centruroides limpidus limpidus
<220> FEATURE:
<221> NAME/KEY: CDS
<222> LOCATION: (1)..(192)
<223> OTHER INFORMATION: Product= Sodium-channel modifier toxin

<400> SEQUENCE: 75

aag gaa ggt tat ctg gtg aac atg aaa acg ggc tgc aaa tac ggg tgc       48
Lys Glu Gly Tyr Leu Val Asn Met Lys Thr Gly Cys Lys Tyr Gly Cys
1               5                   10                  15

tat gaa ttg ggt gac aac ggt tac tgc gat agg aaa tgc aaa gcg gag       96
Tyr Glu Leu Gly Asp Asn Gly Tyr Cys Asp Arg Lys Cys Lys Ala Glu
            20                  25                  30

agc ggt aac tac ggc tat tgc tat act gtt ggg tgc tgg tgc gaa gga      144
Ser Gly Asn Tyr Gly Tyr Cys Tyr Thr Val Gly Cys Trp Cys Glu Gly
        35                  40                  45

ttg ccc aat agt aaa ccg act tgg ccc ctt cct ggt aaa tca tgc agc      192
Leu Pro Asn Ser Lys Pro Thr Trp Pro Leu Pro Gly Lys Ser Cys Ser
    50                  55                  60


<210> SEQ ID NO 76
```

-continued

<211> LENGTH: 64
<212> TYPE: PRT
<213> ORGANISM: Centruroides limpidus limpidus

<400> SEQUENCE: 76

```
Lys Glu Gly Tyr Leu Val Asn Met Lys Thr Gly Cys Lys Tyr Gly Cys
1               5                   10                  15

Tyr Glu Leu Gly Asp Asn Gly Tyr Cys Asp Arg Lys Cys Lys Ala Glu
            20                  25                  30

Ser Gly Asn Tyr Gly Tyr Cys Tyr Thr Val Gly Cys Trp Cys Glu Gly
        35                  40                  45

Leu Pro Asn Ser Lys Pro Thr Trp Pro Leu Pro Gly Lys Ser Cys Ser
    50                  55                  60
```

<210> SEQ ID NO 77
<211> LENGTH: 316
<212> TYPE: DNA
<213> ORGANISM: Centruroides limpidus limpidus
<220> FEATURE:
<221> NAME/KEY: CDS
<222> LOCATION: (5)..(259)
<223> OTHER INFORMATION: Product= Sodium-channel modifier toxin precursor In the mature peptide, the last Cys is amidated, and the last Gly and the last 2 basic aminoacids are cut
<220> FEATURE:
<221> NAME/KEY: 3'UTR
<222> LOCATION: (263)..(316)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:

<400> SEQUENCE: 77

```
gaag atg aat tcg ttg ttg atg atc act gct tgt ttg gtc cta ttc gga      49
     Met Asn Ser Leu Leu Met Ile Thr Ala Cys Leu Val Leu Phe Gly
                     -15                 -10                 -5

aca gtg tgg gca aag gaa ggt tat ctg gtg aac acg tac acg ggc tgc       97
Thr Val Trp Ala Lys Glu Gly Tyr Leu Val Asn Thr Tyr Thr Gly Cys
            -1  1               5                   10

aaa tac att tgc tgg aaa ttg gga gag aac aaa tac tgc att gat gaa      145
Lys Tyr Ile Cys Trp Lys Leu Gly Glu Asn Lys Tyr Cys Ile Asp Glu
        15                  20                  25

tgt aaa gag ata gga gct ggt tac ggc tat tgc tac ggt ttt ggg tgc      193
Cys Lys Glu Ile Gly Ala Gly Tyr Gly Tyr Cys Tyr Gly Phe Gly Cys
    30                  35                  40

tat tgc gaa gga ttt ccc gaa aat aaa ccg acc tgg ccc ctt cct aat      241
Tyr Cys Glu Gly Phe Pro Glu Asn Lys Pro Thr Trp Pro Leu Pro Asn
45                  50                  55                  60

aaa aca tgc ggc aga aaa taatgacaac gtctttttat tgtccaccaa             289
Lys Thr Cys Gly Arg Lys
                65

cagaaatatt gtaacgcttc ttaattg                                        316
```

<210> SEQ ID NO 78
<211> LENGTH: 85
<212> TYPE: PRT
<213> ORGANISM: Centruroides limpidus limpidus -continued

<400> SEQUENCE: 78

```
Met Asn Ser Leu Leu Met Ile Thr Ala Cys Leu Val Leu Phe Gly Thr
                -15                 -10                 -5

Val Trp Ala Lys Glu Gly Tyr Leu Val Asn Thr Tyr Thr Gly Cys Lys
        -1  1               5                   10

Tyr Ile Cys Trp Lys Leu Gly Glu Asn Lys Tyr Cys Ile Asp Glu Cys
    15                  20                  25

Lys Glu Ile Gly Ala Gly Tyr Gly Tyr Cys Tyr Gly Phe Gly Cys Tyr
30                  35                  40                  45

Cys Glu Gly Phe Pro Glu Asn Lys Pro Thr Trp Pro Leu Pro Asn Lys
                50                  55                  60

Thr Cys Gly Arg Lys
            65
```

<210> SEQ ID NO 79
<211> LENGTH: 189
<212> TYPE: DNA
<213> ORGANISM: Centruroides limpidus limpidus
<220> FEATURE:
<221> NAME/KEY: CDS
<222> LOCATION: (1)..(189)
<223> OTHER INFORMATION: Product= Sodium-channel modifier toxin

<400> SEQUENCE: 79

```
aag gaa ggt tat ctg gtg aac acg tac acg ggc tgc aaa tac att tgc       48
Lys Glu Gly Tyr Leu Val Asn Thr Tyr Thr Gly Cys Lys Tyr Ile Cys
1               5                   10                  15

tgg aaa ttg gga gag aac aaa tac tgc att gat gaa tgt aaa gag ata       96
Trp Lys Leu Gly Glu Asn Lys Tyr Cys Ile Asp Glu Cys Lys Glu Ile
            20                  25                  30

gga gct ggt tac ggc tat tgc tac ggt ttt ggg tgc tat tgc gaa gga      144
Gly Ala Gly Tyr Gly Tyr Cys Tyr Gly Phe Gly Cys Tyr Cys Glu Gly
        35                  40                  45

ttt ccc gaa aat aaa ccg acc tgg ccc ctt cct aat aaa aca tgc          189
Phe Pro Glu Asn Lys Pro Thr Trp Pro Leu Pro Asn Lys Thr Cys
    50                  55                  60
```

<210> SEQ ID NO 80
<211> LENGTH: 63
<212> TYPE: PRT
<213> ORGANISM: Centruroides limpidus limpidus

<400> SEQUENCE: 80

```
Lys Glu Gly Tyr Leu Val Asn Thr Tyr Thr Gly Cys Lys Tyr Ile Cys
1               5                   10                  15

Trp Lys Leu Gly Glu Asn Lys Tyr Cys Ile Asp Glu Cys Lys Glu Ile
            20                  25                  30

Gly Ala Gly Tyr Gly Tyr Cys Tyr Gly Phe Gly Cys Tyr Cys Glu Gly
        35                  40                  45

Phe Pro Glu Asn Lys Pro Thr Trp Pro Leu Pro Asn Lys Thr Cys
    50                  55                  60
```

<210> SEQ ID NO 81
<211> LENGTH: 274
<212> TYPE: DNA
<213> ORGANISM: Centruroides limpidus limpidus
<220> FEATURE:
<221> NAME/KEY: CDS
<222> LOCATION: (2)..(217)
<223> OTHER INFORMATION: Product= Sodium-channel modifier toxin
      precursor In the mature peptide, the last Cys is amidated, -continued and the last Gly and the last 2 basic aminoacids are cut
<220> FEATURE:
<221> NAME/KEY: sig_peptide
<222> LOCATION: (2)..(13)
<223> OTHER INFORMATION: Carboxy-end of the signal peptide
<220> FEATURE:
<221> NAME/KEY: mat_peptide
<222> LOCATION: (14)..()
<223> OTHER INFORMATION: Product= Sodium-channel modifier toxin
<220> FEATURE:
<221> NAME/KEY: 3'UTR
<222> LOCATION: (221)..(274)

<400> SEQUENCE: 81

```
a aca gtg tcg gca aaa gaa ggt tat ctg gtg aag aag agc aat ggt tgc      49
  Thr Val Ser Ala Lys Glu Gly Tyr Leu Val Lys Lys Ser Asn Gly Cys
              -1  1               5                   10

aaa tac gag tgc ttt aaa ttg gga gaa aac gaa cac tgc gat acg gaa        97
Lys Tyr Glu Cys Phe Lys Leu Gly Glu Asn Glu His Cys Asp Thr Glu
        15                  20                  25

tgc aaa gcg ccg aac caa gga ggt agt tac ggc tat tgc gac act ttt       145
Cys Lys Ala Pro Asn Gln Gly Gly Ser Tyr Gly Tyr Cys Asp Thr Phe
    30                  35                  40

gag tgt tgg tgc gaa ggt ttg ccc gaa agt aca ccg act tgg cct ctt       193
Glu Cys Trp Cys Glu Gly Leu Pro Glu Ser Thr Pro Thr Trp Pro Leu
45                  50                  55                  60

cct aat aaa tca tgc ggc aaa aaa taatggcaac gtctttttat tgtccaccaa      247
Pro Asn Lys Ser Cys Gly Lys Lys
                65

cagaaatatt gtaacgcttc ttaattg                                         274
```

<210> SEQ ID NO 82
<211> LENGTH: 72
<212> TYPE: PRT
<213> ORGANISM: Centruroides limpidus limpidus

<400> SEQUENCE: 82

```
Thr Val Ser Ala Lys Glu Gly Tyr Leu Val Lys Lys Ser Asn Gly Cys
            -1  1               5                   10

Lys Tyr Glu Cys Phe Lys Leu Gly Glu Asn Glu His Cys Asp Thr Glu
        15                  20                  25

Cys Lys Ala Pro Asn Gln Gly Gly Ser Tyr Gly Tyr Cys Asp Thr Phe
    30                  35                  40

Glu Cys Trp Cys Glu Gly Leu Pro Glu Ser Thr Pro Thr Trp Pro Leu
45                  50                  55                  60

Pro Asn Lys Ser Cys Gly Lys Lys
                65
```

<210> SEQ ID NO 83
<211> LENGTH: 195
<212> TYPE: DNA
<213> ORGANISM: Centruroides limpidus limpidus
<220> FEATURE:
<221> NAME/KEY: CDS
<222> LOCATION: (1)..(195)
<223> OTHER INFORMATION: Product= Sodium-channel modifier toxin

<400> SEQUENCE: 83

```
aaa gaa ggt tat ctg gtg aag aag agc aat ggt tgc aaa tac gag tgc        48
Lys Glu Gly Tyr Leu Val Lys Lys Ser Asn Gly Cys Lys Tyr Glu Cys
1               5                   10                  15

ttt aaa ttg gga gaa aac gaa cac tgc gat acg gaa tgc aaa gcg ccg        96
Phe Lys Leu Gly Glu Asn Glu His Cys Asp Thr Glu Cys Lys Ala Pro
            20                  25                  30
```

-continued

```
aac caa gga ggt agt tac ggc tat tgc gac act ttt gag tgt tgg tgc      144
Asn Gln Gly Gly Ser Tyr Gly Tyr Cys Asp Thr Phe Glu Cys Trp Cys
        35                  40                  45

gaa ggt ttg ccc gaa agt aca ccg act tgg cct ctt cct aat aaa tca      192
Glu Gly Leu Pro Glu Ser Thr Pro Thr Trp Pro Leu Pro Asn Lys Ser
    50                  55                  60

tgc                                                                  195
Cys
65


<210> SEQ ID NO 84
<211> LENGTH: 65
<212> TYPE: PRT
<213> ORGANISM: Centruroides limpidus limpidus

<400> SEQUENCE: 84

Lys Glu Gly Tyr Leu Val Lys Lys Ser Asn Gly Cys Lys Tyr Glu Cys
1               5                   10                  15

Phe Lys Leu Gly Glu Asn Glu His Cys Asp Thr Glu Cys Lys Ala Pro
            20                  25                  30

Asn Gln Gly Gly Ser Tyr Gly Tyr Cys Asp Thr Phe Glu Cys Trp Cys
        35                  40                  45

Glu Gly Leu Pro Glu Ser Thr Pro Thr Trp Pro Leu Pro Asn Lys Ser
    50                  55                  60

Cys
65


<210> SEQ ID NO 85
<211> LENGTH: 323
<212> TYPE: DNA
<213> ORGANISM: Centruroides noxius
<220> FEATURE:
<221> NAME/KEY: CDS
<222> LOCATION: (5)..(265)
<223> OTHER INFORMATION: Product= Sodium-channel modifier toxin
      precursor In the mature peptide, the last Asn is amidated,
      and the last Gly and the last basic aminoacid are cut
<220> FEATURE:
<221> NAME/KEY: 3'UTR
<222> LOCATION: (269)..(323)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:

<400> SEQUENCE: 85

gaag atg aac tcg ttg ttg atg atc act gct tgt ttg gcc ctg gtc gga      49
     Met Asn Ser Leu Leu Met Ile Thr Ala Cys Leu Ala Leu Val Gly
                     -15                 -10                 -5

aca gtg tgg tca aag gaa ggt tat ata gta aac tcg tac acg ggc tgc       97
Thr Val Trp Ser Lys Glu Gly Tyr Ile Val Asn Ser Tyr Thr Gly Cys
            -1  1               5                   10

aaa tac gaa tgc ttg aaa ttg gga gac aac gat tat tgc ttg agg gaa      145
Lys Tyr Glu Cys Leu Lys Leu Gly Asp Asn Asp Tyr Cys Leu Arg Glu
        15                  20                  25

tgc aaa cag cag tac gga aaa ggt gct ggc ggc tat tgt tac gct ttt      193
```

-continued

```
Cys Lys Gln Gln Tyr Gly Lys Gly Ala Gly Gly Tyr Cys Tyr Ala Phe
    30                  35                  40

ggg tgc tgg tgc aca cat ttg tac gaa caa gcg gtg gtc tgg ccc ctt      241
Gly Cys Trp Cys Thr His Leu Tyr Glu Gln Ala Val Val Trp Pro Leu
45                  50                  55                  60

aaa aat aag aca tgc aac gga aaa taatggcaac gactttttat tgcccaccaa     295
Lys Asn Lys Thr Cys Asn Gly Lys
                65

cagaaatatt gtaacgcttc ttaattgg                                       323


<210> SEQ ID NO 86
<211> LENGTH: 87
<212> TYPE: PRT
<213> ORGANISM: Centruroides noxius

<400> SEQUENCE: 86

Met Asn Ser Leu Leu Met Ile Thr Ala Cys Leu Ala Leu Val Gly Thr
                -15                 -10                 -5

Val Trp Ser Lys Glu Gly Tyr Ile Val Asn Ser Tyr Thr Gly Cys Lys
        -1  1               5                   10

Tyr Glu Cys Leu Lys Leu Gly Asp Asn Asp Tyr Cys Leu Arg Glu Cys
    15                  20                  25

Lys Gln Gln Tyr Gly Lys Gly Ala Gly Gly Tyr Cys Tyr Ala Phe Gly
30                  35                  40                  45

Cys Trp Cys Thr His Leu Tyr Glu Gln Ala Val Val Trp Pro Leu Lys
                50                  55                  60

Asn Lys Thr Cys Asn Gly Lys
            65


<210> SEQ ID NO 87
<211> LENGTH: 198
<212> TYPE: DNA
<213> ORGANISM: Centruroides noxius
<220> FEATURE:
<221> NAME/KEY: CDS
<222> LOCATION: (1)..(198)
<223> OTHER INFORMATION: Product= Sodium-channel modifier toxin

<400> SEQUENCE: 87

aag gaa ggt tat ata gta aac tcg tac acg ggc tgc aaa tac gaa tgc       48
Lys Glu Gly Tyr Ile Val Asn Ser Tyr Thr Gly Cys Lys Tyr Glu Cys
1               5                   10                  15

ttg aaa ttg gga gac aac gat tat tgc ttg agg gaa tgc aaa cag cag       96
Leu Lys Leu Gly Asp Asn Asp Tyr Cys Leu Arg Glu Cys Lys Gln Gln
            20                  25                  30

tac gga aaa ggt gct ggc ggc tat tgt tac gct ttt ggg tgc tgg tgc      144
Tyr Gly Lys Gly Ala Gly Gly Tyr Cys Tyr Ala Phe Gly Cys Trp Cys
        35                  40                  45

aca cat ttg tac gaa caa gcg gtg gtc tgg ccc ctt aaa aat aag aca      192
Thr His Leu Tyr Glu Gln Ala Val Val Trp Pro Leu Lys Asn Lys Thr
    50                  55                  60

tgc aac                                                              198
Cys Asn
65


<210> SEQ ID NO 88
<211> LENGTH: 66
<212> TYPE: PRT
<213> ORGANISM: Centruroides noxius

<400> SEQUENCE: 88
```

-continued

```
Lys Glu Gly Tyr Ile Val Asn Ser Tyr Thr Gly Cys Lys Tyr Glu Cys
1               5                   10                  15

Leu Lys Leu Gly Asp Asn Asp Tyr Cys Leu Arg Glu Cys Lys Gln Gln
            20                  25                  30

Tyr Gly Lys Gly Ala Gly Gly Tyr Cys Tyr Ala Phe Gly Cys Trp Cys
        35                  40                  45

Thr His Leu Tyr Glu Gln Ala Val Val Trp Pro Leu Lys Asn Lys Thr
    50                  55                  60

Cys Asn
65


<210> SEQ ID NO 89
<211> LENGTH: 323
<212> TYPE: DNA
<213> ORGANISM: Centruroides noxius
<220> FEATURE:
<221> NAME/KEY: CDS
<222> LOCATION: (5)..(265)
<223> OTHER INFORMATION: Product= Sodium-channel modifier toxin
      precursor In the mature peptide, the last Ser is amidated,
      and the last Gly and the last basic aminoacid are cut
<220> FEATURE:
<221> NAME/KEY: 3'UTR
<222> LOCATION: (269)..(323)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:

<400> SEQUENCE: 89

gaag atg aat tcg ttg ttg atg atc act gct tgt ttg gtc ctg atc gga      49
     Met Asn Ser Leu Leu Met Ile Thr Ala Cys Leu Val Leu Ile Gly
                     -15                 -10                 -5

aca gtg tgc gca aag gaa ggt tat ctg gtg aac aaa agc aca ggc tgt       97
Thr Val Cys Ala Lys Glu Gly Tyr Leu Val Asn Lys Ser Thr Gly Cys
            -1  1               5                   10

aaa tac aac tgc ttg ata ttg gga gaa aac aaa aac tgc gat atg gaa      145
Lys Tyr Asn Cys Leu Ile Leu Gly Glu Asn Lys Asn Cys Asp Met Glu
        15                  20                  25

tgc aaa gcg aag aac caa gga ggt agt tac ggc tat tgc tac gga ttt      193
Cys Lys Ala Lys Asn Gln Gly Gly Ser Tyr Gly Tyr Cys Tyr Gly Phe
    30                  35                  40

ggg tgc tat tgt gaa gga ttg tcc gat agt aca ccg act tgg ccc ctt      241
Gly Cys Tyr Cys Glu Gly Leu Ser Asp Ser Thr Pro Thr Trp Pro Leu
45                  50                  55                  60

cct aat aaa aca tgc agc gga aaa taatggcaac gactttttat tgtccaccaa     295
Pro Asn Lys Thr Cys Ser Gly Lys
                65

cagaaatagt gtaacgcttc ttaattgc                                       323


<210> SEQ ID NO 90
<211> LENGTH: 87
<212> TYPE: PRT
<213> ORGANISM: Centruroides noxius

<400> SEQUENCE: 90
```

-continued

```
Met Asn Ser Leu Leu Met Ile Thr Ala Cys Leu Val Leu Ile Gly Thr
                -15                 -10                 -5

Val Cys Ala Lys Glu Gly Tyr Leu Val Asn Lys Ser Thr Gly Cys Lys
        -1  1               5                   10

Tyr Asn Cys Leu Ile Leu Gly Glu Asn Lys Asn Cys Asp Met Glu Cys
    15                  20                  25

Lys Ala Lys Asn Gln Gly Gly Ser Tyr Gly Tyr Cys Tyr Gly Phe Gly
30                  35                  40                  45

Cys Tyr Cys Glu Gly Leu Ser Asp Ser Thr Pro Thr Trp Pro Leu Pro
                50                  55                  60

Asn Lys Thr Cys Ser Gly Lys
            65


<210> SEQ ID NO 91
<211> LENGTH: 198
<212> TYPE: DNA
<213> ORGANISM: Centruroides noxius
<220> FEATURE:
<221> NAME/KEY: CDS
<222> LOCATION: (1)..(198)
<223> OTHER INFORMATION: Product= Sodium-channel modifier toxin

<400> SEQUENCE: 91

aag gaa ggt tat ctg gtg aac aaa agc aca ggc tgt aaa tac aac tgc       48
Lys Glu Gly Tyr Leu Val Asn Lys Ser Thr Gly Cys Lys Tyr Asn Cys
1               5                   10                  15

ttg ata ttg gga gaa aac aaa aac tgc gat atg gaa tgc aaa gcg aag       96
Leu Ile Leu Gly Glu Asn Lys Asn Cys Asp Met Glu Cys Lys Ala Lys
            20                  25                  30

aac caa gga ggt agt tac ggc tat tgc tac gga ttt ggg tgc tat tgt      144
Asn Gln Gly Gly Ser Tyr Gly Tyr Cys Tyr Gly Phe Gly Cys Tyr Cys
        35                  40                  45

gaa gga ttg tcc gat agt aca ccg act tgg ccc ctt cct aat aaa aca      192
Glu Gly Leu Ser Asp Ser Thr Pro Thr Trp Pro Leu Pro Asn Lys Thr
    50                  55                  60

tgc agc                                                              198
Cys Ser
65


<210> SEQ ID NO 92
<211> LENGTH: 66
<212> TYPE: PRT
<213> ORGANISM: Centruroides noxius

<400> SEQUENCE: 92

Lys Glu Gly Tyr Leu Val Asn Lys Ser Thr Gly Cys Lys Tyr Asn Cys
1               5                   10                  15

Leu Ile Leu Gly Glu Asn Lys Asn Cys Asp Met Glu Cys Lys Ala Lys
            20                  25                  30

Asn Gln Gly Gly Ser Tyr Gly Tyr Cys Tyr Gly Phe Gly Cys Tyr Cys
        35                  40                  45

Glu Gly Leu Ser Asp Ser Thr Pro Thr Trp Pro Leu Pro Asn Lys Thr
    50                  55                  60

Cys Ser
65


<210> SEQ ID NO 93
<211> LENGTH: 323
<212> TYPE: DNA
<213> ORGANISM: Centruroides elegans
<220> FEATURE:
```

-continued

```
<221> NAME/KEY: CDS
<222> LOCATION: (5)..(265)
<223> OTHER INFORMATION: Product= Sodium-channel modifier toxin
      precursor In the mature peptide, the last Asn is amidated,
      and the last Gly and the last basic aminoacid are cut
<220> FEATURE:
<221> NAME/KEY: 3'UTR
<222> LOCATION: (269)..(323)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (68)..()
<223> OTHER INFORMATION: Product= Sodium-channel modifier toxin
<220> FEATURE:
<221> NAME/KEY: sig_peptide
<222> LOCATION: (5)..(67)
<223> OTHER INFORMATION:

<400> SEQUENCE: 93

gaag atg aac tcg ttg ttg atg atc act gct tgt ttg gcc ctg atc gga      49
     Met Asn Ser Leu Leu Met Ile Thr Ala Cys Leu Ala Leu Ile Gly
         -20                 -15                 -10

aca gtg tgg gca aag gaa ggt tat att gta aac tac cac gat ggc tgc       97
Thr Val Trp Ala Lys Glu Gly Tyr Ile Val Asn Tyr His Asp Gly Cys
    -5              -1  1               5                   10

aaa tac gaa tgc tat aaa ttg gga gat aac gat tat tgc cta agg gaa      145
Lys Tyr Glu Cys Tyr Lys Leu Gly Asp Asn Asp Tyr Cys Leu Arg Glu
                15                  20                  25

tgc aaa ttg aga tac gga aaa ggt gct ggc ggc tat tgc tac gct ttt      193
Cys Lys Leu Arg Tyr Gly Lys Gly Ala Gly Gly Tyr Cys Tyr Ala Phe
            30                  35                  40

ggg tgc tgg tgc aca cat ttg tac gaa caa gcg gtg gtc tgg ccc ctt      241
Gly Cys Trp Cys Thr His Leu Tyr Glu Gln Ala Val Val Trp Pro Leu
        45                  50                  55

cct aaa aaa aga tgc aat gga aaa taatggcaac gactttttat tgtccaccaa     295
Pro Lys Lys Arg Cys Asn Gly Lys
    60                  65

cagaaatatt gtaacgcttc ttaattgc                                       323


<210> SEQ ID NO 94
<211> LENGTH: 87
<212> TYPE: PRT
<213> ORGANISM: Centruroides elegans

<400> SEQUENCE: 94

Met Asn Ser Leu Leu Met Ile Thr Ala Cys Leu Ala Leu Ile Gly Thr
    -20                 -15                 -10

Val Trp Ala Lys Glu Gly Tyr Ile Val Asn Tyr His Asp Gly Cys Lys
-5              -1  1               5                   10

Tyr Glu Cys Tyr Lys Leu Gly Asp Asn Asp Tyr Cys Leu Arg Glu Cys
            15                  20                  25

Lys Leu Arg Tyr Gly Lys Gly Ala Gly Gly Tyr Cys Tyr Ala Phe Gly
        30                  35                  40

Cys Trp Cys Thr His Leu Tyr Glu Gln Ala Val Val Trp Pro Leu Pro
    45                  50                  55

Lys Lys Arg Cys Asn Gly Lys
60                  65


<210> SEQ ID NO 95
<211> LENGTH: 192
```

-continued

```
<212> TYPE: DNA
<213> ORGANISM: Centruroides elegans
<220> FEATURE:
<221> NAME/KEY: CDS
<222> LOCATION: (1)..(192)
<223> OTHER INFORMATION: Product= Sodium-channel modifier toxin

<400> SEQUENCE: 95

ggt tat att gta aac tac cac gat ggc tgc aaa tac gaa tgc tat aaa       48
Gly Tyr Ile Val Asn Tyr His Asp Gly Cys Lys Tyr Glu Cys Tyr Lys
1               5                   10                  15

ttg gga gat aac gat tat tgc cta agg gaa tgc aaa ttg aga tac gga       96
Leu Gly Asp Asn Asp Tyr Cys Leu Arg Glu Cys Lys Leu Arg Tyr Gly
            20                  25                  30

aaa ggt gct ggc ggc tat tgc tac gct ttt ggg tgc tgg tgc aca cat      144
Lys Gly Ala Gly Gly Tyr Cys Tyr Ala Phe Gly Cys Trp Cys Thr His
        35                  40                  45

ttg tac gaa caa gcg gtg gtc tgg ccc ctt cct aaa aaa aga tgc aat      192
Leu Tyr Glu Gln Ala Val Val Trp Pro Leu Pro Lys Lys Arg Cys Asn
    50                  55                  60


<210> SEQ ID NO 96
<211> LENGTH: 64
<212> TYPE: PRT
<213> ORGANISM: Centruroides elegans

<400> SEQUENCE: 96

Gly Tyr Ile Val Asn Tyr His Asp Gly Cys Lys Tyr Glu Cys Tyr Lys
1               5                   10                  15

Leu Gly Asp Asn Asp Tyr Cys Leu Arg Glu Cys Lys Leu Arg Tyr Gly
            20                  25                  30

Lys Gly Ala Gly Gly Tyr Cys Tyr Ala Phe Gly Cys Trp Cys Thr His
        35                  40                  45

Leu Tyr Glu Gln Ala Val Val Trp Pro Leu Pro Lys Lys Arg Cys Asn
    50                  55                  60


<210> SEQ ID NO 97
<211> LENGTH: 323
<212> TYPE: DNA
<213> ORGANISM: Centruroides elegans
<220> FEATURE:
<221> NAME/KEY: CDS
<222> LOCATION: (5)..(265)
<223> OTHER INFORMATION: Product= Sodium-channel modifier toxin
      precursor In the mature peptide, the last 2 basic aminoacids
      are cut
<220> FEATURE:
<221> NAME/KEY: 3'UTR
<222> LOCATION: (269)..(323)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (68)..()
<223> OTHER INFORMATION: Product= Sodium-channel modifier toxin
<220> FEATURE:
<221> NAME/KEY: sig_peptide
<222> LOCATION: (5)..(67)
<223> OTHER INFORMATION:

<400> SEQUENCE: 97

gaag atg aat tcg ttg ttg atg atc act gct tgt ttg gtc cta ttc gga      49
     Met Asn Ser Leu Leu Met Ile Thr Ala Cys Leu Val Leu Phe Gly
         -20                 -15                 -10
```

-continued

```
aca gtg aaa gca aaa gaa ggt tat ctg gta aac aag agc acg ggc tgc        97
Thr Val Lys Ala Lys Glu Gly Tyr Leu Val Asn Lys Ser Thr Gly Cys
    -5              -1  1               5                   10

aaa tac ggt tgc ctc ttg tta aga aaa aac gaa ggc tgc gat aag gaa       145
Lys Tyr Gly Cys Leu Leu Leu Arg Lys Asn Glu Gly Cys Asp Lys Glu
                15                  20                  25

tgc aaa gcg aag aac caa gga ggt agt tac ggc tat tgc tac tct ttt       193
Cys Lys Ala Lys Asn Gln Gly Gly Ser Tyr Gly Tyr Cys Tyr Ser Phe
            30                  35                  40

gca tgc tgg tgc gaa ggt ttg ccc gaa agt aca ccg act tat ccc ctt       241
Ala Cys Trp Cys Glu Gly Leu Pro Glu Ser Thr Pro Thr Tyr Pro Leu
        45                  50                  55

cct aat aaa tca tgc agc aaa aaa taatggcaac gatttttat tgtccaccaa      295
Pro Asn Lys Ser Cys Ser Lys Lys
    60                  65

cagaaatatt gtaacgcttc ttaatttc                                        323


<210> SEQ ID NO 98
<211> LENGTH: 87
<212> TYPE: PRT
<213> ORGANISM: Centruroides elegans

<400> SEQUENCE: 98

Met Asn Ser Leu Leu Met Ile Thr Ala Cys Leu Val Leu Phe Gly Thr
    -20                 -15                 -10

Val Lys Ala Lys Glu Gly Tyr Leu Val Asn Lys Ser Thr Gly Cys Lys
-5              -1  1               5                   10

Tyr Gly Cys Leu Leu Leu Arg Lys Asn Glu Gly Cys Asp Lys Glu Cys
            15                  20                  25

Lys Ala Lys Asn Gln Gly Gly Ser Tyr Gly Tyr Cys Tyr Ser Phe Ala
        30                  35                  40

Cys Trp Cys Glu Gly Leu Pro Glu Ser Thr Pro Thr Tyr Pro Leu Pro
    45                  50                  55

Asn Lys Ser Cys Ser Lys Lys
60                  65


<210> SEQ ID NO 99
<211> LENGTH: 192
<212> TYPE: DNA
<213> ORGANISM: Centruroides elegans
<220> FEATURE:
<221> NAME/KEY: CDS
<222> LOCATION: (1)..(192)
<223> OTHER INFORMATION: Product= Sodium-channel modifier toxin

<400> SEQUENCE: 99

ggt tat ctg gta aac aag agc acg ggc tgc aaa tac ggt tgc ctc ttg        48
Gly Tyr Leu Val Asn Lys Ser Thr Gly Cys Lys Tyr Gly Cys Leu Leu
1               5                   10                  15

tta aga aaa aac gaa ggc tgc gat aag gaa tgc aaa gcg aag aac caa        96
Leu Arg Lys Asn Glu Gly Cys Asp Lys Glu Cys Lys Ala Lys Asn Gln
            20                  25                  30

gga ggt agt tac ggc tat tgc tac tct ttt gca tgc tgg tgc gaa ggt       144
Gly Gly Ser Tyr Gly Tyr Cys Tyr Ser Phe Ala Cys Trp Cys Glu Gly
        35                  40                  45

ttg ccc gaa agt aca ccg act tat ccc ctt cct aat aaa tca tgc agc       192
Leu Pro Glu Ser Thr Pro Thr Tyr Pro Leu Pro Asn Lys Ser Cys Ser
    50                  55                  60


<210> SEQ ID NO 100
<211> LENGTH: 64
```

-continued

<212> TYPE: PRT
<213> ORGANISM: Centruroides elegans

<400> SEQUENCE: 100

```
Gly Tyr Leu Val Asn Lys Ser Thr Gly Cys Lys Tyr Gly Cys Leu Leu
1               5                   10                  15

Leu Arg Lys Asn Glu Gly Cys Asp Lys Glu Cys Lys Ala Lys Asn Gln
            20                  25                  30

Gly Gly Ser Tyr Gly Tyr Cys Tyr Ser Phe Ala Cys Trp Cys Glu Gly
        35                  40                  45

Leu Pro Glu Ser Thr Pro Thr Tyr Pro Leu Pro Asn Lys Ser Cys Ser
    50                  55                  60
```

<210> SEQ ID NO 101
<211> LENGTH: 323
<212> TYPE: DNA
<213> ORGANISM: Centruroides elegans
<220> FEATURE:
<221> NAME/KEY: CDS
<222> LOCATION: (5)..(265)
<223> OTHER INFORMATION: Product= Sodium-channel modifier toxin precursor In the mature peptide, the last Cys is amidated, and the last Gly and the last 2 basic aminoacids are cut
<220> FEATURE:
<221> NAME/KEY: 3'UTR
<222> LOCATION: (269)..(323)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (65)..()
<223> OTHER INFORMATION: Product= Sodium-channel modifier toxin
<220> FEATURE:
<221> NAME/KEY: sig_peptide
<222> LOCATION: (5)..(64)
<223> OTHER INFORMATION:

<400> SEQUENCE: 101

```
gaag atg aat tcg ttg ttg atg atc act gct tgc ttg gtc ctg atc gga      49
     Met Asn Ser Leu Leu Met Ile Thr Ala Cys Leu Val Leu Ile Gly
     -20                 -15                 -10

aca gtg tgt gca aag gaa ggt tat ctg gta aac aag agc acg ggc tgc       97
Thr Val Cys Ala Lys Glu Gly Tyr Leu Val Asn Lys Ser Thr Gly Cys
-5              -1  1               5                   10

aaa tac agt tgc gtg tta ttg gga aaa aac gaa aac tgc gat aag gaa      145
Lys Tyr Ser Cys Val Leu Leu Gly Lys Asn Glu Asn Cys Asp Lys Glu
            15                  20                  25

tgc aaa gcg aag aac caa gga ggt agt tac ggc tat tgc tac gct ttt      193
Cys Lys Ala Lys Asn Gln Gly Gly Ser Tyr Gly Tyr Cys Tyr Ala Phe
        30                  35                  40

ggg tgc tgg tgt gaa gga ttg ccc gaa agt aca ccg act tat ccc att      241
Gly Cys Trp Cys Glu Gly Leu Pro Glu Ser Thr Pro Thr Tyr Pro Ile
    45                  50                  55

cct ggt aaa tca tgc ggc aga aaa taacggcaac gatattttat tgtttaccaa     295
Pro Gly Lys Ser Cys Gly Arg Lys
60                  65

cagaaatatt gtaacgcttc ttaatttc                                        323
```

<210> SEQ ID NO 102
<211> LENGTH: 87
<212> TYPE: PRT
<213> ORGANISM: Centruroides elegans -continued

<400> SEQUENCE: 102

```
Met Asn Ser Leu Leu Met Ile Thr Ala Cys Leu Val Leu Ile Gly Thr
-20                 -15                 -10                 -5

Val Cys Ala Lys Glu Gly Tyr Leu Val Asn Lys Ser Thr Gly Cys Lys
            -1  1               5                   10

Tyr Ser Cys Val Leu Leu Gly Lys Asn Glu Asn Cys Asp Lys Glu Cys
        15                  20                  25

Lys Ala Lys Asn Gln Gly Gly Ser Tyr Gly Tyr Cys Tyr Ala Phe Gly
    30                  35                  40

Cys Trp Cys Glu Gly Leu Pro Glu Ser Thr Pro Thr Tyr Pro Ile Pro
45                  50                  55                  60

Gly Lys Ser Cys Gly Arg Lys
                65
```

<210> SEQ ID NO 103
<211> LENGTH: 192
<212> TYPE: DNA
<213> ORGANISM: Centruroides elegans
<220> FEATURE:
<221> NAME/KEY: CDS
<222> LOCATION: (1)..(192)
<223> OTHER INFORMATION: Product= Sodium-channel modifier toxin

<400> SEQUENCE: 103

```
gaa ggt tat ctg gta aac aag agc acg ggc tgc aaa tac agt tgc gtg       48
Glu Gly Tyr Leu Val Asn Lys Ser Thr Gly Cys Lys Tyr Ser Cys Val
1               5                   10                  15

tta ttg gga aaa aac gaa aac tgc gat aag gaa tgc aaa gcg aag aac       96
Leu Leu Gly Lys Asn Glu Asn Cys Asp Lys Glu Cys Lys Ala Lys Asn
            20                  25                  30

caa gga ggt agt tac ggc tat tgc tac gct ttt ggg tgc tgg tgt gaa      144
Gln Gly Gly Ser Tyr Gly Tyr Cys Tyr Ala Phe Gly Cys Trp Cys Glu
        35                  40                  45

gga ttg ccc gaa agt aca ccg act tat ccc att cct ggt aaa tca tgc      192
Gly Leu Pro Glu Ser Thr Pro Thr Tyr Pro Ile Pro Gly Lys Ser Cys
    50                  55                  60
```

<210> SEQ ID NO 104
<211> LENGTH: 64
<212> TYPE: PRT
<213> ORGANISM: Centruroides elegans

<400> SEQUENCE: 104

```
Glu Gly Tyr Leu Val Asn Lys Ser Thr Gly Cys Lys Tyr Ser Cys Val
1               5                   10                  15

Leu Leu Gly Lys Asn Glu Asn Cys Asp Lys Glu Cys Lys Ala Lys Asn
            20                  25                  30

Gln Gly Gly Ser Tyr Gly Tyr Cys Tyr Ala Phe Gly Cys Trp Cys Glu
        35                  40                  45

Gly Leu Pro Glu Ser Thr Pro Thr Tyr Pro Ile Pro Gly Lys Ser Cys
    50                  55                  60
```

<210> SEQ ID NO 105
<211> LENGTH: 323
<212> TYPE: DNA
<213> ORGANISM: Centruroides elegans
<220> FEATURE:
<221> NAME/KEY: CDS
<222> LOCATION: (5)..(265)
<223> OTHER INFORMATION: Product= Sodium-channel modifier toxin
precursor In the mature peptide, the last Cys is amidated,
and the last Gly and the last 2 basic aminoacids are cut -continued

```
<220> FEATURE:
<221> NAME/KEY: 3'UTR
<222> LOCATION: (269)..(323)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (65)..()
<223> OTHER INFORMATION: Product= Sodium-channel modifier toxin Ce6b
<220> FEATURE:
<221> NAME/KEY: sig_peptide
<222> LOCATION: (5)..(64)
<223> OTHER INFORMATION:

<400> SEQUENCE: 105

gaag atg aat tcg ttg ttg atg atc act gct tgt ttg gtc ctg atc gga      49
     Met Asn Ser Leu Leu Met Ile Thr Ala Cys Leu Val Leu Ile Gly
     -20                -15                 -10

aca gtt tgc gca aag gat ggt tat ctg gta aac aag agc acg ggc tgc       97
Thr Val Cys Ala Lys Asp Gly Tyr Leu Val Asn Lys Ser Thr Gly Cys
-5              -1  1               5                   10

aaa tac agt tgc ggg aaa ttg gga gaa aac gaa cac tgc gat aag gaa      145
Lys Tyr Ser Cys Gly Lys Leu Gly Glu Asn Glu His Cys Asp Lys Glu
            15                  20                  25

tgc aaa gcg aag aac caa gga ggt agt tac ggc tat tgc tat gct ttt      193
Cys Lys Ala Lys Asn Gln Gly Gly Ser Tyr Gly Tyr Cys Tyr Ala Phe
        30                  35                  40

ggg tgc tgg tgt gaa gga ttg ccc gaa agt acc ccg act tat ccc att      241
Gly Cys Trp Cys Glu Gly Leu Pro Glu Ser Thr Pro Thr Tyr Pro Ile
    45                  50                  55

cct ggt aaa tca tgc ggc aga aaa taacggcaac gatattttat tgtttaccaa     295
Pro Gly Lys Ser Cys Gly Arg Lys
60                  65

cagaaatatt gtaacgcttc ttaattgc                                       323


<210> SEQ ID NO 106
<211> LENGTH: 87
<212> TYPE: PRT
<213> ORGANISM: Centruroides elegans

<400> SEQUENCE: 106

Met Asn Ser Leu Leu Met Ile Thr Ala Cys Leu Val Leu Ile Gly Thr
-20                 -15                 -10                 -5

Val Cys Ala Lys Asp Gly Tyr Leu Val Asn Lys Ser Thr Gly Cys Lys
            -1  1               5                   10

Tyr Ser Cys Gly Lys Leu Gly Glu Asn Glu His Cys Asp Lys Glu Cys
        15                  20                  25

Lys Ala Lys Asn Gln Gly Gly Ser Tyr Gly Tyr Cys Tyr Ala Phe Gly
    30                  35                  40

Cys Trp Cys Glu Gly Leu Pro Glu Ser Thr Pro Thr Tyr Pro Ile Pro
45                  50                  55                  60

Gly Lys Ser Cys Gly Arg Lys
                65


<210> SEQ ID NO 107
<211> LENGTH: 192
<212> TYPE: DNA
<213> ORGANISM: Centruroides elegans
<220> FEATURE:
<221> NAME/KEY: CDS
<222> LOCATION: (1)..(192)
```

-continued

```
<223> OTHER INFORMATION: Product= Sodium-channel modifier toxin

<400> SEQUENCE: 107

gat ggt tat ctg gta aac aag agc acg ggc tgc aaa tac agt tgc ggg       48
Asp Gly Tyr Leu Val Asn Lys Ser Thr Gly Cys Lys Tyr Ser Cys Gly
1               5                   10                  15

aaa ttg gga gaa aac gaa cac tgc gat aag gaa tgc aaa gcg aag aac       96
Lys Leu Gly Glu Asn Glu His Cys Asp Lys Glu Cys Lys Ala Lys Asn
            20                  25                  30

caa gga ggt agt tac ggc tat tgc tat gct ttt ggg tgc tgg tgt gaa      144
Gln Gly Gly Ser Tyr Gly Tyr Cys Tyr Ala Phe Gly Cys Trp Cys Glu
        35                  40                  45

gga ttg ccc gaa agt acc ccg act tat ccc att cct ggt aaa tca tgc      192
Gly Leu Pro Glu Ser Thr Pro Thr Tyr Pro Ile Pro Gly Lys Ser Cys
    50                  55                  60


<210> SEQ ID NO 108
<211> LENGTH: 64
<212> TYPE: PRT
<213> ORGANISM: Centruroides elegans

<400> SEQUENCE: 108

Asp Gly Tyr Leu Val Asn Lys Ser Thr Gly Cys Lys Tyr Ser Cys Gly
1               5                   10                  15

Lys Leu Gly Glu Asn Glu His Cys Asp Lys Glu Cys Lys Ala Lys Asn
            20                  25                  30

Gln Gly Gly Ser Tyr Gly Tyr Cys Tyr Ala Phe Gly Cys Trp Cys Glu
        35                  40                  45

Gly Leu Pro Glu Ser Thr Pro Thr Tyr Pro Ile Pro Gly Lys Ser Cys
    50                  55                  60


<210> SEQ ID NO 109
<211> LENGTH: 311
<212> TYPE: DNA
<213> ORGANISM: Centruroides elegans
<220> FEATURE:
<221> NAME/KEY: CDS
<222> LOCATION: (5)..(256)
<223> OTHER INFORMATION: Product= Sodium-channel modifier toxin
      precursor In the mature peptide, the last Cys is amidated,
      and the last Gly and the last 2 basic aminoacids are cut
<220> FEATURE:
<221> NAME/KEY: 3'UTR
<222> LOCATION: (260)..(311)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (59)..()
<223> OTHER INFORMATION: Product= Sodium-channel modifier toxin
<220> FEATURE:
<221> NAME/KEY: sig_peptide
<222> LOCATION: (5)..(58)
<223> OTHER INFORMATION:

<400> SEQUENCE: 109

gaag atg aat tcg ttg ttg atg atc act gct tgt ttg gtc cta ttc gga      49
     Met Asn Ser Leu Leu Met Ile Thr Ala Cys Leu Val Leu Phe Gly
                 -15                 -10                 -5

aat gtg tgg gca aag gac ggt tat ctg gtg aac aag acg ggc tgc aaa       97
Asn Val Trp Ala Lys Asp Gly Tyr Leu Val Asn Lys Thr Gly Cys Lys
        -1  1               5                   10

tac aat tgc tgg ata ttg gga gaa aac aaa tac tgc aat tcg gaa tgc      145
```

-continued

Tyr Asn Cys Trp Ile Leu Gly Glu Asn Lys Tyr Cys Asn Ser Glu Cys
15 20 25 aaa gag gta ggt gct ggt tac ggc tat tgc tat gct ttt ggg tgc tat 193
Lys Glu Val Gly Ala Gly Tyr Gly Tyr Cys Tyr Ala Phe Gly Cys Tyr
30 35 40 45 tgc gaa gga tta ccc gaa agc gta ctg acc tgg ccc ctt tct gat aaa 241
Cys Glu Gly Leu Pro Glu Ser Val Leu Thr Trp Pro Leu Ser Asp Lys
50 55 60 aca tgc ggc aga aaa taatggcaac gtctttttat tgtccaccaa cagaaatatt 296
Thr Cys Gly Arg Lys
65 gtaacgcttc ttaat 311

<210> SEQ ID NO 110
<211> LENGTH: 84
<212> TYPE: PRT
<213> ORGANISM: Centruroides elegans

<400> SEQUENCE: 110

Met Asn Ser Leu Leu Met Ile Thr Ala Cys Leu Val Leu Phe Gly Asn
-15 -10 -5

Val Trp Ala Lys Asp Gly Tyr Leu Val Asn Lys Thr Gly Cys Lys Tyr
-1 1 5 10

Asn Cys Trp Ile Leu Gly Glu Asn Lys Tyr Cys Asn Ser Glu Cys Lys
15 20 25 30

Glu Val Gly Ala Gly Tyr Gly Tyr Cys Tyr Ala Phe Gly Cys Tyr Cys
35 40 45

Glu Gly Leu Pro Glu Ser Val Leu Thr Trp Pro Leu Ser Asp Lys Thr
50 55 60

Cys Gly Arg Lys
65

<210> SEQ ID NO 111
<211> LENGTH: 189
<212> TYPE: DNA
<213> ORGANISM: Centruroides elegans
<220> FEATURE:
<221> NAME/KEY: CDS
<222> LOCATION: (1)..(189)
<223> OTHER INFORMATION: Product= Sodium-channel modifier toxin

<400> SEQUENCE: 111 gca aag gac ggt tat ctg gtg aac aag acg ggc tgc aaa tac aat tgc 48
Ala Lys Asp Gly Tyr Leu Val Asn Lys Thr Gly Cys Lys Tyr Asn Cys
1 5 10 15 tgg ata ttg gga gaa aac aaa tac tgc aat tcg gaa tgc aaa gag gta 96
Trp Ile Leu Gly Glu Asn Lys Tyr Cys Asn Ser Glu Cys Lys Glu Val
20 25 30 ggt gct ggt tac ggc tat tgc tat gct ttt ggg tgc tat tgc gaa gga 144
Gly Ala Gly Tyr Gly Tyr Cys Tyr Ala Phe Gly Cys Tyr Cys Glu Gly
35 40 45 tta ccc gaa agc gta ctg acc tgg ccc ctt tct gat aaa aca tgc 189
Leu Pro Glu Ser Val Leu Thr Trp Pro Leu Ser Asp Lys Thr Cys
50 55 60

<210> SEQ ID NO 112
<211> LENGTH: 63
<212> TYPE: PRT
<213> ORGANISM: Centruroides elegans

<400> SEQUENCE: 112

-continued

Ala Lys Asp Gly Tyr Leu Val Asn Lys Thr Gly Cys Lys Tyr Asn Cys
1 5 10 15

Trp Ile Leu Gly Glu Asn Lys Tyr Cys Asn Ser Glu Cys Lys Glu Val
20 25 30

Gly Ala Gly Tyr Gly Tyr Cys Tyr Ala Phe Gly Cys Tyr Cys Glu Gly
35 40 45

Leu Pro Glu Ser Val Leu Thr Trp Pro Leu Ser Asp Lys Thr Cys
50 55 60

<210> SEQ ID NO 113
<211> LENGTH: 323
<212> TYPE: DNA
<213> ORGANISM: Centruroides elegans
<220> FEATURE:
<221> NAME/KEY: CDS
<222> LOCATION: (5)..(265)
<223> OTHER INFORMATION: Product= Sodium-channel modifier toxin precursor In the mature peptide, the last Cys is amidated, and the last Gly and the last 2 basic aminoacids are cut
<220> FEATURE:
<221> NAME/KEY: 3'UTR
<222> LOCATION: (269)..(323)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (65)..()
<223> OTHER INFORMATION: Product= Sodium-channel modifier toxin
<220> FEATURE:
<221> NAME/KEY: sig_peptide
<222> LOCATION: (5)..(64)
<223> OTHER INFORMATION:

<400> SEQUENCE: 113 gaag atg aat tcg ttg ttg atg atc act gct tgt ttg gtc atg ttc gga 49
Met Asn Ser Leu Leu Met Ile Thr Ala Cys Leu Val Met Phe Gly
-20 -15 -10 aca gtg tgg gca aaa aaa gac ggt tat ctg gtg gac aag acg ggc tgc 97
Thr Val Trp Ala Lys Lys Asp Gly Tyr Leu Val Asp Lys Thr Gly Cys
-5 -1 1 5 10 aaa tac act tgc tgg ata ttg gga gaa aac aaa tac tgc aat agg gaa 145
Lys Tyr Thr Cys Trp Ile Leu Gly Glu Asn Lys Tyr Cys Asn Arg Glu
15 20 25 tgc aca tgg aag cac cga gga ggt aat tac ggc tat tgc tac gga ttt 193
Cys Thr Trp Lys His Arg Gly Gly Asn Tyr Gly Tyr Cys Tyr Gly Phe
30 35 40 ggg tgc tat tgc gaa gga ttg tcc gat agt aca ccg act tgg ccc ctt 241
Gly Cys Tyr Cys Glu Gly Leu Ser Asp Ser Thr Pro Thr Trp Pro Leu
45 50 55 tct aat aaa aga tgc ggc aaa aaa taatggcaac gactttttat tgtccaccaa 295
Ser Asn Lys Arg Cys Gly Lys Lys
60 65 cagaaatatt gtaacgcttc ttaattgc 323

<210> SEQ ID NO 114
<211> LENGTH: 87
<212> TYPE: PRT
<213> ORGANISM: Centruroides elegans

<400> SEQUENCE: 114

Met Asn Ser Leu Leu Met Ile Thr Ala Cys Leu Val Met Phe Gly Thr
-20 -15 -10 -5

-continued

```
Val Trp Ala Lys Lys Asp Gly Tyr Leu Val Asp Lys Thr Gly Cys Lys
            -1  1               5                   10

Tyr Thr Cys Trp Ile Leu Gly Glu Asn Lys Tyr Cys Asn Arg Glu Cys
        15                  20                  25

Thr Trp Lys His Arg Gly Gly Asn Tyr Gly Tyr Cys Tyr Gly Phe Gly
    30                  35                  40

Cys Tyr Cys Glu Gly Leu Ser Asp Ser Thr Pro Thr Trp Pro Leu Ser
45                  50                  55                  60

Asn Lys Arg Cys Gly Lys Lys
                65
```

<210> SEQ ID NO 115
<211> LENGTH: 192
<212> TYPE: DNA
<213> ORGANISM: Centruroides elegans
<220> FEATURE:
<221> NAME/KEY: CDS
<222> LOCATION: (1)..(192)
<223> OTHER INFORMATION: Product= Sodium-channel modifier toxin

<400> SEQUENCE: 115

```
aaa gac ggt tat ctg gtg gac aag acg ggc tgc aaa tac act tgc tgg       48
Lys Asp Gly Tyr Leu Val Asp Lys Thr Gly Cys Lys Tyr Thr Cys Trp
1               5                   10                  15

ata ttg gga gaa aac aaa tac tgc aat agg gaa tgc aca tgg aag cac       96
Ile Leu Gly Glu Asn Lys Tyr Cys Asn Arg Glu Cys Thr Trp Lys His
            20                  25                  30

cga gga ggt aat tac ggc tat tgc tac gga ttt ggg tgc tat tgc gaa      144
Arg Gly Gly Asn Tyr Gly Tyr Cys Tyr Gly Phe Gly Cys Tyr Cys Glu
        35                  40                  45

gga ttg tcc gat agt aca ccg act tgg ccc ctt tct aat aaa aga tgc      192
Gly Leu Ser Asp Ser Thr Pro Thr Trp Pro Leu Ser Asn Lys Arg Cys
    50                  55                  60
```

<210> SEQ ID NO 116
<211> LENGTH: 64
<212> TYPE: PRT
<213> ORGANISM: Centruroides elegans

<400> SEQUENCE: 116

```
Lys Asp Gly Tyr Leu Val Asp Lys Thr Gly Cys Lys Tyr Thr Cys Trp
1               5                   10                  15

Ile Leu Gly Glu Asn Lys Tyr Cys Asn Arg Glu Cys Thr Trp Lys His
            20                  25                  30

Arg Gly Gly Asn Tyr Gly Tyr Cys Tyr Gly Phe Gly Cys Tyr Cys Glu
        35                  40                  45

Gly Leu Ser Asp Ser Thr Pro Thr Trp Pro Leu Ser Asn Lys Arg Cys
    50                  55                  60
```

<210> SEQ ID NO 117
<211> LENGTH: 323
<212> TYPE: DNA
<213> ORGANISM: Centruroides elegans
<220> FEATURE:
<221> NAME/KEY: CDS
<222> LOCATION: (5)..(265)
<223> OTHER INFORMATION: Product= Sodium-channel modifier toxin
precursor In the mature peptide, the last Cys is amidated,
and the last Gly and the last 2 basic aminoacids are cut
<220> FEATURE:
<221> NAME/KEY: 3'UTR
<222> LOCATION: (269)..(323)
<223> OTHER INFORMATION:
<220> FEATURE:

-continued

```
<221> NAME/KEY: 5'UTR
<222> LOCATION: (1)..(4)
<223> OTHER INFORMATION:
<220> FEATURE:
<221> NAME/KEY: mat_peptide
<222> LOCATION: (65)..()
<223> OTHER INFORMATION: Product= Sodium-channel modifier toxin
<220> FEATURE:
<221> NAME/KEY: sig_peptide
<222> LOCATION: (5)..(64)
<223> OTHER INFORMATION:

<400> SEQUENCE: 117

gaag atg aat tcg ttg ttg atg atc act gct tgt ttg gtc atg ttc gga      49
     Met Asn Ser Leu Leu Met Ile Thr Ala Cys Leu Val Met Phe Gly
     -20                -15                 -10

aca gtg tgg gca aaa aaa gac ggt tat ctg gtg gac aag acg ggc tgc       97
Thr Val Trp Ala Lys Lys Asp Gly Tyr Leu Val Asp Lys Thr Gly Cys
-5              -1  1               5                   10

aaa tac act tgc tgg ata ttg gga gaa aac aaa tac tgc aat agg gaa      145
Lys Tyr Thr Cys Trp Ile Leu Gly Glu Asn Lys Tyr Cys Asn Arg Glu
            15                  20                  25

tgc aca tgg aag cac cga gga ggt aat tac ggc tat tgc tac gga ttt      193
Cys Thr Trp Lys His Arg Gly Gly Asn Tyr Gly Tyr Cys Tyr Gly Phe
        30                  35                  40

ggg tgc tat tgc gaa gga ttg tcc gat agt aca ccg act tgg ccc ctt      241
Gly Cys Tyr Cys Glu Gly Leu Ser Asp Ser Thr Pro Thr Trp Pro Leu
    45                  50                  55

cct aat aaa aga tgc ggc aaa aaa taatggcaac gactttttat tgtccaccaa     295
Pro Asn Lys Arg Cys Gly Lys Lys
60                  65

cagaaatagt gtaacgcttc ttaattgc                                       323


<210> SEQ ID NO 118
<211> LENGTH: 87
<212> TYPE: PRT
<213> ORGANISM: Centruroides elegans

<400> SEQUENCE: 118

Met Asn Ser Leu Leu Met Ile Thr Ala Cys Leu Val Met Phe Gly Thr
-20                 -15                 -10                 -5

Val Trp Ala Lys Lys Asp Gly Tyr Leu Val Asp Lys Thr Gly Cys Lys
            -1  1               5                   10

Tyr Thr Cys Trp Ile Leu Gly Glu Asn Lys Tyr Cys Asn Arg Glu Cys
        15                  20                  25

Thr Trp Lys His Arg Gly Gly Asn Tyr Gly Tyr Cys Tyr Gly Phe Gly
    30                  35                  40

Cys Tyr Cys Glu Gly Leu Ser Asp Ser Thr Pro Thr Trp Pro Leu Pro
45                  50                  55                  60

Asn Lys Arg Cys Gly Lys Lys
                65


<210> SEQ ID NO 119
<211> LENGTH: 192
<212> TYPE: DNA
<213> ORGANISM: Centruroides elegans
<220> FEATURE:
<221> NAME/KEY: CDS
<222> LOCATION: (1)..(192)
<223> OTHER INFORMATION: Product= Sodium-channel modifier toxin

<400> SEQUENCE: 119

aaa gac ggt tat ctg gtg gac aag acg ggc tgc aaa tac act tgc tgg       48
```

-continued

```
Lys Asp Gly Tyr Leu Val Asp Lys Thr Gly Cys Lys Tyr Thr Cys Trp
1               5                   10                  15

ata ttg gga gaa aac aaa tac tgc aat agg gaa tgc aca tgg aag cac        96
Ile Leu Gly Glu Asn Lys Tyr Cys Asn Arg Glu Cys Thr Trp Lys His
            20                  25                  30

cga gga ggt aat tac ggc tat tgc tac gga ttt ggg tgc tat tgc gaa       144
Arg Gly Gly Asn Tyr Gly Tyr Cys Tyr Gly Phe Gly Cys Tyr Cys Glu
        35                  40                  45

gga ttg tcc gat agt aca ccg act tgg ccc ctt cct aat aaa aga tgc       192
Gly Leu Ser Asp Ser Thr Pro Thr Trp Pro Leu Pro Asn Lys Arg Cys
    50                  55                  60


<210> SEQ ID NO 120
<211> LENGTH: 64
<212> TYPE: PRT
<213> ORGANISM: Centruroides elegans

<400> SEQUENCE: 120

Lys Asp Gly Tyr Leu Val Asp Lys Thr Gly Cys Lys Tyr Thr Cys Trp
1               5                   10                  15

Ile Leu Gly Glu Asn Lys Tyr Cys Asn Arg Glu Cys Thr Trp Lys His
            20                  25                  30

Arg Gly Gly Asn Tyr Gly Tyr Cys Tyr Gly Phe Gly Cys Tyr Cys Glu
        35                  40                  45

Gly Leu Ser Asp Ser Thr Pro Thr Trp Pro Leu Pro Asn Lys Arg Cys
    50                  55                  60


<210> SEQ ID NO 121
<211> LENGTH: 323
<212> TYPE: DNA
<213> ORGANISM: Centruroides gracilis
<220> FEATURE:
<221> NAME/KEY: CDS
<222> LOCATION: (5)..(265)
<223> OTHER INFORMATION: Product= Sodium-channel modifier toxin
      precursor In the mature peptide, the last Cys is amidated,
      and the last Gly and the last 2 basic aminoacids are cut
<220> FEATURE:
<221> NAME/KEY: 5'UTR
<222> LOCATION: (1)..(4)
<223> OTHER INFORMATION:
<220> FEATURE:
<221> NAME/KEY: 3'UTR
<222> LOCATION: (269)..(323)
<223> OTHER INFORMATION:
<220> FEATURE:
<221> NAME/KEY: mat_peptide
<222> LOCATION: (71)..()
<223> OTHER INFORMATION: Product= Sodium-channel modifier toxin
<220> FEATURE:
<221> NAME/KEY: sig_peptide
<222> LOCATION: (5)..(70)
<223> OTHER INFORMATION:

<400> SEQUENCE: 121

gaag atg aat tcg ttg ttg atg atc act gct tgt ttg gtc ctg atc gga       49
     Met Asn Ser Leu Leu Met Ile Thr Ala Cys Leu Val Leu Ile Gly
             -20                 -15                 -10

acc gtg tgg gca aag gac ggt tat ctg gtg aag aag agc gac ggc tgc        97
Thr Val Trp Ala Lys Asp Gly Tyr Leu Val Lys Lys Ser Asp Gly Cys
        -5              -1  1               5

aaa tac ggt tgc atg ctc aag ata gga gac gct ggc tgt gat aag gaa       145
Lys Tyr Gly Cys Met Leu Lys Ile Gly Asp Ala Gly Cys Asp Lys Glu
10                  15                  20                  25

tgc aaa gcg ccg aac caa gga ggt agt tac ggc tat tgc tac ctt ctt       193
Cys Lys Ala Pro Asn Gln Gly Gly Ser Tyr Gly Tyr Cys Tyr Leu Leu
```

-continued

```
                30                  35                  40

ggg tgc tgg tgc gaa ggt atg cct gaa agt aca ccg act tat ccc ctt      241
Gly Cys Trp Cys Glu Gly Met Pro Glu Ser Thr Pro Thr Tyr Pro Leu
            45                  50                  55

cct ggt aaa tca tgc ggc aaa aaa taatggcaac gtctttttat tgtccactaa     295
Pro Gly Lys Ser Cys Gly Lys Lys
        60                  65

cagaaatatt gtaacgcttc ttaattgc                                       323


<210> SEQ ID NO 122
<211> LENGTH: 87
<212> TYPE: PRT
<213> ORGANISM: Centruroides gracilis

<400> SEQUENCE: 122

Met Asn Ser Leu Leu Met Ile Thr Ala Cys Leu Val Leu Ile Gly Thr
        -20                 -15                 -10

Val Trp Ala Lys Asp Gly Tyr Leu Val Lys Lys Ser Asp Gly Cys Lys
    -5              -1  1               5                   10

Tyr Gly Cys Met Leu Lys Ile Gly Asp Ala Gly Cys Asp Lys Glu Cys
                15                  20                  25

Lys Ala Pro Asn Gln Gly Gly Ser Tyr Gly Tyr Cys Tyr Leu Leu Gly
            30                  35                  40

Cys Trp Cys Glu Gly Met Pro Glu Ser Thr Pro Thr Tyr Pro Leu Pro
        45                  50                  55

Gly Lys Ser Cys Gly Lys Lys
    60                  65


<210> SEQ ID NO 123
<211> LENGTH: 186
<212> TYPE: DNA
<213> ORGANISM: Centruroides gracilis
<220> FEATURE:
<221> NAME/KEY: CDS
<222> LOCATION: (1)..(186)
<223> OTHER INFORMATION: Product= Sodium-channel modifier toxin

<400> SEQUENCE: 123

tat ctg gtg aag aag agc gac ggc tgc aaa tac ggt tgc atg ctc aag       48
Tyr Leu Val Lys Lys Ser Asp Gly Cys Lys Tyr Gly Cys Met Leu Lys
1               5                   10                  15

ata gga gac gct ggc tgt gat aag gaa tgc aaa gcg ccg aac caa gga       96
Ile Gly Asp Ala Gly Cys Asp Lys Glu Cys Lys Ala Pro Asn Gln Gly
            20                  25                  30

ggt agt tac ggc tat tgc tac ctt ctt ggg tgc tgg tgc gaa ggt atg      144
Gly Ser Tyr Gly Tyr Cys Tyr Leu Leu Gly Cys Trp Cys Glu Gly Met
        35                  40                  45

cct gaa agt aca ccg act tat ccc ctt cct ggt aaa tca tgc              186
Pro Glu Ser Thr Pro Thr Tyr Pro Leu Pro Gly Lys Ser Cys
    50                  55                  60


<210> SEQ ID NO 124
<211> LENGTH: 62
<212> TYPE: PRT
<213> ORGANISM: Centruroides gracilis

<400> SEQUENCE: 124

Tyr Leu Val Lys Lys Ser Asp Gly Cys Lys Tyr Gly Cys Met Leu Lys
1               5                   10                  15

Ile Gly Asp Ala Gly Cys Asp Lys Glu Cys Lys Ala Pro Asn Gln Gly
            20                  25                  30
```

```
Gly Ser Tyr Gly Tyr Cys Tyr Leu Leu Gly Cys Trp Cys Glu Gly Met
        35                  40                  45

Pro Glu Ser Thr Pro Thr Tyr Pro Leu Pro Gly Lys Ser Cys
    50                  55                  60


<210> SEQ ID NO 125
<211> LENGTH: 323
<212> TYPE: DNA
<213> ORGANISM: Centruroides gracilis
<220> FEATURE:
<221> NAME/KEY: CDS
<222> LOCATION: (5)..(265)
<223> OTHER INFORMATION: Product= Sodium-channel modifier toxin
      precursor In the mature peptide, the last Cys is amidated,
      and the last Gly and the last 2 basic aminoacids are cut
<220> FEATURE:
<221> NAME/KEY: 5'UTR
<222> LOCATION: (1)..(4)
<223> OTHER INFORMATION:
<220> FEATURE:
<221> NAME/KEY: 3'UTR
<222> LOCATION: (269)..(323)
<223> OTHER INFORMATION:
<220> FEATURE:
<221> NAME/KEY: sig_peptide
<222> LOCATION: (5)..(70)
<223> OTHER INFORMATION:
<220> FEATURE:
<221> NAME/KEY: mat_peptide
<222> LOCATION: (71)..()
<223> OTHER INFORMATION: Product= Sodium-channel modifier toxin

<400> SEQUENCE: 125

gaag atg aac tcg ttg ttg atg atc act gct tgt ttg gtc ctg atc gga      49
     Met Asn Ser Leu Leu Met Ile Thr Ala Cys Leu Val Leu Ile Gly
             -20                 -15                 -10

acc gtg tgg gca aag gac ggt tat ctg gtg aag gag agc gac ggc tgc       97
Thr Val Trp Ala Lys Asp Gly Tyr Leu Val Lys Glu Ser Asp Gly Cys
        -5              -1  1               5

aaa tac ggt tgc atg ctc aag ata gga gac gct ggc tgt gat aag gaa      145
Lys Tyr Gly Cys Met Leu Lys Ile Gly Asp Ala Gly Cys Asp Lys Glu
10                  15                  20                  25

tgc aaa gcg ccg aac caa gga ggt agt tac ggc tat tgc tac ctt ctt      193
Cys Lys Ala Pro Asn Gln Gly Gly Ser Tyr Gly Tyr Cys Tyr Leu Leu
                30                  35                  40

ggg tgc tgg tgc gaa ggt atg cct gaa agt aca ccg act tat ccc ctt      241
Gly Cys Trp Cys Glu Gly Met Pro Glu Ser Thr Pro Thr Tyr Pro Leu
            45                  50                  55

cct ggt aaa tca tgc ggc aaa aaa taatggcaac gtctttttat tgtccactaa     295
Pro Gly Lys Ser Cys Gly Lys Lys
        60                  65

cagaaatatt gtaacgcttc ttaattgc                                       323


<210> SEQ ID NO 126
<211> LENGTH: 87
<212> TYPE: PRT
<213> ORGANISM: Centruroides gracilis

<400> SEQUENCE: 126

Met Asn Ser Leu Leu Met Ile Thr Ala Cys Leu Val Leu Ile Gly Thr
        -20                 -15                 -10

Val Trp Ala Lys Asp Gly Tyr Leu Val Lys Glu Ser Asp Gly Cys Lys
    -5              -1  1               5                   10

Tyr Gly Cys Met Leu Lys Ile Gly Asp Ala Gly Cys Asp Lys Glu Cys
                15                  20                  25
```

```
Lys Ala Pro Asn Gln Gly Gly Ser Tyr Gly Tyr Cys Tyr Leu Leu Gly
            30                  35                  40

Cys Trp Cys Glu Gly Met Pro Glu Ser Thr Pro Thr Tyr Pro Leu Pro
        45                  50                  55

Gly Lys Ser Cys Gly Lys Lys
    60                  65


<210> SEQ ID NO 127
<211> LENGTH: 186
<212> TYPE: DNA
<213> ORGANISM: Centruroides gracilis
<220> FEATURE:
<221> NAME/KEY: CDS
<222> LOCATION: (1)..(186)
<223> OTHER INFORMATION: Product= Sodium-channel modifier toxin

<400> SEQUENCE: 127

tat ctg gtg aag gag agc gac ggc tgc aaa tac ggt tgc atg ctc aag       48
Tyr Leu Val Lys Glu Ser Asp Gly Cys Lys Tyr Gly Cys Met Leu Lys
1               5                   10                  15

ata gga gac gct ggc tgt gat aag gaa tgc aaa gcg ccg aac caa gga       96
Ile Gly Asp Ala Gly Cys Asp Lys Glu Cys Lys Ala Pro Asn Gln Gly
            20                  25                  30

ggt agt tac ggc tat tgc tac ctt ctt ggg tgc tgg tgc gaa ggt atg      144
Gly Ser Tyr Gly Tyr Cys Tyr Leu Leu Gly Cys Trp Cys Glu Gly Met
        35                  40                  45

cct gaa agt aca ccg act tat ccc ctt cct ggt aaa tca tgc              186
Pro Glu Ser Thr Pro Thr Tyr Pro Leu Pro Gly Lys Ser Cys
    50                  55                  60


<210> SEQ ID NO 128
<211> LENGTH: 62
<212> TYPE: PRT
<213> ORGANISM: Centruroides gracilis

<400> SEQUENCE: 128

Tyr Leu Val Lys Glu Ser Asp Gly Cys Lys Tyr Gly Cys Met Leu Lys
1               5                   10                  15

Ile Gly Asp Ala Gly Cys Asp Lys Glu Cys Lys Ala Pro Asn Gln Gly
            20                  25                  30

Gly Ser Tyr Gly Tyr Cys Tyr Leu Leu Gly Cys Trp Cys Glu Gly Met
        35                  40                  45

Pro Glu Ser Thr Pro Thr Tyr Pro Leu Pro Gly Lys Ser Cys
    50                  55                  60


<210> SEQ ID NO 129
<211> LENGTH: 323
<212> TYPE: DNA
<213> ORGANISM: Centruroides gracilis
<220> FEATURE:
<221> NAME/KEY: CDS
<222> LOCATION: (5)..(265)
<223> OTHER INFORMATION: Product= Sodium-channel modifier toxin
      precursor
<220> FEATURE:
<221> NAME/KEY: 5'UTR
<222> LOCATION: (1)..(4)
<223> OTHER INFORMATION:
<220> FEATURE:
<221> NAME/KEY: 3'UTR
<222> LOCATION: (269)..(323)
<223> OTHER INFORMATION:
<220> FEATURE:
<221> NAME/KEY: mat_peptide
<222> LOCATION: (62)..()
```

-continued

```
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:

<400> SEQUENCE: 129

gaag atg aat tcg ttg ttg atg atc act gct tgt ttg gtc ctg atc gga      49
     Met Asn Ser Leu Leu Met Ile Thr Ala Cys Leu Val Leu Ile Gly
                     -15                 -10                 -5

acg gtg tgg gca aag gac ggt tat ctg gtg aac aag agc acg ggc tgc       97
Thr Val Trp Ala Lys Asp Gly Tyr Leu Val Asn Lys Ser Thr Gly Cys
            -1  1               5                   10

aaa tac agt tgc ata gaa aat ata aac gac agt cac tgc aat gag gaa      145
Lys Tyr Ser Cys Ile Glu Asn Ile Asn Asp Ser His Cys Asn Glu Glu
        15                  20                  25

tgt ata tcg tcg atc cgc aaa ggt agt tac ggc tat tgc tac aaa ttt      193
Cys Ile Ser Ser Ile Arg Lys Gly Ser Tyr Gly Tyr Cys Tyr Lys Phe
    30                  35                  40

tac tgt tat tgc ata ggt atg ccc gat agt aca cag gtt tat cct att      241
Tyr Cys Tyr Cys Ile Gly Met Pro Asp Ser Thr Gln Val Tyr Pro Ile
45                  50                  55                  60

cct ggt aaa act tgc agc aca gaa taatggcaac gtctttttat tgtccaccaa     295
Pro Gly Lys Thr Cys Ser Thr Glu
                65

cagaaatatt gtaacgcttc ttaattgc                                       323


<210> SEQ ID NO 130
<211> LENGTH: 87
<212> TYPE: PRT
<213> ORGANISM: Centruroides gracilis

<400> SEQUENCE: 130

Met Asn Ser Leu Leu Met Ile Thr Ala Cys Leu Val Leu Ile Gly Thr
                -15                 -10                 -5

Val Trp Ala Lys Asp Gly Tyr Leu Val Asn Lys Ser Thr Gly Cys Lys
        -1  1               5                   10

Tyr Ser Cys Ile Glu Asn Ile Asn Asp Ser His Cys Asn Glu Glu Cys
    15                  20                  25

Ile Ser Ser Ile Arg Lys Gly Ser Tyr Gly Tyr Cys Tyr Lys Phe Tyr
30                  35                  40                  45

Cys Tyr Cys Ile Gly Met Pro Asp Ser Thr Gln Val Tyr Pro Ile Pro
                50                  55                  60

Gly Lys Thr Cys Ser Thr Glu
            65


<210> SEQ ID NO 131
<211> LENGTH: 204
<212> TYPE: DNA
<213> ORGANISM: Centruroides gracilis
<220> FEATURE:
<221> NAME/KEY: CDS
<222> LOCATION: (1)..(204)
<223> OTHER INFORMATION: Product= Sodium-channel modifier toxin

<400> SEQUENCE: 131

aag gac ggt tat ctg gtg aac aag agc acg ggc tgc aaa tac agt tgc       48
Lys Asp Gly Tyr Leu Val Asn Lys Ser Thr Gly Cys Lys Tyr Ser Cys
1               5                   10                  15

ata gaa aat ata aac gac agt cac tgc aat gag gaa tgt ata tcg tcg       96
Ile Glu Asn Ile Asn Asp Ser His Cys Asn Glu Glu Cys Ile Ser Ser
            20                  25                  30
```

-continued

```
atc cgc aaa ggt agt tac ggc tat tgc tac aaa ttt tac tgt tat tgc      144
Ile Arg Lys Gly Ser Tyr Gly Tyr Cys Tyr Lys Phe Tyr Cys Tyr Cys
        35                  40                  45

ata ggt atg ccc gat agt aca cag gtt tat cct att cct ggt aaa act      192
Ile Gly Met Pro Asp Ser Thr Gln Val Tyr Pro Ile Pro Gly Lys Thr
    50                  55                  60

tgc agc aca gaa                                                      204
Cys Ser Thr Glu
65


<210> SEQ ID NO 132
<211> LENGTH: 68
<212> TYPE: PRT
<213> ORGANISM: Centruroides gracilis

<400> SEQUENCE: 132

Lys Asp Gly Tyr Leu Val Asn Lys Ser Thr Gly Cys Lys Tyr Ser Cys
1               5                   10                  15

Ile Glu Asn Ile Asn Asp Ser His Cys Asn Glu Glu Cys Ile Ser Ser
            20                  25                  30

Ile Arg Lys Gly Ser Tyr Gly Tyr Cys Tyr Lys Phe Tyr Cys Tyr Cys
        35                  40                  45

Ile Gly Met Pro Asp Ser Thr Gln Val Tyr Pro Ile Pro Gly Lys Thr
    50                  55                  60

Cys Ser Thr Glu
65


<210> SEQ ID NO 133
<211> LENGTH: 323
<212> TYPE: DNA
<213> ORGANISM: Centruroides gracilis
<220> FEATURE:
<221> NAME/KEY: CDS
<222> LOCATION: (5)..(265)
<223> OTHER INFORMATION: Product= Sodium-channel modifier toxin
      precursor In the mature peptide, the last Cys is amidated,
      and the last Gly and the last 2 basic aminoacids are cut
<220> FEATURE:
<221> NAME/KEY: 5'UTR
<222> LOCATION: (1)..(4)
<223> OTHER INFORMATION:
<220> FEATURE:
<221> NAME/KEY: 3'UTR
<222> LOCATION: (269)..(323)
<223> OTHER INFORMATION:
<220> FEATURE:
<221> NAME/KEY: mat_peptide
<222> LOCATION: (71)..()
<223> OTHER INFORMATION: Product= Sodium-channel modifier toxin
<220> FEATURE:
<221> NAME/KEY: sig_peptide
<222> LOCATION: (5)..(70)
<223> OTHER INFORMATION:

<400> SEQUENCE: 133

gaag atg aac tcg ttg ttg atg atc act gct tgt ttg gtc ctg atc gga      49
     Met Asn Ser Leu Leu Met Ile Thr Ala Cys Leu Val Leu Ile Gly
             -20                 -15                 -10

acc gtg tgg aca aag gac ggt tat ctg gtg aag aag agc gac ggc tgc       97
Thr Val Trp Thr Lys Asp Gly Tyr Leu Val Lys Lys Ser Asp Gly Cys
        -5              -1  1               5

aaa tac ggt tgc gta atg ttg gtc gga gac agt ggc tgc gat acg gaa      145
Lys Tyr Gly Cys Val Met Leu Val Gly Asp Ser Gly Cys Asp Thr Glu
10                  15                  20                  25

tgc aaa gcg aag aat caa ggt ggt aaa aaa gga tgg tgc tac gcc ttt      193
```

-continued

```
Cys Lys Ala Lys Asn Gln Gly Gly Lys Lys Gly Trp Cys Tyr Ala Phe
                30                  35                  40

ggg tgc tgg tgc aca ggt atg ccc gac agt aca cag gtt tat ccc ctt      241
Gly Cys Trp Cys Thr Gly Met Pro Asp Ser Thr Gln Val Tyr Pro Leu
            45                  50                  55

cct gat aaa tca tgc ggc aaa aaa taatggcaac gtctttttat tgtccaccaa     295
Pro Asp Lys Ser Cys Gly Lys Lys
        60                  65

cagaaatagt gtaacgcttc ttaattgc                                       323


<210> SEQ ID NO 134
<211> LENGTH: 87
<212> TYPE: PRT
<213> ORGANISM: Centruroides gracilis

<400> SEQUENCE: 134

Met Asn Ser Leu Leu Met Ile Thr Ala Cys Leu Val Leu Ile Gly Thr
        -20                 -15                 -10

Val Trp Thr Lys Asp Gly Tyr Leu Val Lys Lys Ser Asp Gly Cys Lys
    -5              -1  1               5                   10

Tyr Gly Cys Val Met Leu Val Gly Asp Ser Gly Cys Asp Thr Glu Cys
                15                  20                  25

Lys Ala Lys Asn Gln Gly Gly Lys Lys Gly Trp Cys Tyr Ala Phe Gly
            30                  35                  40

Cys Trp Cys Thr Gly Met Pro Asp Ser Thr Gln Val Tyr Pro Leu Pro
        45                  50                  55

Asp Lys Ser Cys Gly Lys Lys
    60                  65


<210> SEQ ID NO 135
<211> LENGTH: 186
<212> TYPE: DNA
<213> ORGANISM: Centruroides gracilis
<220> FEATURE:
<221> NAME/KEY: CDS
<222> LOCATION: (1)..(186)
<223> OTHER INFORMATION: Product= Sodium-channel modifier toxin

<400> SEQUENCE: 135

tat ctg gtg aag aag agc gac ggc tgc aaa tac ggt tgc gta atg ttg       48
Tyr Leu Val Lys Lys Ser Asp Gly Cys Lys Tyr Gly Cys Val Met Leu
1               5                   10                  15

gtc gga gac agt ggc tgc gat acg gaa tgc aaa gcg aag aat caa ggt       96
Val Gly Asp Ser Gly Cys Asp Thr Glu Cys Lys Ala Lys Asn Gln Gly
            20                  25                  30

ggt aaa aaa gga tgg tgc tac gcc ttt ggg tgc tgg tgc aca ggt atg      144
Gly Lys Lys Gly Trp Cys Tyr Ala Phe Gly Cys Trp Cys Thr Gly Met
        35                  40                  45

ccc gac agt aca cag gtt tat ccc ctt cct gat aaa tca tgc              186
Pro Asp Ser Thr Gln Val Tyr Pro Leu Pro Asp Lys Ser Cys
    50                  55                  60


<210> SEQ ID NO 136
<211> LENGTH: 62
<212> TYPE: PRT
<213> ORGANISM: Centruroides gracilis

<400> SEQUENCE: 136

Tyr Leu Val Lys Lys Ser Asp Gly Cys Lys Tyr Gly Cys Val Met Leu
1               5                   10                  15

Val Gly Asp Ser Gly Cys Asp Thr Glu Cys Lys Ala Lys Asn Gln Gly
```

-continued

```
            20                  25                  30

Gly Lys Lys Gly Trp Cys Tyr Ala Phe Gly Cys Trp Cys Thr Gly Met
        35                  40                  45

Pro Asp Ser Thr Gln Val Tyr Pro Leu Pro Asp Lys Ser Cys
    50                  55                  60


<210> SEQ ID NO 137
<211> LENGTH: 323
<212> TYPE: DNA
<213> ORGANISM: Centruroides sculpturatus
<220> FEATURE:
<221> NAME/KEY: CDS
<222> LOCATION: (5)..(265)
<223> OTHER INFORMATION: Product= Sodium-channel modifier toxin
      precursor In the mature peptide, the last Cys is amidated,
      and the last Gly and the last 2 basic aminoacids are cut
<220> FEATURE:
<221> NAME/KEY: 3'UTR
<222> LOCATION: (269)..(323)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing, that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (5)..(265)

<400> SEQUENCE: 137

gaag atg aat tcg ttg ttg atc atc act gtt tgt ttg ttc ctg atc gga      49
     Met Asn Ser Leu Leu Ile Ile Thr Val Cys Leu Phe Leu Ile Gly
                     -15                 -10                 -5

acc gtg tgg gca aaa gaa ggt tat ctg gta aac aag agc acg ggc tgc       97
Thr Val Trp Ala Lys Glu Gly Tyr Leu Val Asn Lys Ser Thr Gly Cys
            -1  1               5                   10

aaa tac gat tgc ttt tgg ttg gga aaa aac gaa cac tgc gat ttg gaa      145
Lys Tyr Asp Cys Phe Trp Leu Gly Lys Asn Glu His Cys Asp Leu Glu
        15                  20                  25

tgc aaa gcg aag aac caa gga ggt agt tac ggg tat tgc tac gct ttc      193
Cys Lys Ala Lys Asn Gln Gly Gly Ser Tyr Gly Tyr Cys Tyr Ala Phe
    30                  35                  40

gca tgc tgg tgc gaa ggt ttg ccc gaa agt aca ccg act tat ccc ctt      241
Ala Cys Trp Cys Glu Gly Leu Pro Glu Ser Thr Pro Thr Tyr Pro Leu
45                  50                  55                  60

cct aat aaa tca tgc ggc aaa aaa taatagcaac aactttttat tgtccaccaa     295
Pro Asn Lys Ser Cys Gly Lys Lys
                65

cagaaatatt gtaacgcttc ttaattgc                                       323


<210> SEQ ID NO 138
<211> LENGTH: 87
```

-continued

<212> TYPE: PRT
<213> ORGANISM: Centruroides sculpturatus

<400> SEQUENCE: 138

```
Met Asn Ser Leu Leu Ile Ile Thr Val Cys Leu Phe Leu Ile Gly Thr
                -15                 -10                 -5

Val Trp Ala Lys Glu Gly Tyr Leu Val Asn Lys Ser Thr Gly Cys Lys
        -1  1               5                   10

Tyr Asp Cys Phe Trp Leu Gly Lys Asn Glu His Cys Asp Leu Glu Cys
    15                  20                  25

Lys Ala Lys Asn Gln Gly Gly Ser Tyr Gly Tyr Cys Tyr Ala Phe Ala
30                  35                  40                  45

Cys Trp Cys Glu Gly Leu Pro Glu Ser Thr Pro Thr Tyr Pro Leu Pro
                50                  55                  60

Asn Lys Ser Cys Gly Lys Lys
            65
```

<210> SEQ ID NO 139
<211> LENGTH: 195
<212> TYPE: DNA
<213> ORGANISM: Centruroides sculpturatus
<220> FEATURE:
<221> NAME/KEY: CDS
<222> LOCATION: (1)..(195)
<223> OTHER INFORMATION: Product= Sodium-channel modifier toxin
<300> PUBLICATION INFORMATION:
<301> AUTHORS: Corona, M., Valdez-Cruz, N.A., Merino, E., Zurita, M. & Possani L.D.
<302> TITLE: Genes and peptides from the scorpion Centruroides sculpturatus Ewing, that recognize Na+-channeLs
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (1)..(195)

<400> SEQUENCE: 139

```
aaa gaa ggt tat ctg gta aac aag agc acg ggc tgc aaa tac gat tgc       48
Lys Glu Gly Tyr Leu Val Asn Lys Ser Thr Gly Cys Lys Tyr Asp Cys
1               5                   10                  15

ttt tgg ttg gga aaa aac gaa cac tgc gat ttg gaa tgc aaa gcg aag       96
Phe Trp Leu Gly Lys Asn Glu His Cys Asp Leu Glu Cys Lys Ala Lys
            20                  25                  30

aac caa gga ggt agt tac ggg tat tgc tac gct ttc gca tgc tgg tgc      144
Asn Gln Gly Gly Ser Tyr Gly Tyr Cys Tyr Ala Phe Ala Cys Trp Cys
        35                  40                  45

gaa ggt ttg ccc gaa agt aca ccg act tat ccc ctt cct aat aaa tca      192
Glu Gly Leu Pro Glu Ser Thr Pro Thr Tyr Pro Leu Pro Asn Lys Ser
    50                  55                  60

tgc                                                                  195
Cys
65
```

<210> SEQ ID NO 140
<211> LENGTH: 65
<212> TYPE: PRT
<213> ORGANISM: Centruroides sculpturatus

<400> SEQUENCE: 140

```
Lys Glu Gly Tyr Leu Val Asn Lys Ser Thr Gly Cys Lys Tyr Asp Cys
1               5                   10                  15

Phe Trp Leu Gly Lys Asn Glu His Cys Asp Leu Glu Cys Lys Ala Lys
```

-continued

```
            20                  25                  30

Asn Gln Gly Gly Ser Tyr Gly Tyr Cys Tyr Ala Phe Ala Cys Trp Cys
        35                  40                  45

Glu Gly Leu Pro Glu Ser Thr Pro Thr Tyr Pro Leu Pro Asn Lys Ser
    50                  55                  60

Cys
65


<210> SEQ ID NO 141
<211> LENGTH: 323
<212> TYPE: DNA
<213> ORGANISM: Centruroides sculpturatus
<220> FEATURE:
<221> NAME/KEY: CDS
<222> LOCATION: (5)..(265)
<223> OTHER INFORMATION: Product= Sodium-channel modifier toxin
      precursor In the mature peptide, the last Cys is amidated,
      and the last Gly and the last 2 basic aminoacids are cut
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:
<220> FEATURE:
<221> NAME/KEY: 3'UTR
<222> LOCATION: (269)..(323)
<223> OTHER INFORMATION:
<220> FEATURE:
<221> NAME/KEY: 5'UTR
<222> LOCATION: (1)..(4)
<223> OTHER INFORMATION:
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing, that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (5)..(265)

<400> SEQUENCE: 141

gaag atg aat tcg ttg ttg atg atc act gct tgt ttc gcc ctg gtc gga      49
     Met Asn Ser Leu Leu Met Ile Thr Ala Cys Phe Ala Leu Val Gly
                     -15                 -10                 -5

aca gtg tgg gca aag gaa ggt tat ctg gtg aag aag agc gat ggc tgc       97
Thr Val Trp Ala Lys Glu Gly Tyr Leu Val Lys Lys Ser Asp Gly Cys
            -1  1               5                   10

aaa tac gat tgc ttt tgg ttg gga aaa aac gaa cac tgc gat ttg gaa      145
Lys Tyr Asp Cys Phe Trp Leu Gly Lys Asn Glu His Cys Asp Leu Glu
        15                  20                  25

tgc aaa gcg aag aac caa gga ggt agt tac ggg tat tgc tac gct ttc      193
Cys Lys Ala Lys Asn Gln Gly Gly Ser Tyr Gly Tyr Cys Tyr Ala Phe
    30                  35                  40

gca tgc tgg tgc gaa ggt ttg ccc gaa agt aca ccg act tat ccc ctt      241
Ala Cys Trp Cys Glu Gly Leu Pro Glu Ser Thr Pro Thr Tyr Pro Leu
45                  50                  55                  60

cct aat aaa tca tgc ggc aaa aaa taatagcaac aactttttat tgtccaccaa     295
Pro Asn Lys Ser Cys Gly Lys Lys
                65

cagaaatagt gtaacgcttc ttaattgc                                       323
```

-continued

<210> SEQ ID NO 142
<211> LENGTH: 87
<212> TYPE: PRT
<213> ORGANISM: Centruroides sculpturatus

<400> SEQUENCE: 142

Met Asn Ser Leu Leu Met Ile Thr Ala Cys Phe Ala Leu Val Gly Thr
-15 -10 -5

Val Trp Ala Lys Glu Gly Tyr Leu Val Lys Lys Ser Asp Gly Cys Lys
-1 1 5 10

Tyr Asp Cys Phe Trp Leu Gly Lys Asn Glu His Cys Asp Leu Glu Cys
15 20 25

Lys Ala Lys Asn Gln Gly Gly Ser Tyr Gly Tyr Cys Tyr Ala Phe Ala
30 35 40 45

Cys Trp Cys Glu Gly Leu Pro Glu Ser Thr Pro Thr Tyr Pro Leu Pro
50 55 60

Asn Lys Ser Cys Gly Lys Lys
65

<210> SEQ ID NO 143
<211> LENGTH: 195
<212> TYPE: DNA
<213> ORGANISM: Centruroides sculpturatus
<220> FEATURE:
<221> NAME/KEY: CDS
<222> LOCATION: (1)..(195)
<223> OTHER INFORMATION: Product= Sodium-channel modifier toxin
<300> PUBLICATION INFORMATION:
<301> AUTHORS: Corona, M., Valdez-Cruz, N.A., Merino, E., Zurita, M. & Possani L.D.
<302> TITLE: Genes and peptides from the scorpion Centruroides sculpturatus Ewing, that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (1)..(195)

<400> SEQUENCE: 143 aag gaa ggt tat ctg gtg aag aag agc gat ggc tgc aaa tac gat tgc 48
Lys Glu Gly Tyr Leu Val Lys Lys Ser Asp Gly Cys Lys Tyr Asp Cys
1 5 10 15 ttt tgg ttg gga aaa aac gaa cac tgc gat ttg gaa tgc aaa gcg aag 96
Phe Trp Leu Gly Lys Asn Glu His Cys Asp Leu Glu Cys Lys Ala Lys
20 25 30 aac caa gga ggt agt tac ggg tat tgc tac gct ttc gca tgc tgg tgc 144
Asn Gln Gly Gly Ser Tyr Gly Tyr Cys Tyr Ala Phe Ala Cys Trp Cys
35 40 45 gaa ggt ttg ccc gaa agt aca ccg act tat ccc ctt cct aat aaa tca 192
Glu Gly Leu Pro Glu Ser Thr Pro Thr Tyr Pro Leu Pro Asn Lys Ser
50 55 60 tgc 195
Cys
65

<210> SEQ ID NO 144
<211> LENGTH: 65
<212> TYPE: PRT
<213> ORGANISM: Centruroides sculpturatus

<400> SEQUENCE: 144

Lys Glu Gly Tyr Leu Val Lys Lys Ser Asp Gly Cys Lys Tyr Asp Cys

-continued

```
1               5                   10                  15

Phe Trp Leu Gly Lys Asn Glu His Cys Asp Leu Glu Cys Lys Ala Lys
            20                  25                  30

Asn Gln Gly Gly Ser Tyr Gly Tyr Cys Tyr Ala Phe Ala Cys Trp Cys
        35                  40                  45

Glu Gly Leu Pro Glu Ser Thr Pro Thr Tyr Pro Leu Pro Asn Lys Ser
    50                  55                  60

Cys
65


<210> SEQ ID NO 145
<211> LENGTH: 323
<212> TYPE: DNA
<213> ORGANISM: Centruroides sculpturatus
<220> FEATURE:
<221> NAME/KEY: CDS
<222> LOCATION: (5)..(265)
<223> OTHER INFORMATION: Product= Sodium-channel modifier toxin
      precursor In the mature peptide, the last Cys is amidated,
      and the last Gly and the last 2 basic aminoacids are cut
<220> FEATURE:
<221> NAME/KEY: 3'UTR
<222> LOCATION: (269)..(323)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:
<220> FEATURE:
<221> NAME/KEY: 5'UTR
<222> LOCATION: (1)..(4)
<223> OTHER INFORMATION:
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing, that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (5)..(265)

<400> SEQUENCE: 145

gaag atg aac tcg ttg ttg atg atc act gct tgt ttg ttc ctg atc gga      49
     Met Asn Ser Leu Leu Met Ile Thr Ala Cys Leu Phe Leu Ile Gly
                     -15                 -10                 -5

acc gtg tgg gca aaa gaa ggt tat ctg gta aac aag agc acg ggc tgc       97
Thr Val Trp Ala Lys Glu Gly Tyr Leu Val Asn Lys Ser Thr Gly Cys
            -1  1               5                   10

aaa tac ggt tgc ctg aaa ttg gga gaa aac gaa ggc tgc gat aag gaa      145
Lys Tyr Gly Cys Leu Lys Leu Gly Glu Asn Glu Gly Cys Asp Lys Glu
        15                  20                  25

tgc aaa gcg aag aac caa gga ggt agt tac ggg tat tgc tac gct ttc      193
Cys Lys Ala Lys Asn Gln Gly Gly Ser Tyr Gly Tyr Cys Tyr Ala Phe
    30                  35                  40

gca tgc tgg tgc gaa ggt ttg ccc gaa agt aca ccg act tat ccc ctt      241
Ala Cys Trp Cys Glu Gly Leu Pro Glu Ser Thr Pro Thr Tyr Pro Leu
45                  50                  55                  60

cct aat aaa tca tgc ggc aaa aaa taatagcaac aactttttat tgtccaccaa     295
Pro Asn Lys Ser Cys Gly Lys Lys
                65
```

```
cagaaatatt gtaacgcttc ttaattgc                                         323


<210> SEQ ID NO 146
<211> LENGTH: 87
<212> TYPE: PRT
<213> ORGANISM: Centruroides sculpturatus

<400> SEQUENCE: 146

Met Asn Ser Leu Leu Met Ile Thr Ala Cys Leu Phe Leu Ile Gly Thr
                -15                 -10                 -5

Val Trp Ala Lys Glu Gly Tyr Leu Val Asn Lys Ser Thr Gly Cys Lys
        -1  1               5                   10

Tyr Gly Cys Leu Lys Leu Gly Glu Asn Glu Gly Cys Asp Lys Glu Cys
    15                  20                  25

Lys Ala Lys Asn Gln Gly Gly Ser Tyr Gly Tyr Cys Tyr Ala Phe Ala
30                  35                  40                  45

Cys Trp Cys Glu Gly Leu Pro Glu Ser Thr Pro Thr Tyr Pro Leu Pro
                50                  55                  60

Asn Lys Ser Cys Gly Lys Lys
            65


<210> SEQ ID NO 147
<211> LENGTH: 195
<212> TYPE: DNA
<213> ORGANISM: Centruroides sculpturatus
<220> FEATURE:
<221> NAME/KEY: CDS
<222> LOCATION: (1)..(195)
<223> OTHER INFORMATION: Product= Sodium-channel modifier toxin
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing, that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (1)..(195)

<400> SEQUENCE: 147

aaa gaa ggt tat ctg gta aac aag agc acg ggc tgc aaa tac ggt tgc       48
Lys Glu Gly Tyr Leu Val Asn Lys Ser Thr Gly Cys Lys Tyr Gly Cys
1               5                   10                  15

ctg aaa ttg gga gaa aac gaa ggc tgc gat aag gaa tgc aaa gcg aag       96
Leu Lys Leu Gly Glu Asn Glu Gly Cys Asp Lys Glu Cys Lys Ala Lys
            20                  25                  30

aac caa gga ggt agt tac ggg tat tgc tac gct ttc gca tgc tgg tgc      144
Asn Gln Gly Gly Ser Tyr Gly Tyr Cys Tyr Ala Phe Ala Cys Trp Cys
        35                  40                  45

gaa ggt ttg ccc gaa agt aca ccg act tat ccc ctt cct aat aaa tca      192
Glu Gly Leu Pro Glu Ser Thr Pro Thr Tyr Pro Leu Pro Asn Lys Ser
    50                  55                  60

tgc                                                                  195
Cys
65


<210> SEQ ID NO 148
<211> LENGTH: 65
<212> TYPE: PRT
<213> ORGANISM: Centruroides sculpturatus
```

-continued

<400> SEQUENCE: 148

```
Lys Glu Gly Tyr Leu Val Asn Lys Ser Thr Gly Cys Lys Tyr Gly Cys
1               5                   10                  15

Leu Lys Leu Gly Glu Asn Glu Gly Cys Asp Lys Glu Cys Lys Ala Lys
            20                  25                  30

Asn Gln Gly Gly Ser Tyr Gly Tyr Cys Tyr Ala Phe Ala Cys Trp Cys
        35                  40                  45

Glu Gly Leu Pro Glu Ser Thr Pro Thr Tyr Pro Leu Pro Asn Lys Ser
    50                  55                  60

Cys
65
```

<210> SEQ ID NO 149
<211> LENGTH: 320
<212> TYPE: DNA
<213> ORGANISM: Centruroides sculpturatus
<220> FEATURE:
<221> NAME/KEY: CDS
<222> LOCATION: (5)..(262)
<223> OTHER INFORMATION: Product= Sodium-channel modifier toxin precursor In the mature peptide, the last Cys is amidated, and the last Gly and the last 2 basic aminoacids are cut
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:
<220> FEATURE:
<221> NAME/KEY: 3'UTR
<222> LOCATION: (266)..(320)
<223> OTHER INFORMATION:
<220> FEATURE:
<221> NAME/KEY: 5'UTR
<222> LOCATION: (1)..(4)
<223> OTHER INFORMATION:
<300> PUBLICATION INFORMATION:
<301> AUTHORS: Corona, M., Valdez-Cruz, N.A., Merino, E., Zurita, M. & Possani L.D.
<302> TITLE: Genes and peptides from the scorpion Centruroides sculpturatus Ewing, that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (5)..(262)

<400> SEQUENCE: 149

```
gaag atg aat tcg ttg ttg atg att act gct tgt ttg gtc ctg atc gga       49
     Met Asn Ser Leu Leu Met Ile Thr Ala Cys Leu Val Leu Ile Gly
                     -15                 -10                 -5

aca gtg tgg gca aag gac ggt tat cta gtg gaa aag acg ggc tgc aaa       97
Thr Val Trp Ala Lys Asp Gly Tyr Leu Val Glu Lys Thr Gly Cys Lys
            -1  1               5                   10

aag act tgc tac aaa ttg gga gaa aac gat ttt tgc aat agg gaa tgc      145
Lys Thr Cys Tyr Lys Leu Gly Glu Asn Asp Phe Cys Asn Arg Glu Cys
        15                  20                  25

aaa tgg aag cac ata gga ggt agt tat ggc tat ttc tac gga ttt ggg      193
Lys Trp Lys His Ile Gly Gly Ser Tyr Gly Tyr Phe Tyr Gly Phe Gly
    30                  35                  40

tgc tat tgc gaa gga ttg ccc gat agt aca cag act tgg ccc ctt cct      241
Cys Tyr Cys Glu Gly Leu Pro Asp Ser Thr Gln Thr Trp Pro Leu Pro
45                  50                  55                  60
```

-continued

```
aat aaa aca tgc ggc aaa aaa taatggcaac gactttttat tgttcaccaa         292
Asn Lys Thr Cys Gly Lys Lys
                65

aagaaatagt gtaacgcttc ttaatttc                                       320


<210> SEQ ID NO 150
<211> LENGTH: 86
<212> TYPE: PRT
<213> ORGANISM: Centruroides sculpturatus

<400> SEQUENCE: 150

Met Asn Ser Leu Leu Met Ile Thr Ala Cys Leu Val Leu Ile Gly Thr
                -15                 -10                 -5

Val Trp Ala Lys Asp Gly Tyr Leu Val Glu Lys Thr Gly Cys Lys Lys
        -1  1               5                   10

Thr Cys Tyr Lys Leu Gly Glu Asn Asp Phe Cys Asn Arg Glu Cys Lys
    15                  20                  25

Trp Lys His Ile Gly Gly Ser Tyr Gly Tyr Phe Tyr Gly Phe Gly Cys
30                  35                  40                  45

Tyr Cys Glu Gly Leu Pro Asp Ser Thr Gln Thr Trp Pro Leu Pro Asn
                50                  55                  60

Lys Thr Cys Gly Lys Lys
            65


<210> SEQ ID NO 151
<211> LENGTH: 192
<212> TYPE: DNA
<213> ORGANISM: Centruroides sculpturatus
<220> FEATURE:
<221> NAME/KEY: CDS
<222> LOCATION: (1)..(192)
<223> OTHER INFORMATION: Product= Sodium-channel modifier toxin
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing, that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (1)..(192)

<400> SEQUENCE: 151

aag gac ggt tat cta gtg gaa aag acg ggc tgc aaa aag act tgc tac       48
Lys Asp Gly Tyr Leu Val Glu Lys Thr Gly Cys Lys Lys Thr Cys Tyr
1               5                   10                  15

aaa ttg gga gaa aac gat ttt tgc aat agg gaa tgc aaa tgg aag cac       96
Lys Leu Gly Glu Asn Asp Phe Cys Asn Arg Glu Cys Lys Trp Lys His
            20                  25                  30

ata gga ggt agt tat ggc tat ttc tac gga ttt ggg tgc tat tgc gaa      144
Ile Gly Gly Ser Tyr Gly Tyr Phe Tyr Gly Phe Gly Cys Tyr Cys Glu
        35                  40                  45

gga ttg ccc gat agt aca cag act tgg ccc ctt cct aat aaa aca tgc      192
Gly Leu Pro Asp Ser Thr Gln Thr Trp Pro Leu Pro Asn Lys Thr Cys
    50                  55                  60


<210> SEQ ID NO 152
<211> LENGTH: 64
<212> TYPE: PRT
<213> ORGANISM: Centruroides sculpturatus

<400> SEQUENCE: 152
```

-continued

```
Lys Asp Gly Tyr Leu Val Glu Lys Thr Gly Cys Lys Lys Thr Cys Tyr
1               5                   10                  15

Lys Leu Gly Glu Asn Asp Phe Cys Asn Arg Glu Cys Lys Trp Lys His
            20                  25                  30

Ile Gly Gly Ser Tyr Gly Tyr Phe Tyr Gly Phe Gly Cys Tyr Cys Glu
        35                  40                  45

Gly Leu Pro Asp Ser Thr Gln Thr Trp Pro Leu Pro Asn Lys Thr Cys
    50                  55                  60


<210> SEQ ID NO 153
<211> LENGTH: 319
<212> TYPE: DNA
<213> ORGANISM: Centruroides sculpturatus
<220> FEATURE:
<221> NAME/KEY: CDS
<222> LOCATION: (1)..(261)
<223> OTHER INFORMATION: Product= Sodium-channel modifier toxin
      precursor In the mature peptide, the last 2 basic aminoacids
      are cut
<220> FEATURE:
<221> NAME/KEY: 3'UTR
<222> LOCATION: (265)..(319)
<223> OTHER INFORMATION:
<220> FEATURE:
<221> NAME/KEY: mat_peptide
<222> LOCATION: (58)..()
<223> OTHER INFORMATION:
<220> FEATURE:
<221> NAME/KEY: sig_peptide
<222> LOCATION: (1)..(57)
<223> OTHER INFORMATION:
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing, that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (1)..(261)

<400> SEQUENCE: 153

atg aat tcg ttg ttg atc atc act gct tgt ttg ttc ctg atc gga acc       48
Met Asn Ser Leu Leu Ile Ile Thr Ala Cys Leu Phe Leu Ile Gly Thr
                -15                 -10                 -5

gtg tgg gca aaa gaa ggt tat ctg gta aac aag agc acg ggc tgc aaa       96
Val Trp Ala Lys Glu Gly Tyr Leu Val Asn Lys Ser Thr Gly Cys Lys
        -1  1               5                   10

tac ggt tgc ctg aaa ttg gga gaa aac gaa ggc tgc gat aag gaa tgc      144
Tyr Gly Cys Leu Lys Leu Gly Glu Asn Glu Gly Cys Asp Lys Glu Cys
    15                  20                  25

aaa gcg gag aac caa gga ggt agt tac ggg tat tgc tac gct ttc gca      192
Lys Ala Glu Asn Gln Gly Gly Ser Tyr Gly Tyr Cys Tyr Ala Phe Ala
30                  35                  40                  45

tgc tgg tgc gaa ggt ttg ccc gaa agt aca ccg act tat cct ctt ccc      240
Cys Trp Cys Glu Gly Leu Pro Glu Ser Thr Pro Thr Tyr Pro Leu Pro
                50                  55                  60

aat aaa tca tgc agc aga aaa taatggcaac gactttttat tgtccaccaa         291
Asn Lys Ser Cys Ser Arg Lys
            65

cagaaatatt gtaacgcttc ttaattgc                                       319


<210> SEQ ID NO 154
```

-continued

```
<211> LENGTH: 87
<212> TYPE: PRT
<213> ORGANISM: Centruroides sculpturatus

<400> SEQUENCE: 154

Met Asn Ser Leu Leu Ile Ile Thr Ala Cys Leu Phe Leu Ile Gly Thr
                -15                 -10                 -5

Val Trp Ala Lys Glu Gly Tyr Leu Val Asn Lys Ser Thr Gly Cys Lys
        -1  1               5                   10

Tyr Gly Cys Leu Lys Leu Gly Glu Asn Glu Gly Cys Asp Lys Glu Cys
    15                  20                  25

Lys Ala Glu Asn Gln Gly Gly Ser Tyr Gly Tyr Cys Tyr Ala Phe Ala
30                  35                  40                  45

Cys Trp Cys Glu Gly Leu Pro Glu Ser Thr Pro Thr Tyr Pro Leu Pro
                50                  55                  60

Asn Lys Ser Cys Ser Arg Lys
            65


<210> SEQ ID NO 155
<211> LENGTH: 198
<212> TYPE: DNA
<213> ORGANISM: Centruroides sculpturatus
<220> FEATURE:
<221> NAME/KEY: CDS
<222> LOCATION: (1)..(198)
<223> OTHER INFORMATION: Product= Sodium-channel modifier toxin
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing, that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (1)..(198)

<400> SEQUENCE: 155

aaa gaa ggt tat ctg gta aac aag agc acg ggc tgc aaa tac ggt tgc       48
Lys Glu Gly Tyr Leu Val Asn Lys Ser Thr Gly Cys Lys Tyr Gly Cys
1               5                   10                  15

ctg aaa ttg gga gaa aac gaa ggc tgc gat aag gaa tgc aaa gcg gag       96
Leu Lys Leu Gly Glu Asn Glu Gly Cys Asp Lys Glu Cys Lys Ala Glu
            20                  25                  30

aac caa gga ggt agt tac ggg tat tgc tac gct ttc gca tgc tgg tgc      144
Asn Gln Gly Gly Ser Tyr Gly Tyr Cys Tyr Ala Phe Ala Cys Trp Cys
        35                  40                  45

gaa ggt ttg ccc gaa agt aca ccg act tat cct ctt ccc aat aaa tca      192
Glu Gly Leu Pro Glu Ser Thr Pro Thr Tyr Pro Leu Pro Asn Lys Ser
    50                  55                  60

tgc agc                                                              198
Cys Ser
65


<210> SEQ ID NO 156
<211> LENGTH: 66
<212> TYPE: PRT
<213> ORGANISM: Centruroides sculpturatus

<400> SEQUENCE: 156

Lys Glu Gly Tyr Leu Val Asn Lys Ser Thr Gly Cys Lys Tyr Gly Cys
1               5                   10                  15
```

-continued

```
Leu Lys Leu Gly Glu Asn Glu Gly Cys Asp Lys Glu Cys Lys Ala Glu
            20                  25                  30

Asn Gln Gly Gly Ser Tyr Gly Tyr Cys Tyr Ala Phe Ala Cys Trp Cys
        35                  40                  45

Glu Gly Leu Pro Glu Ser Thr Pro Thr Tyr Pro Leu Pro Asn Lys Ser
    50                  55                  60

Cys Ser
65


<210> SEQ ID NO 157
<211> LENGTH: 323
<212> TYPE: DNA
<213> ORGANISM: Centruroides sculpturatus
<220> FEATURE:
<221> NAME/KEY: CDS
<222> LOCATION: (5)..(265)
<223> OTHER INFORMATION: Product= Sodium-channel modifier toxin
      precursor In the mature peptide, the last 2 basic aminoacids
      are cut
<220> FEATURE:
<221> NAME/KEY: 3'UTR
<222> LOCATION: (269)..(323)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: sig_peptide
<222> LOCATION: (5)..(61)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing, that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (5)..(265)

<400> SEQUENCE: 157

gaag atg aat tcg ttg ttg atg atc act gct tgt ttg ttc ctg atc gga      49
     Met Asn Ser Leu Leu Met Ile Thr Ala Cys Leu Phe Leu Ile Gly
                     -15                 -10                 -5

acc gtg tgg gca aga gaa ggt tat ctg gta aac aag agc acg ggc tgc       97
Thr Val Trp Ala Arg Glu Gly Tyr Leu Val Asn Lys Ser Thr Gly Cys
            -1  1               5                   10

aaa tac ggt tgc ctg aaa ttg gga gaa aac gaa ggc tgc gat aag gaa      145
Lys Tyr Gly Cys Leu Lys Leu Gly Glu Asn Glu Gly Cys Asp Lys Glu
        15                  20                  25

tgc aaa gcg aag aac caa gga ggt agt tac ggg tat tgc tac gct ttc      193
Cys Lys Ala Lys Asn Gln Gly Gly Ser Tyr Gly Tyr Cys Tyr Ala Phe
    30                  35                  40

gca tgc tgg tgc gaa ggt ttg ccc gaa agt aca ccg act tat cct ctt      241
Ala Cys Trp Cys Glu Gly Leu Pro Glu Ser Thr Pro Thr Tyr Pro Leu
45                  50                  55                  60

cct aat aaa tca tgc agc aga aaa taatggcaac gactttttat tgtccaccaa     295
Pro Asn Lys Ser Cys Ser Arg Lys
                65

cagaaatagt gtaacgcttc ttaatttc                                       323
```

-continued

```
<210> SEQ ID NO 158
<211> LENGTH: 87
<212> TYPE: PRT
<213> ORGANISM: Centruroides sculpturatus

<400> SEQUENCE: 158

Met Asn Ser Leu Leu Met Ile Thr Ala Cys Leu Phe Leu Ile Gly Thr
                -15                 -10                 -5

Val Trp Ala Arg Glu Gly Tyr Leu Val Asn Lys Ser Thr Gly Cys Lys
        -1  1               5                   10

Tyr Gly Cys Leu Lys Leu Gly Glu Asn Glu Gly Cys Asp Lys Glu Cys
    15                  20                  25

Lys Ala Lys Asn Gln Gly Gly Ser Tyr Gly Tyr Cys Tyr Ala Phe Ala
30                  35                  40                  45

Cys Trp Cys Glu Gly Leu Pro Glu Ser Thr Pro Thr Tyr Pro Leu Pro
                50                  55                  60

Asn Lys Ser Cys Ser Arg Lys
            65


<210> SEQ ID NO 159
<211> LENGTH: 198
<212> TYPE: DNA
<213> ORGANISM: Centruroides sculpturatus
<220> FEATURE:
<221> NAME/KEY: CDS
<222> LOCATION: (1)..(198)
<223> OTHER INFORMATION: Product= Sodium-channel modifier toxin
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing, that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (1)..(198)

<400> SEQUENCE: 159

aga gaa ggt tat ctg gta aac aag agc acg ggc tgc aaa tac ggt tgc       48
Arg Glu Gly Tyr Leu Val Asn Lys Ser Thr Gly Cys Lys Tyr Gly Cys
1               5                   10                  15

ctg aaa ttg gga gaa aac gaa ggc tgc gat aag gaa tgc aaa gcg aag       96
Leu Lys Leu Gly Glu Asn Glu Gly Cys Asp Lys Glu Cys Lys Ala Lys
            20                  25                  30

aac caa gga ggt agt tac ggg tat tgc tac gct ttc gca tgc tgg tgc      144
Asn Gln Gly Gly Ser Tyr Gly Tyr Cys Tyr Ala Phe Ala Cys Trp Cys
        35                  40                  45

gaa ggt ttg ccc gaa agt aca ccg act tat cct ctt cct aat aaa tca      192
Glu Gly Leu Pro Glu Ser Thr Pro Thr Tyr Pro Leu Pro Asn Lys Ser
    50                  55                  60

tgc agc                                                              198
Cys Ser
65


<210> SEQ ID NO 160
<211> LENGTH: 66
<212> TYPE: PRT
<213> ORGANISM: Centruroides sculpturatus

<400> SEQUENCE: 160
```

-continued

```
Arg Glu Gly Tyr Leu Val Asn Lys Ser Thr Gly Cys Lys Tyr Gly Cys
1               5                   10                  15

Leu Lys Leu Gly Glu Asn Glu Gly Cys Asp Lys Glu Cys Lys Ala Lys
            20                  25                  30

Asn Gln Gly Gly Ser Tyr Gly Tyr Cys Tyr Ala Phe Ala Cys Trp Cys
        35                  40                  45

Glu Gly Leu Pro Glu Ser Thr Pro Thr Tyr Pro Leu Pro Asn Lys Ser
    50                  55                  60

Cys Ser
65


<210> SEQ ID NO 161
<211> LENGTH: 323
<212> TYPE: DNA
<213> ORGANISM: Centruroides sculpturatus
<220> FEATURE:
<221> NAME/KEY: CDS
<222> LOCATION: (5)..(265)
<223> OTHER INFORMATION: Product= Sodium-channel modifier toxin
      precursor
      In the mature peptide, the last 2 basic aminoacids are cut
<220> FEATURE:
<221> NAME/KEY: 3'UTR
<222> LOCATION: (269)..(323)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: 5'UTR
<222> LOCATION: (1)..(4)
<223> OTHER INFORMATION:
<220> FEATURE:
<221> NAME/KEY: sig_peptide
<222> LOCATION: (5)..(61)
<223> OTHER INFORMATION:
<300> PUBLICATION INFORMATION:
<301> AUTHORS: Genes and peptides from the scorpion Centruroides
      sculpturatus Ewing, that recognize Na+-channels
<302> TITLE: Corona, M., Valdez-Cruz, N.A., Merino, E., Zurita, M.
      & Possani L.D.
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (5)..(265)

<400> SEQUENCE: 161

gaag atg aac tcg ttg ttg atg atc act gct tgt ttg ttc ctg atc gga      49
     Met Asn Ser Leu Leu Met Ile Thr Ala Cys Leu Phe Leu Ile Gly
                     -15                 -10                 -5

acc gtg tgg gca aaa gaa ggt tat ctg gta aac aag agc acg gcc tgc       97
Thr Val Trp Ala Lys Glu Gly Tyr Leu Val Asn Lys Ser Thr Ala Cys
            -1  1               5                   10

aaa tac ggt tgc ctg aaa ttg gga gaa aac gaa ggc tgc gat aag gaa      145
Lys Tyr Gly Cys Leu Lys Leu Gly Glu Asn Glu Gly Cys Asp Lys Glu
        15                  20                  25

tgc aaa gcg aag aac caa gga ggt agt tac ggg tat tgc tac gct ttc      193
Cys Lys Ala Lys Asn Gln Gly Gly Ser Tyr Gly Tyr Cys Tyr Ala Phe
    30                  35                  40

gca tgc tgg tgc gaa ggt ttg ccc gaa agt aca ccg act tat cct ctt      241
Ala Cys Trp Cys Glu Gly Leu Pro Glu Ser Thr Pro Thr Tyr Pro Leu
45                  50                  55                  60

cct aat aaa tca tgc agc aga aaa taatggcaac gactttttat tgtccaccaa     295
Pro Asn Lys Ser Cys Ser Arg Lys
```

-continued

```
                65

cagaaatatt gtaacgcttc ttaattga                                          323


<210> SEQ ID NO 162
<211> LENGTH: 87
<212> TYPE: PRT
<213> ORGANISM: Centruroides sculpturatus

<400> SEQUENCE: 162

Met Asn Ser Leu Leu Met Ile Thr Ala Cys Leu Phe Leu Ile Gly Thr
                -15                 -10                 -5

Val Trp Ala Lys Glu Gly Tyr Leu Val Asn Lys Ser Thr Ala Cys Lys
        -1  1               5                   10

Tyr Gly Cys Leu Lys Leu Gly Glu Asn Glu Gly Cys Asp Lys Glu Cys
    15                  20                  25

Lys Ala Lys Asn Gln Gly Gly Ser Tyr Gly Tyr Cys Tyr Ala Phe Ala
30                  35                  40                  45

Cys Trp Cys Glu Gly Leu Pro Glu Ser Thr Pro Thr Tyr Pro Leu Pro
                50                  55                  60

Asn Lys Ser Cys Ser Arg Lys
            65


<210> SEQ ID NO 163
<211> LENGTH: 198
<212> TYPE: DNA
<213> ORGANISM: Centruroides sculpturatus
<220> FEATURE:
<221> NAME/KEY: CDS
<222> LOCATION: (1)..(198)
<223> OTHER INFORMATION: Product= Sodium-channel modifier toxin
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing, that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (1)..(198)

<400> SEQUENCE: 163

aaa gaa ggt tat ctg gta aac aag agc acg gcc tgc aaa tac ggt tgc       48
Lys Glu Gly Tyr Leu Val Asn Lys Ser Thr Ala Cys Lys Tyr Gly Cys
1               5                   10                  15

ctg aaa ttg gga gaa aac gaa ggc tgc gat aag gaa tgc aaa gcg aag       96
Leu Lys Leu Gly Glu Asn Glu Gly Cys Asp Lys Glu Cys Lys Ala Lys
            20                  25                  30

aac caa gga ggt agt tac ggg tat tgc tac gct ttc gca tgc tgg tgc      144
Asn Gln Gly Gly Ser Tyr Gly Tyr Cys Tyr Ala Phe Ala Cys Trp Cys
        35                  40                  45

gaa ggt ttg ccc gaa agt aca ccg act tat cct ctt cct aat aaa tca      192
Glu Gly Leu Pro Glu Ser Thr Pro Thr Tyr Pro Leu Pro Asn Lys Ser
    50                  55                  60

tgc agc                                                              198
Cys Ser
65


<210> SEQ ID NO 164
<211> LENGTH: 66
<212> TYPE: PRT
<213> ORGANISM: Centruroides sculpturatus
```

-continued

<400> SEQUENCE: 164

```
Lys Glu Gly Tyr Leu Val Asn Lys Ser Thr Ala Cys Lys Tyr Gly Cys
1               5                   10                  15

Leu Lys Leu Gly Glu Asn Glu Gly Cys Asp Lys Glu Cys Lys Ala Lys
            20                  25                  30

Asn Gln Gly Gly Ser Tyr Gly Tyr Cys Tyr Ala Phe Ala Cys Trp Cys
        35                  40                  45

Glu Gly Leu Pro Glu Ser Thr Pro Thr Tyr Pro Leu Pro Asn Lys Ser
    50                  55                  60

Cys Ser
65
```

<210> SEQ ID NO 165
<211> LENGTH: 323
<212> TYPE: DNA
<213> ORGANISM: Centruroides sculpturatus
<220> FEATURE:
<221> NAME/KEY: CDS
<222> LOCATION: (5)..(265)
<223> OTHER INFORMATION: Product= Sodium-channel modifier toxin
      precursor
      In the mature peptide, the last Cys is amidated, and the last Gly
      and the last 2 basic aminoacids are cut
<220> FEATURE:
<221> NAME/KEY: 3'UTR
<222> LOCATION: (269)..(323)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing, that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (5)..(265)

<400> SEQUENCE: 165

```
gaag atg aat tcg ttg ttg atc atc act gct tgt ttc gcc ctg gtc gga      49
     Met Asn Ser Leu Leu Ile Ile Thr Ala Cys Phe Ala Leu Val Gly
                     -15                 -10                 -5

aca gtg tgg gca aag gaa ggt tat ctg gtg aag aag agc gat ggc tgc       97
Thr Val Trp Ala Lys Glu Gly Tyr Leu Val Lys Lys Ser Asp Gly Cys
            -1  1               5                   10

aaa tac gat tgc ttt tgg ttg gga aaa aac gaa cac tgc gat acg gaa      145
Lys Tyr Asp Cys Phe Trp Leu Gly Lys Asn Glu His Cys Asp Thr Glu
        15                  20                  25

tgc aaa gcg aag aac caa gga ggt agt tac ggg tat tgc tac gct ttc      193
Cys Lys Ala Lys Asn Gln Gly Gly Ser Tyr Gly Tyr Cys Tyr Ala Phe
    30                  35                  40

gca tgc tgg tgc gaa ggt ttg ccc gaa agt aca ccg act tat ccc ctt      241
Ala Cys Trp Cys Glu Gly Leu Pro Glu Ser Thr Pro Thr Tyr Pro Leu
```

-continued

```
45                  50                  55                  60

cct aat aaa tca tgc ggc aaa aaa taatagcaac aactttttat tgtccaccaa     295
Pro Asn Lys Ser Cys Gly Lys Lys
                65

cggaaatagt gtaacgcttc ttaattgc                                       323
```

<210> SEQ ID NO 166
<211> LENGTH: 87
<212> TYPE: PRT
<213> ORGANISM: Centruroides sculpturatus

<400> SEQUENCE: 166

```
Met Asn Ser Leu Leu Ile Ile Thr Ala Cys Phe Ala Leu Val Gly Thr
                -15                 -10                 -5

Val Trp Ala Lys Glu Gly Tyr Leu Val Lys Lys Ser Asp Gly Cys Lys
        -1  1               5                   10

Tyr Asp Cys Phe Trp Leu Gly Lys Asn Glu His Cys Asp Thr Glu Cys
    15                  20                  25

Lys Ala Lys Asn Gln Gly Gly Ser Tyr Gly Tyr Cys Tyr Ala Phe Ala
30                  35                  40                  45

Cys Trp Cys Glu Gly Leu Pro Glu Ser Thr Pro Thr Tyr Pro Leu Pro
                50                  55                  60

Asn Lys Ser Cys Gly Lys Lys
            65
```

<210> SEQ ID NO 167
<211> LENGTH: 195
<212> TYPE: DNA
<213> ORGANISM: Centruroides sculpturatus
<220> FEATURE:
<221> NAME/KEY: CDS
<222> LOCATION: (1)..(195)
<223> OTHER INFORMATION: Product= Sodium-channel modifier toxin
<300> PUBLICATION INFORMATION:
<301> AUTHORS: Corona, M., Valdez-Cruz, N.A., Merino, E., Zurita, M. & Possani L.D.
<302> TITLE: Genes and peptides from the scorpion Centruroides sculpturatus Ewing, that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (1)..(195)

<400> SEQUENCE: 167

```
aag gaa ggt tat ctg gtg aag aag agc gat ggc tgc aaa tac gat tgc       48
Lys Glu Gly Tyr Leu Val Lys Lys Ser Asp Gly Cys Lys Tyr Asp Cys
1               5                   10                  15

ttt tgg ttg gga aaa aac gaa cac tgc gat acg gaa tgc aaa gcg aag       96
Phe Trp Leu Gly Lys Asn Glu His Cys Asp Thr Glu Cys Lys Ala Lys
            20                  25                  30

aac caa gga ggt agt tac ggg tat tgc tac gct ttc gca tgc tgg tgc      144
Asn Gln Gly Gly Ser Tyr Gly Tyr Cys Tyr Ala Phe Ala Cys Trp Cys
        35                  40                  45

gaa ggt ttg ccc gaa agt aca ccg act tat ccc ctt cct aat aaa tca      192
Glu Gly Leu Pro Glu Ser Thr Pro Thr Tyr Pro Leu Pro Asn Lys Ser
    50                  55                  60

tgc                                                                  195
Cys
65
```

-continued

```
<210> SEQ ID NO 168
<211> LENGTH: 65
<212> TYPE: PRT
<213> ORGANISM: Centruroides sculpturatus

<400> SEQUENCE: 168

Lys Glu Gly Tyr Leu Val Lys Lys Ser Asp Gly Cys Lys Tyr Asp Cys
1               5                   10                  15

Phe Trp Leu Gly Lys Asn Glu His Cys Asp Thr Glu Cys Lys Ala Lys
            20                  25                  30

Asn Gln Gly Gly Ser Tyr Gly Tyr Cys Tyr Ala Phe Ala Cys Trp Cys
        35                  40                  45

Glu Gly Leu Pro Glu Ser Thr Pro Thr Tyr Pro Leu Pro Asn Lys Ser
    50                  55                  60

Cys
65


<210> SEQ ID NO 169
<211> LENGTH: 323
<212> TYPE: DNA
<213> ORGANISM: Centruroides sculpturatus
<220> FEATURE:
<221> NAME/KEY: CDS
<222> LOCATION: (5)..(265)
<223> OTHER INFORMATION: Product= Sodium-channel modifier toxin
      precursor
      In the mature peptide, the last Cys is amidated, and the last Gly
      and the last 2 basic aminoacids are cut
<220> FEATURE:
<221> NAME/KEY: 3'UTR
<222> LOCATION: (269)..(323)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing, that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (5)..(265)

<400> SEQUENCE: 169

gaag atg aat tcg ttg ttg atg atc act gct tgt ttc gcc ctg gtc gga      49
     Met Asn Ser Leu Leu Met Ile Thr Ala Cys Phe Ala Leu Val Gly
                     -15                 -10                 -5

aca gtg tgg gca aag gaa ggt tat ctg gtg aag aag agc gat ggc tgc       97
Thr Val Trp Ala Lys Glu Gly Tyr Leu Val Lys Lys Ser Asp Gly Cys
            -1  1               5                   10

aaa tac gat tgc ttt tgg ttg gga gaa aac gaa ggc tgc gat aag gaa      145
Lys Tyr Asp Cys Phe Trp Leu Gly Glu Asn Glu Gly Cys Asp Lys Glu
        15                  20                  25

tgc aaa gcg aag aac caa gga ggt agt tac ggg tat tgc tac gct ttc      193
```

-continued

```
Cys Lys Ala Lys Asn Gln Gly Gly Ser Tyr Gly Tyr Cys Tyr Ala Phe
    30                  35                  40

gca tgc tgg tgc gaa ggt ttg ccc gaa agt aca ccg act tat ccc ctt      241
Ala Cys Trp Cys Glu Gly Leu Pro Glu Ser Thr Pro Thr Tyr Pro Leu
45                  50                  55                  60

cct aat aaa tca tgc ggc aaa aaa taatagcaac aactttttat tgtccaccaa     295
Pro Asn Lys Ser Cys Gly Lys Lys
                65

cagaaatagt gtaacgcttc ttaattgc                                       323


<210> SEQ ID NO 170
<211> LENGTH: 87
<212> TYPE: PRT
<213> ORGANISM: Centruroides sculpturatus

<400> SEQUENCE: 170

Met Asn Ser Leu Leu Met Ile Thr Ala Cys Phe Ala Leu Val Gly Thr
                -15                 -10                 -5

Val Trp Ala Lys Glu Gly Tyr Leu Val Lys Lys Ser Asp Gly Cys Lys
        -1  1               5                   10

Tyr Asp Cys Phe Trp Leu Gly Glu Asn Glu Gly Cys Asp Lys Glu Cys
    15                  20                  25

Lys Ala Lys Asn Gln Gly Gly Ser Tyr Gly Tyr Cys Tyr Ala Phe Ala
30                  35                  40                  45

Cys Trp Cys Glu Gly Leu Pro Glu Ser Thr Pro Thr Tyr Pro Leu Pro
                50                  55                  60

Asn Lys Ser Cys Gly Lys Lys
            65


<210> SEQ ID NO 171
<211> LENGTH: 195
<212> TYPE: DNA
<213> ORGANISM: Centruroides sculpturatus
<220> FEATURE:
<221> NAME/KEY: CDS
<222> LOCATION: (1)..(195)
<223> OTHER INFORMATION: Product= Sodium-channel modifier toxin
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing,
      that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (1)..(195)

<400> SEQUENCE: 171

aag gaa ggt tat ctg gtg aag aag agc gat ggc tgc aaa tac gat tgc       48
Lys Glu Gly Tyr Leu Val Lys Lys Ser Asp Gly Cys Lys Tyr Asp Cys
1               5                   10                  15

ttt tgg ttg gga gaa aac gaa ggc tgc gat aag gaa tgc aaa gcg aag       96
Phe Trp Leu Gly Glu Asn Glu Gly Cys Asp Lys Glu Cys Lys Ala Lys
            20                  25                  30

aac caa gga ggt agt tac ggg tat tgc tac gct ttc gca tgc tgg tgc      144
Asn Gln Gly Gly Ser Tyr Gly Tyr Cys Tyr Ala Phe Ala Cys Trp Cys
        35                  40                  45

gaa ggt ttg ccc gaa agt aca ccg act tat ccc ctt cct aat aaa tca      192
Glu Gly Leu Pro Glu Ser Thr Pro Thr Tyr Pro Leu Pro Asn Lys Ser
    50                  55                  60
```

-continued

```
tgc                                                                  195
Cys
65


<210> SEQ ID NO 172
<211> LENGTH: 65
<212> TYPE: PRT
<213> ORGANISM: Centruroides sculpturatus

<400> SEQUENCE: 172

Lys Glu Gly Tyr Leu Val Lys Lys Ser Asp Gly Cys Lys Tyr Asp Cys
1               5                   10                  15

Phe Trp Leu Gly Glu Asn Glu Gly Cys Asp Lys Glu Cys Lys Ala Lys
            20                  25                  30

Asn Gln Gly Gly Ser Tyr Gly Tyr Cys Tyr Ala Phe Ala Cys Trp Cys
        35                  40                  45

Glu Gly Leu Pro Glu Ser Thr Pro Thr Tyr Pro Leu Pro Asn Lys Ser
    50                  55                  60

Cys
65


<210> SEQ ID NO 173
<211> LENGTH: 323
<212> TYPE: DNA
<213> ORGANISM: Centruroides sculpturatus
<220> FEATURE:
<221> NAME/KEY: CDS
<222> LOCATION: (5)..(265)
<223> OTHER INFORMATION: Product= Sodium-channel modifier toxin
      precursor
      In the mature peptide, the last 2 basic aminoacids are cut
<220> FEATURE:
<221> NAME/KEY: 3'clip
<222> LOCATION: (269)..(323)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing,
      that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (5)..(265)

<400> SEQUENCE: 173

gaag atg aac tcg ttg ttg atc atc act gct tgt ttg ttc ctg atc gga      49
     Met Asn Ser Leu Leu Ile Ile Thr Ala Cys Leu Phe Leu Ile Gly
                     -15                 -10                 -5

acc gtg tgg gca aaa gaa ggt tat ctg gta aac aag agc acg ggc tgc       97
Thr Val Trp Ala Lys Glu Gly Tyr Leu Val Asn Lys Ser Thr Gly Cys
            -1  1               5                   10
```

-continued

```
aaa tac ggt tgc ctg aaa ttg gga gaa aac gaa ggc tgc gat aag gaa      145
Lys Tyr Gly Cys Leu Lys Leu Gly Glu Asn Glu Gly Cys Asp Lys Glu
        15                  20                  25

tgc aaa gcg aag aac caa gga ggt agt tac ggc tat tgc tac gct ttc      193
Cys Lys Ala Lys Asn Gln Gly Gly Ser Tyr Gly Tyr Cys Tyr Ala Phe
    30                  35                  40

gca tgc tgg tgc gaa ggt ttg ccc gaa agt aca ccg act tat cct ctt      241
Ala Cys Trp Cys Glu Gly Leu Pro Glu Ser Thr Pro Thr Tyr Pro Leu
45                  50                  55                  60

cct aat aaa tca tgc agc aga aaa taatggcaac gactttttat tgtccaccaa     295
Pro Asn Lys Ser Cys Ser Arg Lys
                65

cagaaatagt gtaacgcttc ttaattgc                                       323


<210> SEQ ID NO 174
<211> LENGTH: 87
<212> TYPE: PRT
<213> ORGANISM: Centruroides sculpturatus

<400> SEQUENCE: 174

Met Asn Ser Leu Leu Ile Ile Thr Ala Cys Leu Phe Leu Ile Gly Thr
                -15                 -10                 -5

Val Trp Ala Lys Glu Gly Tyr Leu Val Asn Lys Ser Thr Gly Cys Lys
        -1  1               5                   10

Tyr Gly Cys Leu Lys Leu Gly Glu Asn Glu Gly Cys Asp Lys Glu Cys
    15                  20                  25

Lys Ala Lys Asn Gln Gly Gly Ser Tyr Gly Tyr Cys Tyr Ala Phe Ala
30                  35                  40                  45

Cys Trp Cys Glu Gly Leu Pro Glu Ser Thr Pro Thr Tyr Pro Leu Pro
                50                  55                  60

Asn Lys Ser Cys Ser Arg Lys
            65


<210> SEQ ID NO 175
<211> LENGTH: 198
<212> TYPE: DNA
<213> ORGANISM: Centruroides sculpturatus
<220> FEATURE:
<221> NAME/KEY: CDS
<222> LOCATION: (1)..(198)
<223> OTHER INFORMATION: Product= Sodium-channel modifier toxin
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing,
      that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (1)..(198)

<400> SEQUENCE: 175

aaa gaa ggt tat ctg gta aac aag agc acg ggc tgc aaa tac ggt tgc       48
Lys Glu Gly Tyr Leu Val Asn Lys Ser Thr Gly Cys Lys Tyr Gly Cys
1               5                   10                  15

ctg aaa ttg gga gaa aac gaa ggc tgc gat aag gaa tgc aaa gcg aag       96
Leu Lys Leu Gly Glu Asn Glu Gly Cys Asp Lys Glu Cys Lys Ala Lys
            20                  25                  30

aac caa gga ggt agt tac ggc tat tgc tac gct ttc gca tgc tgg tgc      144
Asn Gln Gly Gly Ser Tyr Gly Tyr Cys Tyr Ala Phe Ala Cys Trp Cys
```

-continued

```
        35                  40                  45

gaa ggt ttg ccc gaa agt aca ccg act tat cct ctt cct aat aaa tca      192
Glu Gly Leu Pro Glu Ser Thr Pro Thr Tyr Pro Leu Pro Asn Lys Ser
    50                  55                  60

tgc agc                                                              198
Cys Ser
65


<210> SEQ ID NO 176
<211> LENGTH: 66
<212> TYPE: PRT
<213> ORGANISM: Centruroides sculpturatus

<400> SEQUENCE: 176

Lys Glu Gly Tyr Leu Val Asn Lys Ser Thr Gly Cys Lys Tyr Gly Cys
1               5                   10                  15

Leu Lys Leu Gly Glu Asn Glu Gly Cys Asp Lys Glu Cys Lys Ala Lys
            20                  25                  30

Asn Gln Gly Gly Ser Tyr Gly Tyr Cys Tyr Ala Phe Ala Cys Trp Cys
        35                  40                  45

Glu Gly Leu Pro Glu Ser Thr Pro Thr Tyr Pro Leu Pro Asn Lys Ser
    50                  55                  60

Cys Ser
65


<210> SEQ ID NO 177
<211> LENGTH: 313
<212> TYPE: DNA
<213> ORGANISM: Centruroides sculpturatus
<220> FEATURE:
<221> NAME/KEY: CDS
<222> LOCATION: (5)..(256)
<223> OTHER INFORMATION: Product= Sodium-channel modifier toxin
<220> FEATURE:
<221> NAME/KEY: 3'UTR
<222> LOCATION: (260)..(313)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing,
      that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (5)..(256)

<400> SEQUENCE: 177

gaag atg aat tcg ttg ttg atg att act act tgt ttg att ctg atc gga      49
     Met Asn Ser Leu Leu Met Ile Thr Thr Cys Leu Ile Leu Ile Gly
                     -15                 -10                 -5

act gtg ttg gca gag gat ggt tat ttg ttt gac aag aga aag cgc tgc       97
```

-continued

```
Thr Val Leu Ala Glu Asp Gly Tyr Leu Phe Asp Lys Arg Lys Arg Cys
            -1  1               5                   10

aca ctc gaa tgc ata gac aag aca gga gac aaa aat tgc gat agg aat      145
Thr Leu Glu Cys Ile Asp Lys Thr Gly Asp Lys Asn Cys Asp Arg Asn
        15                  20                  25

tgc aag aat gaa gga ggt agt ttt ggc aaa tgc tcc tat ttt gca tgc      193
Cys Lys Asn Glu Gly Gly Ser Phe Gly Lys Cys Ser Tyr Phe Ala Cys
    30                  35                  40

tgg tgc aaa gga ttg ccc gga att aca ccg att tca cgt act cct ggt      241
Trp Cys Lys Gly Leu Pro Gly Ile Thr Pro Ile Ser Arg Thr Pro Gly
45                  50                  55                  60

aaa aca tgt aaa ata taatggcaac ttttttattt gtgcaccaac agaaatagtg      296
Lys Thr Cys Lys Ile
                65

taacgcttct taattgc                                                   313


<210> SEQ ID NO 178
<211> LENGTH: 84
<212> TYPE: PRT
<213> ORGANISM: Centruroides sculpturatus

<400> SEQUENCE: 178

Met Asn Ser Leu Leu Met Ile Thr Thr Cys Leu Ile Leu Ile Gly Thr
                -15                 -10                 -5

Val Leu Ala Glu Asp Gly Tyr Leu Phe Asp Lys Arg Lys Arg Cys Thr
        -1  1               5                   10

Leu Glu Cys Ile Asp Lys Thr Gly Asp Lys Asn Cys Asp Arg Asn Cys
    15                  20                  25

Lys Asn Glu Gly Gly Ser Phe Gly Lys Cys Ser Tyr Phe Ala Cys Trp
30                  35                  40                  45

Cys Lys Gly Leu Pro Gly Ile Thr Pro Ile Ser Arg Thr Pro Gly Lys
                50                  55                  60

Thr Cys Lys Ile
            65


<210> SEQ ID NO 179
<211> LENGTH: 195
<212> TYPE: DNA
<213> ORGANISM: Centruroides sculpturatus
<220> FEATURE:
<221> NAME/KEY: CDS
<222> LOCATION: (1)..(195)
<223> OTHER INFORMATION: Product= Sodium-channel modifier toxin
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing,
      that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (1)..(195)

<400> SEQUENCE: 179

gag gat ggt tat ttg ttt gac aag aga aag cgc tgc aca ctc gaa tgc       48
Glu Asp Gly Tyr Leu Phe Asp Lys Arg Lys Arg Cys Thr Leu Glu Cys
1               5                   10                  15

ata gac aag aca gga gac aaa aat tgc gat agg aat tgc aag aat gaa       96
Ile Asp Lys Thr Gly Asp Lys Asn Cys Asp Arg Asn Cys Lys Asn Glu
            20                  25                  30
```

-continued

```
gga ggt agt ttt ggc aaa tgc tcc tat ttt gca tgc tgg tgc aaa gga      144
Gly Gly Ser Phe Gly Lys Cys Ser Tyr Phe Ala Cys Trp Cys Lys Gly
        35                  40                  45

ttg ccc gga att aca ccg att tca cgt act cct ggt aaa aca tgt aaa      192
Leu Pro Gly Ile Thr Pro Ile Ser Arg Thr Pro Gly Lys Thr Cys Lys
    50                  55                  60

ata                                                                  195
Ile
65


<210> SEQ ID NO 180
<211> LENGTH: 65
<212> TYPE: PRT
<213> ORGANISM: Centruroides sculpturatus

<400> SEQUENCE: 180

Glu Asp Gly Tyr Leu Phe Asp Lys Arg Lys Arg Cys Thr Leu Glu Cys
1               5                   10                  15

Ile Asp Lys Thr Gly Asp Lys Asn Cys Asp Arg Asn Cys Lys Asn Glu
            20                  25                  30

Gly Gly Ser Phe Gly Lys Cys Ser Tyr Phe Ala Cys Trp Cys Lys Gly
        35                  40                  45

Leu Pro Gly Ile Thr Pro Ile Ser Arg Thr Pro Gly Lys Thr Cys Lys
    50                  55                  60

Ile
65


<210> SEQ ID NO 181
<211> LENGTH: 313
<212> TYPE: DNA
<213> ORGANISM: Centruroides sculpturatus
<220> FEATURE:
<221> NAME/KEY: CDS
<222> LOCATION: (5)..(256)
<223> OTHER INFORMATION: Product= Sodium-channel modifier toxin
      precursor
<220> FEATURE:
<221> NAME/KEY: 5'UTR
<222> LOCATION: (260)..(313)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing,
      that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (5)..(256)

<400> SEQUENCE: 181

gaag atg aat tcg ttg ttg atc att act act tgt ttg att ctg atc gga      49
```

-continued

```
     Met Asn Ser Leu Leu Ile Ile Thr Thr Cys Leu Ile Leu Ile Gly
                     -15                 -10                 -5

act gtg ttg gca gag gat ggt tat ttg ttt gac aag aga aag cgc tgc       97
Thr Val Leu Ala Glu Asp Gly Tyr Leu Phe Asp Lys Arg Lys Arg Cys
            -1  1               5                   10

aca ctc gaa tgc ata gac atg aca gga gac aaa aat tgc gat agg aat      145
Thr Leu Glu Cys Ile Asp Met Thr Gly Asp Lys Asn Cys Asp Arg Asn
        15                  20                  25

tgc aag aag gaa gga ggt agt ttt ggc aaa tgc tcc tat ttt gca tgc      193
Cys Lys Lys Glu Gly Gly Ser Phe Gly Lys Cys Ser Tyr Phe Ala Cys
    30                  35                  40

tgg tgc aaa gga ttg ccc gga att aca ccg att tca cgt act cct ggt      241
Trp Cys Lys Gly Leu Pro Gly Ile Thr Pro Ile Ser Arg Thr Pro Gly
45                  50                  55                  60

aaa aca tgt aaa ata taatggcaac tttttttatt gtgcaccaac agaaatattg      296
Lys Thr Cys Lys Ile
                65

taacgcttct taatttc                                                   313
```

<210> SEQ ID NO 182
<211> LENGTH: 84
<212> TYPE: PRT
<213> ORGANISM: Centruroides sculpturatus

<400> SEQUENCE: 182

```
Met Asn Ser Leu Leu Ile Ile Thr Thr Cys Leu Ile Leu Ile Gly Thr
                -15                 -10                 -5

Val Leu Ala Glu Asp Gly Tyr Leu Phe Asp Lys Arg Lys Arg Cys Thr
        -1  1               5                   10

Leu Glu Cys Ile Asp Met Thr Gly Asp Lys Asn Cys Asp Arg Asn Cys
    15                  20                  25

Lys Lys Glu Gly Gly Ser Phe Gly Lys Cys Ser Tyr Phe Ala Cys Trp
30                  35                  40                  45

Cys Lys Gly Leu Pro Gly Ile Thr Pro Ile Ser Arg Thr Pro Gly Lys
                50                  55                  60

Thr Cys Lys Ile
            65
```

<210> SEQ ID NO 183
<211> LENGTH: 195
<212> TYPE: DNA
<213> ORGANISM: Centruroides sculpturatus
<220> FEATURE:
<221> NAME/KEY: CDS
<222> LOCATION: (1)..(195)
<223> OTHER INFORMATION: Product= Sodium-channel modifier toxin
<300> PUBLICATION INFORMATION:
<301> AUTHORS: Corona, M., Valdez-Cruz, N.A., Merino, E., Zurita, M. & Possani L.D.
<302> TITLE: Genes and peptides from the scorpion Centruroides sculpturatus Ewing, that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (1)..(195)

<400> SEQUENCE: 183

```
gag gat ggt tat ttg ttt gac aag aga aag cgc tgc aca ctc gaa tgc       48
Glu Asp Gly Tyr Leu Phe Asp Lys Arg Lys Arg Cys Thr Leu Glu Cys
1               5                   10                  15
```

-continued

```
ata gac atg aca gga gac aaa aat tgc gat agg aat tgc aag aag gaa       96
Ile Asp Met Thr Gly Asp Lys Asn Cys Asp Arg Asn Cys Lys Lys Glu
            20                  25                  30

gga ggt agt ttt ggc aaa tgc tcc tat ttt gca tgc tgg tgc aaa gga      144
Gly Gly Ser Phe Gly Lys Cys Ser Tyr Phe Ala Cys Trp Cys Lys Gly
        35                  40                  45

ttg ccc gga att aca ccg att tca cgt act cct ggt aaa aca tgt aaa      192
Leu Pro Gly Ile Thr Pro Ile Ser Arg Thr Pro Gly Lys Thr Cys Lys
    50                  55                  60

ata                                                                  195
Ile
65


<210> SEQ ID NO 184
<211> LENGTH: 65
<212> TYPE: PRT
<213> ORGANISM: Centruroides sculpturatus

<400> SEQUENCE: 184

Glu Asp Gly Tyr Leu Phe Asp Lys Arg Lys Arg Cys Thr Leu Glu Cys
1               5                   10                  15

Ile Asp Met Thr Gly Asp Lys Asn Cys Asp Arg Asn Cys Lys Lys Glu
            20                  25                  30

Gly Gly Ser Phe Gly Lys Cys Ser Tyr Phe Ala Cys Trp Cys Lys Gly
        35                  40                  45

Leu Pro Gly Ile Thr Pro Ile Ser Arg Thr Pro Gly Lys Thr Cys Lys
    50                  55                  60

Ile
65


<210> SEQ ID NO 185
<211> LENGTH: 314
<212> TYPE: DNA
<213> ORGANISM: Centruroides sculpturatus
<220> FEATURE:
<221> NAME/KEY: CDS
<222> LOCATION: (2)..(256)
<223> OTHER INFORMATION: Product= Sodium-channel modifier toxin
      precursor
      In the mature peptide, the last Cys is amidated, and the last Gly
      and the last 2 basic aminoacids are cut
<220> FEATURE:
<221> NAME/KEY: 5'UTR
<222> LOCATION: (260)..(314)
<223> OTHER INFORMATION:
<220> FEATURE:
<221> NAME/KEY: 5'UTR
<222> LOCATION: (1)..(1)
<223> OTHER INFORMATION:
<220> FEATURE:
<221> NAME/KEY: mat_peptide
<222> LOCATION: (59)..()
<223> OTHER INFORMATION: Product= Sodium-channel modifier toxin
<220> FEATURE:
<221> NAME/KEY: sig_peptide
<222> LOCATION: (2)..(58)
<223> OTHER INFORMATION:
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing,
      that recognize Na+-channels
<303> JOURNAL: Toxicon
<304> VOLUME: 39
<305> ISSUE: 12
<306> PAGES: 1893-1898
<307> DATE: 2001-12-01
```

-continued

```
<309> DATABASE ENTRY DATE:
<313> RELEVANT RESIDUES: (5)..(256)

<400> SEQUENCE: 185

g atg aac tcg ttg ttg atg atc act gct tgt ttg gtc cta ttc gga aca      49
  Met Asn Ser Leu Leu Met Ile Thr Ala Cys Leu Val Leu Phe Gly Thr
                  -15                 -10                 -5

gtc tgg tca gag aaa ggt tat ctg gtg cat gag gac acg ggc tgc aga       97
Val Trp Ser Glu Lys Gly Tyr Leu Val His Glu Asp Thr Gly Cys Arg
        -1  1               5                   10

tac aag tgc act ttt tcg gga gaa aat agt tac tgc gat aag gaa tgc      145
Tyr Lys Cys Thr Phe Ser Gly Glu Asn Ser Tyr Cys Asp Lys Glu Cys
    15                  20                  25

aag agc caa gga ggt gat tct ggc att tgc caa tct aag gcg tgt tat      193
Lys Ser Gln Gly Gly Asp Ser Gly Ile Cys Gln Ser Lys Ala Cys Tyr
30                  35                  40                  45

tgc caa ggt ttg ccc gaa gat aca aag act tgg ccc ctt att ggt aaa      241
Cys Gln Gly Leu Pro Glu Asp Thr Lys Thr Trp Pro Leu Ile Gly Lys
                50                  55                  60

tta tgc ggc aga aaa taatggcttc gtctttttat tgttcaccaa caaaaatagt      296
Leu Cys Gly Arg Lys
            65

gtaacgcttc ttaatttc                                                  314


<210> SEQ ID NO 186
<211> LENGTH: 85
<212> TYPE: PRT
<213> ORGANISM: Centruroides sculpturatus

<400> SEQUENCE: 186

Met Asn Ser Leu Leu Met Ile Thr Ala Cys Leu Val Leu Phe Gly Thr
                -15                 -10                 -5

Val Trp Ser Glu Lys Gly Tyr Leu Val His Glu Asp Thr Gly Cys Arg
        -1  1               5                   10

Tyr Lys Cys Thr Phe Ser Gly Glu Asn Ser Tyr Cys Asp Lys Glu Cys
    15                  20                  25

Lys Ser Gln Gly Gly Asp Ser Gly Ile Cys Gln Ser Lys Ala Cys Tyr
30                  35                  40                  45

Cys Gln Gly Leu Pro Glu Asp Thr Lys Thr Trp Pro Leu Ile Gly Lys
                50                  55                  60

Leu Cys Gly Arg Lys
            65


<210> SEQ ID NO 187
<211> LENGTH: 189
<212> TYPE: DNA
<213> ORGANISM: Centruroides sculpturatus
<220> FEATURE:
<221> NAME/KEY: CDS
<222> LOCATION: (1)..(189)
<223> OTHER INFORMATION: Product= Sodium-channel modifier toxin
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing,
      that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (1)..(189)
```

-continued

<400> SEQUENCE: 187

```
gag aaa ggt tat ctg gtg cat gag gac acg ggc tgc aga tac aag tgc       48
Glu Lys Gly Tyr Leu Val His Glu Asp Thr Gly Cys Arg Tyr Lys Cys
1               5                   10                  15

act ttt tcg gga gaa aat agt tac tgc gat aag gaa tgc aag agc caa       96
Thr Phe Ser Gly Glu Asn Ser Tyr Cys Asp Lys Glu Cys Lys Ser Gln
            20                  25                  30

gga ggt gat tct ggc att tgc caa tct aag gcg tgt tat tgc caa ggt      144
Gly Gly Asp Ser Gly Ile Cys Gln Ser Lys Ala Cys Tyr Cys Gln Gly
        35                  40                  45

ttg ccc gaa gat aca aag act tgg ccc ctt att ggt aaa tta tgc          189
Leu Pro Glu Asp Thr Lys Thr Trp Pro Leu Ile Gly Lys Leu Cys
    50                  55                  60
```

<210> SEQ ID NO 188
<211> LENGTH: 63
<212> TYPE: PRT
<213> ORGANISM: Centruroides sculpturatus

<400> SEQUENCE: 188

```
Glu Lys Gly Tyr Leu Val His Glu Asp Thr Gly Cys Arg Tyr Lys Cys
1               5                   10                  15

Thr Phe Ser Gly Glu Asn Ser Tyr Cys Asp Lys Glu Cys Lys Ser Gln
            20                  25                  30

Gly Gly Asp Ser Gly Ile Cys Gln Ser Lys Ala Cys Tyr Cys Gln Gly
        35                  40                  45

Leu Pro Glu Asp Thr Lys Thr Trp Pro Leu Ile Gly Lys Leu Cys
    50                  55                  60
```

<210> SEQ ID NO 189
<211> LENGTH: 321
<212> TYPE: DNA
<213> ORGANISM: Centruroides sculpturatus
<220> FEATURE:
<221> NAME/KEY: CDS
<222> LOCATION: (5)..(265)
<223> OTHER INFORMATION: Product= Sodium-channel modifier toxin precursor
In the mature peptide, the last Asn is amidated, and the last Gly and the last basic aminoacid are cut
<220> FEATURE:
<221> NAME/KEY: 3'UTR
<222> LOCATION: (269)..(321)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:
<300> PUBLICATION INFORMATION:
<301> AUTHORS: Corona, M., Valdez-Cruz, N.A., Merino, E., Zurita, M. & Possani L.D.
<302> TITLE: Genes and peptides from the scorpion Centruroides sculpturatus Ewing,
that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:

-continued

```
<313> RELEVANT RESIDUES: (5)..(265)

<400> SEQUENCE: 189

gaag atg aac tcg ttg ttg atc atc gct gct tgt ttg gcc ctg atc gga      49
     Met Asn Ser Leu Leu Ile Ile Ala Ala Cys Leu Ala Leu Ile Gly
                    -15                 -10                 -5

aca gtc tgg gca aag gaa ggt tat att gtg aac tat cac acg ggc tgc       97
Thr Val Trp Ala Lys Glu Gly Tyr Ile Val Asn Tyr His Thr Gly Cys
            -1  1               5                   10

aaa tac gaa tgc ttt aaa ttg gga gac aac gat tat tgc ctg agg gaa      145
Lys Tyr Glu Cys Phe Lys Leu Gly Asp Asn Asp Tyr Cys Leu Arg Glu
        15                  20                  25

tgc aaa ttg aga cac gga aaa ggt agt ggc ggc tat tgc tac gct ttt      193
Cys Lys Leu Arg His Gly Lys Gly Ser Gly Gly Tyr Cys Tyr Ala Phe
    30                  35                  40

ggg tgc tgg tgc aca cac ttg tac gaa caa gca gtg gtt tgg ccc ctt      241
Gly Cys Trp Cys Thr His Leu Tyr Glu Gln Ala Val Val Trp Pro Leu
45                  50                  55                  60

cct aag aaa aaa tgc aac gga aaa taatggcaac gactttttat tgtccaccaa     295
Pro Lys Lys Lys Cys Asn Gly Lys
                65

cagaaatagt gtaacgcttc ttaatt                                         321


<210> SEQ ID NO 190
<211> LENGTH: 87
<212> TYPE: PRT
<213> ORGANISM: Centruroides sculpturatus

<400> SEQUENCE: 190

Met Asn Ser Leu Leu Ile Ile Ala Ala Cys Leu Ala Leu Ile Gly Thr
                -15                 -10                 -5

Val Trp Ala Lys Glu Gly Tyr Ile Val Asn Tyr His Thr Gly Cys Lys
        -1  1               5                   10

Tyr Glu Cys Phe Lys Leu Gly Asp Asn Asp Tyr Cys Leu Arg Glu Cys
    15                  20                  25

Lys Leu Arg His Gly Lys Gly Ser Gly Gly Tyr Cys Tyr Ala Phe Gly
30                  35                  40                  45

Cys Trp Cys Thr His Leu Tyr Glu Gln Ala Val Val Trp Pro Leu Pro
                50                  55                  60

Lys Lys Lys Cys Asn Gly Lys
            65


<210> SEQ ID NO 191
<211> LENGTH: 198
<212> TYPE: DNA
<213> ORGANISM: Centruroides sculpturatus
<220> FEATURE:
<221> NAME/KEY: CDS
<222> LOCATION: (1)..(198)
<223> OTHER INFORMATION: Product= Sodium-channel modifier toxin
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing,
      that recognize Na+-channels
<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (1)..(198)
```

-continued

```
<400> SEQUENCE: 191

aag gaa ggt tat att gtg aac tat cac acg ggc tgc aaa tac gaa tgc       48
Lys Glu Gly Tyr Ile Val Asn Tyr His Thr Gly Cys Lys Tyr Glu Cys
1               5                   10                  15

ttt aaa ttg gga gac aac gat tat tgc ctg agg gaa tgc aaa ttg aga       96
Phe Lys Leu Gly Asp Asn Asp Tyr Cys Leu Arg Glu Cys Lys Leu Arg
            20                  25                  30

cac gga aaa ggt agt ggc ggc tat tgc tac gct ttt ggg tgc tgg tgc      144
His Gly Lys Gly Ser Gly Gly Tyr Cys Tyr Ala Phe Gly Cys Trp Cys
        35                  40                  45

aca cac ttg tac gaa caa gca gtg gtt tgg ccc ctt cct aag aaa aaa      192
Thr His Leu Tyr Glu Gln Ala Val Val Trp Pro Leu Pro Lys Lys Lys
    50                  55                  60

tgc aac                                                              198
Cys Asn
65


<210> SEQ ID NO 192
<211> LENGTH: 66
<212> TYPE: PRT
<213> ORGANISM: Centruroides sculpturatus

<400> SEQUENCE: 192

Lys Glu Gly Tyr Ile Val Asn Tyr His Thr Gly Cys Lys Tyr Glu Cys
1               5                   10                  15

Phe Lys Leu Gly Asp Asn Asp Tyr Cys Leu Arg Glu Cys Lys Leu Arg
            20                  25                  30

His Gly Lys Gly Ser Gly Gly Tyr Cys Tyr Ala Phe Gly Cys Trp Cys
        35                  40                  45

Thr His Leu Tyr Glu Gln Ala Val Val Trp Pro Leu Pro Lys Lys Lys
    50                  55                  60

Cys Asn
65


<210> SEQ ID NO 193
<211> LENGTH: 320
<212> TYPE: DNA
<213> ORGANISM: Centruroides sculpturatus
<220> FEATURE:
<221> NAME/KEY: CDS
<222> LOCATION: (5)..(262)
<223> OTHER INFORMATION: Product= Sodium-channel modifier toxin
      precursor
      In the mature peptide, the last Cys is amidated, and the last Gly
      and the last 2 basic aminoacids are cut
<220> FEATURE:
<221> NAME/KEY: 5'clip
<222> LOCATION: (266)..(320)
<223> OTHER INFORMATION:
<220> FEATURE:
<221> NAME/KEY: 5'UTR
<222> LOCATION: (1)..(4)
<223> OTHER INFORMATION:
<220> FEATURE:
<221> NAME/KEY: mat_peptide
<222> LOCATION: (62)..()
<223> OTHER INFORMATION: Product= Sodium-channel modifier toxin
<220> FEATURE:
<221> NAME/KEY: sig_peptide
<222> LOCATION: (5)..(61)
<223> OTHER INFORMATION:
<300> PUBLICATION INFORMATION:
<301> AUTHORS: Corona, M., Valdez-Cruz, N.A., Merino, E., Zurita, M.
      & Possani L.D.
<302> TITLE: Genes and peptides from the scorpion Centruroides
      sculpturatus Ewing,
      that recognize Na+-channels
```

-continued

<303> JOURNAL: Toxicon
<304> VOLUME: 39
<305> ISSUE: 12
<306> PAGES: 1893-1898
<307> DATE: 2001-12-01
<309> DATABASE ENTRY DATE:
<313> RELEVANT RESIDUES: (5)..(262)

<400> SEQUENCE: 193 gaag atg aat tcg ttg ttg atg atc act gct tgt ttg gtc gtg atc gga 49
Met Asn Ser Leu Leu Met Ile Thr Ala Cys Leu Val Val Ile Gly
-15 -10 -5 aca gtg tgg gca aag gaa ggt tat ctg gtg gac gta aag ggc tgc aaa 97
Thr Val Trp Ala Lys Glu Gly Tyr Leu Val Asp Val Lys Gly Cys Lys
-1 1 5 10 aaa aat tgc tgg aaa ttg gga gat aac gat tat tgc aat agg gaa tgt 145
Lys Asn Cys Trp Lys Leu Gly Asp Asn Asp Tyr Cys Asn Arg Glu Cys
15 20 25 aaa tgg aag cac ata gga ggt agt tac ggc tat tgc tac gga ttt ggg 193
Lys Trp Lys His Ile Gly Gly Ser Tyr Gly Tyr Cys Tyr Gly Phe Gly
30 35 40 tgc tat tgc gaa gga ttg ccc gat agt aca cag act tgg ccc ctt cct 241
Cys Tyr Cys Glu Gly Leu Pro Asp Ser Thr Gln Thr Trp Pro Leu Pro
45 50 55 60 aat aaa aca tgc ggc aaa aaa taatggcaac gactttttat tgtctaccaa 292
Asn Lys Thr Cys Gly Lys Lys
65 cagaaatagt gtaacgcttc ttaattgc 320

<210> SEQ ID NO 194
<211> LENGTH: 86
<212> TYPE: PRT
<213> ORGANISM: Centruroides sculpturatus

<400> SEQUENCE: 194

Met Asn Ser Leu Leu Met Ile Thr Ala Cys Leu Val Val Ile Gly Thr
-15 -10 -5

Val Trp Ala Lys Glu Gly Tyr Leu Val Asp Val Lys Gly Cys Lys Lys
-1 1 5 10

Asn Cys Trp Lys Leu Gly Asp Asn Asp Tyr Cys Asn Arg Glu Cys Lys
15 20 25

Trp Lys His Ile Gly Gly Ser Tyr Gly Tyr Cys Tyr Gly Phe Gly Cys
30 35 40 45

Tyr Cys Glu Gly Leu Pro Asp Ser Thr Gln Thr Trp Pro Leu Pro Asn
50 55 60

Lys Thr Cys Gly Lys Lys
65

<210> SEQ ID NO 195
<211> LENGTH: 192
<212> TYPE: DNA
<213> ORGANISM: Centruroides sculpturatus
<220> FEATURE:
<221> NAME/KEY: CDS
<222> LOCATION: (1)..(192)
<223> OTHER INFORMATION: Product= Sodium-channel modifier toxin
<300> PUBLICATION INFORMATION:
<301> AUTHORS: Corona, M., Valdez-Cruz, N.A., Merino, E., Zurita, M. & Possani L.D.
<302> TITLE: Genes and peptides from the scorpion Centruroides sculpturatus Ewing,
that recognize Na+-channels
<303> JOURNAL: Toxicon
<304> VOLUME: 39

-continued

<305> ISSUE: 12
<306> PAGES: 1893-1898
<307> DATE: 2001-12-01
<309> DATABASE ENTRY DATE:
<313> RELEVANT RESIDUES: (1)..(192)

<400> SEQUENCE: 195

```
aag gaa ggt tat ctg gtg gac gta aag ggc tgc aaa aaa aat tgc tgg       48
Lys Glu Gly Tyr Leu Val Asp Val Lys Gly Cys Lys Lys Asn Cys Trp
1               5                   10                  15

aaa ttg gga gat aac gat tat tgc aat agg gaa tgt aaa tgg aag cac       96
Lys Leu Gly Asp Asn Asp Tyr Cys Asn Arg Glu Cys Lys Trp Lys His
            20                  25                  30

ata gga ggt agt tac ggc tat tgc tac gga ttt ggg tgc tat tgc gaa      144
Ile Gly Gly Ser Tyr Gly Tyr Cys Tyr Gly Phe Gly Cys Tyr Cys Glu
        35                  40                  45

gga ttg ccc gat agt aca cag act tgg ccc ctt cct aat aaa aca tgc      192
Gly Leu Pro Asp Ser Thr Gln Thr Trp Pro Leu Pro Asn Lys Thr Cys
    50                  55                  60
```

<210> SEQ ID NO 196
<211> LENGTH: 64
<212> TYPE: PRT
<213> ORGANISM: Centruroides sculpturatus

<400> SEQUENCE: 196

```
Lys Glu Gly Tyr Leu Val Asp Val Lys Gly Cys Lys Lys Asn Cys Trp
1               5                   10                  15

Lys Leu Gly Asp Asn Asp Tyr Cys Asn Arg Glu Cys Lys Trp Lys His
            20                  25                  30

Ile Gly Gly Ser Tyr Gly Tyr Cys Tyr Gly Phe Gly Cys Tyr Cys Glu
        35                  40                  45

Gly Leu Pro Asp Ser Thr Gln Thr Trp Pro Leu Pro Asn Lys Thr Cys
    50                  55                  60
```

<210> SEQ ID NO 197
<211> LENGTH: 190
<212> TYPE: DNA
<213> ORGANISM: Centruroides exilicauda
<220> FEATURE:
<221> NAME/KEY: CDS
<222> LOCATION: (1)..(129)
<223> OTHER INFORMATION: Product= Erg-channel modifier toxin precursor
<220> FEATURE:
<221> NAME/KEY: 3'UTR
<222> LOCATION: (130)..(190)
<223> OTHER INFORMATION:

<400> SEQUENCE: 197

```
gat aga gat agc tgt gtt gat aaa tca cga tgc gca aaa tat gga tac       48
Asp Arg Asp Ser Cys Val Asp Lys Ser Arg Cys Ala Lys Tyr Gly Tyr
1               5                   10                  15

tac caa gag tgt cag gat tgt tgt aag aaa gct gga cac agt gga gga       96
Tyr Gln Glu Cys Gln Asp Cys Cys Lys Lys Ala Gly His Ser Gly Gly
            20                  25                  30

acc tgt atg ttt ttc aag tgt aaa tgt gcg taa actcgaaaat cagttaataa    149
Thr Cys Met Phe Phe Lys Cys Lys Cys Ala
        35                  40

tatcaaagtt gtaagctatt tatgaagtga aaaataaaga t                        190
```

<210> SEQ ID NO 198
<211> LENGTH: 42
<212> TYPE: PRT
<213> ORGANISM: Centruroides exilicauda -continued

<400> SEQUENCE: 198

```
Asp Arg Asp Ser Cys Val Asp Lys Ser Arg Cys Ala Lys Tyr Gly Tyr
1               5                   10                  15

Tyr Gln Glu Cys Gln Asp Cys Cys Lys Lys Ala Gly His Ser Gly Gly
            20                  25                  30

Thr Cys Met Phe Phe Lys Cys Lys Cys Ala
        35                  40
```

<210> SEQ ID NO 199
<211> LENGTH: 126
<212> TYPE: DNA
<213> ORGANISM: Centruroides exilicauda
<220> FEATURE:
<221> NAME/KEY: CDS
<222> LOCATION: (1)..(126)
<223> OTHER INFORMATION: Product= Erg-channel modifier toxin

<400> SEQUENCE: 199

```
gat aga gat agc tgt gtt gat aaa tca cga tgc gca aaa tat gga tac       48
Asp Arg Asp Ser Cys Val Asp Lys Ser Arg Cys Ala Lys Tyr Gly Tyr
1               5                   10                  15

tac caa gag tgt cag gat tgt tgt aag aaa gct gga cac agt gga gga       96
Tyr Gln Glu Cys Gln Asp Cys Cys Lys Lys Ala Gly His Ser Gly Gly
            20                  25                  30

acc tgt atg ttt ttc aag tgt aaa tgt gcg                              126
Thr Cys Met Phe Phe Lys Cys Lys Cys Ala
        35                  40
```

<210> SEQ ID NO 200
<211> LENGTH: 42
<212> TYPE: PRT
<213> ORGANISM: Centruroides exilicauda

<400> SEQUENCE: 200

```
Asp Arg Asp Ser Cys Val Asp Lys Ser Arg Cys Ala Lys Tyr Gly Tyr
1               5                   10                  15

Tyr Gln Glu Cys Gln Asp Cys Cys Lys Lys Ala Gly His Ser Gly Gly
            20                  25                  30

Thr Cys Met Phe Phe Lys Cys Lys Cys Ala
        35                  40
```

<210> SEQ ID NO 201
<211> LENGTH: 197
<212> TYPE: DNA
<213> ORGANISM: Centruroides exilicauda
<220> FEATURE:
<221> NAME/KEY: CDS
<222> LOCATION: (1)..(132)
<223> OTHER INFORMATION: Product= Erg-channel modifier toxin precursor
<220> FEATURE:
<221> NAME/KEY: 3'UTR
<222> LOCATION: (133)..(197)
<223> OTHER INFORMATION:

<400> SEQUENCE: 201

```
gat aga gat agc tgt gtt gat aaa tca aaa tgc gga aaa tat gga tac       48
Asp Arg Asp Ser Cys Val Asp Lys Ser Lys Cys Gly Lys Tyr Gly Tyr
1               5                   10                  15

tac ggt caa tgt gat gaa tgt tgc aag aaa gct gga gac cgt gca gga       96
Tyr Gly Gln Cys Asp Glu Cys Cys Lys Lys Ala Gly Asp Arg Ala Gly
            20                  25                  30

atc tgc gag tat tac aag tgt aaa tgt aac cca taa actcgaatgt          142
Ile Cys Glu Tyr Tyr Lys Cys Lys Cys Asn Pro
```

-continued

```
        35                  40

gaattaagaa tatcaaagct ggaagctgtt taaaaagtga aaaataaaga ttatt         197


<210> SEQ ID NO 202
<211> LENGTH: 43
<212> TYPE: PRT
<213> ORGANISM: Centruroides exilicauda

<400> SEQUENCE: 202

Asp Arg Asp Ser Cys Val Asp Lys Ser Lys Cys Gly Lys Tyr Gly Tyr
1               5                   10                  15

Tyr Gly Gln Cys Asp Glu Cys Cys Lys Lys Ala Gly Asp Arg Ala Gly
            20                  25                  30

Ile Cys Glu Tyr Tyr Lys Cys Lys Cys Asn Pro
        35                  40


<210> SEQ ID NO 203
<211> LENGTH: 129
<212> TYPE: DNA
<213> ORGANISM: Centruroides exilicauda
<220> FEATURE:
<221> NAME/KEY: CDS
<222> LOCATION: (1)..(129)
<223> OTHER INFORMATION: Product= Erg-channel modifier toxin

<400> SEQUENCE: 203

gat aga gat agc tgt gtt gat aaa tca aaa tgc gga aaa tat gga tac       48
Asp Arg Asp Ser Cys Val Asp Lys Ser Lys Cys Gly Lys Tyr Gly Tyr
1               5                   10                  15

tac ggt caa tgt gat gaa tgt tgc aag aaa gct gga gac cgt gca gga       96
Tyr Gly Gln Cys Asp Glu Cys Cys Lys Lys Ala Gly Asp Arg Ala Gly
            20                  25                  30

atc tgc gag tat tac aag tgt aaa tgt aac cca                          129
Ile Cys Glu Tyr Tyr Lys Cys Lys Cys Asn Pro
        35                  40


<210> SEQ ID NO 204
<211> LENGTH: 43
<212> TYPE: PRT
<213> ORGANISM: Centruroides exilicauda

<400> SEQUENCE: 204

Asp Arg Asp Ser Cys Val Asp Lys Ser Lys Cys Gly Lys Tyr Gly Tyr
1               5                   10                  15

Tyr Gly Gln Cys Asp Glu Cys Cys Lys Lys Ala Gly Asp Arg Ala Gly
            20                  25                  30

Ile Cys Glu Tyr Tyr Lys Cys Lys Cys Asn Pro
        35                  40


<210> SEQ ID NO 205
<211> LENGTH: 196
<212> TYPE: DNA
<213> ORGANISM: Centruroides exilicauda
<220> FEATURE:
<221> NAME/KEY: CDS
<222> LOCATION: (1)..(132)
<223> OTHER INFORMATION: Product= Erg-channel modifier toxin precursor
<220> FEATURE:
<221> NAME/KEY: 3'UTR
<222> LOCATION: (133)..(196)
<223> OTHER INFORMATION:

<400> SEQUENCE: 205

gat aga gat agc tgt gtt gat aaa tca aaa tgc gca aaa tat gga tac       48
```

-continued

```
Asp Arg Asp Ser Cys Val Asp Lys Ser Lys Cys Ala Lys Tyr Gly Tyr
1               5                   10                  15

tac tat caa tgt gat gaa tgt tgc aag aaa gct gga gac cgt gca gga       96
Tyr Tyr Gln Cys Asp Glu Cys Cys Lys Lys Ala Gly Asp Arg Ala Gly
            20                  25                  30

acc tgc gag tat ttc aag tgt aaa tgt aac cca taa actcgaatgt           142
Thr Cys Glu Tyr Phe Lys Cys Lys Cys Asn Pro
        35                  40

gaattaagaa tatcaaagct ggaagctgtt taagaagtga aaaataaaga ttat          196


<210> SEQ ID NO 206
<211> LENGTH: 43
<212> TYPE: PRT
<213> ORGANISM: Centruroides exilicauda

<400> SEQUENCE: 206

Asp Arg Asp Ser Cys Val Asp Lys Ser Lys Cys Ala Lys Tyr Gly Tyr
1               5                   10                  15

Tyr Tyr Gln Cys Asp Glu Cys Cys Lys Lys Ala Gly Asp Arg Ala Gly
            20                  25                  30

Thr Cys Glu Tyr Phe Lys Cys Lys Cys Asn Pro
        35                  40


<210> SEQ ID NO 207
<211> LENGTH: 129
<212> TYPE: DNA
<213> ORGANISM: Centruroides exilicauda
<220> FEATURE:
<221> NAME/KEY: CDS
<222> LOCATION: (1)..(129)
<223> OTHER INFORMATION: Product= Erg-channel modifier toxin

<400> SEQUENCE: 207

gat aga gat agc tgt gtt gat aaa tca aaa tgc gca aaa tat gga tac       48
Asp Arg Asp Ser Cys Val Asp Lys Ser Lys Cys Ala Lys Tyr Gly Tyr
1               5                   10                  15

tac tat caa tgt gat gaa tgt tgc aag aaa gct gga gac cgt gca gga       96
Tyr Tyr Gln Cys Asp Glu Cys Cys Lys Lys Ala Gly Asp Arg Ala Gly
            20                  25                  30

acc tgc gag tat ttc aag tgt aaa tgt aac cca                          129
Thr Cys Glu Tyr Phe Lys Cys Lys Cys Asn Pro
        35                  40


<210> SEQ ID NO 208
<211> LENGTH: 43
<212> TYPE: PRT
<213> ORGANISM: Centruroides exilicauda

<400> SEQUENCE: 208

Asp Arg Asp Ser Cys Val Asp Lys Ser Lys Cys Ala Lys Tyr Gly Tyr
1               5                   10                  15

Tyr Tyr Gln Cys Asp Glu Cys Cys Lys Lys Ala Gly Asp Arg Ala Gly
            20                  25                  30

Thr Cys Glu Tyr Phe Lys Cys Lys Cys Asn Pro
        35                  40


<210> SEQ ID NO 209
<211> LENGTH: 196
<212> TYPE: DNA
<213> ORGANISM: Centruroides exilicauda
<220> FEATURE:
<221> NAME/KEY: CDS
<222> LOCATION: (1)..(132)
```

-continued

```
<223> OTHER INFORMATION: Product= Erg-channel modifier toxin precursor
<220> FEATURE:
<221> NAME/KEY: 3'UTR
<222> LOCATION: (133)..(196)
<223> OTHER INFORMATION:

<400> SEQUENCE: 209

gat aga gat agc tgt gtt gat aaa tca caa tgc gca aaa tat gga tac       48
Asp Arg Asp Ser Cys Val Asp Lys Ser Gln Cys Ala Lys Tyr Gly Tyr
1               5                   10                  15

tac tat caa tgt gat gaa tgt tgc aag aaa gct gga gac cgt gca gga       96
Tyr Tyr Gln Cys Asp Glu Cys Cys Lys Lys Ala Gly Asp Arg Ala Gly
            20                  25                  30

acc tgc gag tat ttc aag tgt aaa tgt aac cca taa actcgaatgt          142
Thr Cys Glu Tyr Phe Lys Cys Lys Cys Asn Pro
        35                  40

gaattaagaa tatcaaagct ggaagctgtt taagaagtga aaaataaaga ttag         196


<210> SEQ ID NO 210
<211> LENGTH: 43
<212> TYPE: PRT
<213> ORGANISM: Centruroides exilicauda

<400> SEQUENCE: 210

Asp Arg Asp Ser Cys Val Asp Lys Ser Gln Cys Ala Lys Tyr Gly Tyr
1               5                   10                  15

Tyr Tyr Gln Cys Asp Glu Cys Cys Lys Lys Ala Gly Asp Arg Ala Gly
            20                  25                  30

Thr Cys Glu Tyr Phe Lys Cys Lys Cys Asn Pro
        35                  40


<210> SEQ ID NO 211
<211> LENGTH: 129
<212> TYPE: DNA
<213> ORGANISM: Centruroides exilicauda
<220> FEATURE:
<221> NAME/KEY: CDS
<222> LOCATION: (1)..(129)
<223> OTHER INFORMATION: Product= Erg-channel modifier toxin

<400> SEQUENCE: 211

gat aga gat agc tgt gtt gat aaa tca caa tgc gca aaa tat gga tac       48
Asp Arg Asp Ser Cys Val Asp Lys Ser Gln Cys Ala Lys Tyr Gly Tyr
1               5                   10                  15

tac tat caa tgt gat gaa tgt tgc aag aaa gct gga gac cgt gca gga       96
Tyr Tyr Gln Cys Asp Glu Cys Cys Lys Lys Ala Gly Asp Arg Ala Gly
            20                  25                  30

acc tgc gag tat ttc aag tgt aaa tgt aac cca                         129
Thr Cys Glu Tyr Phe Lys Cys Lys Cys Asn Pro
        35                  40


<210> SEQ ID NO 212
<211> LENGTH: 43
<212> TYPE: PRT
<213> ORGANISM: Centruroides exilicauda

<400> SEQUENCE: 212

Asp Arg Asp Ser Cys Val Asp Lys Ser Gln Cys Ala Lys Tyr Gly Tyr
1               5                   10                  15

Tyr Tyr Gln Cys Asp Glu Cys Cys Lys Lys Ala Gly Asp Arg Ala Gly
            20                  25                  30

Thr Cys Glu Tyr Phe Lys Cys Lys Cys Asn Pro
        35                  40
```

-continued

<210> SEQ ID NO 213
<211> LENGTH: 202
<212> TYPE: DNA
<213> ORGANISM: Centruroides limpidus limpidus
<220> FEATURE:
<221> NAME/KEY: CDS
<222> LOCATION: (1)..(129)
<223> OTHER INFORMATION: Product= Erg-channel modifier toxin precursor
<220> FEATURE:
<221> NAME/KEY: 3'UTR
<222> LOCATION: (130)..(202)
<223> OTHER INFORMATION:

<400> SEQUENCE: 213 gat aga gat agc tgt gtt gat aaa tca cga tgc tca aaa tat gga tac 48
Asp Arg Asp Ser Cys Val Asp Lys Ser Arg Cys Ser Lys Tyr Gly Tyr
1 5 10 15 tac caa gag tgt cag gat tgt tgc aag aaa gct gga cac aat gga gga 96
Tyr Gln Glu Cys Gln Asp Cys Cys Lys Lys Ala Gly His Asn Gly Gly
20 25 30 acc tgc atg ttt ttc aag tgt aaa tgt gcg taa actcgaagat gaattaacaa 149
Thr Cys Met Phe Phe Lys Cys Lys Cys Ala
35 40 tatcaaagct gtaatctatt tatgaagtaa aaaataaagt ttttgaaatt tcc 202

<210> SEQ ID NO 214
<211> LENGTH: 42
<212> TYPE: PRT
<213> ORGANISM: Centruroides limpidus limpidus

<400> SEQUENCE: 214

Asp Arg Asp Ser Cys Val Asp Lys Ser Arg Cys Ser Lys Tyr Gly Tyr
1 5 10 15

Tyr Gln Glu Cys Gln Asp Cys Cys Lys Lys Ala Gly His Asn Gly Gly
20 25 30

Thr Cys Met Phe Phe Lys Cys Lys Cys Ala
35 40

<210> SEQ ID NO 215
<211> LENGTH: 126
<212> TYPE: DNA
<213> ORGANISM: Centruroides limpidus limpidus
<220> FEATURE:
<221> NAME/KEY: CDS
<222> LOCATION: (1)..(126)
<223> OTHER INFORMATION: Product= Erg-channel modifier toxin

<400> SEQUENCE: 215 gat aga gat agc tgt gtt gat aaa tca cga tgc tca aaa tat gga tac 48
Asp Arg Asp Ser Cys Val Asp Lys Ser Arg Cys Ser Lys Tyr Gly Tyr
1 5 10 15 tac caa gag tgt cag gat tgt tgc aag aaa gct gga cac aat gga gga 96
Tyr Gln Glu Cys Gln Asp Cys Cys Lys Lys Ala Gly His Asn Gly Gly
20 25 30 acc tgc atg ttt ttc aag tgt aaa tgt gcg 126
Thr Cys Met Phe Phe Lys Cys Lys Cys Ala
35 40

<210> SEQ ID NO 216
<211> LENGTH: 42
<212> TYPE: PRT
<213> ORGANISM: Centruroides limpidus limpidus

<400> SEQUENCE: 216

-continued

```
Asp Arg Asp Ser Cys Val Asp Lys Ser Arg Cys Ser Lys Tyr Gly Tyr
1               5                   10                  15

Tyr Gln Glu Cys Gln Asp Cys Cys Lys Lys Ala Gly His Asn Gly Gly
            20                  25                  30

Thr Cys Met Phe Phe Lys Cys Lys Cys Ala
        35                  40


<210> SEQ ID NO 217
<211> LENGTH: 207
<212> TYPE: DNA
<213> ORGANISM: Centruroides limpidus limpidus
<220> FEATURE:
<221> NAME/KEY: CDS
<222> LOCATION: (1)..(132)
<223> OTHER INFORMATION: Product= Erg-channel modifier toxin precursor
<220> FEATURE:
<221> NAME/KEY: 3'UTR
<222> LOCATION: (133)..(207)
<223> OTHER INFORMATION:

<400> SEQUENCE: 217

gat aga gat agc tgt gtt gat aaa tca aaa tgt tca aaa tat gga tac       48
Asp Arg Asp Ser Cys Val Asp Lys Ser Lys Cys Ser Lys Tyr Gly Tyr
1               5                   10                  15

tac ggt caa tgt gat gag tgt tgc aag aaa gct gga gac cgt gca gga       96
Tyr Gly Gln Cys Asp Glu Cys Cys Lys Lys Ala Gly Asp Arg Ala Gly
            20                  25                  30

aac tgc gtg tat ttc aag tgt aaa tgt aac cca taa actcgaatgt           142
Asn Cys Val Tyr Phe Lys Cys Lys Cys Asn Pro
        35                  40

gaattaagaa tatcaaagct ggaagctatt taagaagtga aaaataaaga ttattaaatt    202
tccgc                                                                207


<210> SEQ ID NO 218
<211> LENGTH: 43
<212> TYPE: PRT
<213> ORGANISM: Centruroides limpidus limpidus

<400> SEQUENCE: 218

Asp Arg Asp Ser Cys Val Asp Lys Ser Lys Cys Ser Lys Tyr Gly Tyr
1               5                   10                  15

Tyr Gly Gln Cys Asp Glu Cys Cys Lys Lys Ala Gly Asp Arg Ala Gly
            20                  25                  30

Asn Cys Val Tyr Phe Lys Cys Lys Cys Asn Pro
        35                  40


<210> SEQ ID NO 219
<211> LENGTH: 129
<212> TYPE: DNA
<213> ORGANISM: Centruroides limpidus limpidus
<220> FEATURE:
<221> NAME/KEY: CDS
<222> LOCATION: (1)..(129)
<223> OTHER INFORMATION: Product= Erg-channel modifier toxin

<400> SEQUENCE: 219

gat aga gat agc tgt gtt gat aaa tca aaa tgt tca aaa tat gga tac       48
Asp Arg Asp Ser Cys Val Asp Lys Ser Lys Cys Ser Lys Tyr Gly Tyr
1               5                   10                  15

tac ggt caa tgt gat gag tgt tgc aag aaa gct gga gac cgt gca gga       96
Tyr Gly Gln Cys Asp Glu Cys Cys Lys Lys Ala Gly Asp Arg Ala Gly
            20                  25                  30

aac tgc gtg tat ttc aag tgt aaa tgt aac cca                          129
```

-continued

```
Asn Cys Val Tyr Phe Lys Cys Lys Cys Asn Pro
        35                  40


<210> SEQ ID NO 220
<211> LENGTH: 43
<212> TYPE: PRT
<213> ORGANISM: Centruroides limpidus limpidus

<400> SEQUENCE: 220

Asp Arg Asp Ser Cys Val Asp Lys Ser Lys Cys Ser Lys Tyr Gly Tyr
1               5                   10                  15

Tyr Gly Gln Cys Asp Glu Cys Cys Lys Lys Ala Gly Asp Arg Ala Gly
            20                  25                  30

Asn Cys Val Tyr Phe Lys Cys Lys Cys Asn Pro
        35                  40


<210> SEQ ID NO 221
<211> LENGTH: 209
<212> TYPE: DNA
<213> ORGANISM: Centruroides limpidus limpidus
<220> FEATURE:
<221> NAME/KEY: CDS
<222> LOCATION: (1)..(132)
<223> OTHER INFORMATION: Product= Erg-channel modifier toxin precursor
<220> FEATURE:
<221> NAME/KEY: 3'UTR
<222> LOCATION: (133)..(209)
<223> OTHER INFORMATION: Product= Erg-channel modifier toxin

<400> SEQUENCE: 221

gat agg gat agc tgc gtt gac aaa tca aaa tgt tca aaa tat gga tac       48
Asp Arg Asp Ser Cys Val Asp Lys Ser Lys Cys Ser Lys Tyr Gly Tyr
1               5                   10                  15

tat ggt caa tgt gat aag tgt tgc aag aaa gct gga gac cgt gca gga       96
Tyr Gly Gln Cys Asp Lys Cys Cys Lys Lys Ala Gly Asp Arg Ala Gly
            20                  25                  30

aac tgc gtg tat ttc aag tgt aaa tgt aac caa taa actcgaatgt           142
Asn Cys Val Tyr Phe Lys Cys Lys Cys Asn Gln
        35                  40

gaacttaaga atatcaaagc tggaagctta tttaagaagt gaaaaataaa gattattaaa    202

taagaga                                                              209


<210> SEQ ID NO 222
<211> LENGTH: 43
<212> TYPE: PRT
<213> ORGANISM: Centruroides limpidus limpidus

<400> SEQUENCE: 222

Asp Arg Asp Ser Cys Val Asp Lys Ser Lys Cys Ser Lys Tyr Gly Tyr
1               5                   10                  15

Tyr Gly Gln Cys Asp Lys Cys Cys Lys Lys Ala Gly Asp Arg Ala Gly
            20                  25                  30

Asn Cys Val Tyr Phe Lys Cys Lys Cys Asn Gln
        35                  40


<210> SEQ ID NO 223
<211> LENGTH: 129
<212> TYPE: DNA
<213> ORGANISM: Centruroides limpidus limpidus
<220> FEATURE:
<221> NAME/KEY: CDS
<222> LOCATION: (1)..(129)
<223> OTHER INFORMATION: Product= Erg-channel modifier toxin
```

-continued

<400> SEQUENCE: 223

```
gat agg gat agc tgc gtt gac aaa tca aaa tgt tca aaa tat gga tac       48
Asp Arg Asp Ser Cys Val Asp Lys Ser Lys Cys Ser Lys Tyr Gly Tyr
1               5                   10                  15

tat ggt caa tgt gat aag tgt tgc aag aaa gct gga gac cgt gca gga       96
Tyr Gly Gln Cys Asp Lys Cys Cys Lys Lys Ala Gly Asp Arg Ala Gly
            20                  25                  30

aac tgc gtg tat ttc aag tgt aaa tgt aac caa                          129
Asn Cys Val Tyr Phe Lys Cys Lys Cys Asn Gln
        35                  40
```

<210> SEQ ID NO 224
<211> LENGTH: 43
<212> TYPE: PRT
<213> ORGANISM: Centruroides limpidus limpidus

<400> SEQUENCE: 224

```
Asp Arg Asp Ser Cys Val Asp Lys Ser Lys Cys Ser Lys Tyr Gly Tyr
1               5                   10                  15

Tyr Gly Gln Cys Asp Lys Cys Cys Lys Lys Ala Gly Asp Arg Ala Gly
            20                  25                  30

Asn Cys Val Tyr Phe Lys Cys Lys Cys Asn Gln
        35                  40
```

<210> SEQ ID NO 225
<211> LENGTH: 141
<212> TYPE: DNA
<213> ORGANISM: Centruroides limpidus limpidus
<220> FEATURE:
<221> NAME/KEY: CDS
<222> LOCATION: (1)..(132)
<223> OTHER INFORMATION: Product= Erg-channel modifier toxin precursor
<220> FEATURE:
<221> NAME/KEY: 3'UTR
<222> LOCATION: (1)..(132)
<223> OTHER INFORMATION:

<400> SEQUENCE: 225

```
gat agg gat agc tgc gtt gac aaa tca aaa tgc gca aaa tat gga tac       48
Asp Arg Asp Ser Cys Val Asp Lys Ser Lys Cys Ala Lys Tyr Gly Tyr
1               5                   10                  15

tat ggt caa tgt gat gag tgt tgc aag aaa gct gga gac cgt gca gga       96
Tyr Gly Gln Cys Asp Glu Cys Cys Lys Lys Ala Gly Asp Arg Ala Gly
            20                  25                  30

aac tgc gtg tat tta aag tgt aaa tgt aac caa taa actcgaatg            141
Asn Cys Val Tyr Leu Lys Cys Lys Cys Asn Gln
        35                  40
```

<210> SEQ ID NO 226
<211> LENGTH: 43
<212> TYPE: PRT
<213> ORGANISM: Centruroides limpidus limpidus

<400> SEQUENCE: 226

```
Asp Arg Asp Ser Cys Val Asp Lys Ser Lys Cys Ala Lys Tyr Gly Tyr
1               5                   10                  15

Tyr Gly Gln Cys Asp Glu Cys Cys Lys Lys Ala Gly Asp Arg Ala Gly
            20                  25                  30

Asn Cys Val Tyr Leu Lys Cys Lys Cys Asn Gln
        35                  40
```

<210> SEQ ID NO 227
<211> LENGTH: 129

```
<212> TYPE: DNA
<213> ORGANISM: Centruroides limpidus limpidus
<220> FEATURE:
<221> NAME/KEY: CDS
<222> LOCATION: (1)..(129)
<223> OTHER INFORMATION: Product= Erg-channel modifier toxin

<400> SEQUENCE: 227

gat agg gat agc tgc gtt gac aaa tca aaa tgc gca aaa tat gga tac       48
Asp Arg Asp Ser Cys Val Asp Lys Ser Lys Cys Ala Lys Tyr Gly Tyr
1               5                   10                  15

tat ggt caa tgt gat gag tgt tgc aag aaa gct gga gac cgt gca gga       96
Tyr Gly Gln Cys Asp Glu Cys Cys Lys Lys Ala Gly Asp Arg Ala Gly
            20                  25                  30

aac tgc gtg tat tta aag tgt aaa tgt aac caa                          129
Asn Cys Val Tyr Leu Lys Cys Lys Cys Asn Gln
        35                  40


<210> SEQ ID NO 228
<211> LENGTH: 43
<212> TYPE: PRT
<213> ORGANISM: Centruroides limpidus limpidus

<400> SEQUENCE: 228

Asp Arg Asp Ser Cys Val Asp Lys Ser Lys Cys Ala Lys Tyr Gly Tyr
1               5                   10                  15

Tyr Gly Gln Cys Asp Glu Cys Cys Lys Lys Ala Gly Asp Arg Ala Gly
            20                  25                  30

Asn Cys Val Tyr Leu Lys Cys Lys Cys Asn Gln
        35                  40


<210> SEQ ID NO 229
<211> LENGTH: 244
<212> TYPE: DNA
<213> ORGANISM: Centruroides noxius
<220> FEATURE:
<221> NAME/KEY: CDS
<222> LOCATION: (1)..(132)
<223> OTHER INFORMATION: Product= Erg-channel modifier toxin precursor
<220> FEATURE:
<221> NAME/KEY: 3'UTR
<222> LOCATION: (133)..(244)
<223> OTHER INFORMATION:

<400> SEQUENCE: 229

gat aga gat agc tgt gtt gat aaa tca aaa tgc gga aaa tat gga tac       48
Asp Arg Asp Ser Cys Val Asp Lys Ser Lys Cys Gly Lys Tyr Gly Tyr
1               5                   10                  15

tac ggt caa tgt gat gag tgt tgc aag aaa gct gga gac cgt gca gga       96
Tyr Gly Gln Cys Asp Glu Cys Cys Lys Lys Ala Gly Asp Arg Ala Gly
            20                  25                  30

acc tgc gtg tat tac aag tgt aaa tgt aac cca taa actcgaatgt          142
Thr Cys Val Tyr Tyr Lys Cys Lys Cys Asn Pro
        35                  40

gaattaagaa tatcaaagct ggaagctgtt taagaagtga aaaataagat tattaaattt    202

ccgcacaaac caaccaaaaa aaagtatcga tcgtatcgta tc                       244


<210> SEQ ID NO 230
<211> LENGTH: 43
<212> TYPE: PRT
<213> ORGANISM: Centruroides noxius

<400> SEQUENCE: 230

Asp Arg Asp Ser Cys Val Asp Lys Ser Lys Cys Gly Lys Tyr Gly Tyr
```

-continued

```
1               5                   10                  15

Tyr Gly Gln Cys Asp Glu Cys Cys Lys Lys Ala Gly Asp Arg Ala Gly
            20                  25                  30

Thr Cys Val Tyr Tyr Lys Cys Lys Cys Asn Pro
        35                  40


<210> SEQ ID NO 231
<211> LENGTH: 129
<212> TYPE: DNA
<213> ORGANISM: Centruroides noxius
<220> FEATURE:
<221> NAME/KEY: CDS
<222> LOCATION: (1)..(129)
<223> OTHER INFORMATION: Product= Erg-channel modifier toxin

<400> SEQUENCE: 231

gat aga gat agc tgt gtt gat aaa tca aaa tgc gga aaa tat gga tac       48
Asp Arg Asp Ser Cys Val Asp Lys Ser Lys Cys Gly Lys Tyr Gly Tyr
1               5                   10                  15

tac ggt caa tgt gat gag tgt tgc aag aaa gct gga gac cgt gca gga       96
Tyr Gly Gln Cys Asp Glu Cys Cys Lys Lys Ala Gly Asp Arg Ala Gly
            20                  25                  30

acc tgc gtg tat tac aag tgt aaa tgt aac cca                          129
Thr Cys Val Tyr Tyr Lys Cys Lys Cys Asn Pro
        35                  40


<210> SEQ ID NO 232
<211> LENGTH: 43
<212> TYPE: PRT
<213> ORGANISM: Centruroides noxius

<400> SEQUENCE: 232

Asp Arg Asp Ser Cys Val Asp Lys Ser Lys Cys Gly Lys Tyr Gly Tyr
1               5                   10                  15

Tyr Gly Gln Cys Asp Glu Cys Cys Lys Lys Ala Gly Asp Arg Ala Gly
            20                  25                  30

Thr Cys Val Tyr Tyr Lys Cys Lys Cys Asn Pro
        35                  40


<210> SEQ ID NO 233
<211> LENGTH: 212
<212> TYPE: DNA
<213> ORGANISM: Centruroides noxius
<220> FEATURE:
<221> NAME/KEY: CDS
<222> LOCATION: (1)..(132)
<223> OTHER INFORMATION: Product= Erg-channel modifier toxin precursor
<220> FEATURE:
<221> NAME/KEY: 3'UTR
<222> LOCATION: (133)..(212)
<223> OTHER INFORMATION:

<400> SEQUENCE: 233

gat aga gat agc tgt gtt gat aaa tca caa tgc gga aaa tat gga tac       48
Asp Arg Asp Ser Cys Val Asp Lys Ser Gln Cys Gly Lys Tyr Gly Tyr
1               5                   10                  15

tac ggt caa tgt gat gag tgt tgc aag aaa gct gga gaa cgt gta gga       96
Tyr Gly Gln Cys Asp Glu Cys Cys Lys Lys Ala Gly Glu Arg Val Gly
            20                  25                  30

acc tgc gtg tat tac aag tgt aaa tgt aac cca taa actcgaatgt          142
Thr Cys Val Tyr Tyr Lys Cys Lys Cys Asn Pro
        35                  40

gaattaagaa tatcaaagct ggaagctgtt taagaagtga aaaataaaga ttattaaatt    202
```

-continued

```
tccgcaaatt                                                   212


<210> SEQ ID NO 234
<211> LENGTH: 43
<212> TYPE: PRT
<213> ORGANISM: Centruroides noxius

<400> SEQUENCE: 234

Asp Arg Asp Ser Cys Val Asp Lys Ser Gln Cys Gly Lys Tyr Gly Tyr
1               5                   10                  15

Tyr Gly Gln Cys Asp Glu Cys Cys Lys Lys Ala Gly Glu Arg Val Gly
            20                  25                  30

Thr Cys Val Tyr Tyr Lys Cys Lys Cys Asn Pro
        35                  40


<210> SEQ ID NO 235
<211> LENGTH: 129
<212> TYPE: DNA
<213> ORGANISM: Centruroides noxius
<220> FEATURE:
<221> NAME/KEY: CDS
<222> LOCATION: (1)..(129)
<223> OTHER INFORMATION: Product= Erg-channel modifier toxin

<400> SEQUENCE: 235

gat aga gat agc tgt gtt gat aaa tca caa tgc gga aaa tat gga tac       48
Asp Arg Asp Ser Cys Val Asp Lys Ser Gln Cys Gly Lys Tyr Gly Tyr
1               5                   10                  15

tac ggt caa tgt gat gag tgt tgc aag aaa gct gga gaa cgt gta gga       96
Tyr Gly Gln Cys Asp Glu Cys Cys Lys Lys Ala Gly Glu Arg Val Gly
            20                  25                  30

acc tgc gtg tat tac aag tgt aaa tgt aac cca                          129
Thr Cys Val Tyr Tyr Lys Cys Lys Cys Asn Pro
        35                  40


<210> SEQ ID NO 236
<211> LENGTH: 43
<212> TYPE: PRT
<213> ORGANISM: Centruroides noxius

<400> SEQUENCE: 236

Asp Arg Asp Ser Cys Val Asp Lys Ser Gln Cys Gly Lys Tyr Gly Tyr
1               5                   10                  15

Tyr Gly Gln Cys Asp Glu Cys Cys Lys Lys Ala Gly Glu Arg Val Gly
            20                  25                  30

Thr Cys Val Tyr Tyr Lys Cys Lys Cys Asn Pro
        35                  40


<210> SEQ ID NO 237
<211> LENGTH: 212
<212> TYPE: DNA
<213> ORGANISM: Centruroides noxius
<220> FEATURE:
<221> NAME/KEY: CDS
<222> LOCATION: (1)..(132)
<223> OTHER INFORMATION: Product= Erg-channel modifier toxin precursor
<220> FEATURE:
<221> NAME/KEY: 3'UTR
<222> LOCATION: (133)..(212)
<223> OTHER INFORMATION:

<400> SEQUENCE: 237

gat aga gat agc tgt gtt gat aaa tca aaa tgc gga aaa tat gga tac       48
Asp Arg Asp Ser Cys Val Asp Lys Ser Lys Cys Gly Lys Tyr Gly Tyr
1               5                   10                  15
```

-continued

```
tac caa gag tgt cag gat tgt tgc aag aat gct gga cac aat gga gga       96
Tyr Gln Glu Cys Gln Asp Cys Cys Lys Asn Ala Gly His Asn Gly Gly
            20                  25                  30

acc tgc gtg tat tac aag tgt aaa tgt aac cca taa actcgaatgt          142
Thr Cys Val Tyr Tyr Lys Cys Lys Cys Asn Pro
        35                  40

gaattaagaa tatcaaagct ggaagctgtt taagaagtga aaaataaaga ttattaaatt    202

tccgcaaatt                                                           212


<210> SEQ ID NO 238
<211> LENGTH: 43
<212> TYPE: PRT
<213> ORGANISM: Centruroides noxius

<400> SEQUENCE: 238

Asp Arg Asp Ser Cys Val Asp Lys Ser Lys Cys Gly Lys Tyr Gly Tyr
1               5                   10                  15

Tyr Gln Glu Cys Gln Asp Cys Cys Lys Asn Ala Gly His Asn Gly Gly
            20                  25                  30

Thr Cys Val Tyr Tyr Lys Cys Lys Cys Asn Pro
        35                  40


<210> SEQ ID NO 239
<211> LENGTH: 129
<212> TYPE: DNA
<213> ORGANISM: Centruroides noxius
<220> FEATURE:
<221> NAME/KEY: CDS
<222> LOCATION: (1)..(129)
<223> OTHER INFORMATION: Product= Erg-channel modifier toxin

<400> SEQUENCE: 239

gat aga gat agc tgt gtt gat aaa tca aaa tgc gga aaa tat gga tac       48
Asp Arg Asp Ser Cys Val Asp Lys Ser Lys Cys Gly Lys Tyr Gly Tyr
1               5                   10                  15

tac caa gag tgt cag gat tgt tgc aag aat gct gga cac aat gga gga       96
Tyr Gln Glu Cys Gln Asp Cys Cys Lys Asn Ala Gly His Asn Gly Gly
            20                  25                  30

acc tgc gtg tat tac aag tgt aaa tgt aac cca                          129
Thr Cys Val Tyr Tyr Lys Cys Lys Cys Asn Pro
        35                  40


<210> SEQ ID NO 240
<211> LENGTH: 43
<212> TYPE: PRT
<213> ORGANISM: Centruroides noxius

<400> SEQUENCE: 240

Asp Arg Asp Ser Cys Val Asp Lys Ser Lys Cys Gly Lys Tyr Gly Tyr
1               5                   10                  15

Tyr Gln Glu Cys Gln Asp Cys Cys Lys Asn Ala Gly His Asn Gly Gly
            20                  25                  30

Thr Cys Val Tyr Tyr Lys Cys Lys Cys Asn Pro
        35                  40


<210> SEQ ID NO 241
<211> LENGTH: 194
<212> TYPE: DNA
<213> ORGANISM: Centruroides elegans
<220> FEATURE:
<221> NAME/KEY: CDS
<222> LOCATION: (1)..(129)
```

-continued

```
<223> OTHER INFORMATION: Product= Erg-channel modifier toxin precursor
<220> FEATURE:
<221> NAME/KEY: 3'UTR
<222> LOCATION: (130)..(194)
<223> OTHER INFORMATION:

<400> SEQUENCE: 241

gat aga gat agc tgt gtt gat aaa tca cga tgc gca aaa tat gga tac       48
Asp Arg Asp Ser Cys Val Asp Lys Ser Arg Cys Ala Lys Tyr Gly Tyr
1               5                   10                  15

tac caa gag tgt aca gat tgt tgc aag aaa tat gga cac aat ggg gga       96
Tyr Gln Glu Cys Thr Asp Cys Cys Lys Lys Tyr Gly His Asn Gly Gly
            20                  25                  30

acc tgc atg ttt ttc aag tgt aaa tgt gcg taa actcgaagat aaattaataa    149
Thr Cys Met Phe Phe Lys Cys Lys Cys Ala
        35                  40

tatcaaagct gtaagctatt tatgaagtga aaaataaaga ttatg                    194


<210> SEQ ID NO 242
<211> LENGTH: 42
<212> TYPE: PRT
<213> ORGANISM: Centruroides elegans

<400> SEQUENCE: 242

Asp Arg Asp Ser Cys Val Asp Lys Ser Arg Cys Ala Lys Tyr Gly Tyr
1               5                   10                  15

Tyr Gln Glu Cys Thr Asp Cys Cys Lys Lys Tyr Gly His Asn Gly Gly
            20                  25                  30

Thr Cys Met Phe Phe Lys Cys Lys Cys Ala
        35                  40


<210> SEQ ID NO 243
<211> LENGTH: 126
<212> TYPE: DNA
<213> ORGANISM: Centruroides elegans
<220> FEATURE:
<221> NAME/KEY: CDS
<222> LOCATION: (1)..(126)
<223> OTHER INFORMATION: Product= Erg-channel modifier toxin

<400> SEQUENCE: 243

gat aga gat agc tgt gtt gat aaa tca cga tgc gca aaa tat gga tac       48
Asp Arg Asp Ser Cys Val Asp Lys Ser Arg Cys Ala Lys Tyr Gly Tyr
1               5                   10                  15

tac caa gag tgt aca gat tgt tgc aag aaa tat gga cac aat ggg gga       96
Tyr Gln Glu Cys Thr Asp Cys Cys Lys Lys Tyr Gly His Asn Gly Gly
            20                  25                  30

acc tgc atg ttt ttc aag tgt aaa tgt gcg                              126
Thr Cys Met Phe Phe Lys Cys Lys Cys Ala
        35                  40


<210> SEQ ID NO 244
<211> LENGTH: 42
<212> TYPE: PRT
<213> ORGANISM: Centruroides elegans

<400> SEQUENCE: 244

Asp Arg Asp Ser Cys Val Asp Lys Ser Arg Cys Ala Lys Tyr Gly Tyr
1               5                   10                  15

Tyr Gln Glu Cys Thr Asp Cys Cys Lys Lys Tyr Gly His Asn Gly Gly
            20                  25                  30

Thr Cys Met Phe Phe Lys Cys Lys Cys Ala
        35                  40
```

-continued

<210> SEQ ID NO 245
<211> LENGTH: 197
<212> TYPE: DNA
<213> ORGANISM: Centruroides elegans
<220> FEATURE:
<221> NAME/KEY: CDS
<222> LOCATION: (1)..(132)
<223> OTHER INFORMATION: Product= Erg-channel modifier toxin precursor
<220> FEATURE:
<221> NAME/KEY: 3'UTR
<222> LOCATION: (133)..(197)
<223> OTHER INFORMATION:

<400> SEQUENCE: 245

```
gat aga gat agc tgt gtt gat aaa tca aga tgc gca aaa tat gga tac       48
Asp Arg Asp Ser Cys Val Asp Lys Ser Arg Cys Ala Lys Tyr Gly Tyr
1               5                   10                  15

tac caa cag tgt gaa att tgt tgc aag aaa gct gga cac aga gga gga       96
Tyr Gln Gln Cys Glu Ile Cys Cys Lys Lys Ala Gly His Arg Gly Gly
            20                  25                  30

acc tgc gaa ttt ttc aag tgt aaa tgt aaa gta taa actcgaatgt          142
Thr Cys Glu Phe Phe Lys Cys Lys Cys Lys Val
        35                  40

gaattaagaa tatcaaagct gggaactgtt tacgatgtga aaaataaaga ttatt        197
```

<210> SEQ ID NO 246
<211> LENGTH: 43
<212> TYPE: PRT
<213> ORGANISM: Centruroides elegans

<400> SEQUENCE: 246

```
Asp Arg Asp Ser Cys Val Asp Lys Ser Arg Cys Ala Lys Tyr Gly Tyr
1               5                   10                  15

Tyr Gln Gln Cys Glu Ile Cys Cys Lys Lys Ala Gly His Arg Gly Gly
            20                  25                  30

Thr Cys Glu Phe Phe Lys Cys Lys Cys Lys Val
        35                  40
```

<210> SEQ ID NO 247
<211> LENGTH: 129
<212> TYPE: DNA
<213> ORGANISM: Centruroides elegans
<220> FEATURE:
<221> NAME/KEY: CDS
<222> LOCATION: (1)..(129)
<223> OTHER INFORMATION: Product= Erg-channel modifier toxin

<400> SEQUENCE: 247

```
gat aga gat agc tgt gtt gat aaa tca aga tgc gca aaa tat gga tac       48
Asp Arg Asp Ser Cys Val Asp Lys Ser Arg Cys Ala Lys Tyr Gly Tyr
1               5                   10                  15

tac caa cag tgt gaa att tgt tgc aag aaa gct gga cac aga gga gga       96
Tyr Gln Gln Cys Glu Ile Cys Cys Lys Lys Ala Gly His Arg Gly Gly
            20                  25                  30

acc tgc gaa ttt ttc aag tgt aaa tgt aaa gta                          129
Thr Cys Glu Phe Phe Lys Cys Lys Cys Lys Val
        35                  40
```

<210> SEQ ID NO 248
<211> LENGTH: 43
<212> TYPE: PRT
<213> ORGANISM: Centruroides elegans

<400> SEQUENCE: 248

-continued

```
Asp Arg Asp Ser Cys Val Asp Lys Ser Arg Cys Ala Lys Tyr Gly Tyr
1               5                   10                  15

Tyr Gln Gln Cys Glu Ile Cys Cys Lys Lys Ala Gly His Arg Gly Gly
            20                  25                  30

Thr Cys Glu Phe Phe Lys Cys Lys Cys Lys Val
        35                  40


<210> SEQ ID NO 249
<211> LENGTH: 196
<212> TYPE: DNA
<213> ORGANISM: Centruroides elegans
<220> FEATURE:
<221> NAME/KEY: CDS
<222> LOCATION: (1)..(132)
<223> OTHER INFORMATION: Product= Erg-channel modifier toxin precursor
<220> FEATURE:
<221> NAME/KEY: 3'UTR
<222> LOCATION: (133)..(196)
<223> OTHER INFORMATION:

<400> SEQUENCE: 249

gat aga gat agc tgt gtt gat aaa tca aaa tgc gga aaa tat gga tac       48
Asp Arg Asp Ser Cys Val Asp Lys Ser Lys Cys Gly Lys Tyr Gly Tyr
1               5                   10                  15

tat cat caa tgt gat gag tgt tgc aag aaa gct gga gac cgt gca gga       96
Tyr His Gln Cys Asp Glu Cys Cys Lys Lys Ala Gly Asp Arg Ala Gly
            20                  25                  30

aac tgc gtg tat tac aag tgt aaa tgt aac cca taa actcgaatgt          142
Asn Cys Val Tyr Tyr Lys Cys Lys Cys Asn Pro
        35                  40

gaattaagaa tatgaaagat ggaagctgtt taagaagtga aaaataaaga ttat          196


<210> SEQ ID NO 250
<211> LENGTH: 43
<212> TYPE: PRT
<213> ORGANISM: Centruroides elegans

<400> SEQUENCE: 250

Asp Arg Asp Ser Cys Val Asp Lys Ser Lys Cys Gly Lys Tyr Gly Tyr
1               5                   10                  15

Tyr His Gln Cys Asp Glu Cys Cys Lys Lys Ala Gly Asp Arg Ala Gly
            20                  25                  30

Asn Cys Val Tyr Tyr Lys Cys Lys Cys Asn Pro
        35                  40


<210> SEQ ID NO 251
<211> LENGTH: 129
<212> TYPE: DNA
<213> ORGANISM: Centruroides elegans
<220> FEATURE:
<221> NAME/KEY: CDS
<222> LOCATION: (1)..(129)
<223> OTHER INFORMATION: Product= Erg-channel modifier toxin

<400> SEQUENCE: 251

gat aga gat agc tgt gtt gat aaa tca aaa tgc gga aaa tat gga tac       48
Asp Arg Asp Ser Cys Val Asp Lys Ser Lys Cys Gly Lys Tyr Gly Tyr
1               5                   10                  15

tat cat caa tgt gat gag tgt tgc aag aaa gct gga gac cgt gca gga       96
Tyr His Gln Cys Asp Glu Cys Cys Lys Lys Ala Gly Asp Arg Ala Gly
            20                  25                  30

aac tgc gtg tat tac aag tgt aaa tgt aac cca                          129
Asn Cys Val Tyr Tyr Lys Cys Lys Cys Asn Pro
```

-continued

```
        35                  40


<210> SEQ ID NO 252
<211> LENGTH: 43
<212> TYPE: PRT
<213> ORGANISM: Centruroides elegans

<400> SEQUENCE: 252

Asp Arg Asp Ser Cys Val Asp Lys Ser Lys Cys Gly Lys Tyr Gly Tyr
1               5                   10                  15

Tyr His Gln Cys Asp Glu Cys Cys Lys Lys Ala Gly Asp Arg Ala Gly
            20                  25                  30

Asn Cys Val Tyr Tyr Lys Cys Lys Cys Asn Pro
        35                  40


<210> SEQ ID NO 253
<211> LENGTH: 193
<212> TYPE: DNA
<213> ORGANISM: Centruroides gracilis
<220> FEATURE:
<221> NAME/KEY: CDS
<222> LOCATION: (1)..(129)
<223> OTHER INFORMATION: Product= Erg-channel modifier toxin precursor
<220> FEATURE:
<221> NAME/KEY: 3'UTR
<222> LOCATION: (130)..(193)
<223> OTHER INFORMATION:

<400> SEQUENCE: 253

gat aga gat agc tgt gtt gat aaa tca cga tgc gcg aaa tat gga cac       48
Asp Arg Asp Ser Cys Val Asp Lys Ser Arg Cys Ala Lys Tyr Gly His
1               5                   10                  15

tac caa gag tgt acg gat tgt tgc aag aaa tac gga cac aat gga gga       96
Tyr Gln Glu Cys Thr Asp Cys Cys Lys Lys Tyr Gly His Asn Gly Gly
            20                  25                  30

acc tgc atg ttc ttc aag tgt aaa tgt gcg taa actcgaagat gaattaataa    149
Thr Cys Met Phe Phe Lys Cys Lys Cys Ala
        35                  40

tataaaagct gtaagctatt tacgaagtga aaaataaaga ttat                     193


<210> SEQ ID NO 254
<211> LENGTH: 42
<212> TYPE: PRT
<213> ORGANISM: Centruroides gracilis

<400> SEQUENCE: 254

Asp Arg Asp Ser Cys Val Asp Lys Ser Arg Cys Ala Lys Tyr Gly His
1               5                   10                  15

Tyr Gln Glu Cys Thr Asp Cys Cys Lys Lys Tyr Gly His Asn Gly Gly
            20                  25                  30

Thr Cys Met Phe Phe Lys Cys Lys Cys Ala
        35                  40


<210> SEQ ID NO 255
<211> LENGTH: 126
<212> TYPE: DNA
<213> ORGANISM: Centruroides gracilis
<220> FEATURE:
<221> NAME/KEY: CDS
<222> LOCATION: (1)..(126)
<223> OTHER INFORMATION: Product= Erg-channel modifier toxin

<400> SEQUENCE: 255

gat aga gat agc tgt gtt gat aaa tca cga tgc gcg aaa tat gga cac       48
```

-continued

```
Asp Arg Asp Ser Cys Val Asp Lys Ser Arg Cys Ala Lys Tyr Gly His
1               5                   10                  15

tac caa gag tgt acg gat tgt tgc aag aaa tac gga cac aat gga gga       96
Tyr Gln Glu Cys Thr Asp Cys Cys Lys Lys Tyr Gly His Asn Gly Gly
            20                  25                  30

acc tgc atg ttc ttc aag tgt aaa tgt gcg                              126
Thr Cys Met Phe Phe Lys Cys Lys Cys Ala
        35                  40


<210> SEQ ID NO 256
<211> LENGTH: 42
<212> TYPE: PRT
<213> ORGANISM: Centruroides gracilis

<400> SEQUENCE: 256

Asp Arg Asp Ser Cys Val Asp Lys Ser Arg Cys Ala Lys Tyr Gly His
1               5                   10                  15

Tyr Gln Glu Cys Thr Asp Cys Cys Lys Lys Tyr Gly His Asn Gly Gly
            20                  25                  30

Thr Cys Met Phe Phe Lys Cys Lys Cys Ala
        35                  40


<210> SEQ ID NO 257
<211> LENGTH: 193
<212> TYPE: DNA
<213> ORGANISM: Centruroides gracilis
<220> FEATURE:
<221> NAME/KEY: CDS
<222> LOCATION: (1)..(129)
<223> OTHER INFORMATION: Product= Erg-channel modifier toxin precursor
<220> FEATURE:
<221> NAME/KEY: 3'UTR
<222> LOCATION: (130)..(193)
<223> OTHER INFORMATION:

<400> SEQUENCE: 257

gat aga gat agc tgt gtt gat aaa tca cga tgc caa aaa tat gga aac       48
Asp Arg Asp Ser Cys Val Asp Lys Ser Arg Cys Gln Lys Tyr Gly Asn
1               5                   10                  15

tac gct cag tgt acg gcc tgt tgc aag aag gct gga cac aat aaa gga       96
Tyr Ala Gln Cys Thr Ala Cys Cys Lys Lys Ala Gly His Asn Lys Gly
            20                  25                  30

acc tgc gac ttt ttc aag tgt aaa tgt acg taa tctcgaagaa gaattaatta    149
Thr Cys Asp Phe Phe Lys Cys Lys Cys Thr
        35                  40

tatcaaagct tggaaccaat taccgaagtg gaaaaattaa gaat                     193


<210> SEQ ID NO 258
<211> LENGTH: 42
<212> TYPE: PRT
<213> ORGANISM: Centruroides gracilis

<400> SEQUENCE: 258

Asp Arg Asp Ser Cys Val Asp Lys Ser Arg Cys Gln Lys Tyr Gly Asn
1               5                   10                  15

Tyr Ala Gln Cys Thr Ala Cys Cys Lys Lys Ala Gly His Asn Lys Gly
            20                  25                  30

Thr Cys Asp Phe Phe Lys Cys Lys Cys Thr
        35                  40


<210> SEQ ID NO 259
<211> LENGTH: 126
<212> TYPE: DNA
```

-continued

```
<213> ORGANISM: Centruroides gracilis
<220> FEATURE:
<221> NAME/KEY: CDS
<222> LOCATION: (1)..(126)
<223> OTHER INFORMATION: Product= Erg-channel modifier toxin

<400> SEQUENCE: 259

gat aga gat agc tgt gtt gat aaa tca cga tgc caa aaa tat gga aac       48
Asp Arg Asp Ser Cys Val Asp Lys Ser Arg Cys Gln Lys Tyr Gly Asn
1               5                   10                  15

tac gct cag tgt acg gcc tgt tgc aag aag gct gga cac aat aaa gga       96
Tyr Ala Gln Cys Thr Ala Cys Cys Lys Lys Ala Gly His Asn Lys Gly
            20                  25                  30

acc tgc gac ttt ttc aag tgt aaa tgt acg                              126
Thr Cys Asp Phe Phe Lys Cys Lys Cys Thr
        35                  40


<210> SEQ ID NO 260
<211> LENGTH: 42
<212> TYPE: PRT
<213> ORGANISM: Centruroides gracilis

<400> SEQUENCE: 260

Asp Arg Asp Ser Cys Val Asp Lys Ser Arg Cys Gln Lys Tyr Gly Asn
1               5                   10                  15

Tyr Ala Gln Cys Thr Ala Cys Cys Lys Lys Ala Gly His Asn Lys Gly
            20                  25                  30

Thr Cys Asp Phe Phe Lys Cys Lys Cys Thr
        35                  40


<210> SEQ ID NO 261
<211> LENGTH: 197
<212> TYPE: DNA
<213> ORGANISM: Centruroides gracilis
<220> FEATURE:
<221> NAME/KEY: CDS
<222> LOCATION: (1)..(141)
<223> OTHER INFORMATION: Product= Erg-channel modifier toxin precursor
      In the mature peptide, the last Ser is amidated, and the last Gly
      and the last basic aminoacid are cut
<220> FEATURE:
<221> NAME/KEY: 3'UTR
<222> LOCATION: (142)..(197)
<223> OTHER INFORMATION:

<400> SEQUENCE: 261

gat aga gat agc tgt gtt gat aaa tca cga tgc caa aaa tat gga ccc       48
Asp Arg Asp Ser Cys Val Asp Lys Ser Arg Cys Gln Lys Tyr Gly Pro
1               5                   10                  15

tac gga cag tgt acg gac tgt tgc aag aaa gct gga cac act gga gga       96
Tyr Gly Gln Cys Thr Asp Cys Cys Lys Lys Ala Gly His Thr Gly Gly
            20                  25                  30

acc tgc ata tat ttc aag tgt aaa tgt ggc gca gaa agt gga aga          141
Thr Cys Ile Tyr Phe Lys Cys Lys Cys Gly Ala Glu Ser Gly Arg
        35                  40                  45

tgaatttata atatcaaagc tgtaagctat ttacgaagtg aaaaataaag attatt        197


<210> SEQ ID NO 262
<211> LENGTH: 47
<212> TYPE: PRT
<213> ORGANISM: Centruroides gracilis

<400> SEQUENCE: 262

Asp Arg Asp Ser Cys Val Asp Lys Ser Arg Cys Gln Lys Tyr Gly Pro
1               5                   10                  15
```

-continued

```
Tyr Gly Gln Cys Thr Asp Cys Cys Lys Lys Ala Gly His Thr Gly Gly
            20                  25                  30

Thr Cys Ile Tyr Phe Lys Cys Lys Cys Gly Ala Glu Ser Gly Arg
        35                  40                  45
```

<210> SEQ ID NO 263
<211> LENGTH: 135
<212> TYPE: DNA
<213> ORGANISM: Centruroides gracilis
<220> FEATURE:
<221> NAME/KEY: CDS
<222> LOCATION: (1)..(135)
<223> OTHER INFORMATION: Product= Erg channel modifier toxin

<400> SEQUENCE: 263

```
gat aga gat agc tgt gtt gat aaa tca cga tgc caa aaa tat gga ccc       48
Asp Arg Asp Ser Cys Val Asp Lys Ser Arg Cys Gln Lys Tyr Gly Pro
1               5                   10                  15

tac gga cag tgt acg gac tgt tgc aag aaa gct gga cac act gga gga       96
Tyr Gly Gln Cys Thr Asp Cys Cys Lys Lys Ala Gly His Thr Gly Gly
            20                  25                  30

acc tgc ata tat ttc aag tgt aaa tgt ggc gca gaa agt                  135
Thr Cys Ile Tyr Phe Lys Cys Lys Cys Gly Ala Glu Ser
        35                  40                  45
```

<210> SEQ ID NO 264
<211> LENGTH: 45
<212> TYPE: PRT
<213> ORGANISM: Centruroides gracilis

<400> SEQUENCE: 264

```
Asp Arg Asp Ser Cys Val Asp Lys Ser Arg Cys Gln Lys Tyr Gly Pro
1               5                   10                  15

Tyr Gly Gln Cys Thr Asp Cys Cys Lys Lys Ala Gly His Thr Gly Gly
            20                  25                  30

Thr Cys Ile Tyr Phe Lys Cys Lys Cys Gly Ala Glu Ser
        35                  40                  45
```

<210> SEQ ID NO 265
<211> LENGTH: 194
<212> TYPE: DNA
<213> ORGANISM: Centruroides sculpturatus
<220> FEATURE:
<221> NAME/KEY: CDS
<222> LOCATION: (1)..(129)
<223> OTHER INFORMATION: Product= Erg-channel modifier toxin precursor
<220> FEATURE:
<221> NAME/KEY: 3'UTR
<222> LOCATION: (130)..(194)
<223> OTHER INFORMATION:

<400> SEQUENCE: 265

```
gat aga gat agc tgt gtt gat aaa tca cga tgc gca aaa tat gga tac       48
Asp Arg Asp Ser Cys Val Asp Lys Ser Arg Cys Ala Lys Tyr Gly Tyr
1               5                   10                  15

tac caa gag tgt cag gat tgt tgc aag aaa gct gga cat aat gga gga       96
Tyr Gln Glu Cys Gln Asp Cys Cys Lys Lys Ala Gly His Asn Gly Gly
            20                  25                  30

acc tgt atg ttt ttc aag tgt aaa tgt gcg taa actcgaagat gaattaataa    149
Thr Cys Met Phe Phe Lys Cys Lys Cys Ala
        35                  40

tatcaaagct gtaagctatt tatgaagtga aaaataaaga ttatt                    194
```

-continued

```
<210> SEQ ID NO 266
<211> LENGTH: 42
<212> TYPE: PRT
<213> ORGANISM: Centruroides sculpturatus

<400> SEQUENCE: 266

Asp Arg Asp Ser Cys Val Asp Lys Ser Arg Cys Ala Lys Tyr Gly Tyr
1               5                   10                  15

Tyr Gln Glu Cys Gln Asp Cys Cys Lys Lys Ala Gly His Asn Gly Gly
            20                  25                  30

Thr Cys Met Phe Phe Lys Cys Lys Cys Ala
        35                  40


<210> SEQ ID NO 267
<211> LENGTH: 126
<212> TYPE: DNA
<213> ORGANISM: Centruroides sculpturatus
<220> FEATURE:
<221> NAME/KEY: CDS
<222> LOCATION: (1)..(126)
<223> OTHER INFORMATION: Product= Erg-channel modifier toxin

<400> SEQUENCE: 267

gat aga gat agc tgt gtt gat aaa tca cga tgc gca aaa tat gga tac       48
Asp Arg Asp Ser Cys Val Asp Lys Ser Arg Cys Ala Lys Tyr Gly Tyr
1               5                   10                  15

tac caa gag tgt cag gat tgt tgc aag aaa gct gga cat aat gga gga       96
Tyr Gln Glu Cys Gln Asp Cys Cys Lys Lys Ala Gly His Asn Gly Gly
            20                  25                  30

acc tgt atg ttt ttc aag tgt aaa tgt gcg                              126
Thr Cys Met Phe Phe Lys Cys Lys Cys Ala
        35                  40


<210> SEQ ID NO 268
<211> LENGTH: 42
<212> TYPE: PRT
<213> ORGANISM: Centruroides sculpturatus

<400> SEQUENCE: 268

Asp Arg Asp Ser Cys Val Asp Lys Ser Arg Cys Ala Lys Tyr Gly Tyr
1               5                   10                  15

Tyr Gln Glu Cys Gln Asp Cys Cys Lys Lys Ala Gly His Asn Gly Gly
            20                  25                  30

Thr Cys Met Phe Phe Lys Cys Lys Cys Ala
        35                  40


<210> SEQ ID NO 269
<211> LENGTH: 197
<212> TYPE: DNA
<213> ORGANISM: Centruroides sculpturatus
<220> FEATURE:
<221> NAME/KEY: CDS
<222> LOCATION: (1)..(132)
<223> OTHER INFORMATION: precursorProduct= Erg-channel modifier toxin
<220> FEATURE:
<221> NAME/KEY: 3'UTR
<222> LOCATION: (133)..(197)
<223> OTHER INFORMATION:

<400> SEQUENCE: 269

gat aga gat agc tgt gtt gat aaa tca cga tgc gca aaa tat gga tac       48
Asp Arg Asp Ser Cys Val Asp Lys Ser Arg Cys Ala Lys Tyr Gly Tyr
1               5                   10                  15

tac ggt caa tgt gaa gtt tgt tgt aag aaa gct gga cat aga gga gga       96
Tyr Gly Gln Cys Glu Val Cys Cys Lys Lys Ala Gly His Arg Gly Gly
```

-continued

```
            20                  25                  30

acc tgc gat ttt ttc aag tgt aaa tgt aaa gta taa actcgaatgt           142
Thr Cys Asp Phe Phe Lys Cys Lys Cys Lys Val
        35                  40

gaattaagaa tatcaaagct gggaactgtt tacgaagtga aaaataaaga ttttg         197
```

```
<210> SEQ ID NO 270
<211> LENGTH: 43
<212> TYPE: PRT
<213> ORGANISM: Centruroides sculpturatus

<400> SEQUENCE: 270

Asp Arg Asp Ser Cys Val Asp Lys Ser Arg Cys Ala Lys Tyr Gly Tyr
1               5                   10                  15

Tyr Gly Gln Cys Glu Val Cys Cys Lys Lys Ala Gly His Arg Gly Gly
            20                  25                  30

Thr Cys Asp Phe Phe Lys Cys Lys Cys Lys Val
        35                  40
```

```
<210> SEQ ID NO 271
<211> LENGTH: 129
<212> TYPE: DNA
<213> ORGANISM: Centruroides sculpturatus
<220> FEATURE:
<221> NAME/KEY: CDS
<222> LOCATION: (1)..(129)
<223> OTHER INFORMATION: Product= Erg-channel modifier toxin

<400> SEQUENCE: 271

gat aga gat agc tgt gtt gat aaa tca cga tgc gca aaa tat gga tac       48
Asp Arg Asp Ser Cys Val Asp Lys Ser Arg Cys Ala Lys Tyr Gly Tyr
1               5                   10                  15

tac ggt caa tgt gaa gtt tgt tgt aag aaa gct gga cat aga gga gga       96
Tyr Gly Gln Cys Glu Val Cys Cys Lys Lys Ala Gly His Arg Gly Gly
            20                  25                  30

acc tgc gat ttt ttc aag tgt aaa tgt aaa gta                          129
Thr Cys Asp Phe Phe Lys Cys Lys Cys Lys Val
        35                  40
```

```
<210> SEQ ID NO 272
<211> LENGTH: 43
<212> TYPE: PRT
<213> ORGANISM: Centruroides sculpturatus

<400> SEQUENCE: 272

Asp Arg Asp Ser Cys Val Asp Lys Ser Arg Cys Ala Lys Tyr Gly Tyr
1               5                   10                  15

Tyr Gly Gln Cys Glu Val Cys Cys Lys Lys Ala Gly His Arg Gly Gly
            20                  25                  30

Thr Cys Asp Phe Phe Lys Cys Lys Cys Lys Val
        35                  40
```

```
<210> SEQ ID NO 273
<211> LENGTH: 197
<212> TYPE: DNA
<213> ORGANISM: Centruroides sculpturatus
<220> FEATURE:
<221> NAME/KEY: CDS
<222> LOCATION: (1)..(132)
<223> OTHER INFORMATION: Product= Erg-channel modifier toxin precursor
<220> FEATURE:
<221> NAME/KEY: 3'UTR
<222> LOCATION: (133)..(197)
<223> OTHER INFORMATION:
```

-continued

<400> SEQUENCE: 273

```
gat aga gat agc tgt gtt gat aaa tca cga tgc gga aaa tat gga tac       48
Asp Arg Asp Ser Cys Val Asp Lys Ser Arg Cys Gly Lys Tyr Gly Tyr
1               5                   10                  15

tac ggt caa tgt gat gac tgt tgc aag aaa gct gga gac cgt gca gga       96
Tyr Gly Gln Cys Asp Asp Cys Cys Lys Lys Ala Gly Asp Arg Ala Gly
            20                  25                  30

acc tgc gtg tat tac aag tgt aaa tgt aac cca taa actcgaatgt          142
Thr Cys Val Tyr Tyr Lys Cys Lys Cys Asn Pro
        35                  40

gaattaagaa tatcaaagct ggaagctgtt taagaagtga aaaataaaga ttatt        197
```

<210> SEQ ID NO 274
<211> LENGTH: 43
<212> TYPE: PRT
<213> ORGANISM: Centruroides sculpturatus

<400> SEQUENCE: 274

```
Asp Arg Asp Ser Cys Val Asp Lys Ser Arg Cys Gly Lys Tyr Gly Tyr
1               5                   10                  15

Tyr Gly Gln Cys Asp Asp Cys Cys Lys Lys Ala Gly Asp Arg Ala Gly
            20                  25                  30

Thr Cys Val Tyr Tyr Lys Cys Lys Cys Asn Pro
        35                  40
```

<210> SEQ ID NO 275
<211> LENGTH: 129
<212> TYPE: DNA
<213> ORGANISM: Centruroides sculpturatus
<220> FEATURE:
<221> NAME/KEY: CDS
<222> LOCATION: (1)..(129)
<223> OTHER INFORMATION: Product= Erg-channel modifier toxin

<400> SEQUENCE: 275

```
gat aga gat agc tgt gtt gat aaa tca cga tgc gga aaa tat gga tac       48
Asp Arg Asp Ser Cys Val Asp Lys Ser Arg Cys Gly Lys Tyr Gly Tyr
1               5                   10                  15

tac ggt caa tgt gat gac tgt tgc aag aaa gct gga gac cgt gca gga       96
Tyr Gly Gln Cys Asp Asp Cys Cys Lys Lys Ala Gly Asp Arg Ala Gly
            20                  25                  30

acc tgc gtg tat tac aag tgt aaa tgt aac cca                          129
Thr Cys Val Tyr Tyr Lys Cys Lys Cys Asn Pro
        35                  40
```

<210> SEQ ID NO 276
<211> LENGTH: 43
<212> TYPE: PRT
<213> ORGANISM: Centruroides sculpturatus

<400> SEQUENCE: 276

```
Asp Arg Asp Ser Cys Val Asp Lys Ser Arg Cys Gly Lys Tyr Gly Tyr
1               5                   10                  15

Tyr Gly Gln Cys Asp Asp Cys Cys Lys Lys Ala Gly Asp Arg Ala Gly
            20                  25                  30

Thr Cys Val Tyr Tyr Lys Cys Lys Cys Asn Pro
        35                  40
```

<210> SEQ ID NO 277
<211> LENGTH: 195
<212> TYPE: DNA

-continued

```
<213> ORGANISM: Centruroides sculpturatus
<220> FEATURE:
<221> NAME/KEY: CDS
<222> LOCATION: (1)..(132)
<223> OTHER INFORMATION: Product= Erg-channel modifier toxin precursor
<220> FEATURE:
<221> NAME/KEY: 3'UTR
<222> LOCATION: (133)..(195)
<223> OTHER INFORMATION:

<400> SEQUENCE: 277

gat aga gat agc tgt gtt gat aaa tca cga tgc gga aaa tat gga tac       48
Asp Arg Asp Ser Cys Val Asp Lys Ser Arg Cys Gly Lys Tyr Gly Tyr
1               5                   10                  15

tac ggt caa tgt gat gaa tgt tgc aag aaa gct gga gac cgt gca gga       96
Tyr Gly Gln Cys Asp Glu Cys Cys Lys Lys Ala Gly Asp Arg Ala Gly
            20                  25                  30

acc tgc gtg tat tac aag tgt aaa tgt aac cca taa actcgaatgt          142
Thr Cys Val Tyr Tyr Lys Cys Lys Cys Asn Pro
        35                  40

gaattaagaa tatcaaagct ggaagctgtt taagaagtga aaaataaaga tta          195


<210> SEQ ID NO 278
<211> LENGTH: 43
<212> TYPE: PRT
<213> ORGANISM: Centruroides sculpturatus

<400> SEQUENCE: 278

Asp Arg Asp Ser Cys Val Asp Lys Ser Arg Cys Gly Lys Tyr Gly Tyr
1               5                   10                  15

Tyr Gly Gln Cys Asp Glu Cys Cys Lys Lys Ala Gly Asp Arg Ala Gly
            20                  25                  30

Thr Cys Val Tyr Tyr Lys Cys Lys Cys Asn Pro
        35                  40


<210> SEQ ID NO 279
<211> LENGTH: 129
<212> TYPE: DNA
<213> ORGANISM: Centruroides sculpturatus
<220> FEATURE:
<221> NAME/KEY: CDS
<222> LOCATION: (1)..(129)
<223> OTHER INFORMATION: Product= Erg-channel modifier toxin

<400> SEQUENCE: 279

gat aga gat agc tgt gtt gat aaa tca cga tgc gga aaa tat gga tac       48
Asp Arg Asp Ser Cys Val Asp Lys Ser Arg Cys Gly Lys Tyr Gly Tyr
1               5                   10                  15

tac ggt caa tgt gat gaa tgt tgc aag aaa gct gga gac cgt gca gga       96
Tyr Gly Gln Cys Asp Glu Cys Cys Lys Lys Ala Gly Asp Arg Ala Gly
            20                  25                  30

acc tgc gtg tat tac aag tgt aaa tgt aac cca                          129
Thr Cys Val Tyr Tyr Lys Cys Lys Cys Asn Pro
        35                  40


<210> SEQ ID NO 280
<211> LENGTH: 43
<212> TYPE: PRT
<213> ORGANISM: Centruroides sculpturatus

<400> SEQUENCE: 280

Asp Arg Asp Ser Cys Val Asp Lys Ser Arg Cys Gly Lys Tyr Gly Tyr
1               5                   10                  15
```

-continued

```
Tyr Gly Gln Cys Asp Glu Cys Cys Lys Lys Ala Gly Asp Arg Ala Gly
            20                  25                  30

Thr Cys Val Tyr Tyr Lys Cys Lys Cys Asn Pro
        35                  40
```

<210> SEQ ID NO 281
<211> LENGTH: 192
<212> TYPE: DNA
<213> ORGANISM: Centruroides sculpturatus
<220> FEATURE:
<221> NAME/KEY: CDS
<222> LOCATION: (1)..(144)
<223> OTHER INFORMATION: Product= Erg-channel modifier toxin precursor
<220> FEATURE:
<221> NAME/KEY: 3'UTR
<222> LOCATION: (145)..(192)
<223> OTHER INFORMATION:

<400> SEQUENCE: 281

```
gat aga gat agc tgt gtt gat aaa tca cga tgc gca aaa tat gga tac       48
Asp Arg Asp Ser Cys Val Asp Lys Ser Arg Cys Ala Lys Tyr Gly Tyr
1               5                   10                  15

tac ggt caa tgt gaa gtt tgt tgt aag aaa gct gga cat aat gga gga       96
Tyr Gly Gln Cys Glu Val Cys Cys Lys Lys Ala Gly His Asn Gly Gly
            20                  25                  30

acc tgt atg ttt ttc aag tgt atg tgc gta aac tcg aag atg aat taa      144
Thr Cys Met Phe Phe Lys Cys Met Cys Val Asn Ser Lys Met Asn
        35                  40                  45

taatatcaaa gctgtaagct atttatgaag tgaaaaataa agattatt                 192
```

<210> SEQ ID NO 282
<211> LENGTH: 47
<212> TYPE: PRT
<213> ORGANISM: Centruroides sculpturatus

<400> SEQUENCE: 282

```
Asp Arg Asp Ser Cys Val Asp Lys Ser Arg Cys Ala Lys Tyr Gly Tyr
1               5                   10                  15

Tyr Gly Gln Cys Glu Val Cys Cys Lys Lys Ala Gly His Asn Gly Gly
            20                  25                  30

Thr Cys Met Phe Phe Lys Cys Met Cys Val Asn Ser Lys Met Asn
        35                  40                  45
```

SEQ ID NO 283
<211> LENGTH: 141
<212> TYPE: DNA
<213> ORGANISM: Centruroides sculpturatus
<220> FEATURE:
<221> NAME/KEY: CDS
<222> LOCATION: (1)..(141)
<223> OTHER INFORMATION: Product= Erg-channel modifier toxin

<400> SEQUENCE: 283

```
gat aga gat agc tgt gtt gat aaa tca cga tgc gca aaa tat gga tac       48
Asp Arg Asp Ser Cys Val Asp Lys Ser Arg Cys Ala Lys Tyr Gly Tyr
1               5                   10                  15

tac ggt caa tgt gaa gtt tgt tgt aag aaa gct gga cat aat gga gga       96
Tyr Gly Gln Cys Glu Val Cys Cys Lys Lys Ala Gly His Asn Gly Gly
            20                  25                  30

acc tgt atg ttt ttc aag tgt atg tgc gta aac tcg aag atg aat          141
Thr Cys Met Phe Phe Lys Cys Met Cys Val Asn Ser Lys Met Asn
        35                  40                  45
```

<210> SEQ ID NO 284
<211> LENGTH: 47
<212> TYPE: PRT
<213> ORGANISM: Centruroides sculpturatus

<400> SEQUENCE: 284

Asp Arg Asp Ser Cys Val Asp Lys Ser Arg Cys Ala Lys Tyr Gly Tyr
1               5                   10                  15

Tyr Gly Gln Cys Glu Val Cys Cys Lys Lys Ala Gly His Asn Gly Gly
            20                  25                  30

Thr Cys Met Phe Phe Lys Cys Met Cys Val Asn Ser Lys Met Asn
        35                  40                  45

<210> SEQ ID NO 285
<211> LENGTH: 24
<212> TYPE: DNA
<213> ORGANISM: Artificial
<220> FEATURE:
<223> OTHER INFORMATION: PCR Reverse oligonucleotide primer
<220> FEATURE:
<221> NAME/KEY: misc_feature
<222> LOCATION: (23)..(23)
<223> OTHER INFORMATION: n is a, t, g, or c
<220> FEATURE:
<221> NAME/KEY: primer_bind
<222> LOCATION: (1)..(24)
<223> OTHER INFORMATION: oligonucleotite T22NN
<220> FEATURE:
<221> NAME/KEY: misc_feature
<222> LOCATION: (24)..(24)
<223> OTHER INFORMATION: n is a, t, g, or c

<400> SEQUENCE: 285
tttttttttt tttttttttt ttnn                                          24

<210> SEQ ID NO 286
<211> LENGTH: 25
<212> TYPE: DNA
<213> ORGANISM: Artificial
<220> FEATURE:
<223> OTHER INFORMATION: PCR Direct oligonucleotide primer
<220> FEATURE:
<221> NAME/KEY: misc_feature
<222> LOCATION: (24)..(24)
<223> OTHER INFORMATION: y is c or t
<220> FEATURE:
<221> NAME/KEY: primer_bind
<222> LOCATION: (1)..(25)
<223> OTHER INFORMATION: Oligonucleotide D1

<400> SEQUENCE: 286
gagatgaatt cgttgttgat gatya                                         25

<210> SEQ ID NO 287
<211> LENGTH: 22
<212> TYPE: DNA
<213> ORGANISM: Artificial
<220> FEATURE:
<223> OTHER INFORMATION: PCR Reverse oligonucleotide primer

<400> SEQUENCE: 287
gcaattaaga agcgttacaa ta                                            22

<210> SEQ ID NO 288
<211> LENGTH: 16
<212> TYPE: DNA
<213> ORGANISM: Artificial

-continued

<220> FEATURE:
<223> OTHER INFORMATION: PCR Direct oligonucleotide primer
<220> FEATURE:
<221> NAME/KEY: misc_feature
<222> LOCATION: (2)..(2)
<223> OTHER INFORMATION: m is a or c
<220> FEATURE:
<221> NAME/KEY: primer_bind
<222> LOCATION: (1)..(16)
<223> OTHER INFORMATION: Direct oligonucleotide CexD2
<220> FEATURE:
<221> NAME/KEY: misc_feature
<222> LOCATION: (5)..(5)
<223> OTHER INFORMATION: r is a or g
<220> FEATURE:
<221> NAME/KEY: misc_feature
<222> LOCATION: (9)..(9)
<223> OTHER INFORMATION: r is a or g

<400> SEQUENCE: 288
gmaarggarg gttatc 16

<210> SEQ ID NO 289
<211> LENGTH: 16
<212> TYPE: DNA
<213> ORGANISM: Artificial
<220> FEATURE:
<223> OTHER INFORMATION: PCR Direct oligonucleotide primer
<220> FEATURE:
<221> NAME/KEY: misc_feature
<222> LOCATION: (1)..(1)
<223> OTHER INFORMATION: r is a or g
<220> FEATURE:
<221> NAME/KEY: primer_bind
<222> LOCATION: (1)..(16)
<223> OTHER INFORMATION: Direct oligonucleotide CexD3
<220> FEATURE:
<221> NAME/KEY: misc_feature
<222> LOCATION: (16)..(16)
<223> OTHER INFORMATION: b is c or g
<220> FEATURE:
<221> NAME/KEY: misc_feature
<222> LOCATION: (7)..(7)
<223> OTHER INFORMATION: s is c or g

<400> SEQUENCE: 289
raaggasggt tatccb 16

<210> SEQ ID NO 290
<211> LENGTH: 17
<212> TYPE: DNA
<213> ORGANISM: Artificial
<220> FEATURE:
<223> OTHER INFORMATION: PCR Reverse oligonucleotide primer
<220> FEATURE:
<221> NAME/KEY: primer_bind
<222> LOCATION: (1)..(17)
<223> OTHER INFORMATION: Reverse Oligonucleotide ErgR1
<220> FEATURE:
<221> NAME/KEY: misc_feature
<222> LOCATION: (2)..(2)
<223> OTHER INFORMATION: m is a or c
<220> FEATURE:
<221> NAME/KEY: misc_feature
<222> LOCATION: (1)..(1)
<223> OTHER INFORMATION: m is a or c

<400> SEQUENCE: 290
mmtaatcttt atttttc 17

-continued

<210> SEQ ID NO 291
<211> LENGTH: 17
<212> TYPE: DNA
<213> ORGANISM: Artificial
<220> FEATURE:
<223> OTHER INFORMATION: PCR Reverse oligonucleotide primer
<220> FEATURE:
<221> NAME/KEY: primer_bind
<222> LOCATION: (1)..(17)
<223> OTHER INFORMATION: Reverse Oligonucleotide ErgR2
<220> FEATURE:
<221> NAME/KEY: misc_feature
<222> LOCATION: (16)..(16)
<223> OTHER INFORMATION: m is a or c
<220> FEATURE:
<221> NAME/KEY: misc_feature
<222> LOCATION: (17)..(17)
<223> OTHER INFORMATION: m is a or c

<400> SEQUENCE: 291
aatttgcgga aatttmm 17

<210> SEQ ID NO 292
<211> LENGTH: 27
<212> TYPE: DNA
<213> ORGANISM: Artificial
<220> FEATURE:
<223> OTHER INFORMATION: PCR Direct oligonucleotide primer
<220> FEATURE:
<221> NAME/KEY: primer_bind
<222> LOCATION: (1)..(27)
<223> OTHER INFORMATION: Direct oligonucleotide ErgD1

<400> SEQUENCE: 292
gatagagata gctgtgttga taaatca 27

<210> SEQ ID NO 293
<211> LENGTH: 24
<212> TYPE: DNA
<213> ORGANISM: Artificial
<220> FEATURE:
<223> OTHER INFORMATION: PCR Direct oligonucleotide primer
<220> FEATURE:
<221> NAME/KEY: primer_bind
<222> LOCATION: (1)..(24)
<223> OTHER INFORMATION: Oligonucleotide
<220> FEATURE:
<221> NAME/KEY: primer_bind
<222> LOCATION: (1)..(24)
<223> OTHER INFORMATION: Direct oligonucleotide

<400> SEQUENCE: 293
atgaaagaag gttatctggt aaac 24

<210> SEQ ID NO 294
<211> LENGTH: 24
<212> TYPE: DNA
<213> ORGANISM: Artificial
<220> FEATURE:
<223> OTHER INFORMATION: PCR Reverse oligonucleotide primer
<220> FEATURE:
<221> NAME/KEY: primer_bind
<222> LOCATION: (1)..(24)
<223> OTHER INFORMATION: Reverse oligonucleotide

<400> SEQUENCE: 294
ttagctgcaa gatttattag gaag 24

What is claimed is:

1. An isolated nucleic acid comprising the sequence of SEQ ID NO:115.

2. An isolated polynucleotide comprising a nucleic acid sequence encoding an amino acid sequence at least 95% identical to the sequence of SEQ ID NO: 116, wherein said isolated polynucleotide encodes a toxin that binds to a sodium channel.

3. An isolated polynucleotide comprising a nucleic acid sequence at least 99% identical to the sequence of SEQ ID NO: 115, wherein said isolated polynucleotide encodes a toxin that binds to a sodium channel.

4. A recombinant vector comprising the nucleic acid of claim 1.

5. A recombinant vector comprising the nucleic acid of claim 1 operatively associated with a regulatory sequence that controls gene expression.

6. A genetically engineered host cell comprising the vector of claim 5.

7. A method for producing a polypeptide, comprising:

a) culturing the genetically engineered host cell of claim 6 under conditions suitable to produce the polypeptide; and b) recovering the polypeptide from the cell culture.

8. A recombinant vector comprising the polynucleotide of claim 2.

9. A recombinant vector comprising the polynucleotide of claim 2 operatively associated with a regulatory sequence that controls gene expression.

10. A genetically engineered host cell comprising the vector of claim 9.

11. A method for producing a polypeptide, comprising:

a) culturing the genetically engineered host cell of claim 10 under conditions suitable to produce the polypeptide; and b) recovering the polypeptide from the cell culture.

12. A recombinant vector comprising the polynucleotide of claim 3.

13. A recombinant vector comprising the polynucleotide of claim 3 operatively associated with a regulatory sequence that controls gene expression.

14. A genetically engineered host cell comprising the vector of claim 13.

15. A method for producing a polypeptide, comprising:

a) culturing the genetically engineered host cell of claim 14 under conditions suitable to produce the polypeptide; and b) recovering the polypeptide from the cell culture.

16. An isolated polynucleotide acid that encodes SEQ ID NO:116.

17. A recombinant vector comprising the polynucleotide of claim 16.

18. A recombinant vector comprising the polynucleotide of claim 16 operatively associated with a regulatory sequence that controls gene expression.

19. A genetically engineered host cell comprising the vector of claim 18.

20. A method for producing a polypeptide, comprising:

a) culturing the genetically engineered host cell of claim 19 under conditions suitable to produce the polypeptide; and b) recovering the polypeptide from the cell culture.

* * * * *

UNITED STATES PATENT AND TRADEMARK OFFICE
CERTIFICATE OF CORRECTION

PATENT NO. : 7,335,759 B2
APPLICATION NO. : 10/721793
DATED : February 26, 2008
INVENTOR(S) : Villegas et al.

It is certified that error appears in the above-identified patent and that said Letters Patent is hereby corrected as shown below:

On the front of the patent please replace the assignee name "Universidad Nacional Autónoma de Méxica (UNAM)" with --Universidad Nacional Autónoma de México (UNAM)--

Sequence Listing, SEQ ID NO: 11, please replace codon/aa No. "1" with -- -20--

Sequence Listing, SEQ ID NO: 12, please replace codon/aa No. "1" with -- -20--

Sequence Listing, SEQ ID NO: 15, please replace codon/aa No. "1" with -- -7--

Sequence Listing, SEQ ID NO: 16, please replace codon/aa No. "1" with -- -7--

Sequence Listing, SEQ ID NO: 19, please delete amino acids 66-68

Sequence Listing, SEQ ID NO: 20, please delete amino acids 66-68

Sequence Listing, SEQ ID NO: 93, please replace "68 .. ( )" with --62 .. ( )--

Sequence Listing, SEQ ID NO: 94, please replace codon/aa No. "-2" with --1--

Sequence Listing, SEQ ID NO: 95, please insert nucleic acids --aag gaa-- encoding amino acids Lys Glu at the beginning of the sequence Sequence Listing, SEQ ID NO: 96, please insert amino acids --Lys Glu-- at the beginning of the sequence Sequence Listing, SEQ ID NO: 97, please replace "68 .. ( )" with --62 .. ( )--

Sequence Listing, SEQ ID NO: 98, please replace codon/aa No. "-2" with --1--

Sequence Listing, SEQ ID NO: 99, please insert nucleic acids --aaa gaa-- encoding amino acids Lys Glu at the beginning of the sequence Sequence Listing, SEQ ID NO: 100, please insert amino acids --Lys Glu-- at the beginning of the sequence Sequence Listing, SEQ ID NO: 101, please replace "65 .. ( )" with --62 .. ( )--

Sequence Listing, SEQ ID NO: 102, please replace codon/aa No. "-1" with --1--

UNITED STATES PATENT AND TRADEMARK OFFICE
CERTIFICATE OF CORRECTION

PATENT NO. : 7,335,759 B2

APPLICATION NO. : 10/721793
DATED : February 26, 2008
INVENTOR(S) : Villegas et al.

It is certified that error appears in the above-identified patent and that said Letters Patent is hereby corrected as shown below:

Sequence Listing, SEQ ID NO: 103, please insert nucleic acids --aag-- encoding the amino acid Lys at the beginning of the sequence Sequence Listing, SEQ ID NO: 104, please insert amino acid --Lys-- at the beginning of the sequence Sequence Listing, SEQ ID NO: 105, please replace "65 . . ( )" with --62 . . ( )--

Sequence Listing, SEQ ID NO: 106, please replace codon/aa No. "-1" with --1--

Sequence Listing, SEQ ID NO: 107, please insert nucleic acids --aag-- encoding the amino acid Lys at the beginning of the sequence Sequence Listing, SEQ ID NO: 108, please insert amino acid --Lys-- at the beginning of the sequence Sequence Listing, SEQ ID NO: 109, please replace "59 . . ( )" with --62 . . ( )--

Sequence Listing, SEQ ID NO: 110, please replace codon/aa No. "2" with --1--

Sequence Listing, SEQ ID NO: 111, please delete nucleic acids "gca" from the beginning of the sequence Sequence Listing, SEQ ID NO: 112, please delete amino acid "Ala" from the beginning of the sequence Sequence Listing, SEQ ID NO: 121, please replace "71 . . ( )" with --62 . . ( )--

Sequence Listing, SEQ ID NO: 122, please replace codon/aa No. "-3" with --1--

Sequence Listing, SEQ ID NO: 123, please insert nucleic acids --aag gac ggt-- encoding the amino acids Lys Asp Gly at the beginning of the sequence Sequence Listing, SEQ ID NO: 124, please insert amino acids --Lys Asp Gly-- at the beginning of the sequence Sequence Listing, SEQ ID NO: 125, please replace "71 . . ( )" with --62 . . ( )--

Sequence Listing, SEQ ID NO: 126, please replace codon/aa No. "-3" with --1--

UNITED STATES PATENT AND TRADEMARK OFFICE

CERTIFICATE OF CORRECTION

PATENT NO. : 7,335,759 B2
APPLICATION NO. : 10/721793
DATED : February 26, 2008
INVENTOR(S) : Villegas et al.

It is certified that error appears in the above-identified patent and that said Letters Patent is hereby corrected as shown below:

Sequence Listing, SEQ ID NO: 127, please insert nucleic acids --aag gac ggt-- encoding amino acids Lys Asp Gly at the beginning of the sequence Sequence Listing, SEQ ID NO: 128, please insert amino acids --Lys Asp Gly-- at the beginning of the sequence Sequence Listing, SEQ ID NO: 133, please replace "71 . . ( )" with --62 . . ( )--

Sequence Listing, SEQ ID NO: 134, please replace codon/aa No. "-3" with --1--

Sequence Listing, SEQ ID NO: 135, please insert nucleic acids --aag gac ggt-- encoding amino acids Lys Asp Gly at the beginning of the sequence Sequence Listing, SEQ ID NO: 136, please insert amino acids --Lys Asp Gly-- at the beginning of the sequence Signed and Sealed this Second Day of September, 2008

JON W. DUDAS
*Director of the United States Patent and Trademark Office*